US012751653B2

(12) United States Patent
Bullington et al.

(10) Patent No.: US 12,751,653 B2
(45) Date of Patent: Oct. 6, 2026

(54) FLUID CONTROL DEVICES AND METHODS OF USING THE SAME

(71) Applicant: Magnolia Medical Technologies, Inc., Seattle, WA (US)

(72) Inventors: Gregory J. Bullington, Seattle, WA (US); Jay M. Miazga, Langley, WA (US); Shan E. Gaw, Seattle, WA (US); Timothy F. Ramsey, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

(21) Appl. No.: 18/680,466

(22) Filed: May 31, 2024

(65) Prior Publication Data

US 2024/0315624 A1 Sep. 26, 2024

Related U.S. Application Data

(63) Continuation of application No. 18/407,010, filed on Jan. 8, 2024, which is a continuation of application
(Continued)

(51) Int. Cl.
*A61B 5/15* (2006.01)
*B01L 3/00* (2006.01)

(52) U.S. Cl.
CPC .... *A61B 5/150946* (2013.01); *A61B 5/15003* (2013.01); *A61B 5/150099* (2013.01);
(Continued)

(58) Field of Classification Search
CPC .......... A61B 5/15003; A61B 5/150221; A61B 5/150992; A61B 5/154; A61B 5/1545;
(Continued)

(56) References Cited

U.S. PATENT DOCUMENTS

| | | | |
|---|---|---|---|
| 2,674,265 | A | 4/1954 | Lee |
| 2,697,435 | A | 12/1954 | Benjamin |

(Continued)

FOREIGN PATENT DOCUMENTS

| | | | |
|---|---|---|---|
| AT | 310345 | B | 9/1973 |
| AT | E219383 | T1 | 7/2002 |

(Continued)

OTHER PUBLICATIONS

Arenas et al., "Asynchronous Testing of 2 Specimen-Diversion Devices to reduce Blood Culture Contamination: A Single-Site Product Supply Quality Improvement Project," J. Emergency Nursing, vol. 47, No. 2, pp. 256-264.e6 (Mar. 2021), 15 pages.

(Continued)

*Primary Examiner* — Jeffrey G. Hoekstra
(74) *Attorney, Agent, or Firm* — COOLEY LLP

(57) ABSTRACT

A fluid control device includes an inlet configured to be placed directly or indirectly in fluid communication with a bodily fluid source and an outlet configured to be placed in fluid communication with a fluid collection device. The fluid control device has a first state in which a negative pressure differential produced from an external source such as the fluid collection device is applied to the fluid control device to draw an initial volume of bodily fluid from the bodily fluid source, through the inlet, and into a sequestration portion of the fluid control device. The fluid control device has a second state in which (1) the sequestration portion sequesters the initial volume, and (2) the negative pressure differential draws a subsequent volume of bodily fluid, being substantially free of contaminants, from the bodily fluid source, through the fluid control device, and into the fluid collection device.

13 Claims, 29 Drawing Sheets

Related U.S. Application Data

No. 18/299,680, filed on Apr. 12, 2023, now Pat. No. 11,903,710, which is a continuation of application No. 18/130,207, filed on Apr. 3, 2023, now Pat. No. 11,903,709, which is a continuation of application No. 17/883,340, filed on Aug. 8, 2022, now Pat. No. 11,653,863, which is a continuation of application No. 17/390,249, filed on Jul. 30, 2021, now Pat. No. 12,290,363, which is a continuation of application No. 16/129,066, filed on Sep. 12, 2018, now Pat. No. 11,076,787.

(60) Provisional application No. 62/678,632, filed on May 31, 2018, provisional application No. 62/634,569, filed on Feb. 23, 2018, provisional application No. 62/557,530, filed on Sep. 12, 2017.

(52) U.S. Cl.
CPC .. *A61B 5/150213* (2013.01); *A61B 5/150221* (2013.01); *A61B 5/150251* (2013.01); *A61B 5/150992* (2013.01); *B01L 3/502* (2013.01); *B01L 2200/026* (2013.01); *B01L 2200/027* (2013.01); *B01L 2200/0684* (2013.01); *B01L 2200/0689* (2013.01); *B01L 2200/141* (2013.01); *B01L 2300/0681* (2013.01); *B01L 2300/14* (2013.01); *B01L 2400/0478* (2013.01); *B01L 2400/0487* (2013.01)

(58) Field of Classification Search
CPC ........ A61B 5/150213; A61B 5/150473; A61B 5/1438; A61B 5/150343; A61B 5/150229; A61B 5/150244; A61B 5/150206; A61B 5/150267; A61B 5/150488; A61B 5/150496; A61B 5/150099
See application file for complete search history.

(56) References Cited

U.S. PATENT DOCUMENTS

| | | | |
|---|---|---|---|
| 2,707,953 | A | 5/1955 | Ryan |
| 2,876,769 | A | 3/1959 | Juan |
| 2,952,258 | A | 9/1960 | Chandler |
| 2,992,974 | A | 7/1961 | Belcove et al. |
| 3,013,557 | A | 12/1961 | Pallotta |
| 3,098,016 | A | 7/1963 | Sam et al. |
| 3,382,865 | A | 5/1968 | Worrall, Jr. |
| 3,405,706 | A | 10/1968 | Paul |
| 3,467,021 | A | 9/1969 | Green, Jr. |
| 3,467,095 | A | 9/1969 | Ross |
| 3,494,351 | A | 2/1970 | Horn |
| 3,494,352 | A | 2/1970 | Russo et al. |
| 3,577,980 | A | 5/1971 | Cohen |
| 3,596,652 | A | 8/1971 | Winkelman |
| 3,604,410 | A | 9/1971 | Whitacre |
| 3,635,798 | A | 1/1972 | Kirkham et al. |
| 3,640,267 | A | 2/1972 | Hurtig et al. |
| 3,648,684 | A | 3/1972 | Barnwell et al. |
| 3,650,093 | A | 3/1972 | Rosenberg |
| 3,680,558 | A | 8/1972 | Kapelowitz |
| 3,696,806 | A | 10/1972 | Sausse |
| 3,705,018 | A | 12/1972 | Taylor |
| 3,730,168 | A | 5/1973 | McWhorter |
| 3,741,197 | A | 6/1973 | Sanz et al. |
| 3,749,084 | A | 7/1973 | Cucchiara |
| 3,777,773 | A | 12/1973 | Tolbert |
| 3,779,383 | A | 12/1973 | Ayres |
| 3,803,810 | A | 4/1974 | Rosenberg |
| 3,817,240 | A | 6/1974 | Ayres |
| 3,831,602 | A | 8/1974 | Broadwin |
| 3,834,372 | A | 9/1974 | Turney |
| 3,835,835 | A | 9/1974 | Thompson et al. |
| 3,848,579 | A | 11/1974 | Villa |
| 3,848,581 | A | 11/1974 | Cinqualbre et al. |
| 3,859,998 | A | 1/1975 | Thomas et al. |
| 3,874,367 | A | 4/1975 | Ayres |
| 3,886,930 | A | 6/1975 | Ryan |
| 3,890,203 | A | 6/1975 | Mehl |
| 3,890,968 | A | 6/1975 | Pierce et al. |
| 3,937,211 | A | 2/1976 | Merten |
| 3,943,917 | A | 3/1976 | Johansen |
| 3,945,380 | A | 3/1976 | Dabney et al. |
| 3,960,139 | A | 6/1976 | Bailey |
| 3,978,846 | A | 9/1976 | Bailey |
| 3,996,923 | A | 12/1976 | Guerra |
| 4,056,101 | A | 11/1977 | Geissler et al. |
| 4,057,050 | A | 11/1977 | Sarstedt |
| 4,062,360 | A | 12/1977 | Bentley |
| 4,063,460 | A | 12/1977 | Svensson |
| 4,077,395 | A | 3/1978 | Woolner |
| 4,106,491 | A | 8/1978 | Guerra |
| 4,106,497 | A | 8/1978 | Percarpio |
| 4,133,304 | A | 1/1979 | Bailey |
| 4,133,863 | A | 1/1979 | Koenig |
| 4,150,089 | A | 4/1979 | Linet |
| 4,154,229 | A | 5/1979 | Nugent |
| 4,166,450 | A | 9/1979 | Abramson |
| 4,190,426 | A | 2/1980 | Ruschke |
| 4,193,400 | A | 3/1980 | Loveless et al. |
| 4,202,764 | A | 5/1980 | Afflerbaugh et al. |
| 4,206,282 | A | 6/1980 | Hochstein |
| 4,207,870 | A | 6/1980 | Eldridge |
| 4,210,173 | A | 7/1980 | Choksi et al. |
| 4,212,308 | A | 7/1980 | Percarpio |
| 4,226,236 | A | 10/1980 | Genese |
| 4,238,207 | A | 12/1980 | Ruschke |
| 4,257,416 | A | 3/1981 | Prager |
| 4,275,730 | A | 6/1981 | Hussein |
| 4,298,358 | A | 11/1981 | Ruschke |
| 4,312,362 | A | 1/1982 | Kaufman |
| 4,317,456 | A | 3/1982 | Percarpio |
| 4,327,746 | A | 5/1982 | Feaster |
| 4,340,067 | A | 7/1982 | Rattenborg |
| 4,340,068 | A | 7/1982 | Kaufman |
| 4,349,035 | A | 9/1982 | Thomas et al. |
| 4,354,507 | A | 10/1982 | Raitto |
| 4,370,987 | A | 2/1983 | Bazell et al. |
| 4,373,535 | A | 2/1983 | Martell |
| 4,398,544 | A | 8/1983 | Nugent et al. |
| 4,411,275 | A | 10/1983 | Raitto |
| 4,412,548 | A | 11/1983 | Hoch |
| 4,416,290 | A | 11/1983 | Lutkowski |
| 4,416,291 | A | 11/1983 | Kaufman |
| 4,425,235 | A | 1/1984 | Cornell et al. |
| 4,436,098 | A | 3/1984 | Kaufman |
| 4,444,203 | A | 4/1984 | Engelman |
| 4,459,997 | A | 7/1984 | Sarstedt |
| 4,496,458 | A | 1/1985 | Lee |
| 4,509,534 | A | 4/1985 | Tassin, Jr. |
| 4,551,131 | A | 11/1985 | Miles et al. |
| 4,581,014 | A | 4/1986 | Millerd et al. |
| 4,608,996 | A | 9/1986 | Brown |
| 4,626,248 | A | 12/1986 | Scheller |
| 4,654,027 | A | 3/1987 | Dragan et al. |
| 4,657,027 | A | 4/1987 | Paulsen |
| 4,657,160 | A | 4/1987 | Woods et al. |
| 4,673,386 | A | 6/1987 | Gordon |
| 4,676,256 | A | 6/1987 | Golden |
| 4,679,571 | A | 7/1987 | Frankel et al. |
| 4,690,154 | A | 9/1987 | Woodford et al. |
| 4,699,612 | A | 10/1987 | Hamacher |
| 4,703,763 | A | 11/1987 | McAlister et al. |
| 4,705,497 | A | 11/1987 | Shitaokoshi et al. |
| 4,714,461 | A | 12/1987 | Gabel |
| 4,715,854 | A | 12/1987 | Vaillancourt |
| 4,772,273 | A | 9/1988 | Alchas |
| 4,820,287 | A | 4/1989 | Leonard |
| 4,838,855 | A | 6/1989 | Lynn |
| 4,865,583 | A | 9/1989 | Tu |
| 4,879,098 | A | 11/1989 | Oberhardt et al. |
| 4,886,072 | A | 12/1989 | Percarpio et al. |

(56) References Cited

U.S. PATENT DOCUMENTS

| | | | |
|---|---|---|---|
| 4,890,627 | A | 1/1990 | Haber et al. |
| 4,904,240 | A | 2/1990 | Hoover |
| 4,936,315 | A | 6/1990 | Lineback |
| 4,980,297 | A | 12/1990 | Haynes et al. |
| 4,988,339 | A | 1/1991 | Vadher |
| 5,006,114 | A | 4/1991 | Rogers et al. |
| 5,009,847 | A | 4/1991 | Solomons |
| 5,027,827 | A | 7/1991 | Cody et al. |
| 5,032,116 | A | 7/1991 | Peterson et al. |
| 5,032,288 | A | 7/1991 | Columbus et al. |
| 5,035,688 | A | 7/1991 | Inui |
| 5,045,185 | A | 9/1991 | Ohnaka et al. |
| 5,052,403 | A | 10/1991 | Haber et al. |
| 5,054,498 | A | 10/1991 | Melet |
| 5,066,284 | A | 11/1991 | Mersch et al. |
| 5,084,034 | A | 1/1992 | Zanotti |
| 5,097,842 | A | 3/1992 | Bonn |
| 5,100,394 | A | 3/1992 | Dudar et al. |
| 5,108,927 | A | 4/1992 | Dorn |
| 5,116,323 | A | 5/1992 | Kreuzer et al. |
| 5,122,129 | A | 6/1992 | Olson et al. |
| 5,126,054 | A | 6/1992 | Matkovich |
| 5,135,489 | A | 8/1992 | Jepson et al. |
| 5,147,329 | A | 9/1992 | Brannon |
| 5,208,160 | A | 5/1993 | Kikyotani et al. |
| 5,222,502 | A | 6/1993 | Kurose |
| 5,269,317 | A | 12/1993 | Bennett |
| 5,286,279 | A | 2/1994 | Wu |
| 5,330,464 | A | 7/1994 | Mathias et al. |
| 5,334,162 | A | 8/1994 | Harris |
| 5,354,537 | A | 10/1994 | Moreno |
| 5,360,011 | A | 11/1994 | McCallister |
| 5,372,143 | A | 12/1994 | Bernes et al. |
| 5,395,339 | A | 3/1995 | Talonn et al. |
| 5,417,673 | A | 5/1995 | Gordon |
| 5,429,610 | A | 7/1995 | Vaillancourt |
| 5,431,811 | A | 7/1995 | Tusini et al. |
| 5,439,022 | A | 8/1995 | Summers et al. |
| 5,439,450 | A | 8/1995 | Haedt |
| 5,450,856 | A | 9/1995 | Norris |
| 5,451,321 | A | 9/1995 | Matkovich |
| 5,454,786 | A | 10/1995 | Harris |
| 5,466,228 | A | 11/1995 | Evans |
| 5,472,605 | A | 12/1995 | Zuk, Jr. |
| 5,485,854 | A | 1/1996 | Hollister |
| 5,507,299 | A | 4/1996 | Roland |
| 5,520,193 | A | 5/1996 | Suzuki et al. |
| 5,522,804 | A | 6/1996 | Lynn |
| 5,573,510 | A | 11/1996 | Isaacson |
| 5,573,951 | A | 11/1996 | Gombrich et al. |
| 5,575,777 | A | 11/1996 | Cover et al. |
| 5,577,513 | A | 11/1996 | Van Vlasselaer |
| 5,603,700 | A | 2/1997 | Daneshvar |
| 5,632,906 | A | 5/1997 | Ishida et al. |
| 5,634,893 | A | 6/1997 | Rishton |
| 5,649,912 | A | 7/1997 | Peterson |
| 5,658,271 | A | 8/1997 | Loubser |
| 5,685,846 | A | 11/1997 | Michaels, Jr. |
| 5,691,486 | A | 11/1997 | Behringer et al. |
| 5,749,857 | A | 5/1998 | Cuppy |
| 5,759,160 | A | 6/1998 | Neese et al. |
| 5,762,633 | A | 6/1998 | Whisson |
| 5,772,608 | A | 6/1998 | Dhas |
| 5,785,682 | A | 7/1998 | Grabenkort |
| 5,811,658 | A | 9/1998 | Van Driel et al. |
| 5,824,001 | A | 10/1998 | Erskine |
| 5,857,983 | A | 1/1999 | Douglas et al. |
| 5,865,803 | A | 2/1999 | Major |
| 5,865,812 | A | 2/1999 | Correia |
| 5,871,699 | A | 2/1999 | Ruggeri |
| 5,873,841 | A | 2/1999 | Brannon |
| 5,876,926 | A | 3/1999 | Beecham |
| 5,882,318 | A | 3/1999 | Boyde |
| D410,081 | S | 5/1999 | Sweeney et al. |
| 5,911,705 | A | 6/1999 | Howell |
| 5,922,551 | A | 7/1999 | Durbin et al. |
| RE36,273 | E | 8/1999 | Brannon |
| 5,947,932 | A | 9/1999 | Desecki et al. |
| 5,961,472 | A | 10/1999 | Swendson et al. |
| 5,971,956 | A | 10/1999 | Epstein |
| 5,980,830 | A | 11/1999 | Savage et al. |
| 6,001,307 | A | 12/1999 | Naka et al. |
| 6,010,633 | A | 1/2000 | Zuk, Jr. et al. |
| 6,013,037 | A | 1/2000 | Brannon |
| 6,016,712 | A | 1/2000 | Warden et al. |
| 6,050,957 | A | 4/2000 | Desch |
| 6,103,271 | A | 8/2000 | Morrison et al. |
| 6,106,509 | A | 8/2000 | Loubser |
| 6,126,643 | A | 10/2000 | Vaillancouert |
| 6,146,360 | A | 11/2000 | Rogers et al. |
| 6,159,164 | A | 12/2000 | Neese et al. |
| 6,171,493 | B1 | 1/2001 | Zia et al. |
| 6,190,855 | B1 | 2/2001 | Herman et al. |
| 6,210,909 | B1 | 4/2001 | Guirguis |
| 6,224,561 | B1 | 5/2001 | Swendson et al. |
| 6,254,581 | B1 | 7/2001 | Scott |
| 6,296,020 | B1 | 10/2001 | Mcneely et al. |
| 6,299,131 | B1 | 10/2001 | Ryan |
| 6,306,614 | B1 | 10/2001 | Romaschin et al. |
| 6,325,975 | B1 | 12/2001 | Naka et al. |
| 6,328,726 | B1 | 12/2001 | Ishida et al. |
| 6,355,023 | B1 | 3/2002 | Roth et al. |
| 6,364,847 | B1 | 4/2002 | Shulze et al. |
| 6,364,890 | B1 | 4/2002 | Lum et al. |
| 6,368,306 | B1 | 4/2002 | Koska |
| 6,387,086 | B2 | 5/2002 | Mathias et al. |
| 6,398,743 | B1 | 6/2002 | Halseth et al. |
| 6,403,381 | B1 | 6/2002 | Mann et al. |
| 6,416,496 | B1 | 7/2002 | Rogers et al. |
| 6,440,725 | B1 | 8/2002 | Pourahmadi et al. |
| 6,478,775 | B1 | 11/2002 | Galt et al. |
| 6,506,182 | B2 | 1/2003 | Estabrook et al. |
| 6,511,439 | B1 | 1/2003 | Tabata et al. |
| 6,520,948 | B1 | 2/2003 | Mathias et al. |
| 6,569,117 | B1 | 5/2003 | Ziv et al. |
| 6,592,555 | B1 | 7/2003 | Wen-Pi et al. |
| 6,592,613 | B1 | 7/2003 | Ishida et al. |
| 6,626,884 | B1 | 9/2003 | Dillon et al. |
| 6,629,959 | B2 | 10/2003 | Kuracina et al. |
| 6,638,252 | B2 | 10/2003 | Moulton et al. |
| 6,638,263 | B1 | 10/2003 | Theeuwes et al. |
| 6,648,835 | B1 | 11/2003 | Shemesh |
| 6,692,479 | B2 | 2/2004 | Kraus et al. |
| 6,695,004 | B1 | 2/2004 | Raybuck |
| 6,712,963 | B2 | 3/2004 | Schick |
| 6,716,187 | B1 | 4/2004 | Jorgensen et al. |
| 6,716,396 | B1 | 4/2004 | Anderson et al. |
| 6,733,433 | B1 | 5/2004 | Fell |
| 6,736,783 | B2 | 5/2004 | Blake et al. |
| 6,746,420 | B1 | 6/2004 | Prestidge et al. |
| 6,772,513 | B1 | 8/2004 | Frye-Mason et al. |
| 6,843,775 | B2 | 1/2005 | Hyun |
| 6,860,871 | B2 | 3/2005 | Kuracina et al. |
| 6,905,483 | B2 | 6/2005 | Newby et al. |
| 6,913,580 | B2 | 7/2005 | Stone |
| 6,945,948 | B2 | 9/2005 | Bainbridge et al. |
| 6,979,323 | B2 | 12/2005 | Rogers et al. |
| 7,002,468 | B2 | 2/2006 | Eveland et al. |
| 7,044,941 | B2 | 5/2006 | Mathias et al. |
| 7,052,603 | B2 | 5/2006 | Schick |
| 7,055,401 | B2 | 6/2006 | Prybella et al. |
| 7,087,047 | B2 | 8/2006 | Kraus et al. |
| 7,130,396 | B2 | 10/2006 | Rogers et al. |
| 7,141,097 | B2 | 11/2006 | Leahey |
| 7,241,281 | B2 | 7/2007 | Coelho et al. |
| 7,264,608 | B2 | 9/2007 | Bischof et al. |
| 7,306,736 | B2 | 12/2007 | Collins et al. |
| 7,314,452 | B2 | 1/2008 | Madonia |
| 7,316,662 | B2 | 1/2008 | Delnevo et al. |
| 7,335,188 | B2 | 2/2008 | Graf |
| 7,351,228 | B2 | 4/2008 | Keane et al. |
| 7,384,416 | B2 | 6/2008 | Goudaliez et al. |
| 7,435,231 | B2 | 10/2008 | Mathias et al. |
| 7,461,671 | B2 | 12/2008 | Ehwald et al. |

(56) References Cited

U.S. PATENT DOCUMENTS 7,479,131 B2 1/2009 Mathias et al.
7,544,324 B2 6/2009 Tung et al.
7,614,857 B2 11/2009 Fuechslin et al.
7,615,033 B2 11/2009 Leong
7,618,407 B2 11/2009 Demay et al.
7,648,491 B2 1/2010 Rogers
7,666,166 B1 2/2010 Emmert et al.
7,744,573 B2 6/2010 Gordon et al.
7,766,879 B2 8/2010 Tan et al.
7,780,794 B2 8/2010 Rogers et al.
7,896,817 B2 3/2011 Garrison
7,914,508 B2 3/2011 Engstrom
7,923,053 B2 4/2011 Kitching et al.
7,963,950 B2 6/2011 Madonia
7,985,302 B2 7/2011 Rogers et al.
8,070,725 B2 12/2011 Christensen
8,109,157 B2 2/2012 Kanayama et al.
RE43,283 E 3/2012 Ishida et al.
8,197,420 B2 6/2012 Patton
8,206,318 B2 6/2012 Uchiyama et al.
8,206,514 B2 6/2012 Rogers et al.
8,231,546 B2 7/2012 Patton
8,282,605 B2 10/2012 Tan et al.
8,287,499 B2 10/2012 Miyasaka
8,290,129 B2 10/2012 Rogers et al.
8,337,418 B2 12/2012 Patton
8,349,254 B2 1/2013 Hoshino et al.
8,356,644 B2 1/2013 Chong et al.
8,377,040 B2 2/2013 Burkholz et al.
8,382,712 B2 2/2013 Kim
8,383,044 B2 2/2013 Davis et al.
8,412,300 B2 4/2013 Sonderegger
8,523,826 B2 9/2013 Layton, Jr.
8,535,241 B2 9/2013 Bullington et al.
8,540,663 B2 9/2013 Davey et al.
8,568,371 B2 10/2013 Siopes et al.
8,574,203 B2 11/2013 Stout et al.
8,603,009 B2 12/2013 Tan et al.
8,647,286 B2 2/2014 Patton
8,679,063 B2 3/2014 Stout et al.
8,747,779 B2 6/2014 Sprague et al.
8,772,046 B2 7/2014 Fraden et al.
8,795,198 B2 8/2014 Tan et al.
8,808,202 B2 8/2014 Brancazio
8,827,958 B2 9/2014 Bierman et al.
8,832,894 B2 9/2014 Rogers et al.
8,834,650 B2 9/2014 Rogers et al.
8,864,684 B2 10/2014 Bullington et al.
8,876,734 B2 11/2014 Patton
8,992,505 B2 3/2015 Thorne, Jr. et al.
8,999,073 B2 4/2015 Rogers et al.
9,022,950 B2 5/2015 Bullington et al.
9,022,951 B2 5/2015 Bullington et al.
9,060,724 B2 6/2015 Bullington et al.
9,060,725 B2 6/2015 Bullington et al.
9,138,572 B2 9/2015 Zeytoonian et al.
9,149,576 B2 10/2015 Bullington et al.
9,155,495 B2 10/2015 Bullington et al.
9,204,864 B2 12/2015 Bullington et al.
9,205,198 B2 12/2015 Py
9,233,208 B2 1/2016 Tekeste
RE45,896 E 2/2016 Stout et al.
9,259,284 B2 2/2016 Rogers et al.
9,314,201 B2 4/2016 Burkholz et al.
9,320,459 B2 4/2016 Chin et al.
9,820,682 B2 11/2017 Rogers et al.
9,855,001 B2 1/2018 Patton
9,855,002 B2 1/2018 Patton
9,855,386 B2 1/2018 Close et al.
9,861,306 B2 1/2018 Patton
9,872,645 B2 1/2018 Patton
9,877,674 B2 1/2018 Holmes et al.
9,877,675 B2 1/2018 Baid
9,895,092 B2 2/2018 Burkholz
9,931,466 B2 4/2018 Bullington et al.
9,950,084 B2 4/2018 Bullington et al.
9,962,489 B2 5/2018 Hopkins
9,999,383 B2 6/2018 Bullington et al.
10,010,282 B2 7/2018 Rogers et al.
10,022,079 B2 7/2018 Hopkins
10,022,530 B2 7/2018 Tekeste
10,028,687 B2 7/2018 Patton
10,028,688 B2 7/2018 Patton
10,028,689 B2 7/2018 Patton
10,039,483 B2 8/2018 Bullington et al.
10,045,724 B2 8/2018 Patton
10,052,053 B2 8/2018 Patton
10,080,516 B2 9/2018 Ellis et al.
10,086,142 B2 10/2018 Tekeste
10,143,412 B2 12/2018 Rogers et al.
10,143,413 B2 12/2018 Garrett et al.
10,206,613 B2 2/2019 Bullington et al.
10,220,139 B2 3/2019 Bullington et al.
10,238,326 B2 3/2019 Gil et al.
10,251,590 B2 4/2019 Bullington et al.
10,265,007 B2 4/2019 Bullington et al.
10,292,633 B2 5/2019 Bullington et al.
10,299,713 B2 5/2019 Patton
10,369,285 B2 8/2019 Hopkins
10,433,779 B2 10/2019 Bullington et al.
10,463,792 B2 11/2019 Hopkins
10,596,315 B2 3/2020 Bullington et al.
10,624,977 B2 4/2020 Bullington et al.
10,736,554 B2 8/2020 Bullington et al.
10,772,548 B2 9/2020 Bullington et al.
10,813,579 B2 10/2020 Baid
10,827,964 B2 11/2020 Rogers et al.
10,856,791 B2 12/2020 McHale et al.
10,881,343 B2 1/2021 Bullington et al.
10,888,262 B2 1/2021 Russ et al.
10,912,506 B2 2/2021 Bullington et al.
11,076,787 B2 8/2021 Bullington et al.
11,116,904 B2 9/2021 Hopkins
11,167,085 B2 11/2021 Hopkins
11,234,626 B2 2/2022 Bullington et al.
11,253,649 B2 2/2022 Hopkins
11,259,727 B2 3/2022 Bullington et al.
11,311,218 B2 4/2022 Bullington et al.
11,317,838 B2 5/2022 Bullington et al.
11,318,459 B2 5/2022 Shi et al.
11,395,611 B2 7/2022 Bullington et al.
11,395,612 B2 7/2022 Bullington et al.
11,419,531 B2 8/2022 Bullington et al.
11,529,081 B2 12/2022 Bullington et al.
11,589,786 B2 2/2023 Bullington et al.
11,607,159 B2 3/2023 Bullington et al.
11,653,863 B2 5/2023 Bullington et al.
11,660,030 B2 5/2023 Bullington et al.
11,737,693 B2 8/2023 Bullington et al.
11,786,155 B2 10/2023 Bullington et al.
11,789,017 B2 10/2023 Bullington et al.
11,819,329 B2 11/2023 Bullington et al.
11,857,321 B2 1/2024 Bullington et al.
11,890,452 B2 2/2024 Bullington et al.
11,903,709 B2 2/2024 Bullington et al.
11,903,710 B2 2/2024 Bullington et al.
11,998,332 B2 6/2024 Bullington et al.
12,083,234 B2 9/2024 Bullington et al.
12,133,968 B2 11/2024 Bullington et al.
12,138,052 B1 11/2024 Rogers et al.
12,150,763 B2 11/2024 Bullington et al.
12,186,080 B2 1/2025 Bullington et al.
12,193,816 B2 1/2025 Bullington et al.
12,290,363 B2 5/2025 Bullington et al.
12,471,815 B2 11/2025 Bullington et al.
12,471,816 B2 11/2025 Bullington et al.
12,478,300 B2 11/2025 Bullington et al.
12,478,301 B2 11/2025 Bullington et al.
12,502,109 B2 12/2025 Bullington et al.
12,551,150 B2 2/2026 Bullington et al.
2001/0031932 A1 10/2001 Blake et al.
2001/0039058 A1 11/2001 Iheme et al.
2002/0002349 A1 1/2002 Flaherty et al.
2002/0004647 A1 1/2002 Leong

(56) References Cited

U.S. PATENT DOCUMENTS

2002/0107469 A1 8/2002 Bolan et al.
2002/0183651 A1 12/2002 Hyun
2002/0193751 A1 12/2002 Theeuwes et al.
2003/0013991 A1 1/2003 Stone
2003/0040708 A1 2/2003 Rogers et al.
2003/0055381 A1 3/2003 Wilkinson
2003/0069543 A1 4/2003 Carpenter et al.
2003/0105414 A1 6/2003 Leong
2003/0208151 A1 11/2003 Kraus et al.
2004/0000309 A1 1/2004 Alston
2004/0009542 A1 1/2004 Dumont et al.
2004/0010228 A1 1/2004 Swenson et al.
2004/0054283 A1 3/2004 Corey et al.
2004/0054333 A1 3/2004 Theeuwes et al.
2004/0073171 A1 4/2004 Rogers et al.
2004/0124389 A1 7/2004 Phillips
2004/0127816 A1 7/2004 Galvao
2004/0147855 A1 7/2004 Marsden
2005/0004524 A1 1/2005 Newby et al.
2005/0010136 A1 1/2005 Restelli et al.
2005/0054949 A1 3/2005 McKinnon et al.
2005/0082218 A1 4/2005 Verri et al.
2005/0148993 A1 7/2005 Mathias et al.
2005/0154368 A1 7/2005 Lim et al.
2005/0161112 A1 7/2005 Ehwald et al.
2005/0199077 A1 9/2005 Prybella et al.
2005/0240161 A1 10/2005 Crawford
2005/0245885 A1 11/2005 Brown
2005/0273019 A1 12/2005 Conway et al.
2005/0277848 A1 12/2005 Graf
2005/0281713 A1 12/2005 Hampsch et al.
2006/0009713 A1 1/2006 Flaherty
2006/0018790 A1 1/2006 Naka et al.
2006/0111667 A1 5/2006 Matsuura et al.
2006/0155212 A1 7/2006 Madonia
2006/0251622 A1 11/2006 Suzuki et al.
2006/0287639 A1 12/2006 Sharp
2007/0083162 A1 4/2007 O'Reagan et al.
2007/0088279 A1 4/2007 Shue et al.
2007/0100250 A1 5/2007 Kline
2007/0119508 A1 5/2007 West et al.
2007/0172389 A1 7/2007 Wilding et al.
2007/0191716 A1 8/2007 Goldberger et al.
2007/0287948 A1 12/2007 Sakiewicz
2008/0086085 A1 4/2008 Brown
2008/0108954 A1 5/2008 Mathias et al.
2008/0114304 A1 5/2008 Nalesso et al.
2008/0145933 A1 6/2008 Patton
2008/0167577 A1 7/2008 Weilbacher et al.
2008/0185056 A1 8/2008 Diodati et al.
2008/0200837 A1 8/2008 Frazier et al.
2008/0254471 A1 10/2008 Bordano
2008/0255523 A1 10/2008 Grinberg
2008/0312576 A1 12/2008 Mckinnon et al.
2008/0319346 A1 12/2008 Crawford et al.
2009/0076441 A1 3/2009 Sebban
2009/0173685 A1 7/2009 Imai et al.
2009/0177117 A1 7/2009 Amano et al.
2009/0192447 A1 7/2009 Andersen et al.
2009/0215159 A1 8/2009 Kirby
2009/0227896 A1 9/2009 Alvin Tan et al.
2009/0301317 A1 12/2009 Andrews
2009/0306601 A1 12/2009 Shaw et al.
2010/0010372 A1 1/2010 Brown et al.
2010/0042048 A1 2/2010 Christensen
2010/0057004 A1 3/2010 Christensen et al.
2010/0094171 A1 4/2010 Conway et al.
2010/0152681 A1 6/2010 Mathias
2010/0185134 A1 7/2010 Houwen et al.
2010/0234768 A1 9/2010 Uchiyama et al.
2010/0240964 A1 9/2010 Sterling et al.
2010/0252118 A1 10/2010 Fraden et al.
2010/0255589 A1 10/2010 Saiki et al.
2010/0268118 A1 10/2010 Schweiger
2010/0286513 A1 11/2010 Pollard, Jr. et al.
2010/0298671 A1 11/2010 Asakura et al.
2011/0009717 A1 1/2011 Davis et al.
2011/0046602 A1 2/2011 Grimm et al.
2011/0092856 A1 4/2011 Freeman et al.
2011/0125058 A1 5/2011 Levinson et al.
2011/0178427 A1 7/2011 Tan et al.
2011/0198221 A1 8/2011 Angelescu
2011/0288441 A1 11/2011 Taguchi
2011/0306856 A1 12/2011 Rule et al.
2011/0306899 A1 12/2011 Brown et al.
2011/0313318 A1 12/2011 Rule et al.
2011/0319859 A1 12/2011 Zeytoonian et al.
2012/0004619 A1 1/2012 Stephens et al.
2012/0016266 A1 1/2012 Burkholz
2012/0017999 A1 1/2012 Velschow
2012/0022404 A1 1/2012 Fojtik
2012/0029494 A1 2/2012 Wittenberger et al.
2012/0035540 A1 2/2012 Ferren et al.
2012/0095367 A1 4/2012 Patton
2012/0123297 A1 5/2012 Brancazio
2012/0215131 A1 8/2012 Patton
2012/0226239 A1 9/2012 Green
2012/0245042 A1 9/2012 Liu et al.
2012/0265099 A1 10/2012 Goodnow, II et al.
2012/0265128 A1 10/2012 Kolln
2012/0277697 A1 11/2012 Haghgooie et al.
2012/0323142 A1 12/2012 Allen et al.
2013/0023792 A1 1/2013 Markey et al.
2013/0079604 A1 3/2013 Patton
2013/0085514 A1 4/2013 Lee et al.
2013/0116599 A1 5/2013 Bullington et al.
2013/0158506 A1 6/2013 Harris et al.
2013/0289420 A1 10/2013 Pfeiffer et al.
2013/0295602 A1 11/2013 Fowler et al.
2013/0317391 A1 11/2013 Bullington et al.
2014/0008366 A1 1/2014 Genosar
2014/0039348 A1 2/2014 Bullington et al.
2014/0051062 A1 2/2014 Vanapalli et al.
2014/0066880 A1 3/2014 Prince et al.
2014/0081172 A1 3/2014 Patton
2014/0107564 A1 4/2014 Bullington et al.
2014/0124542 A1 5/2014 Kojima et al.
2014/0128775 A1 5/2014 Andreae et al.
2014/0155781 A1 6/2014 Bullington et al.
2014/0155782 A1 6/2014 Bullington et al.
2014/0163419 A1 6/2014 Bullington et al.
2014/0188002 A1 7/2014 Close et al.
2014/0208978 A1 7/2014 Sunder et al.
2014/0221873 A1 8/2014 Hayakawa et al.
2014/0257249 A1 9/2014 Witt
2014/0276039 A1 9/2014 Cowan et al.
2014/0305196 A1 10/2014 Ellis et al.
2014/0336536 A1 11/2014 Brancazio
2015/0000061 A1 1/2015 Rogers et al.
2015/0011847 A1 1/2015 Hayden
2015/0011910 A1 1/2015 Bullington et al.
2015/0011911 A1 1/2015 Bullington et al.
2015/0018715 A1 1/2015 Walterspiel
2015/0025454 A1 1/2015 Wetzel et al.
2015/0025455 A1 1/2015 Shetty et al.
2015/0025456 A1 1/2015 Shetty et al.
2015/0073304 A1 3/2015 Millerd
2015/0073348 A1 3/2015 Bullington et al.
2015/0094615 A1 4/2015 Patton
2015/0099996 A1 4/2015 Bullington et al.
2015/0151298 A1 6/2015 Hobbs et al.
2015/0257691 A1 9/2015 Bullington et al.
2015/0314105 A1 11/2015 Gasparyan et al.
2015/0342510 A1 12/2015 Bullington et al.
2015/0351678 A1 12/2015 Bullington et al.
2015/0351679 A1 12/2015 Bullington et al.
2015/0359473 A1 12/2015 Garrett et al.
2015/0367069 A1 12/2015 Bullington et al.
2016/0008579 A1 1/2016 Burkholz et al.
2016/0038068 A1 2/2016 Chickering, III et al.
2016/0038684 A1 2/2016 Lum et al.
2016/0081606 A1 3/2016 Russ et al.
2016/0089070 A1 3/2016 Russ et al.
2016/0113560 A1 4/2016 Bullington et al.

(56) References Cited

U.S. PATENT DOCUMENTS

| | | | |
|---|---|---|---|
| 2016/0135724 | A1 | 5/2016 | Bullington et al. |
| 2016/0174888 | A1 | 6/2016 | Berthier et al. |
| 2016/0174948 | A1 | 6/2016 | Kato et al. |
| 2016/0213294 | A1 | 7/2016 | Patton |
| 2016/0257586 | A1 | 9/2016 | Shaamsundarr |
| 2016/0361006 | A1 | 12/2016 | Bullington et al. |
| 2016/0367177 | A1 | 12/2016 | Edelhauser et al. |
| 2017/0020427 | A1 | 1/2017 | Rogers et al. |
| 2017/0020428 | A1 | 1/2017 | Rogers et al. |
| 2017/0059552 | A1 | 3/2017 | Campton et al. |
| 2017/0065733 | A1 | 3/2017 | Bullington et al. |
| 2017/0071519 | A1 | 3/2017 | Gelfand et al. |
| 2017/0150913 | A1 | 6/2017 | Patton |
| 2017/0153165 | A1 | 6/2017 | Nwadigo |
| 2017/0156654 | A1 | 6/2017 | Patton |
| 2017/0172482 | A1 | 6/2017 | Patton |
| 2017/0181683 | A1 | 6/2017 | Patton |
| 2017/0227536 | A1 | 8/2017 | Matsuura |
| 2017/0276679 | A1 | 9/2017 | Chapman et al. |
| 2017/0327867 | A1 | 11/2017 | Dohale et al. |
| 2017/0361019 | A1 | 12/2017 | Hopkins |
| 2018/0078186 | A1 | 3/2018 | Patton |
| 2018/0085042 | A1 | 3/2018 | Patton |
| 2018/0092582 | A1 | 4/2018 | Patton |
| 2018/0092583 | A1 | 4/2018 | Patton |
| 2018/0092584 | A1 | 4/2018 | Bullington et al. |
| 2018/0093077 | A1 | 4/2018 | Harding et al. |
| 2018/0098723 | A1 | 4/2018 | Patton |
| 2018/0116577 | A1 | 5/2018 | Bullington et al. |
| 2018/0160958 | A1 | 6/2018 | Baid |
| 2018/0177445 | A1 | 6/2018 | Rogers et al. |
| 2018/0177943 | A1 | 6/2018 | Bullington et al. |
| 2018/0207300 | A1 | 7/2018 | Bullington et al. |
| 2018/0242890 | A1 | 8/2018 | Chickering, III et al. |
| 2018/0271425 | A1 | 9/2018 | Rogers et al. |
| 2018/0289894 | A1 | 10/2018 | Hopkins |
| 2018/0321270 | A1 | 11/2018 | Iwashita et al. |
| 2018/0353117 | A1 | 12/2018 | Bullington et al. |
| 2019/0000367 | A1 | 1/2019 | Lundquist et al. |
| 2019/0030293 | A1 | 1/2019 | Rogers et al. |
| 2019/0049442 | A1 | 2/2019 | Guirguis |
| 2019/0076074 | A1 | 3/2019 | Bullington et al. |
| 2019/0150818 | A1 | 5/2019 | Bullington et al. |
| 2019/0151536 | A1 | 5/2019 | Bullington et al. |
| 2019/0159711 | A1 | 5/2019 | Rogers et al. |
| 2019/0175085 | A1 | 6/2019 | Bullington et al. |
| 2019/0175087 | A1 | 6/2019 | Bullington et al. |
| 2019/0209066 | A1 | 7/2019 | Bullington et al. |
| 2019/0365303 | A1 | 12/2019 | Bullington et al. |
| 2019/0374145 | A1 | 12/2019 | Breindel et al. |
| 2020/0060595 | A1 | 2/2020 | Bullington et al. |
| 2020/0060596 | A1 | 2/2020 | Patton |
| 2020/0197925 | A1 | 6/2020 | Ivosevic et al. |
| 2020/0214611 | A1 | 7/2020 | Ivosevic |
| 2020/0215211 | A1 | 7/2020 | Bullington et al. |
| 2020/0253524 | A1 | 8/2020 | Bullington et al. |
| 2020/0281514 | A1 | 9/2020 | Rogers et al. |
| 2020/0289039 | A1 | 9/2020 | Bullington et al. |
| 2020/0305780 | A1 | 10/2020 | Rogers et al. |
| 2020/0359951 | A1 | 11/2020 | Bullington et al. |
| 2021/0008280 | A1 | 1/2021 | Bullington et al. |
| 2021/0169387 | A1 | 6/2021 | Bullington et al. |
| 2021/0178389 | A1 | 6/2021 | Bullington et al. |
| 2021/0186392 | A1 | 6/2021 | Bullington et al. |
| 2021/0290123 | A1 | 9/2021 | Sawyer |
| 2021/0353193 | A1 | 11/2021 | Bullington et al. |
| 2021/0353194 | A1 | 11/2021 | Bullington et al. |
| 2021/0361206 | A1 | 11/2021 | Bullington et al. |
| 2021/0361207 | A1 | 11/2021 | Rogers et al. |
| 2022/0023539 | A1 | 1/2022 | Hopkins |
| 2022/0071533 | A1 | 3/2022 | Bullington et al. |
| 2022/0079482 | A1 | 3/2022 | Bullington et al. |
| 2022/0151525 | A1 | 5/2022 | Bullington et al. |
| 2022/0151526 | A1 | 5/2022 | Bullington et al. |
| 2022/0151527 | A1 | 5/2022 | Bullington et al. |
| 2022/0175284 | A1 | 6/2022 | Bullington et al. |
| 2022/0183600 | A1 | 6/2022 | Bullington et al. |
| 2022/0218248 | A1 | 7/2022 | Bullington et al. |
| 2022/0218249 | A1 | 7/2022 | Bullington et al. |
| 2022/0218250 | A1 | 7/2022 | Bullington et al. |
| 2022/0304600 | A1 | 9/2022 | Hammer |
| 2022/0304601 | A1 | 9/2022 | Bullington et al. |
| 2022/0304664 | A1 | 9/2022 | Hammer |
| 2022/0361786 | A1 | 11/2022 | Bullington et al. |
| 2022/0369970 | A1 | 11/2022 | Bullington et al. |
| 2022/0369971 | A1 | 11/2022 | Bullington et al. |
| 2022/0369972 | A1 | 11/2022 | Bullington et al. |
| 2023/0109255 | A1 | 4/2023 | Rogers et al. |
| 2023/0172502 | A1 | 6/2023 | Bullington et al. |
| 2023/0190157 | A1 | 6/2023 | Bullington et al. |
| 2023/0240571 | A1 | 8/2023 | Bullington et al. |
| 2023/0248281 | A1 | 8/2023 | Bullington et al. |
| 2023/0363674 | A1 | 11/2023 | Bullington et al. |
| 2023/0417746 | A1 | 12/2023 | Bullington et al. |
| 2024/0008780 | A1 | 1/2024 | Bullington et al. |
| 2024/0041369 | A1 | 2/2024 | Bullington et al. |
| 2024/0041370 | A1 | 2/2024 | Bullington et al. |
| 2024/0057908 | A1 | 2/2024 | Bullington et al. |
| 2024/0065590 | A1 | 2/2024 | Bullington et al. |
| 2024/0131258 | A1 | 4/2024 | Bullington et al. |
| 2024/0138734 | A1 | 5/2024 | Bullington et al. |
| 2024/0164670 | A1 | 5/2024 | Patton |
| 2024/0306963 | A1 | 9/2024 | Bullington et al. |
| 2024/0306964 | A1 | 9/2024 | Bullington et al. |
| 2024/0315620 | A1 | 9/2024 | Bullington et al. |
| 2024/0315621 | A1 | 9/2024 | Bullington et al. |
| 2024/0315622 | A1 | 9/2024 | Bullington et al. |
| 2024/0315623 | A1 | 9/2024 | Bullington et al. |
| 2025/0082235 | A1 | 3/2025 | Bullington et al. |
| 2025/0120628 | A1 | 4/2025 | Bullington et al. |
| 2025/0235133 | A1 | 7/2025 | Bullington et al. |
| 2025/0235613 | A1 | 7/2025 | Bullington |
| 2025/0275697 | A1 | 9/2025 | Bullington et al. |
| 2026/0033759 | A1 | 2/2026 | Bullington et al. |

FOREIGN PATENT DOCUMENTS

| | | | |
|---|---|---|---|
| AU | 736156 | B2 | 7/2001 |
| AU | 2003244890 | A1 | 1/2004 |
| BR | 112012025546 | A2 | 6/2016 |
| CA | 1264275 | A | 1/1990 |
| CA | 3074105 | A1 | 3/2019 |
| CN | 86103696 | A | 1/1987 |
| CN | 2115767 | U | 9/1992 |
| CN | 1713928 | A | 12/2005 |
| CN | 1784186 | A | 6/2006 |
| CN | 1901955 | A | 1/2007 |
| CN | 2907683 | Y | 6/2007 |
| CN | 1325126 | C | 7/2007 |
| CN | 101060871 | A | 10/2007 |
| CN | 101309641 | A | 11/2008 |
| CN | 101352357 | A | 1/2009 |
| CN | 101437450 | A | 5/2009 |
| CN | 101564301 | A | 10/2009 |
| CN | 101631498 | A | 1/2010 |
| CN | 101676001 | A | 3/2010 |
| CN | 101785676 | A | 7/2010 |
| CN | 101801445 | A | 8/2010 |
| CN | 201617841 | U | 11/2010 |
| CN | 102421362 | A | 4/2012 |
| CN | 102548524 | A | 7/2012 |
| CN | 102811754 | A | 12/2012 |
| CN | 102971040 | A | 3/2013 |
| CN | 103027727 | A | 4/2013 |
| CN | 101626803 | B | 8/2013 |
| CN | 103477201 | A | 12/2013 |
| CN | 103619386 | A | 3/2014 |
| CN | 104902817 | A | 9/2015 |
| CN | 104955392 | A | 9/2015 |
| CN | 104971390 | A | 10/2015 |
| CN | 104981203 | A | 10/2015 |
| CN | 105090005 | A | 11/2015 |
| CN | 105612346 | A | 5/2016 |
| CN | 105813669 | A | 7/2016 |

(56) References Cited

FOREIGN PATENT DOCUMENTS

| | | | |
|---|---|---|---|
| CN | 107736901 | A | 2/2018 |
| CN | 209916854 | U | 1/2020 |
| DE | 7203008 | U | 5/1972 |
| DE | 2203858 | A1 | 5/1973 |
| DE | 2541494 | A1 | 3/1977 |
| DE | 2203858 | B2 | 10/1977 |
| DE | 2946660 | A1 | 5/1981 |
| DE | 3403957 | A1 | 8/1985 |
| DE | 4026732 | A1 | 2/1992 |
| DE | 29913417 | U1 | 12/2000 |
| DE | 10038026 | A1 | 2/2001 |
| DE | 10134913 | A1 | 2/2003 |
| DE | 10134913 | C2 | 6/2003 |
| DE | 10243129 | A1 | 4/2004 |
| DE | 69632870 | T2 | 7/2005 |
| DE | 102009057792 | B4 | 8/2016 |
| EP | 0181957 | A1 | 5/1986 |
| EP | 0207304 | A1 | 1/1987 |
| EP | 0448795 | A2 | 10/1991 |
| EP | 0208053 | B1 | 12/1991 |
| EP | 0329786 | B1 | 1/1993 |
| EP | 0486059 | B1 | 1/1997 |
| EP | 1144026 | B1 | 7/2004 |
| EP | 1505159 | B1 | 5/2008 |
| EP | 1980204 | A1 | 10/2008 |
| EP | 2254472 | A2 | 12/2010 |
| EP | 1381438 | B1 | 5/2012 |
| EP | 2254472 | B1 | 5/2016 |
| EP | 1487369 | B1 | 5/2017 |
| EP | 2986218 | B1 | 12/2017 |
| EP | 2178585 | B1 | 4/2021 |
| ES | 2564496 | T3 | 3/2016 |
| FR | 2110516 | A5 | 6/1972 |
| FR | 2691364 | B1 | 8/1999 |
| FR | 2833175 | B1 | 5/2004 |
| FR | 2851167 | B1 | 10/2005 |
| GB | 1506449 | A | 4/1978 |
| GB | 1562686 | A | 3/1980 |
| IE | 904353 | A1 | 10/1991 |
| IL | 128709 | A | 9/2004 |
| JP | S4846180 | A | 7/1973 |
| JP | S5397289 | A | 8/1978 |
| JP | S56109643 | A | 8/1981 |
| JP | S5789869 | A | 6/1982 |
| JP | S6458241 | A | 3/1989 |
| JP | H0363570 | A | 3/1991 |
| JP | H05501071 | A | 3/1993 |
| JP | H0551222 | B2 | 8/1993 |
| JP | H06500403 | A | 1/1994 |
| JP | H0716219 | A | 1/1995 |
| JP | H0910302 | A | 1/1997 |
| JP | H0951947 | A | 2/1997 |
| JP | H09229828 | A | 9/1997 |
| JP | H10153531 | A | 6/1998 |
| JP | H10211274 | A | 8/1998 |
| JP | H1156821 | A | 3/1999 |
| JP | H1176397 | A | 3/1999 |
| JP | H11197236 | A | 7/1999 |
| JP | 2001159630 | A | 6/2001 |
| JP | 2001161668 | A | 6/2001 |
| JP | 2001276181 | A | 10/2001 |
| JP | 3231086 | B2 | 11/2001 |
| JP | 2002116201 | A | 4/2002 |
| JP | 2002272710 | A | 9/2002 |
| JP | 2002528159 | A | 9/2002 |
| JP | 2003126068 | A | 5/2003 |
| JP | 2005237617 | A | 9/2005 |
| JP | 2006026327 | A | 2/2006 |
| JP | 3813974 | B2 | 8/2006 |
| JP | 2007175534 | A | 7/2007 |
| JP | 2008149076 | A | 7/2008 |
| JP | 2008206734 | A | 9/2008 |
| JP | 2009525819 | A | 7/2009 |
| JP | 2009536554 | A | 10/2009 |
| JP | 4382322 | B2 | 12/2009 |
| JP | 2010514501 | A | 5/2010 |
| JP | 2010524505 | A | 7/2010 |
| JP | 2010189415 | A | 9/2010 |
| JP | 4573538 | B2 | 11/2010 |
| JP | 2010536014 | A | 11/2010 |
| JP | 2011512987 | A | 4/2011 |
| JP | 4861649 | B2 | 1/2012 |
| JP | 4869910 | B2 | 2/2012 |
| JP | 5344252 | B2 | 11/2013 |
| JP | 5620541 | B2 | 11/2014 |
| JP | 2015014552 | A | 1/2015 |
| JP | 2015519145 | A | 7/2015 |
| JP | 2015215355 | A | 12/2015 |
| JP | 2016500278 | A | 1/2016 |
| JP | 2016504075 | A | 2/2016 |
| JP | 2016520827 | A | 7/2016 |
| JP | 2016523591 | A | 8/2016 |
| JP | 5997760 | B2 | 9/2016 |
| JP | 2016527939 | A | 9/2016 |
| JP | 6194415 | B2 | 9/2017 |
| JP | 2018110967 | A | 7/2018 |
| JP | 2018525191 | A | 9/2018 |
| JP | 2020513906 | A | 5/2020 |
| JP | 7204742 | B2 | 1/2023 |
| KR | 20120030087 | A | 3/2012 |
| KR | 101134279 | B1 | 4/2012 |
| KR | 20160088853 | A | 7/2016 |
| TW | 200528066 | A | 9/2005 |
| WO | WO-8605568 | A1 | 9/1986 |
| WO | WO-9004351 | A1 | 5/1990 |
| WO | WO-8403213 | A1 | 10/1990 |
| WO | WO-9118632 | A1 | 12/1991 |
| WO | WO-9216144 | A1 | 10/1992 |
| WO | WO-9407415 | A1 | 4/1994 |
| WO | WO-9412093 | A1 | 6/1994 |
| WO | WO-9415665 | A1 | 7/1994 |
| WO | WO-9511712 | A1 | 5/1995 |
| WO | WO-9516395 | A1 | 6/1995 |
| WO | WO-9521639 | A1 | 8/1995 |
| WO | WO-9524176 | A1 | 9/1995 |
| WO | WO-9621853 | A1 | 7/1996 |
| WO | WO-9718845 | A1 | 5/1997 |
| WO | WO-1997045714 | A1 | 12/1997 |
| WO | WO-1998034532 | A1 | 8/1998 |
| WO | WO-9846136 | A1 | 10/1998 |
| WO | WO-9913925 | A1 | 3/1999 |
| WO | WO-1999029232 | A1 | 6/1999 |
| WO | WO-9948425 | A1 | 9/1999 |
| WO | WO-9955232 | A1 | 11/1999 |
| WO | WO-0024313 | A1 | 5/2000 |
| WO | WO-0040291 | A1 | 7/2000 |
| WO | WO-0041624 | A1 | 7/2000 |
| WO | WO-0108546 | A2 | 2/2001 |
| WO | WO-0191829 | A2 | 12/2001 |
| WO | WO-2002028457 | A1 | 4/2002 |
| WO | WO-0245813 | A1 | 6/2002 |
| WO | WO-02051520 | A1 | 7/2002 |
| WO | WO-03008012 | A2 | 1/2003 |
| WO | WO-03041767 | A1 | 5/2003 |
| WO | WO-03047660 | A1 | 6/2003 |
| WO | WO-03078964 | A2 | 9/2003 |
| WO | WO-03085395 | A1 | 10/2003 |
| WO | WO-2003092573 | A2 | 11/2003 |
| WO | WO-2004082467 | A2 | 9/2004 |
| WO | WO-2004103565 | A2 | 12/2004 |
| WO | WO-2005068011 | A1 | 7/2005 |
| WO | WO-2006031500 | A2 | 3/2006 |
| WO | WO-2006124634 | A1 | 11/2006 |
| WO | WO-2007033319 | A1 | 3/2007 |
| WO | WO-2008028165 | A2 | 3/2008 |
| WO | WO-2008047699 | A1 | 4/2008 |
| WO | WO-2008077047 | A2 | 6/2008 |
| WO | WO-2008101025 | A1 | 8/2008 |
| WO | WO-2008157511 | A1 | 12/2008 |
| WO | WO-2009094345 | A1 | 7/2009 |
| WO | WO-2009113999 | A2 | 9/2009 |
| WO | WO-2010087216 | A1 | 8/2010 |
| WO | WO-2011030282 | A1 | 3/2011 |
| WO | WO-2011050110 | A1 | 4/2011 |

(56) References Cited

FOREIGN PATENT DOCUMENTS

| | | | |
|---|---|---|---|
| WO | WO-2011069145 | A2 | 6/2011 |
| WO | WO-2011114413 | A1 | 9/2011 |
| WO | WO-2011123685 | A2 | 10/2011 |
| WO | WO-2011162772 | A1 | 12/2011 |
| WO | WO-2012012127 | A2 | 1/2012 |
| WO | WO-2012114105 | A1 | 8/2012 |
| WO | WO-2013181352 | A1 | 12/2013 |
| WO | WO-2014022275 | A1 | 2/2014 |
| WO | WO-2014022750 | A1 | 2/2014 |
| WO | WO-2014058945 | A1 | 4/2014 |
| WO | WO-2014085800 | A1 | 6/2014 |
| WO | WO-2014089186 | A1 | 6/2014 |
| WO | WO-2014099266 | A2 | 6/2014 |
| WO | WO-2015091818 | A1 | 6/2015 |
| WO | WO-2016027782 | A1 | 2/2016 |
| WO | WO-2016054252 | A1 | 4/2016 |
| WO | WO-2016201406 | A1 | 12/2016 |
| WO | WO-2017019552 | A1 | 2/2017 |
| WO | WO-2017041087 | A1 | 3/2017 |
| WO | WO-2017133953 | A1 | 8/2017 |
| WO | WO-2017218840 | A1 | 12/2017 |
| WO | WO-2017218848 | A1 | 12/2017 |
| WO | WO-2018125929 | A1 | 7/2018 |
| WO | WO-2018227191 | A1 | 12/2018 |
| WO | WO-2019055487 | A1 | 3/2019 |
| WO | WO-2019113505 | A1 | 6/2019 |
| WO | WO-2019232196 | A1 | 12/2019 |
| WO | WO-2020163744 | A1 | 8/2020 |
| WO | WO-2020185914 | A1 | 9/2020 |
| WO | WO-2021119487 | A1 | 6/2021 |
| WO | WO-2022203747 | A1 | 9/2022 |

OTHER PUBLICATIONS

Arkin, C. F. et al., “Procedures for the Collection of Diagnostic Blood Specimens by Venipuncture; Approved Standard,” Fifth Edition, Clinical and Laboratory Standards Institute, vol. 23, No. 32 (2003), 52 pages.

Avatar: “Is it safe to reinfuse blood drawn from a CVAD via a syringe when checking line patency or drawing blood?” [retrieved online Jul. 31, 2024] URL:https://www.avatargroup.org.au/faq---blood-collection.html, 4 pages.

Barnard, D. R. & Arthur, M. M., “Fibronectin (cold insoluble globulin) in the neonate,” Clinical and Laboratory Observations, 102(3):453-455 (1983).

Bauman et al., “Don’t Stick Me Again! Reducing Blood Culture Contamination,” INOVA Fairfax Medical Campus, Emergency Department (2019), 1 page.

Baxter, “IV Tubing and Access Devices” authored by and published by Baxter, dated Nov. 6, 2006, 105 pages.

BD Saf-T-Intima Closed IV Catheter System, Becton, Dickinson and Company, 2015 Brochure. Retrieved from the Internet (Sep. 11, 2019) https://www.bd.com/en-us/offerings/capabilities/infusion-therapy/iv-catheters/bd-saf-tintima-closed-iv-catheter-system, 2 pages.

BD Vacutainer Passive Shielding Blood Collection Needle Brochure; Becton Dickinson and Company (2005), 2 pages.

Bell et al., Effectiveness of a Novel Specimen Collection System in Reducing Blood Culture Contamination Rates, J. Emergency Nursing, vol. 44, No. 6, 570 (Nov. 2018), 6 pages.

Blakeney, “Reduction of Blood Culture Contaminations Using Initial Specimen Diversion Device,” Beebe Healthcare (Jun. 2018), 1 page.

Brecher, M. E. et al., “Bacterial Contamination of Blood Components,” Clinical Microbiology Reviews, 18(1):195-204 (2005).

Brownfield et al., “Emergency Department Observes 83% Reduction in Blood Culture Contamination with Initial Specimen Diversion Technology Adoption,” Am. J. Infection Control, vol. 49, S14, ADS 34 (Jun. 2021), 1 page.

Bruneau, Cecile, et al.; “Efficacy of a new collection procedure for preventing bacterial contamination of whole-blood donations,” Transfusion (2001); 41(1):74-81.

Calam, R. R., “Recommended ‘Order of Draw’ for Collecting Blood Specimens Into Additive-Containing Tubes,” Letter to the Editor, Clinical Chemistry, 28(6):1399 (1982), 1 page.

Cartridge and Test Information, Abbott, Art: 714258-010 Rev. Date: Aug. 15, 2016, 6 pages.

Case 1: 19-cv-00097-CFC-CJB, *Magnolia Medical Technologies, Inc.*, Plaintiff v. *Kurin, Inc.*, Defendant; Memorandum Opinion, (Document 514) filed Aug. 4, 2023, 38 pages.

Case 1: 19-cv-00097-CFC-CJB, *Magnolia Medical Technologies, Inc.*, Plaintiff v. *Kurin, Inc.*, Defendant; Order, (Document 515) filed Aug. 4, 2023, 1 page.

Case 1: 19-cv-00097-CFC-CJB, *Magnolia Medical Technologies, Inc.*, Plaintiff v. *Kurin, Inc.*, Defendant; Order, (Document 516) filed Aug. 4, 2023, 2 pages.

Challiner, A. et al., Queen Alexandra Hospital, Portsmouth P06 3LY, “Venous/arterial blood management protection system,” Anaesthesia, Correspondence (Feb. 1992); 47(2), p. 169.

Chang et al., “Impact of Blood Culture Diversion Device and Molecular Pathogen Identification on Vancomycin Use,” San Antonio Military Medical Center (2016), 1 page.

Claim Construction Order in *Retractable Technologies, Inc., and Thomas Shaw* v. *Becton Dickinson & Co.*, Civil Action No. 2:07-CV-250 (OF) (Jan. 20, 2009). 32 pages.

Claim Construction Order, *Magnolia Medical Techs*. v. *Kurin*, Case No. 19-00097-CFC-CJB, at 3 (D. Del.) (May 20, 2020), 4 pages.

De Korte, D. et al., “Diversion of first blood vol. results in a reduction of bacterial contamination for whole-blood collections,” Vox Sanguinis, 83:13-16 (2002).

De Korte, D. et al., “Effects of skin disinfection method, deviation bag, and bacterial screening on clinical safety of platelet transfusions in the Netherlands,” Transfusion, 46:476-485 (2006).

Declaration of Dr. Erik K. Antonsson, Ph.D., P.E., NAE (Mar. 21, 2023); 137 pages.

Declaration of Dr. Morten Jensen under 37 C.F.R. § 1.132, Oct. 10, 2023, 400 pages.

Doern et al., “A Comprehensive Update on the Problem of Blood Culture Contamination and a Discussion of Methods for Addressing the Problem,” Clinical Microbiology, vol. 33, No. 1, e00009-19 (Jan. 2020), 21 pages.

Edwards Lifesciences, “Conservation. Safety. Simplicity. Edwards Vamp and Vamp Jr. Systems,” 2002 Brochure. Retrieved from the Internet (Sep. 11, 19) https://www.medline.com/media/catalog/Docs/MKT/VAMPSYSTEMBROCHURE.PDF, 4 pages.

Ernst, D. J et al., “NCCLS simplifies the order of draw: a brief history,” MLO, pp. 26-27 (2004).

Exhibit 01—Defendant’s Invalidity Contentions, Invalidity Claim Chart—U.S. Pat. No. 9,855,001 vs Barnard NPL, Aug. 30, 2019, 8 pages.

Exhibit 02—Defendant’s Invalidity Contentions, Invalidity Claim Chart—U.S. Pat. No. 9,855,001 vs BD Needle NPL, Aug. 30, 2019, 7 pages.

Exhibit 03—Defendant’s Invalidity Contentions, Invalidity Claim Chart—U.S. Pat. No. 9,855,001 vs U.S. Pat. No. 6,626,884, Aug. 30, 2019, 11 pages.

Exhibit 04—Defendant’s Invalidity Contentions, Invalidity Claim Chart—U.S. Pat. No. 9,855,001 vs U.S. Pat. Pub. No. 2005/161112, Aug. 30, 2019, 22 pages.

Exhibit 05—Defendant’s Invalidity Contentions, Invalidity Claim Chart—U.S. Pat. No. 9,855,001 vs U.S. Pat. No. 4,673,386, Aug. 30, 2019, 21 pages.

Exhibit 06—Defendant’s Invalidity Contentions, Invalidity Claim Chart—U.S. Pat. No. 9,855,001 vs U.S. Pat. No. 4,904,240, Aug. 30, 2019, 15 pages.

Exhibit 07—Defendant’s Invalidity Contentions, Invalidity Claim Chart—U.S. Pat. No. 9,855,001 vs Leukotrap NPL, Aug. 30, 2019, 38 pages.

Exhibit 09—Defendant’s Invalidity Contentions, Invalidity Claim Chart—U.S. Pat. No. 9,855,001 vs U.S. Pat. No. 4,106,497, Aug. 30, 2019, 22 pages.

Exhibit 10—Defendant’s Invalidity Contentions, Invalidity Claim Chart—U.S. Pat. No. 9,855,001 vs Stopcock-Syringe NPL, Aug. 30, 2019, 85 pages.

(56) References Cited

OTHER PUBLICATIONS

Exhibit 11—Defendant's Invalidity Contentions, Invalidity Claim Chart—U.S. Pat. No. 9,855,001 vs Ziegler NPL, Aug. 30, 2019, 8 pages.
Exhibit 12—Defendant's Invalidity Contentions, Invalidity Claim Chart—U.S. Pat. No. 10,028,689 vs Barnard NPL, Aug. 30, 2019, 12 pages.
Exhibit 13—Defendant's Invalidity Contentions, Invalidity Claim Chart—U.S. Pat. No. 10,028,689 vs U.S. Pat. No. 6,626,884, Aug. 30, 2019, 29 pages.
Exhibit 14—Defendant's Invalidity Contentions, Invalidity Claim Chart—U.S. Pat. No. 10,028,689 vs U.S. Pat. Pub. No. 2005/161112, Aug. 30, 2019, 48 pages.
Exhibit 15—Defendant's Invalidity Contentions, Invalidity Claim Chart—U.S. Pat. No. 10,028,689 vs U.S. Pat. No. 4,673,386, Aug. 30, 2019, 44 pages.
Exhibit 16—Defendant's Invalidity Contentions, Invalidity Claim Chart—U.S. Pat. No. 10,028,689 vs U.S. Pat. No. 4,904,240, Aug. 30, 2019, 31 pages.
Exhibit 17—Defendant's Invalidity Contentions, Invalidity Claim Chart—U.S. Pat. No. 10,028,689 vs Leukotrap NPL, Aug. 30, 2019, 113 pages.
Exhibit 19—Defendant's Invalidity Contentions, Invalidity Claim Chart—U.S. Pat. No. 10,028,689 vs U.S. Pat. No. 4,106,497, Aug. 30, 2019, 38 pages.
Exhibit 20—Defendant's Invalidity Contentions, Invalidity Claim Chart—U.S. Pat. No. 10,028,689 vs Stopcock-Syringe NPL, Aug. 30, 2019, 268 pages.
Exhibit 21—Defendant's Invalidity Contentions, Invalidity Claim Chart—U.S. Pat. No. 10,220,139 vs U.S. Pat. No. 6,626,884, Aug. 30, 2019, 35 pages.
Exhibit 22—Defendant's Invalidity Contentions, Invalidity Claim Chart—U.S. Pat. No. 10,220,139 vs U.S. Pat. Pub. No. 2005/161112, Aug. 30, 2019, 46 pages.
Exhibit 23—Defendant's Invalidity Contentions, Invalidity Claim Chart—U.S. Pat. No. 10,220,139 vs U.S. Pat. No. 4,207,870, Aug. 30, 2019, 20 pages.
Exhibit 24—Defendant's Invalidity Contentions, Invalidity Claim Chart—U.S. Pat. No. 10,220,139 vs U.S. Pat. No. 6,506,182, Aug. 30, 2019, 15 pages.
Exhibit 25—Defendant's Invalidity Contentions, Invalidity Claim Chart—U.S. Pat. No. 10,220,139 vs U.S. Pat. No. 4,673,386, Aug. 30, 2019, 53 pages.
Exhibit 26—Defendant's Invalidity Contentions, Invalidity Claim Chart—U.S. Pat. No. 10,220,139 vs U.S. Pat. No. 4,904,240, Aug. 30, 2019, 39 pages.
Exhibit 27—Defendant's Invalidity Contentions, Invalidity Claim Chart—U.S. Pat. No. 10,220,139 vs Leukotrap NPL, Aug. 30, 2019, 115 pages.
Exhibit 29—Defendant's Invalidity Contentions, Invalidity Claim Chart—U.S. Pat. No. 10,220,139 vs U.S. Pat. No. 4,106,497, Aug. 30, 2019, 45 pages.
Exhibit 30—Defendant's Invalidity Contentions, Invalidity Claim Chart—U.S. Pat. No. 10,220,139 vs Stopcock-Syringe NPL, Aug. 30, 2019, 246 pages.
Exhibit 31—Defendant's Invalidity Contentions, Invalidity Claim Chart—U.S. Pat. No. 10,220,139 vs U.S. Pat. No. 4,349,035, Aug. 30, 2019, 26 pages.
Exhibit 32—Defendant's Invalidity Contentions, Invalidity Claim Chart—U.S. Pat. No. 10,220,139 vs U.S. Pat. Pub. No. 2008/0145933A1, Aug. 30, 2019, 39 pages.
Exhibit 33—Defendant's Invalidity Contentions, Invalidity Claim Chart—U.S. Pat. No. 10,039,483 vs Barnard NPL, Aug. 30, 2019, 14 pages.
Exhibit 34—Defendant's Invalidity Contentions, Invalidity Claim Chart—U.S. Pat. No. 10,039,483 vs U.S. Pat. No. 6,626,884, Aug. 30, 2019, 22 pages.
Exhibit 35—Defendant's Invalidity Contentions, Invalidity Claim Chart—U.S. Pat. No. 10,039,483 vs U.S. Pat. Pub. No. 2005/161112, Aug. 30, 2019, 45 pages.
Exhibit 36—Defendant's Invalidity Contentions, Invalidity Claim Chart—U.S. Pat. No. 10,039,483 vs U.S. Pat. No. 4,673,386, Aug. 30, 2019, 47 pages.
Exhibit 37—Defendant's Invalidity Contentions, Invalidity Claim Chart—U.S. Pat. No. 10,039,483 vs U.S. Pat. No. 4,904,240, Aug. 30, 2019, 30 pages.
Exhibit 38—Defendant's Invalidity Contentions, Invalidity Claim Chart—U.S. Pat. No. 10,039,483 vs Leukotrap NPL, Aug. 30, 2019, 115 pages.
Exhibit 40—Defendant's Invalidity Contentions, Invalidity Claim Chart—U.S. Pat. No. 10,039,483 vs U.S. Pat. No. 4,106,497, Aug. 30, 2019, 45 pages.
Exhibit 41—Defendant's Invalidity Contentions, Invalidity Claim Chart—U.S. Pat. No. 10,039,483 vs Stopcock-Syringe NPL, Aug. 30, 2019, 214 pages.
Exhibit 42—Defendant's Invalidity Contentions, Invalidity Claim Chart—U.S. Pat. No. 10,039,483 vs U.S. Pat. Pub. No. 2008/0145933A1, Aug. 30, 2019, 38 pages.
Exhibit A1—Defendant's Invalidity Contentions, Invalidity Claim Chart—U.S. Pat. No. 9,855,002 vs U.S. Patent Publication No. 2005/0161112 A1, Jul. 29, 2024, 234 pages.
Exhibit A10—Defendant's Invalidity Contentions, Invalidity Claim Chart—U.S. Pat. No. 9,855,002 vs PortSyringe NPL, Jul. 29, 2024, 230 pages.
Exhibit A11—Defendant's Invalidity Contentions, Invalidity Claim Chart—U.S. Pat. No. 9,855,002 vs U.S. Pat. No. 4,056,101 NPL, Jul. 29, 2024, 111 pages.
Exhibit A12—Defendant's Invalidity Contentions, Invalidity Claim Chart—U.S. Pat. No. 9,855,002 vs U.S. Pat. No. 5,947,932, Jul. 29, 2024, 156 pages.
Exhibit A2—Defendant's Invalidity Contentions, Invalidity Claim Chart—U.S. Pat. No. 9,855,002 vs Japanese Patent Publication No. H10-2112742, Jul. 29, 2024, 281 pages.
Exhibit A3—Defendant's Invalidity Contentions, Invalidity Claim Chart—U.S. Pat. No. 9,855,002 vs U.S. Patent Publication No. 2007/0119508, Jul. 29, 2024, 368 pages.
Exhibit A4—Defendant's Invalidity Contentions, Invalidity Claim Chart—U.S. Pat. No. 9,855,002 vs U.S. Pat. No. 5,573,951, Jul. 29, 2024, 258 pages.
Exhibit A5—Defendant's Invalidity Contentions, Invalidity Claim Chart—U.S. Pat. No. 9,855,002 vs U.S. Pat. No. 6,626,884, Jul. 29, 2024, 116 pages.
Exhibit A6—Defendant's Invalidity Contentions, Invalidity Claim Chart—U.S. Pat. No. 9,855,002 vs U.S. Pat. No. 4,673,386, Jul. 29, 2024, 145 pages.
Exhibit A7—Defendant's Invalidity Contentions, Invalidity Claim Chart—U.S. Pat. No. 9,855,002 vs U.S. Pat. No. 4,904,240, Jul. 29, 2024, 147 pages.
Exhibit A8—Defendant's Invalidity Contentions, Invalidity Claim Chart—U.S. Pat. No. 9,855,002 vs Leukotrap NPL, Jul. 29, 2024, 144 pages.
Exhibit A9—Defendant's Invalidity Contentions, Invalidity Claim Chart—U.S. Pat. No. 9,855,002 vs U.S. Pat. No. 4,106,497, Jul. 29, 2024, 194 pages.
Exhibit B1—Defendant's Invalidity Contentions, Invalidity Claim Chart—U.S. Pat. No. 10,052,053 vs U.S. Patent Publication No. 2005/0161112 A1, Jul. 29, 2024, 237 pages.
Exhibit B10—Defendant's Invalidity Contentions, Invalidity Claim Chart—U.S. Pat. No. 10,052,053 vs PortSyringe NPL, Jul. 29, 2024, 229 pages.
Exhibit B11—Defendant's Invalidity Contentions, Invalidity Claim Chart—U.S. Pat. No. 10,052,053 vs U.S. Pat. No. 4,056,101 NPL, Jul. 29, 2024, 107 pages.
Exhibit B12—Defendant's Invalidity Contentions, Invalidity Claim Chart—U.S. Pat. No. 10,052,053 vs U.S. Pat. No. 5,947,932, Jul. 29, 2024, 154 pages.
Exhibit B2—Defendant's Invalidity Contentions, Invalidity Claim Chart—U.S. Pat. No. 10,052,053 vs Japanese Patent Publication No. H10-2112742, Jul. 29, 2024, 265 pages.
Exhibit B3—Defendant's Invalidity Contentions, Invalidity Claim Chart—U.S. Pat. No. 10,052,053 vs U.S. Patent Publication No. 2007/0119508, Jul. 29, 2024, 373 pages.

(56) References Cited

OTHER PUBLICATIONS

Exhibit B4—Defendant's Invalidity Contentions, Invalidity Claim Chart—U.S. Pat. No. 10,052,053 vs U.S. Pat. No. 5,573,951, Jul. 29, 2024, 264 pages.
Exhibit B5—Defendant's Invalidity Contentions, Invalidity Claim Chart—U.S. Pat. No. 10,052,053 vs U.S. Pat. No. 6,626,884, Jul. 29, 2024, 125 pages.
Exhibit B6—Defendant's Invalidity Contentions, Invalidity Claim Chart—U.S. Pat. No. 10,052,053 vs U.S. Pat. No. 4,673,386, Jul. 29, 2024, 146 pages.
Exhibit B7—Defendant's Invalidity Contentions, Invalidity Claim Chart—U.S. Pat. No. 10,052,053 vs U.S. Pat. No. 4,904,240, Jul. 29, 2024, 143 pages.
Exhibit B8—Defendant's Invalidity Contentions, Invalidity Claim Chart—U.S. Pat. No. 10,052,053 vs Leukotrap NPL, Jul. 29, 2024, 136 pages.
Exhibit B9—Defendant's Invalidity Contentions, Invalidity Claim Chart—U.S. Pat. No. 10,052,053 vs U.S. Pat. No. 4,106,497, Jul. 29, 2024, 191 pages.
Exhibit C1—Defendant's Invalidity Contentions, Invalidity Claim Chart—U.S. Pat. No. 11,529,081 vs U.S. Patent Publication No. 2005/0161112 A1, Jul. 29, 2024, 363 pages.
Exhibit C2—Defendant's Invalidity Contentions, Invalidity Claim Chart—U.S. Pat. No. 11,529,081 vs U.S. Patent Nos. 9,855,002 and 10,052,053, Jul. 29, 2024, 488 pages.
Exhibit C3—Defendant's Invalidity Contentions, Invalidity Claim Chart—U.S. Pat. No. 11,529,081 vs U.S. Pat. No. 4,312,362, Jul. 29, 2024, 354 pages.
Exhibit C4—Defendant's Invalidity Contentions, Invalidity Claim Chart—U.S. Pat. No. 11,529,081 vs Kurin Lock NPL, Jul. 29, 2024, 361 pages.
Exhibit C5—Defendant's Invalidity Contentions, Invalidity Claim Chart—U.S. Pat. No. 11,529,081 vs U.S. Pat. No. 4,207,870, Jul. 29, 2024, 230 pages.
Exhibit C6—Defendant's Invalidity Contentions, Invalidity Claim Chart—U.S. Pat. No. 11,529,081 vs U.S. Patent Publication No. 2018/0177445, Jul. 29, 2024, 479 pages.
Exhibit C7—Defendant's Invalidity Contentions, Invalidity Claim Chart—U.S. Pat. No. 11,529,081 vs U.S. Pat. No. 9,820,682, Jul. 29, 2024, 338 pages.
Exhibit D1—Defendant's Invalidity Contentions, Invalidity Claim Chart—U.S. Pat. No. 11,653,863 vs U.S. Patent Publication No. 2005/0161112 A1, Jul. 29, 2024, 369 pages.
Exhibit D2—Defendant's Invalidity Contentions, Invalidity Claim Chart—U.S. Pat. No. 11,653,863 vs U.S. Patent Nos. 9,855,002 and 10,052,053, Jul. 29, 2024, 481 pages.
Exhibit D3—Defendant's Invalidity Contentions, Invalidity Claim Chart—U.S. Pat. No. 11,653,863 vs U.S. Pat. No. 4,312,362, Jul. 29, 2024, 334 pages.
Exhibit D4—Defendant's Invalidity Contentions, Invalidity Claim Chart—U.S. Pat. No. 11,653,863 vs Kurin Lock NPL, Jul. 29, 2024, 363 pages.
Exhibit D5—Defendant's Invalidity Contentions, Invalidity Claim Chart—U.S. Pat. No. 11,653,863 vs U.S. Pat. No. 4,207,870, Jul. 29, 2024, 219 pages.
Exhibit D6—Defendant's Invalidity Contentions, Invalidity Claim Chart—U.S. Pat. No. 11,653,863 vs U.S. Patent Publication No. 2018/0177445, Jul. 29, 2024, 447 pages.
Exhibit D7—Defendant's Invalidity Contentions, Invalidity Claim Chart—U.S. Pat. No. 11,653,863 vs U.S. Pat. No. 9,820,682, Jul. 29, 2024, 309 pages.
Exhibit E1—Defendant's Invalidity Contentions, Invalidity Claim Chart—U.S. Pat. No. 11,903,709 vs U.S. Patent Publication No. 2005/0161112 A1, Jul. 29, 2024, 442 pages.
Exhibit E2—Defendant's Invalidity Contentions, Invalidity Claim Chart—U.S. Pat. No. 11,903,709 vs U.S. Pat. Nos. 9,855,002 and 10,052,053, Jul. 29, 2024, 517 pages.
Exhibit E3—Defendant's Invalidity Contentions, Invalidity Claim Chart—U.S. Pat. No. 11,903,709 vs U.S. Pat. No. 4,312,362, Jul. 29, 2024, 438 pages.
Exhibit E4—Defendant's Invalidity Contentions, Invalidity Claim Chart—U.S. Pat. No. 11,903,709 vs Kurin Lock NPL, Jul. 29, 2024, 365 pages.
Exhibit E5—Defendant's Invalidity Contentions, Invalidity Claim Chart—U.S. Pat. No. 11,903,709 vs U.S. Pat. No. 4,207,870, Jul. 29, 2024, 351 pages.
Exhibit E6—Defendant's Invalidity Contentions, Invalidity Claim Chart—U.S. Pat. No. 11,903,709 vs U.S. Patent Publication No. 2018/0177445, Jul. 29, 2024, 559 pages.
Exhibit E7—Defendant's Invalidity Contentions, Invalidity Claim Chart—U.S. Pat. No. 11,903,709 vs U.S. Pat. No. 9,820,682, Jul. 29, 2024, 419 pages.
Extended European Search Report for EP Application No. 17204012.3, dated Feb. 14, 2018, 7 pages.
Extended European Search Report for EP Application No. 17206745.6, dated Feb. 19, 2018, 8 pages.
Extended European Search Report for European Application No. 18188136.8, mailed May 16, 2019, 9 pages.
Extended European Search Report for European Application No. 18855938.9, mailed Aug. 2, 2021, 7 pages.
Extended European Search Report for European Application No. 18885543.1, mailed Oct. 8, 2021, 8 pages.
Extended European Search Report for European Application No. 20207898.6, mailed Aug. 30, 2021, 8 pages.
Extended European Search Report for European Application No. 2023029844.2 mailed Mar. 20, 2024, 9 pages.
Extended European Search Report for European Application No. 21167069.0, mailed Nov. 10, 2021, 9 pages.
Extended European Search Report for European Application No. 21167625.9, mailed Oct. 8, 2021, 7 pages.
Extended European Search Report for European Application No. 22172183.0, mailed Sep. 11, 2022, 7 pages.
Extended European Search Report for European Application No. 22194769.0, mailed Feb. 28, 2023, 9 pages.
Extended European Search Report for European Application No. 22210589.2, mailed Apr. 17, 2023, 6 pages.
Extended European Search Report for European Application No. 23182529.0, mailed Dec. 19, 2023, 13 pages.
Extended European Search Report for European Application No. 23218666.8 mailed Apr. 18, 2024, 9 pages.
File History of U.S. Appl. No. 15/832,091, filed Dec. 5, 2017, 360 pages.
First Amended Complaint in *Magnolia Medical Technologies, Inc.* v. *Kurin, Inc.*, C.A. No. 19-CV-00097-CFC, Document 5 (Filed Mar. 7, 2019). 40 pages.
Geisler et al., "Model to Evaluate the Impact of Hospital-Based Interventions Targeting False-Positive Blood Cultures on Economic and Clinical Outcomes," J. Hospital Infection, vol. 102, No. 4, pp. 438-444 (Mar. 2019).
Gottlieb, T., "Hazards of Bacterial Contamination of Blood Products," Anaesth Intens Care, 21:20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, pp. 575-589 (2003).
International Search Report and Written Opinion for International Application No. PCT/US2007/087951, mailed May 16, 2008, 8 pages.
International Search Report and Written Opinion for International Application No. PCT/US2013/043289, mailed Oct. 24, 2013, 15 pages.
International Search Report and Written Opinion for International Application No. PCT/US2013/052493, mailed Nov. 27, 2013, 7 pages.
International Search Report and Written Opinion for International Application No. PCT/US2013/063975, mailed Mar. 20, 2014, 16 pages.
International Search Report and Written Opinion for International Application No. PCT/US2013/071491, mailed Aug. 5, 2014, 9 pages.

(56) References Cited

OTHER PUBLICATIONS

International Search Report and Written Opinion for International Application No. PCT/US2013/072563, mailed Feb. 7, 2014, 11 pages.
International Search Report and Written Opinion for International Application No. PCT/US2013/073080, mailed Feb. 18, 2014, 14 pages.
International Search Report and Written Opinion for International Application No. PCT/US2016/050380, mailed Dec. 1, 2016, 6 pages.
International Search Report and Written Opinion for International Application No. PCT/US2018/036910, mailed Sep. 4, 2018, 13 pages.
International Search Report and Written Opinion for International Application No. PCT/US2018/050621, mailed Nov. 26, 2018, 11 pages.
International Search Report and Written Opinion for International Application No. PCT/US2018/064561, mailed Feb. 11, 2019, 9 pages.
International Search Report and Written Opinion for International Application No. PCT/US2019/034626, mailed Aug. 22, 2019, 16 pages.
International Search Report and Written Opinion for International Application No. PCT/US2020/022125, mailed May 26, 2020, 17 pages.
Kim, J. Y. et al., "The Sum of the Parts is Greater Than the Whole: Reducing Blood Culture Contamination," Annals of Internal Medicine, 154:202-203 (2011).
Kurin, Inc.'s Opening Post-Trial Brief Regarding indefiniteness in *Magnolia Medical Technologies, Inc.* v. *Kurin, Inc.*, C.A. No. 19-097 (CFC)(CJB), Document 451 (Filed Sep. 9, 2022), 24 pages.
Lanteri et al., "Reduction of Blood Culture Contaminations in the Emergency Department," Department of Emergency Medicine, San Antonio Military Medical Center (2016), 1 page.
Levin, P. D. et al., "Use of the Nonwire Central Line Hub to Reduce Blood Culture Contamination," Chest, 143(3):640-645 (2013).
Litigation Search Report CRU 3999 for Reexamination Application No. 90/019,177 dated Mar. 23, 2023, 95 pages.
Liumbruno, G. M. et al., "Reduction of the risk of bacterial contamination of blood components through diversion of the first part of the donation of blood and blood components," Blood Transfus., 7:86-93 (2009).
Li, Y. et al., "Direct labeling and visualization of blood vessels with lipophilic carbocyanine dye Oil," Nature Protocols, 3(11):1703-1708 (2008).
Magnolia's Answer Brief in Opposition to Kurin, Inc.'s Opening Post-Trial Brief Regarding Indefiniteness in *Magnolia Medical Technologies, Inc.* v. *Kurin, Inc.*, C.A. No. 19-097 (CFC)(CJB), Document 463 (Filed Sep. 30, 2022). 25 pages.
Mayer, G. A, "A Method for the Reliable Determination of Clotting Time in Whole Blood," Can Med Assoc J., 72(12):927-929 (1955).
McDonald, C. P., "Interventions Implemented to Reduce the Risk of Transmission of Bacteria by Transfusion in the English National Blood Service," Transfus Med Hemother, 38:255-258 (2011).
McDonald, C.P.; "Bacterial risk reduction by improved donor arm disinfection, diversion and bacterial screening," Transfus Med., (2006); 16(6):381-396.
Meissner, G. F. et al., "A Method Based on the Use of Whole Venous Blood in Capillary Tubes," American Journal of Clinical Pathology, 33(2):29-31 (1963).
Murphy, M., "Better Blood Transfusion," Journal of the Intensive Core Society, 4(3):78-80 (2003).
Napolitano, M. et al., "Quality control of bacterial contamination of blood components: the feasibility of diversion system testing," Blood Transfus., 2:231-232 (2004).
Nielsen et al., "Initial Specimen Diversion Device Reduces Blood Culture Contamination and Vancomycin Use in Academic Medical Centre," J. Hospital Infection, vol. 120:127-133 (Feb. 2022).
Norberg, A et al., "Contamination Rates of Blood Cultures Obtained by Dedicated Phlebotomy vs Intravenous Catheter," JAMA, 289(6):726-729 (2003).
Notice of Allowance and Search Report for Chinese Application No. 20188066848 mailed Jan. 4, 2023, 4 pages.
Office Action and Search Report for Chinese Application No. 202080033513.6, mailed Oct. 9, 2022, with English translation, 19 pages.
Office Action for Australian Application No. 2018334138 mailed Jun. 24, 2023, 3 pages.
Office Action for Australian Application No. 2020218544, mailed Jul. 31, 2024, 3 pages.
Office Action for Australian Application No. 20220200818 mailed May 11, 2023, 4 pages.
Office Action for Canadian Application No. 3120161, mailed Jun. 20, 2022, 4 pages.
Office Action for Canadian Application No. 3136331, mailed Feb. 21, 2023, 4 pages.
Office Action for Chinese Application No. 201380040468.7, mailed Jun. 30, 2016, with English Translation, 9 pages.
Office Action for Chinese Application No. 201380072185.0, mailed Sep. 28, 2016, with English Translation, 17 pages.
Office Action for Chinese Application No. 201711078173.5, mailed Feb. 3, 2020, with English Translation, 14 pages.
Office Action for Chinese Application No. 201811146373.4, mailed Aug. 25, 2021, with English language translation, 10 pages.
Office Action for Chinese Application No. 201811146373.4, mailed Jan. 29, 2022, with English language translation, 21 pages.
Office Action for Chinese Application No. 201811146373.4, mailed Nov. 4, 2020, with English language translation, 17 pages.
Office Action for Chinese Application No. 201880066848.0, mailed Apr. 20, 2022, with English Translation, 10 pages.
Office Action for Chinese Application No. 201880088771.7, mailed Sep. 3, 2021, with English translation, 17 pages.
Office Action for European Application No. 20716348.6, mailed Jul. 12, 2022, 7 pages.
Office Action for Ex Parte Reexamination for U.S. Appl. No. 90/019,177, mailed Aug. 9, 2023, 11 pages.
Office Action for Indian Application No. 202017008581, mailed Mar. 8, 2022, with English translation, 7 pages.
Office Action for Israeli Application No. 273025, mailed Dec. 4, 2022, 3 pages.
Office Action for Israeli Application No. 285289, mailed May 6, 2024, 4 pages.
Office Action for Israeli Application No. 286263, mailed May 12, 2024, 4 pages.
Office Action for Israeli Application No. 309638, mailed Jul. 16, 2024, 3 pages.
Office Action for Japanese Application No. 2015-545813, mailed Jul. 4, 2017, with English Translation, 14 pages.
Office Action for Japanese Application No. 2018-081980, mailed Feb. 21, 2019, with English Translation, 9 pages.
Office Action for Japanese Application No. 2018-081980, mailed Jan. 30, 2020, 11 pages.
Office Action for Japanese Application No. 2018-086721, mailed Mar. 15, 2019, with English Translation, 6 pages.
Office Action for Japanese Application No. 2019-230734, mailed Jan. 22, 2021, with English Translation, 9 pages.
Office Action for Japanese Application No. 2020-075727, mailed Jul. 21, 2021, with English translation, 37 pages.
Office Action for Japanese Application No. 2020-094488, mailed Aug. 2, 2021, with English Translation, 4 pages.
Office Action for Japanese Application No. 2020-094488, mailed Mar. 31, 2022, with English Translation, 6 pages.
Office Action for Japanese Application No. 2020-511930, mailed Aug. 23, 2022, with English translation, 9 pages.
Office Action for Japanese Application No. 2020-566232 mailed Apr. 12, 2023, with English translation, 27 pages.
Office Action for Japanese Application No. 2021-552145, mailed Jan. 15, 2024, with English Translation, 9 pages.
Office Action for Japanese Application No. 2022-184274, mailed Jun. 14, 2024, with English Translation, 4 pages.

(56) References Cited

OTHER PUBLICATIONS

Office Action for Japanese Application No. 2022-184274 mailed Oct. 27, 2023, with English translation, 6 pages.
Office Action for Japanese Application No. 2022-212405, mailed Jun. 20, 2024, with English translation, 6 pages.
Office Action for Japanese Application No. 2022-212405, mailed Nov. 29, 2023, with English translation, 13 pages.
Office Action for Japanese Application No. 2023-075104 mailed Feb. 29, 2024, with English Translation, 9 pages.
Office Action for United Kingdom Application No. GB 1805101.1, mailed May 25, 2018, 8 pages.
Office Action for U.S. Appl. No. 11/955,635, mailed Dec. 3, 2010, 11 pages.
Office Action for U.S. Appl. No. 11/955,635, mailed Jul. 22, 2010, 11 pages.
Office Action for U.S. Appl. No. 13/335,241, mailed Apr. 20, 2012, 12 pages.
Office Action for U.S. Appl. No. 13/458,508, mailed Jul. 24, 2012, 13 pages.
Office Action for U.S. Appl. No. 13/675,295, mailed May 23, 2013, 15 pages.
Office Action for U.S. Appl. No. 13/952,964, mailed Mar. 20, 2015, 11 pages.
Office Action for U.S. Appl. No. 13/954,528, mailed Mar. 17, 2014, 10 pages.
Office Action for U.S. Appl. No. 14/049,326, mailed Apr. 24, 2015, 10 pages.
Office Action for U.S. Appl. No. 14/089,267, mailed Jun. 19, 2014, 13 pages.
Office Action for U.S. Appl. No. 14/096,826, mailed Jul. 26, 2017, 12 pages.
Office Action for U.S. Appl. No. 14/096,826, mailed Mar. 8, 2018, 14 pages.
Office Action for U.S. Appl. No. 14/493,796, mailed Jan. 27, 2015, 7 pages.
Office Action for U.S. Appl. No. 14/494,208, mailed Jan. 27, 2015, 7 pages.
Office Action for U.S. Appl. No. 14/498,102, mailed Oct. 17, 2017, 20 pages.
Office Action for U.S. Appl. No. 14/498,102, mailed Sep. 24, 2018, 18 pages.
Office Action for U.S. Appl. No. 14/662,676, mailed Sep. 5, 2018, 25 pages.
Office Action for U.S. Appl. No. 14/712,437 mailed Oct. 25, 2018, 20 pages.
Office Action for U.S. Appl. No. 14/728,318, mailed Dec. 20, 2018, 26 pages.
Office Action for U.S. Appl. No. 14/728,318, mailed Jan. 8, 2018, 36 pages.
Office Action for U.S. Appl. No. 14/728,318, mailed May 19, 2017, 26 pages.
Office Action for U.S. Appl. No. 14/838,794, mailed Aug. 3, 2017, 8 pages.
Office Action for U.S. Appl. No. 14/880,397, mailed Apr. 17, 2018, 6 pages.
Office Action for U.S. Appl. No. 14/880,397, mailed Sep. 24, 2018, 5 pages.
Office Action for U.S. Appl. No. 14/926,784, mailed Jan. 15, 2019, 15 pages.
Office Action for U.S. Appl. No. 14/926,784, mailed Jan. 21, 2020, 17 pages.
Office Action for U.S. Appl. No. 14/926,784, mailed May 25, 2018, 15 pages.
Office Action for U.S. Appl. No. 15/088,842, mailed Nov. 23, 2016, 20 pages.
Office Action for U.S. Appl. No. 15/432,310, mailed Apr. 12, 2017, 14 pages.
Office Action for U.S. Appl. No. 15/435,684, mailed Jun. 12, 2017, 19 pages.
Office Action for U.S. Appl. No. 15/448,891, mailed Jun. 16, 2017, 25 pages.
Office Action for U.S. Appl. No. 15/457,082, mailed Jun. 15, 2017, 22 pages.
Office Action for U.S. Appl. No. 15/829,015, mailed Feb. 6, 2018, 24 pages.
Office Action for U.S. Appl. No. 15/829,018, mailed Feb. 16, 2018, 13 pages.
Office Action for U.S. Appl. No. 15/829,023, mailed Feb. 7, 2018, 25 pages.
Office Action for U.S. Appl. No. 15/832,055, mailed Feb. 8, 2018, 21 pages.
Office Action for U.S. Appl. No. 15/832,087, mailed Feb. 7, 2018, 24 pages.
Office Action for U.S. Appl. No. 15/832,091, mailed Feb. 22, 2018, 16 pages.
Office Action for U.S. Appl. No. 15/854,273, mailed Jan. 13, 2020, 13 pages.
Office Action for U.S. Appl. No. 15/854,273, mailed Mar. 15, 2019, 19 pages.
Office Action for U.S. Appl. No. 15/854,273, mailed Sep. 7, 2018, 15 pages.
Office Action for U.S. Appl. No. 15/925,159, mailed May 14, 2019, 15 pages.
Office Action for U.S. Appl. No. 15/925,159, mailed Nov. 26, 2018, 11 pages.
Office Action for U.S. Appl. No. 16/004,955, mailed Feb. 16, 2021, 28 pages.
Office Action for U.S. Appl. No. 16/129,066, mailed Sep. 3, 2020, 13 pages.
Office Action for U.S. Appl. No. 16/213,005, mailed Feb. 3, 2021, 15 pages.
Office Action for U.S. Appl. No. 16/255,055, mailed Mar. 18, 2019, 16 pages.
Office Action for U.S. Appl. No. 16/255,058, mailed Mar. 30, 2021, 16 pages.
Office Action for U.S. Appl. No. 16/274,835, mailed Feb. 12, 2021, 17 pages.
Office Action for U.S. Appl. No. 16/299,962, mailed Dec. 26, 2019, 14 pages.
Office Action for U.S. Appl. No. 16/299,962, mailed Dec. 9, 2020, 15 pages.
Office Action for U.S. Appl. No. 16/299,962, mailed Jun. 15, 2021, 17 pages.
Office Action for U.S. Appl. No. 16/299,962, mailed May 2, 2019, 14 pages.
Office Action for U.S. Appl. No. 16/376,745, mailed May 14, 2021, 13 pages.
Office Action for U.S. Appl. No. 16/379,128, mailed Apr. 26, 2022, 14 pages.
Office Action for U.S. Appl. No. 16/426,380, mailed May 7, 2021, 28 pages.
Office Action for U.S. Appl. No. 16/426,380, mailed Oct. 30, 2020, 29 pages.
Office Action for U.S. Appl. No. 16/789,034, mailed Feb. 9, 2023, 11 pages.
Office Action for U.S. Appl. No. 16/815,526, mailed Aug. 18, 2022, 13 pages.
Office Action for U.S. Appl. No. 17/136,882, mailed Apr. 19, 2024, 8 pages.
Office Action for U.S. Appl. No. 17/138,056, mailed Dec. 21, 2022, 11 pages.
Office Action for U.S. Appl. No. 17/388,971, mailed Nov. 23, 2021, 19 pages.
Office Action for U.S. Appl. No. 17/388,979, mailed Dec. 8, 2021, 21 pages.
Office Action for U.S. Appl. No. 17/390,249 mailed Nov. 8, 2023, 9 pages.
Office Action for U.S. Appl. No. 17/403,500, mailed May 20, 2024, 28 pages.
Office Action for U.S. Appl. No. 17/525,682, mailed Feb. 7, 2022, 12 pages.

(56) References Cited

OTHER PUBLICATIONS

Office Action for U.S. Appl. No. 17/532,382, mailed Feb. 7, 2022, 10 pages.
Office Action for U.S. Appl. No. 17/591,237, mailed Aug. 25, 2023, 25 pages.
Office Action for U.S. Appl. No. 17/591,237, mailed Aug. 4, 2022, 26 pages.
Office Action for U.S. Appl. No. 17/591,237, mailed Feb. 16, 2023, 34 pages.
Office Action for U.S. Appl. No. 17/591,237, mailed May 3, 2022, 20 pages.
Office Action for U.S. Appl. No. 17/591,239, mailed Aug. 23, 2023, 23 pages.
Office Action for U.S. Appl. No. 17/591,239, mailed Aug. 4, 2022, 26 pages.
Office Action for U.S. Appl. No. 17/591,239, mailed Feb. 17, 2023, 34 pages.
Office Action for U.S. Appl. No. 17/591,239, mailed May 3, 2022, 21 pages.
Office Action for U.S. Appl. No. 17/684,920, mailed Jan. 31, 2023, 9 pages.
Office Action for U.S. Appl. No. 17/684,920, mailed Jul. 11, 2022, 12 pages.
Office Action for U.S. Appl. No. 17/710,389, mailed Jun. 16, 2022, 25 pages.
Office Action for U.S. Appl. No. 17/710,401, mailed Jul. 6, 2022, 22 pages.
Office Action for U.S. Appl. No. 17/710,411, mailed Jul. 6, 2022, 22 pages.
Office Action for U.S. Appl. No. 17/863,605, mailed Nov. 28, 2023, 15 pages.
Office Action for U.S. Appl. No. 18/130,207 mailed Aug. 21, 2023, 7 pages.
Office Action for U.S. Appl. No. 18/227,185, mailed Apr. 18, 2024, 18 pages.
Office Action for U.S. Appl. No. 18/240,178, mailed Jun. 12, 2024, 16 pages.
Office Action for U.S. Appl. No. 18/299,680, mailed Aug. 15, 2023, 5 pages.
Office Action for U.S. Appl. No. 18/380,259, mailed Jan. 29, 2024, 33 pages.
Office Action for U.S. Appl. No. 18/381,369, mailed Nov. 28, 2023, 16 pages.
Office Action for U.S. Appl. No. 18/399,007, mailed Mar. 7, 2024, 8 pages.
Office Action for U.S. Appl. No. 18/407,010, mailed Mar. 13, 2024, 8 pages.
Office Action for U.S. Appl. No. 18/675,824, mailed Jul. 26, 2024, 13 pages.
Office Action for U.S. Appl. No. 18/676,186, mailed Aug. 5, 2024, 13 pages.
Opening Expert Report of Dr. Juan G. Santiago Regarding Infringement of U.S. Pat. Nos. 9,855,001 and 10,039,483 (Redacted) in *Magnolia Medical Technologies, Inc.* v. *Kurin, Inc.*, CA No. 19-00097-CFC (dated Jan. 15, 2021), 555 pages.
Order of Draw for Multiple Tube Collections, LabNotes, a newsletter from BD Diagnostics,—Preanalytical Systems, 17(1):3 (2007), 1 page.
Original Claims of U.S. Appl. No. 14/712,431, filed May 14, 2015. 6 pages.
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Pall Corp., "Leukotrap Filtration Systems for Whole Blood Derived Platelets: Leukotrap RC PL and Leukotrap PL Systems," 2005 Brochure, 2 pages.
Patel, R. et al., "Optimized Pathogen Detection with 30- Compared to 20-Milliliter Blood Culture Draws." Journal of Clinical Microbiology, 49(12):4047-4051 (2011).
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Povroznik, "Initial Specimen Diversion Device Utilization Mitigates Blood Culture Contamination Across Regional Community Hospital and Acute Care Facility," Am. J. Medical Quality, vol. 37, No. 5, 405 (Mar. 2022), 8 pages.
Proehl, J. A et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Redacted Plaintiff's Answering Brief in Opposition to Defendant's Motion for Summary Judgement (No. 3) of Noninfringement of All Asserted Claims Due to Lack of Sequestration in *Magnolia Medical Technologies, Inc.* v. *Kurin, Inc.*, C.A. No. 19-97 (CFC)(CJB), Document 389 (Filed Jul. 14, 2021), 15 pages.
Reexamination Request Order-Granted, for U.S. Appl. No. 90/019,177, mailed Apr. 26, 2023, 16 pages.
Request for Ex Parte Reexamination for U.S. Pat. No. 10,039,483 Under 35 U.S.C. § 302 and 37 C.F.R. § 1.510 filed Mar. 22, 2023, 84 pages.
Rupp et al., "Reduction in Blood Culture Contamination Through Use of Initial Specimen Diversion Device," Clinical Infectious Diseases, vol. 65, No. 2, 201 (Jul. 15, 2017), 19 pages.
Schuur, J., "Blood Cultures: When Do they Help and When Do They Harm?" Brigham & Women's Hospital, Department of Emergency Medicine, (Jun. 21-23, 2012), 42 pages.
Sheppard, C. A., et al.; "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1):11-19 (2000).
Sibley, C. D., et al.; "Molecular Methods for Pathogen and Microbial Community Detection and Characterization: Current and Potential Application in Diagnostic Microbiology," Infection, Genetics and Evolution 12:505-521 (2012).
Skoglund et al., "Estimated Clinical and Economic Impact through Use of a Novel Blood Collection Device to Reduce Blood Culture Contamination in the Emergency Department: a Cost-Benefit Analysis," J Clin Microbiol. (Jan. 2019); 57(1):e01015-18, 10 pages.
Steed et al., "Study Demonstrates Reduction in Blood Culture Contamination Rates with Novel Blood Culture Collection Device," Clinical Lab Products Magazine (Feb. 2018), 2 pages.
Stohl, S. et al., "Blood Cultures at Central Line Insertion in the Intensive Care Unit: Comparison with Peripheral Venipuncture," Journal of Clinical Microbiology, 49(7):2398-2403 (2011).
Supplementary European Search Report for EP Application No. 13797732.8, dated Dec. 7, 2015, 5 pages.
Supplementary European Search Report for EP Application No. 13845555.5, dated Jul. 12, 2016, 6 pages.
Supplementary European Search Report for EP Application No. 13860741.1, dated Jun. 7, 2016, 5 pages.
Tang, M. et al., "Closed Blood Conservation Device for Reducing Catheter-Related Infections in Children After Cardiac Surgery," Critical Care Nurse, 34(5):53-61 (2014).
Tompkins et al., "Getting to Zero: Impact of A Device to Reduce Blood Culture Contamination and False-Positive Central-Line-Associated Bloodstream Infection," Infection Control & Hospital Epidemiology, pp. 1-5 (Nov. 2022).
Tongma et al., "Significant Reduction of Blood Culture Contamination in the Emergency Department (ED) Using the Steripath® Blood Diversion Device," Open Forum Infectious Diseases, vol. 4, Supp. 1, 2035 (Oct. 2017), 1 page.
Vent Definition & Meaning—Merriam-Webster (https://www.merriam-webster.com/dictionary/vent, accessed Mar. 21, 2023); 16 pages.
Vent, n.2: Oxford English Dictionary (https://www.oed.com/view/Entry/222207?&print, accessed Feb. 16, 2023); 12 pages.

(56) References Cited

OTHER PUBLICATIONS

Verdict Form (Phase 2) (Redacted) in *Magnolia Medical Technologies, Inc.* v. *Kurin, Inc.*, CA No. 19-97-CFC (CJB), Document 443 (Filed Jul. 29, 2022). 5 pages.
Verdict Form (Redacted) in *Magnolia Medical Technologies, Inc.* v. *Kurin, Inc.*, C.A. No. 19-97-CFC (CJB), Document 437 (Filed Jul. 26, 2022). 3 pages.
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23: pp. 63-66 (2012).
Weinbaum, F. I. et al., "Doing It Right the First Time: Quality Improvement and the Contaminant Blood Culture," Journal of Clinical Microbiology, 35(3):563-565 (1997).
Weinstein, M.P., "Current Blood Culture Methods and Systems: Clinical Concepts, Technology, and Interpretation of Results," Clinical Infectious Diseases, 23:40-46 (1996).
Weinstein, M.P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Weinstein, M.P., "Minireview: Blood Culture Contamination: Persisting Problems and Partial Progress," Journal of Clinical Microbiology, 41(6):2275-2278 (2003).
Ziegler, et al., "Controlled Clinical Laboratory Comparison of Two Supplemented Aerobic and Anaerobic Media Used in Automated Blood Culture Systems to Detect Bloodstream Infections," J. Clinical Microbiology, 36(3):657-661 (1998).
Zimmerman et al., "Reducing Blood Culture Contamination Using an Initial Specimen Diversion Device," Am. J. Infection Control, vol. 47, No. 7, pp. 822-826 (Jan. 2019).
Zimmon, D. S. et al., "Effect of Portal Venous Blood Flow Diversion on Portal Pressure," J Clin Invest, 65(6): 1388-1397 (1980).
Zundert, A V., "New Closed IV Catheter System," Acta Anaesth. Belg., 56:283-285 (2005).
Declaration of Dr. Erik K. Antonsson, Ph.D., P.E., NAE, dated Dec. 5, 2024, 138 pages.
Exhibit A to Magnolia Medical Technologies, Inc.'s Frist Amended Disclosure of Asserted Claims and Infringement Contentions, served May 28, 2024, in *Magnolia Medical Technologies, Inc.* v. *Kurin, Inc.*; Case No. 3-24-cv-00428 (S.D. Cal.), 240 pages.
Exhibit B to Magnolia Medical Technologies, Inc.'s Frist Amended Disclosure of Asserted Claims and Infringement Contentions, served May 28, 2024, in *Magnolia Medical Technologies, Inc.* v. *Kurin, Inc.*; Case No. 3-24-cv-00428 (S.D. Cal.), 213 pages.
Extended European Search Report for European Application No. 23217471.4, mailed May 22, 2024, 8 pages.
File History of U.S. Appl. No. 15/432,310, filed Feb. 14, 2017, 246 pages.
File History of U.S. Appl. No. 15/829,023, filed Dec. 1, 2017, 348 pages.
Magnolia's Corrected Opening Claim Construction Brief in *Magnolia Medical Technologies, Inc.* v. *Kurin, Inc.* Case No. CA No. 1:24-01124-CFC (D. Del.), dated Nov. 17, 2024, 32 pages.
Memorandum Opinion in support of Judgment of Non-infringement as a matter of law, entered in *Magnolia Medical Technologies, Inc.* v. *Kurin, Inc.*, C.A. No. 19-97 (CFC)(CJB) (D.Del.), May 14, 2024, 21 pages.
Office Action for Australian Application No. 2020234829, mailed Nov. 15, 2024, 3 pages.
Office Action for Canadian Application No. 3066670, mailed Oct. 4, 2024, 4 pages.
Office Action for Canadian Application No. 3074105, mailed Nov. 15, 2024, 5 pages.
Office Action for Canadian Application No. 3183294, mailed Aug. 19, 2024, 5 pages.
Office Action for Ex Parte Reexamination for U.S. Appl. No. 90/019,177, mailed Dec. 1, 2023, 19 pages.
Office Action for U.S. Appl. No. 17/136,882, mailed Jun. 9, 2023, 11 pages.
Office Action for U.S. Appl. No. 17/136,882, mailed Nov. 8, 2023, 11 pages.
Office Action for U.S. Appl. No. 17/403,500, mailed Nov. 13, 2024, 27 pages.
Office Action for U.S. Appl. No. 18/227,185, mailed Oct. 31, 2024, 17 pages.
Office Action for U.S. Appl. No. 18/380,259, mailed Oct. 16, 2024, 15 pages.
Office Action for U.S. Appl. No. 18/407,010, mailed Sep. 6, 2024, 11 pages.
Partial Judgment entered in *Magnolia Medical Technologies, Inc.* v. *Kurin, Inc.*, C.A. No. 19-97 (CFC)(CJB) (D. Del.), Jun. 10, 2022, 3 pages.
Request for Ex Parte Reexamination for U.S. Pat. No. 10,052,053 Under 35 U.S.C. § 302 and 37 C.F.R. § 1.510, filed Dec. 6, 2024, 144 pages.
Request for Ex Parte Reexamination for U.S. Pat. No. 9,855,002 Under 35 U.S.C. § 302 and 37 C.F.R. § 1.510, filed Dec. 6, 2024, 147 pages.
Transcript of Jury Trial Proceedings of Jul. 25, 2022, in *Magnolia Medical Technologies, Inc.* v. *Kurin, Inc.*, C.A. No. 19-97 (CFC)(CJB) (D. Del.), 402 pages.
Transcript of Jury Trial Proceedings of Jul. 27, 2022, in *Magnolia Medical Technologies, Inc.* v. *Kurin, Inc.*, C.A. No. 19-97 (CFC)(CJB) (D. Del.), 412 pages.
Chamarthy, P., et al.; "Mixing Characteristics in a Serpentine Micro-Channel," IMECE2004-61902; Proceedings of the ASME 2004 International Mechanical Engineering Congress and Exposition. Fluids Engineering. Anaheim, California, USA; Nov. 13-19, 2004, pp. 253-261; Exhibit 4; 10 pages.
Declaration of Dr. Erik K. Antonsson, Ph.D., P.E., NAE, U.S. Pat. No. 11,529,081, dated Jan. 20, 2025, 164 pages.
Declaration of Dr. Erik K. Antonsson, Ph.D., P.E., NAE, U.S. Pat. No. 11,653,863, dated Jan. 20, 2025, 169 pages.
Declaration of Dr. Erik K. Antonsson, Ph.D., P.E., NAE, U.S. Pat. No. 11,903,709, dated Jan. 20, 2025, 161 pages.
Declaration of Dr. Erik K. Antonsson, Ph.D., P.E., NAE, U.S. Pat. No. 9,855,002, dated Dec. 5, 2024, 141 pages.
Declaration of Professor Steven T. Wereley, PH.D., *Magnolia Medical Technologies, Inc.* v. *Kurin, Inc.*, C.A. 24-01124-CFC (D. Del.), Document # 181, dated Apr. 14, 2025, 37 pages.
Exhibit C to Magnolia's First Amended Disclosure of Asserted Claims and Infringement Contentions, *Magnolia Medical Technologies, Inc.* v. *Kurin, Inc.*, C.A. 3-24-cv-00428 (S.D. Cal.), served May 28, 2024, 250 pages.
Exhibit D to Magnolia's First Amended Disclosure of Asserted Claims and Infringement Contentions, *Magnolia Medical Technologies, Inc.* v. *Kurin, Inc.*, C.A. 3-24-cv-00428 (S.D. Cal.), served May 28, 2024, 222 pages.
Exhibit E to Magnolia's First Amended Disclosure of Asserted Claims and Infringement Contentions, *Magnolia Medical Technologies, Inc.* v. *Kurin, Inc.*, C.A. 3-24-cv-00428 (S.D. Cal.), served May 28, 2024, 239 pages.
Extended European Search Report for European Application No. 16808502.5, mailed Jan. 23, 2019, 5 pages.
Extended European Search Report for European Application No. 19156636.3, mailed Aug. 27, 2019, 7 pages.
Extended European Search Report for European Application No. 19190772.4, mailed Feb. 10, 2020, 7 pages.
Extended European Search Report for European Application No. 20176877.7, mailed Dec. 1, 2020, 9 pages.
Extended European Search Report for European Application No. 21197514.9, mailed Mar. 30, 2022, 9 pages.
Extended European Search Report for European Application No. 22158983.1, mailed Aug. 1, 2022, 9 pages.
Extended European Search Report for European Application No. 23153164.1, mailed Aug. 7, 2023, 8 pages.
Extended European Search Report for European Application No. 23171135.9, mailed Oct. 30, 2023, 8 pages.
Extended European Search Report for European Application No. 24217446.4, mailed Apr. 17, 2025, 8 pages.

(56) References Cited

OTHER PUBLICATIONS

File History of U.S. Appl. No. 17/883,339, filed Aug. 8, 2022, 484 pages.
File History of U.S. Appl. No. 17/883,340, filed May 23, 2023, 801 pages.
File History of U.S. Appl. No. 18/130,207, filed Apr. 3, 2023, 476 pages.
File History of U.S. Appl. No. 60/969,394, filed Aug. 31, 2007, Inventor Humes; 95 pages; Exhibit 181-3.
Garstecki, P., et al.; "Formation of droplets and bubbles in a microfluidic T-junction-scaling and mechanism of break-up," Lab Chip; 6(3):437-446 (Mar. 2006).
International Search Report and Written Opinion for International Application No. PCT/US2016/037160, mailed Sep. 30, 2016, 15 pages.
International Search Report and Written Opinion for International Application No. PCT/US2020/017261, mailed May 14, 2020, 13 pages.
Kurin blood culture collection; Device Description; KUR-MAG-DE000147; pp. 1-9; Exhibit 181-6 (2025).
Magnolia's Supplemental Claim Construction Brief, *Magnolia Medical Technologies, Inc.* v. *Kurin, Inc.*, C.A. 24-01124-CFC (D. Del.), Document # 180, dated Apr. 14, 2025, 30 pages.
Marshall, L.A., et al.; "An injection molded microchip for nucleic acid purification from 25 microliter samples using isotachophoresis," J Chromatogr A.; 1331; pp. 139-142 (Feb. 2014).
Office Action for Australian Application No. 2018279941, mailed Mar. 20, 2023, 3 pages.
Office Action for Australian Application No. 2024203105, mailed Jan. 21, 2025, 3 pages.
Office Action for Australian Application No. 2024203140, mailed Apr. 8, 2025, 4 pages.
Office Action for Canadian Application No. 2932536, mailed Nov. 8, 2019, 6 pages.
Office Action for Canadian Application No. 2932536, mailed Oct. 23, 2020, 6 pages.
Office Action for Canadian Application No. 3087992, mailed Mar. 20, 2025, 4 pages.
Office Action for Canadian Application No. 3101972, mailed May 13, 2025, 4 pages.
Office Action for Canadian Application No. 3129065, mailed Feb. 11, 2025, 3 pages.
Office Action for Chinese Application No. 201811146373.4, mailed Apr. 8, 2025, with English translation, 18 pages.
Office Action for Chinese Application No. 201880050862.1, mailed Mar. 14, 2022, with English translation, 19 pages.
Office Action for Chinese Application No. 202080025953.7, mailed Aug. 28, 2024, with English language translation, 26 pages.
Office Action for Chinese Application No. 202080025953.7, mailed Dec. 17, 2024, with English language translation, 22 pages.
Office Action for Chinese Application No. 202080025953.7, mailed Jan. 9, 2024, with English translation, 27 pages.
Office Action for Chinese Application No. 202310257287.5, mailed Apr. 23, 2025, with English translation, 21 pages.
Office Action for European Application No. 20709440.0, mailed Feb. 18, 2025, 6 pages.
Office Action for Ex Parte Re-examination of U.S. Appl. No. 90/019,756, mailed Jun. 17, 2025, 38 pages.
Office Action for Ex Parte Re-examination of U.S. Appl. No. 90/019,757, mailed Jun. 17, 2025, 27 pages.
Office Action for Israeli Application No. 313917, mailed May 29, 2025, 4 pages.
Office Action for Japanese Application No. 2019-230734, mailed Jan. 5, 2022, with English Translation, 6 pages.
Office Action for Japanese Application No. 2020-517772, mailed Dec. 26, 2022, with English Translation, 6 pages.
Office Action for Japanese Application No. 2020-517772, mailed Mar. 14, 2022, with English Translation, 13 pages.
Office Action for Japanese Application No. 2020-550048, mailed Aug. 5, 2022, with English Translation, 5 pages.
Office Action for Japanese Application No. 2021-546225, mailed Dec. 19, 2023, with English translation, 11 pages.
Office Action for Japanese Application No. 2022-074696 mailed Feb. 20, 2023, with English translation, 11 pages.
Office Action for Japanese Application No. 2024-014849, mailed Apr. 30, 2025, with English translation, 9 pages.
Office Action for Japanese Application No. 2024-020482 mailed Mar. 11, 2025, with English Translation, 16 pages.
Office Action for Japanese Application No. 2024-115518, mailed Jun. 11, 2025, with English Translation, 6 pages.
Office Action for Japanese Application No. 2024-187934, mailed Apr. 28, 2025, with English translation, 12 pages.
Office Action for U.S. Appl. No. 14/728,318, mailed Jul. 18, 2019, 27 pages.
Office Action for U.S. Appl. No. 15/180,454, mailed Apr. 1, 2020, 28 pages.
Office Action for U.S. Appl. No. 15/180,454, mailed Jan. 21, 2021, 24 pages.
Office Action for U.S. Appl. No. 15/180,454, mailed Jul. 25, 2019, 27 pages.
Office Action for U.S. Appl. No. 16/785,170, mailed Sep. 14, 2022, 11 pages.
Office Action for U.S. Appl. No. 16/934,975, mailed Oct. 6, 2022, 18 pages.
Office Action for U.S. Appl. No. 17/136,882, mailed Dec. 31, 2024, 6 pages.
Office Action for U.S. Appl. No. 17/403,500, mailed Jul. 28, 2023, 28 pages.
Office Action for U.S. Appl. No. 17/403,500, mailed Sep. 27, 2022, 29 pages.
Office Action for U.S. Appl. No. 17/516,887, mailed Jan. 13, 2025, 42 pages.
Office Action for U.S. Appl. No. 17/583,791, mailed Dec. 23, 2024, 19 pages.
Office Action for U.S. Appl. No. 17/591,237, mailed Jan. 24, 2025, 34 pages.
Office Action for U.S. Appl. No. 17/591,239, mailed Jan. 24, 2025, 32 pages.
Office Action for U.S. Appl. No. 17/869,256, mailed May 5, 2025, 24 pages.
Office Action for U.S. Appl. No. 18/240,178, mailed Feb. 27, 2025, 12 pages.
Office Action for U.S. Appl. No. 18/680,331, mailed Mar. 25, 2025, 8 pages.
Office Action for U.S. Appl. No. 18/680,348, mailed Mar. 25, 2025, 7 pages.
Office Action for U.S. Appl. No. 18/680,377, mailed Mar. 26, 2025, 12 pages.
Office Action for U.S. Appl. No. 18/680,439, mailed Mar. 31, 2025, 8 pages.
Office Action for U.S. Appl. No. 18/960,441, mailed Jan. 17, 2025, 8 pages.
Office Action for U.S. Appl. No. 18/990,547, mailed Jan. 31, 2025, 10 pages.
Order Granting Request for Ex Parte Reexamination for U.S. Appl. No. 90/019,823, dated Feb. 24, 2025, 16 pages.
Order Granting Request for Ex Parte Reexamination for U.S. Appl. No. 90/019,824, dated Feb. 24, 2025, 18 pages.
Order Granting Request for Ex Parte Reexamination for U.S. Appl. No. 90/019,825, dated Feb. 25, 2025, 15 pages.
Preliminary Amendment of U.S. Appl. No. 17/591,237, filed Feb. 2, 2022, 12 pages.
Preliminary Amendment of U.S. Appl. No. 17/591,239, filed Feb. 2, 2022, 12 pages.
Request for Ex Parte Reexamination for U.S. Pat. No. 11,529,081 Under 35 U.S.C. § 302 and 37 C.F.R. § 1.510, filed Jan. 21, 2025, 179 pages.
Request for Ex Parte Reexamination for U.S. Pat. No. 11,653,863 Under 35 U.S.C. § 302 and 37 C.F.R. § 1.510, filed Jan. 21, 2025, 180 pages.
Request for Ex Parte Reexamination for U.S. Pat. No. 11,903,709 Under 35 U.S.C. § 302 and 37 C.F.R. § 1.510, filed Jan. 21, 2025, 176 pages.

(56) References Cited

OTHER PUBLICATIONS

Shen, H., et al.; "A microfluidic chip based sequential injection system with trapped droplet liquid-liquid extraction and chemiluminescence detection," Lab Chip; 6(10):1387-1389 (Oct. 2006).
U.S. Appl. No. 62/439,426, filed Dec. 27, 2016, Inventor Rogers, et al.; 126 pages.
Appellant/Patent Owner (Magnolia's) Opening Brief on Appeal, Document 10, *Magnolia Medical Technologies, Inc.* v. *Kurin, Inc.*, Appeal No. 24-2001 (Fed. Cir.) from C.A. 19-00097-CFC-CJB (D. Del.), dated Aug. 26, 2024; 71 pages.
Appellant/Patent Owner (Magnolia's) Reply Brief on Appeal, Document 25, *Magnolia Medical Technologies, Inc.* v. *Kurin, Inc.*, Appeal No. 24-2001 (Fed. Cir.) from C.A. 19-00097-CFC-CJB (D. Del.), dated Jan. 7, 2025; 44 pages.
Appellee/Requester (Kurin's) Brief on Appeal, Document 21, *Magnolia Medical Technologies, Inc.* v. *Kurin, Inc.*, Appeal No. 24-2001 (Fed. Cir.) from C.A. 19-00097-CFC-CJB (D. Del.), dated Nov. 12, 2024; 89 pages.
AU Application No. 2013267448, Office Action mailed Nov. 5, 2016; Applicant Magnolia Medical Technologies, Inc.; 3 pages.
AU Application No. 2017216493, Office Action mailed Sep. 19, 2018; Applicant Magnolia Medical Technologies, Inc.; 2 pages.
AU Application No. 2019204941, Office Action mailed Jul. 15, 2019; Applicant Magnolia Medical Technologies, Inc.; 4 pages.
AU Application No. 2020213415, Office Action mailed May 21, 2021; Applicant Magnolia Medical Technologies, Inc.; 3 pages.
AU Application No. 2020234829, Office Action mailed Sep. 11, 2025; Applicant Magnolia Medical Technologies, Inc.; 3 pages.
AU Application No. 2024205062, Office Action mailed Sep. 8, 2025; Applicant Magnolia Medical Technologies, Inc.; 2 pages.
Author Unknown, "Bact/Alert® Culture Media: Strong Outside, Strong Inside," [website], Biomerieux, (Publication Date Unknown), [Accessed via Internet, publicly available at URL: https://www.biomerieux.com/us/en/our-offer/clinical-products/bact-alert-culture-media-bottles.html.], 10 pages.
Author Unknown, "BD BACTEC™ Blood Culture System," [website], Becton, Dickinson and Company, (Publication Date Unknown), [Accessed via Internet, publicly available at URL: https://www.bd.com/en-us/products-and-solutions/products/product-families/bd-bactec-blood-culture-system.], 9 pages.
Author Unknown, "Changing Blood Culture Collection in Hospitals Across America, Clinical Evidence, Studies," [website], Kurin, (Publication Date Unknown), [Retrieved from Internet on Sep. 15, 2025 at URL: https://www.kurin.com/studies/.], 22 pages.
Author Unknown, "Changing Blood Culture Collection in Hospitals Across America," [website], Kurin, (Publication Date Unknown), [Retrieved from Internet on Sep. 15, 2025 at URL: https://www.kurin.com/clinical-guidelines/.], 11 pages.
Author Unknown, "False Positive Blood Cultures—Improve the accuracy of blood culture," [website], Kurin, (Publication Date Unknown), [Retrieved from Internet on Sep. 15, 2025 at URL: https://www.kurin.com/false-positive-blood-cultures/.], 5 pages.
Author Unknown, "Kurin® Jet™ Blood Culture Collection Ordering Information," [website], Kurin, (Publication Date Unknown), [Accessed via Internet, publicly available at URL: https://www.kurin.com/kurin-jet/.], 2 pages.
Author Unknown, "Kurin Launches Kurin Jet, Redefining the Blood Culture Contamination Device Market," [website], Kurin, (Publication Date Unknown), [Accessed via Internet, publicly available at URL: https://www.kurin.com/kurin-launches-kurin-jet-redefining-the-blood-culture-contamination-device-market/.], 5 pages.
Author Unknown, "Kurin Lock® with Flash Technology: Better than conventional diversion," [website], Kurin, (Publication Date Unknown), [Retrieved from Internet on Sep. 26, 2025 at URL: https://www.kurin.com/kurin-jet/.], 10 pages.
Author Unknown, "Lowering the 3% Blood Culture Contamination Rate Benchmark," [website], Kurin, (Publication Date Unknown), [Retrieved from Internet on Sep. 15, 2025 at URL: https://www.kurin.com/3-percent-standard/.], 4 pages.
Author Unknown, "Newly Released CLSI National Blood Culture Guidelines Identify Best Practices and Evidence-Based Technology Solutions Such as Steripath® to Improve Patient Safety and Outcomes," [website], Magnolia Medical Technologies, Inc., (May 5, 2022), [Retrieved from Internet on Sep. 15, 2025 at URL: https://magnolia-medical.com/news/newly-released-clsi-national-blood-culture-guidelines-identify-best-practices-and-evidence-based-technology-solutions-such-as-steripath-to-improve-patient-safety-and-outcomes/.], 5 pages.
Author Unknown, "The Financial and Clinical Costs of False Positive Blood Cultures," [website], Kurin, (Publication Date Unknown), [Retrieved from Internet on Sep. 15, 2025 at URL: https://www.kurin.com/false-positives-blood-culture-cost/.], 5 pages.
Buzard, B.A. et al., "Evaluation of an Initial Specimen Diversion Device (ISDD) on Rates of Blood Culture Contamination in the Emergency Department," Kans J Med. Mar. 1, 20219; 14(1): 73-76. eCollection 2021.
CA Application No. 2875118, Office Action mailed Apr. 7, 2020; Applicant Magnolia Medical Technologies, Inc. et al; 4 pages.
CA Application No. 2875118, Office Action mailed Mar. 21, 2019; Applicant Magnolia Medical Technologies, Inc. et al; 5 pages.
CA Application No. 2931983, Office Action mailed Oct. 1, 2020; Applicant Magnolia Medical Technologies, Inc.; 3 pages.
CA Application No. 2931983, Office Action mailed Oct. 16, 2019; Applicant Magnolia Medical Technologies, Inc.; 4 pages.
CA Application No. 2932536, Office Action mailed Jul. 13, 2021; Applicant Magnolia Medical Technologies, Inc.; 4 pages.
CA Application No. 3132981, Office Action mailed Aug. 22, 2025; Applicant Magnolia Medical Technologies, Inc.; 5 pages.
CA Application No. 3164339, Office Action mailed Jan. 26, 2026; Applicant Magnolia Medical Technologies, Inc.; 4 pages.
Callado, G. Y. et al., "Diagnostic Stewardship: A Systematic Review and Meta-analysis of Blood Collection Diversion Devices Used to Reduce Blood Culture Contamination and Improve the Accuracy of Diagnosis in Clinical Settings," Open Forum Infect Dis. Aug. 11, 2023; 10(9): ofad433, 10 pages. eCollection Sep. 2023.
CN Application No. 201380040468.7, Office Action mailed Apr. 12, 2017; Applicant Magnolia Medical Technologies, Inc., with English Translation; 8 pages.
CN Application No. 201380071681.4, Office Action mailed Aug. 16, 2016; Applicant Magnolia Medical Technologies, Inc., with English Translation; 16 pages.
CN Application No. 201380071681.4, Office Action mailed Jun. 28, 2017; Applicant Magnolia Medical Technologies, Inc., with English Translation; 22 pages.
CN Application No. 201811146373.4, Office Action mailed Jul. 28, 2025; Applicant Magnolia Medical Technologies, Inc., with English Translation; 36 pages.
CN Application No. 201880088771.7, Office Action mailed May 7, 2022; Applicant Magnolia Medical Technologies, Inc., with English Translation; 5 pages.
CN Application No. 202011295348.X, Office Action mailed Nov. 29, 2023; Applicant Magnolia Medical Technologies, Inc., with English Translation; 10 pages.
CN Application No. 202080025953.7, Office Action mailed May 24, 2025; Applicant Magnolia Medical Technologies, Inc., with English Translation; 12 pages.
CN Application No. 202080094860.X, Office Action mailed Jan. 10, 2025; Applicant Magnolia Medical Technologies, Inc., with English Translation; 20 pages.
Declaration of Dr. Morten Jensen under 37 C.F.R. § 1.132, U.S. Pat. No. 10,052,053; dated Oct. 1, 2025, 79 pages.
Declaration of Dr. Morten Jensen under 37 C.F.R. § 1.132, U.S. Pat. No. 10,052,053, dated Feb. 10, 2026; 74 pages.
Declaration of Dr. Morten Jensen under 37 C.F.R. § 1.132, U.S. Pat. No. 11,529,081, dated Nov. 25, 2025, 75 pages.
Declaration of Dr. Morten Jensen under 37 C.F.R. § 1.132, U.S. Pat. No. 11,653,863, dated Feb. 16, 2026; 84 pages.
Declaration of Dr. Morten Jensen under 37 C.F.R. § 1.132, U.S. Pat. No. 11,903,709, dated Feb. 3, 2026; 80 pages.
Declaration of Dr. Morten Jensen under 37 C.F.R. 1.132, U.S. Pat. No. 9,855,002; dated Oct. 1, 2025, 61 pages.

(56) References Cited

OTHER PUBLICATIONS

Defendant's Amended Invalidity Contentions, U.S. Pat. No. 11,903,709, *Magnolia Medical Technologies, Inc.*, vs. *Kurin, Inc.*, C.A. No. 24-1124-CFC (D. Del.), dated Dec. 10, 2024; 70 pages.
ENA (Emergency Nurses Association), "Clinical Practice Guideline: Synopsis—Prevention of Blood Culture Contamination," [website], Guidelinecentral, (May 8, 2018; last updated Oct. 18, 2025), [Accessed via Internet, publicly available at URL: https://www.guidelinecentral.com/guideline/308349/#section-420.], 1 page.
EP Application No. 13859067.4, Extended European Search Report mailed Aug. 16, 2017; Applicant Magnolia Medical Technologies, Inc.; 6 pages.
EP Application No. 13859067.4, Extended European Search Report mailed Jan. 27, 2017; Applicant Magnolia Medical Technologies, Inc.; 4 pages.
EP Application No. 13859067.4, Extended European Search Report mailed Jun. 7, 2016; Applicant Magnolia Medical Technologies, Inc.; 4 pages.
EP Application No. 16200112.7, Extended European Search Report mailed Feb. 15, 2018; Applicant Magnolia Medical Technologies, Inc.; 3 pages.
EP Application No. 16200112.7, Extended European Search Report mailed Mar. 1, 2017; Applicant Magnolia Medical Technologies, Inc.; 6 pages.
EP Application No. 16843182.3, Extended European Search Report mailed Mar. 26, 2019; Applicant Magnolia Medical Technologies, Inc.; 4 pages.
EP Application No. 17206745.6, Office Action mailed Feb. 18, 2020; Applicant Magnolia Medical Technologies, Inc.; 4 pages.
EP Application No. 18813278.1, Extended European Search Report mailed Feb. 17, 2021; Applicant Magnolia Medical Technologies, Inc.; 4 pages.
EP Application No. 20167572.5, Extended European Search Report mailed Sep. 30, 2020; Applicant Magnolia Medical Technologies, Inc.; 10 pages.
EP Application No. 23173044.1, Extended European Search Report mailed Oct. 27, 2023; Applicant Magnolia Medical Technologies, Inc.; 8 pages.
EP Application No. 23182529.0, Office Action mailed Jul. 29, 2025; Applicant Magnolia Medical Technologies, Inc.; 6 pages.
EP Application No. 25164992.7, Extended European Search Report mailed Aug. 26, 2025; Applicant Magnolia Medical Technologies, Inc.; 8 pages.
GB Application No. 1506837.2, Office Action mailed Jul. 19, 2017; Applicant Magnolia Medical Technologies, Inc.; 6 pages.
IL Application No. 238991, Office Action mailed Feb. 13, 2020; Applicant Magnolia Medical Technologies, Inc., with English Translation; 10 pages.
IL Application No. 238991, Office Action mailed Nov. 12, 2018; Applicant Magnolia Medical Technologies, Inc., with English Translation; 6 pages.
IL Application No. 286263, Office Action mailed Aug. 5, 2025; Applicant Magnolia Medical Technologies, Inc. et al.; 3 pages. (English Only).
IL Application No. 303591, Office Action mailed Feb. 25, 2024; Applicant Magnolia Medical Technologies, Inc. et al.; 4 pages.
IL Application No. 309638, Office Action mailed Aug. 11, 2025; Applicant Magnolia Medical Technologies, Inc. et al.; 3 pages. (English Only).
IN Application No. 11068/DELNP/2014, Office Action mailed Sep. 28, 2020; Applicant Magnolia Medical Technologies, Inc., with English Translation; 6 pages.
Joint Claim Construction Brief for Kurin, Inc's Asserted Patent of U.S. Pat. Nos. 12,138,052, Document 153; *Magnolia Medical Technologies, Inc.* v. *Kurin, Inc.*, C.A. 1:24-cv-01124-CFC (D. Del.); filed Mar. 10, 2025; 31 pages.
Joint Motion for Entry of Partial Judgment of Non-Infringement of U.S. Pat. Nos. 9,855,002 and 10,052,053, with Proposed Partial Judgment, Document 247; *Magnolia Medical Technologies, Inc.* v. *Kurin, Inc.*, C.A. 1:24-cv-01124-CFC (D. Del.); filed Jul. 25, 2025, 7 pages.
Joint Proposed Final Jury Instructions (Phase 1), Document 357, *Magnolia Medical Technologies, Inc.* v. *Kurin, Inc.*, C.A. 24-01124-CFC (D. Del.), filed Oct. 23, 2025; 59 pages.
JP Application No. 2015-515178, Office Action mailed Feb. 16, 2017; Applicant Magnolia Medical Technologies, Inc. et al., with English Translation; 7 pages.
JP Application No. 2015-545494, Office Action mailed Jun. 19, 2017; Applicant Magnolia Medical Technologies, Inc., with English Translation; 9 pages.
JP Application No. 2017-214629, Office Action mailed Jul. 23, 2019; Applicant Magnolia Medical Technologies, Inc., with English Translation; 8 pages.
JP Application No. 2017-214629, Office Action mailed Sep. 20, 2018; Applicant Magnolia Medical Technologies, Inc., with English Translation; 9 pages.
JP Application No. 2020-075727, Office Action mailed Mar. 28, 2023; Applicant Magnolia Medical Technologies, Inc., with English Translation; 6 pages.
JP Application No. 2020-075727, Office Action mailed May 18, 2022; Applicant Magnolia Medical Technologies, Inc., with English Translation; 11 pages.
JP Application No. 2020-566232, Office Action mailed Sep. 19, 2023; Applicant Magnolia Medical Technologies, Inc., with English Translation; 6 pages.
JP Application No. 2021-552145, Office Action mailed Sep. 11, 2024; Applicant Magnolia Medical Technologies, Inc., with English Translation; 4 pages.
JP Application No. 2022-074696, Office Action mailed Oct. 25, 2023; Applicant Magnolia Medical Technologies, Inc., with English Translation; 7 pages.
JP Application No. 2022-149585, Office Action mailed Sep. 26, 2023; Applicant Magnolia Medical Technologies, Inc., with English Translation; 9 pages.
JP Application No. 2022-184274, Office Action Appeal Decision No. 2024-016403 mailed Nov. 7, 2025, Applicant Magnolia Medical Technologies, Inc., with English translation; 73 pages.
JP Application No. 2022-534220, Office Action mailed Sep. 13, 2024; Applicant Magnolia Medical Technologies, Inc., with English Translation; 8 pages.
JP Application No. 2024-014849, Office Action mailed Jan. 28, 2026; Applicant Magnolia Medical Technologies, Inc., with English Translation; 6 pages.
JP Application No. 2024-127830, Office Action mailed Nov. 4, 2025; Applicant Magnolia Medical Technologies, Inc., with English Translation; 8 pages.
JP Application No. 2024-153369, Office Action mailed Feb. 18, 2026; Applicant Magnolia Medical Technologies, Inc., with English Translation; 6 pages.
JP Application No. 2024-153369, Office Action mailed Sep. 5, 2025; Applicant Magnolia Medical Technologies, Inc., with English Translation; 10 pages.
Judgment in favor of Kurin, Inc. against Magnolia Medical Technologies, Inc., Document 541, *Magnolia Medical Technologies, Inc.* v. *Kurin, Inc.*, C.A. 19-00097-CFC-CJB (D. Del.), dated Jun. 10, 2024; 3 pages.
Memorandum Opinion Concerning Claim Construction, Document 74, *Magnolia Medical Technologies, Inc.* v. *Kurin, Inc.*, C.A. 1:19-cv-00097-CFC-CJB (D. Del.), dated May 20, 2020; 14 pages.
Mohajer, M.A., et al.; "The Impact of Initial Specimen Diversion Systems on Blood Culture Contamination," Open Forum Infect Dis.; 10(5):ofad182; pp. 1-6. doi: 10.1093/ofid/ofad182 (Apr. 5, 2023).
Order Granting Kurin's Motion for Judgment of Non-Infringement as a Matter of Law, Document 537, *Magnolia Medical Technologies, Inc.* v. *Kurin, Inc.*, C.A. 19-00097-CFC-CJB (D. Del.), dated May 14, 2024; 2 pages.
Order *Magnolia Medical Technologies, Inc.* v. *Kurin, Inc.*, C.A. No. 1:24-cv-01124-CFC (D. Del.); Document 390, dated Nov. 17, 2025; 6 pages.

(56) References Cited

OTHER PUBLICATIONS

Partial Judgment of Infringement of U.S. Appl. No. 10/039,483, Document 512 (Exhibit 1022), *Magnolia Medical Technologies, Inc.* v. *Kurin, Inc.*, C.A. 19-00097-CFC-CJB (D. Del.), dated Jul. 26, 2023, 2 pages.
PCT Application No. PCT/US2020/064600, International Search Report and Written Opinion mailed Mar. 18, 2021, Applicant Magnolia Medical Technologies, Inc.; 14 pages.
Snyder, S.R., et al.; "Effectiveness of practices to reduce blood culture contamination: A Laboratory Medicine Best Practices systematic review and meta-analysis," Clin Biochem.; Epub Jun. 16, 2012; 45(Issues 13-14):999-1011. doi: 10.1016/j.clinbiochem.2012.06.007, 13 pages (Sep. 2012).
U.S. Appl. No. 14/264,481, Final Office Action mailed Apr. 13, 2017; Inventor Bullington, Gregory J. et al.; 14 pages.
U.S. Appl. No. 14/264,481, Final Office Action mailed Jul. 14, 2016; Inventor Bullington, Gregory J. et al.; 9 pages.
U.S. Appl. No. 14/264,481, Non-Final Office Action mailed Feb. 26, 2016; Inventor Bullington, Gregory J. et al.; 10 pages.
U.S. Appl. No. 14/264,481, Non-Final Office Action mailed Jul. 1, 2015; Inventor Bullington, Gregory J. et al.; 13 pages.
U.S. Appl. No. 14/264,481, Non-Final Office Action mailed Oct. 21, 2016; Inventor Bullington, Gregory J. et al.; 10 pages.
U.S. Appl. No. 14/264,481, Non-Final Office Action mailed Sep. 7, 2017; Inventor Bullington, Gregory J. et al.; 12 pages.
U.S. Appl. No. 14/712,431, Non-Final Office Action mailed Sep. 14, 2018; Inventor Bullington, Gregory et al.; 10 pages.
U.S. Appl. No. 15/257,185, Non-Final Office Action mailed Aug. 8, 2017; Inventor Bullington, Gregory J. et al.; 5 pages.
U.S. Appl. No. 16/815,521, Non-Final Office Action mailed Oct. 25, 2023; Inventor Bullington, Gregory J. et al.; 9 pages.
U.S. Appl. No. 17/119,732, Non-Final Office Action mailed Aug. 25, 2022; Inventor Bullington, Gregory J. et al.; 30 pages.
U.S. Appl. No. 17/516,887, Final Office Action mailed Aug. 13, 2025; Inventor Bullington, Gregory J. et al.; 24 pages.
U.S. Appl. No. 17/559,081, Non-Final Office Action mailed Jan. 12, 2026; Inventor Bullington, Gregory J. et al.; 10 pages.
U.S. Appl. No. 17/591,237, Final Office Action mailed Aug. 20, 2025; Inventor Bullington, Gregory J. et al.; 24 pages.
U.S. Appl. No. 18/209,327, Non-Final Office Action mailed Dec. 16, 2025; Inventor Patton, Richard G.; 19 pages.
U.S. Appl. No. 18/242,900, Non-Final Office Action mailed Oct. 23, 2025; Inventor Bullington, Gregory J. et al.; 12 pages.
U.S. Appl. No. 18/243,540, Non-Final Office Action mailed Jun. 4, 2025; Inventor Bullington, Gregory J. et al.; 34 pages.
U.S. Appl. No. 18/407,010, Non-Final Office Action mailed Dec. 4, 2025; Inventor Bullington, Gregory J. et al.; 7 pages.
U.S. Appl. No. 18/680,331, Final Office Action mailed Nov. 24, 2025; Inventor Bullington, Gregory J. et al.; 9 pages.
U.S. Appl. No. 18/680,348, Final Office Action mailed Nov. 24, 2025; Inventor Bullington; Gregory J. et al.; 8 pages.
U.S. Appl. No. 18/680,377, Final Office Action mailed Nov. 25, 2025; Inventor Bullington, Gregory J., et al.; 14 pages.
U.S. Appl. No. 18/680,439, Final Office Action mailed Nov. 25, 2025; Inventor Bullington, Gregory J., et al.; 10 pages.
U.S. Appl. No. 19/175,765, Final Office Action mailed Nov. 26, 2025; Inventor Bullington, Gregory J. et al.; 14 pages.
U.S. Appl. No. 19/175,765, Non-Final Office Action mailed Aug. 8, 2025; Inventor Bullington, Gregory J. et al.; 11 pages.
U.S. Appl. No. 19/353,350, Non-Final Office Action mailed Feb. 9, 2026; Inventor Bullington, Gregory et al.; 23 pages.
U.S. Appl. No. 90/015,399, Order Granting Request for Ex Parte Reexamination mailed Oct. 21, 2025; Inventor Bullington, Gregory J., et al.; 43 pages.
U.S. Appl. No. 90/015,399, Request for Ex Parte Reexamination of U.S. Pat. No. 10,039,483 Under 35 U.S.C. § 302 and 37 C.F.R. § 1.510, filed Jul. 21, 2025, Inventor Bullington, Gregory J., et al.; 66 pages.
U.S. Appl. No. 90/019,177, Patent Trial and Appeal Board Decision in Ex Parte Reexamination (Exhibit 1003) mailed May 20, 2025, Inventor Bullington, Gregory J., et al.; 22 pages.
U.S. Appl. No. 90/019,756, Ex Parte Reexamination Interview Summary mailed Sep. 17, 2025, Inventor Patton, Richard G.; 7 pages.
U.S. Appl. No. 90/019,756, Ex Parte Reexamination Non-Final Action mailed Nov. 10, 2025; Inventor Patton, Richard G.; 44 pages.
U.S. Appl. No. 90/019,756, Order Granting Request for Ex Parte Reexamination mailed Jan. 22, 2025, Inventor Patton, Richard G.; 14 pages.
U.S. Appl. No. 90/019,757, Ex Parte Reexamination Final Action mailed Nov. 28, 2025; Inventor Patton, Richard G.; 46 pages.
U.S. Appl. No. 90/019,757, Ex Parte Reexamination Interview Summary mailed Sep. 17, 2025, Inventor Patton, Richard G.; 7 pages.
U.S. Appl. No. 90/019,757, Order Granting Request for Ex Parte Reexamination mailed Jan. 27, 2025, Inventor Patton, Richard G.; 15 pages.
U.S. Appl. No. 90/019,757, Request for Ex Parte Reexamination of U.S. Pat. No. 9,855,002 Under 35 U.S.C. § 302 and 37 C.F.R. § 1.510, filed Dec. 6, 2024, Inventor Patton, Richard G.; 147 pages.
U.S. Appl. No. 90/019,823, Ex Parte Reexamination Interview Summary mailed Nov. 25, 2025; Inventor Bullington, Gregory J.; 31 pages.
U.S. Appl. No. 90/019,823, Ex-Parte Reexamination mailed Aug. 25, 2025; Inventor Bullington, Gregory J. et al.; 30 pages.
U.S. Appl. No. 90/019,823, Response to Office Action in Ex Parte Reexamination filed Nov. 25, 2025; Inventor Bullington, Gregory J.; 211 pages.
U.S. Appl. No. 90/019,824, Ex Parte Reexamination Non-Final Action mailed Nov. 4, 2025; Inventor Bullington, Gregory J., et al.; 22 pages.
U.S. Appl. No. 90/019,824, Examiner Interview Summary mailed Jan. 29, 2026; Inventor Magnolia Medical Technologies, Inc et al.; 3 pages.
U.S. Appl. No. 90/019,825, Ex Parte Reexamination Non-Final Action mailed Nov. 17, 2025; Inventor Bullington, Gregory J., et al.; 25 pages.
U.S. Appl. No. 90/019,825, Examiner Interview Summary mailed Jan. 29, 2026; Inventor Bullington, Gregory J. et al.; 3 pages.
Valleywise Health Medical Center Case Study "In anticipation of CMS changes, AZ hospital identifies solution to blood culture contaminations with new Kurin Jet™," Brochure; 1 page (Publication Date Unknown).
Verdict Form Phase 1 (Redacted), Document 424, *Magnolia Medical Technologies, Inc.* v. *Kurin, Inc.*, C.A. 24-01124-CFC (D. Del.), filed Dec. 16, 2025; 15 pages.
Widmer, A.F., et al.; "Sterilization of skin and catheters before drawing blood cultures," J Clin Microbiol.; 41(10):4910; 1 page (Oct. 2003).
Wilber, E.P., et al.; "Effect of an initial specimen diversion device on blood-culture contamination rates and vancomycin usage: A quasi-experimental study," Epub Aug. 3, 2023; Infect Control Hosp Epidemiol.; 45(1):100-102 (Jan. 2024).
Zwang, O., et al.; "Analysis of strategies to improve cost effectiveness of blood cultures," J Hosp Med.; 1(5):272-276. doi: 10.1002/jhm.115 (Sep. 2006).

FLUID CONTROL DEVICES AND METHODS OF USING THE SAME

CROSS-REFERENCE TO RELATED APPLICATIONS

This application is a continuation of U.S. patent application Ser. No. 18/407,010 entitled, "Fluid Control Devices and Methods of Using the Same." filed Jan. 8, 2024, which is a continuation of U.S. patent application Ser. No. 18/299,680 entitled, "Fluid Control Devices and Methods of Using the Same," filed Apr. 12, 2023 (now U.S. Pat. No. 11,903,710), which is a continuation of U.S. patent application Ser. No. 18/130,207 entitled, "Fluid Control Devices and Methods of Using the Same," filed Apr. 3, 2023 (now U.S. Pat. No. 11,903,709), which is a continuation of U.S. patent application Ser. No. 17/883,340 entitled, "Fluid Control Devices and Methods of Using the Same," filed Aug. 8, 2022 (now U.S. Pat. No. 11,653,863), which is a continuation of U.S. patent application Ser. No. 17/390,249 entitled, "Fluid Control Devices and Methods of Using the Same," filed Jul. 30, 2021, which is a continuation of U.S. patent application Ser. No. 16/129,066 entitled, "Fluid Control Devices and Methods of Using the Same," filed Sep. 12, 2018 (now U.S. Pat. No. 11,076,787), which claims priority to and the benefit of U.S. Provisional Patent Application No. 62/678,632 entitled, "Fluid Control Devices and Methods of Using the Same," filed May 31, 2018, U.S. Provisional Patent Application No. 62/634,569 entitled, "Fluid Control Devices and Methods of Using the Same," filed Feb. 23, 2018, and U.S. Provisional Patent Application No. 62/557,530 entitled, "Fluid Control Devices and Methods of Using the Same," filed Sep. 12, 2017, the disclosure of each of which is incorporated herein by reference in its entirety.

BACKGROUND

The invention relates generally to the parenteral procurement of bodily fluid samples, and more particularly to fluid diversion, sequestration, and/or isolation devices and methods for procuring bodily fluid samples with reduced contaminants such as dermally residing microbes and/or other contaminants exterior to the bodily fluid source.

Health care practitioners routinely perform various types of microbial as well as other broad diagnostic tests on patients using parenterally obtained bodily fluids. As advanced diagnostic technologies evolve and improve, the speed, accuracy (both sensitivity and specificity), and value of information that can be provided to clinicians continues to improve. Maintaining the integrity of the bodily fluid sample during and/or after collection also ensures that analytical diagnostic results are representative of the in vivo conditions of a patient. Examples of diagnostic technologies that are reliant on high quality, non-contaminated, and/or unadulterated bodily fluid samples include but are not limited to microbial detection, molecular diagnostics, genetic sequencing (e.g., deoxyribonucleic acid (DNA), ribonucleic acid (RNA), next-generation sequencing (NGS), etc.), biomarker identification, and the like. When biological matter, which can include cells external to the intended source for sample procurement, and/or other external contaminants are inadvertently included in the bodily fluid sample that is to be analyzed, there is an opportunity for inaccurate test results to be derived. In short, when the purity of the sample intended to be derived or collected from a specific bodily fluid source is compromised during the specimen procurement process, resultant analytical test results may be inaccurate, distorted, adulterated, falsely positive, falsely negative, and/or otherwise not representative of the actual condition of the patient, which in turn, can inform faulty, inaccurate, confused, unsure, low-confidence, and/or otherwise undesired clinical decision making.

In some instances, patient samples (e.g., bodily fluids) are tested for the presence of one or more potentially undesirable microbes, such as bacteria, fungi, or yeast (e.g., *Candida*). In some instances, microbial testing may include incubating patient samples in one or more sterile and/or non-sterile vessels that may contain culture media, common additives, and/or other types of solutions that are conducive to microbial growth. In other instances, the sample in the vessel may be analyzed directly (i.e., not incubated) and may not contain culture media or additives associated with incubating the specimen. In still other instances, various technologies can be employed to assist in the detection of the presence of microbes as well as other types of biological matter, specific types of cells, biomarkers, proteins, antigens, enzymes, blood components, and/or the like during diagnostic testing. Examples include but are not limited to molecular polymerase chain reaction (PCR), magnetic resonance and other magnetic analytical platforms, automated microscopy, spatial clone isolation, flow cytometry, whole blood ("culture free") specimen analysis (e.g. NGS) and associated technologies, morphokinetic cellular analysis, and/or other common or evolving and advanced technologies utilized in the clinical laboratory environment to characterize patient specimens and/or to detect, identify, type, categorize, and/or characterize specific organisms, antibiotic susceptibilities, and/or the like.

In some instances, the detection of the presence of microbes includes allowing the microbes and/or organisms to grow for an amount of time (e.g., a variable amount of time from less than an hour to a few hours to several days-which can be longer or shorter depending on the diagnostic technology employed). The microbe and/or organism growth can then be detected by automated, continuous monitoring, and/or other methods specific to the analytical platform and technology used for detection, identification, and/or the like.

In culture testing, for example, when microbes are present in the patient sample, the microbes flourish over time in the culture medium and, in some instances, automated monitoring technologies can detect carbon dioxide produced by organism growth. The presence of microbes in the culture medium (as indicated by observation of carbon dioxide and/or via other detection methods) suggests the presence of the same microbes in the patient sample which, in turn, suggests the presence of the same microbes in the bodily fluid of the patient from whom the sample was obtained. Accordingly, when microbes are determined to be present in the culture medium (or more generally in the sample used for testing), the patient may be diagnosed and prescribed one or more antibiotics or other treatments specifically designed to treat or otherwise remove the undesired microbes from the patient.

Patient samples, however, can become contaminated during procurement and/or otherwise can be susceptible to false positive or false negative results. For example, microbes from a bodily surface (e.g., dermally residing microbes) that are dislodged during the specimen procurement process (which can include needle insertion into a patient, specimen procurement via a lumen-containing device such as a peripheral IV catheter (PIV), a central line (PICC) and/or other indwelling catheter(s), collection with a syringe or any other suitable means employed to collect a patient specimen), either directly or indirectly via tissue fragments, hair follicles, sweat glands, and other skin adnexal structures, can be subsequently transferred to a culture medium, test vial, or other suitable specimen collection or transfer vessel with the patient sample and/or included in the specimen that is to be analyzed for non-culture based testing. Another possible source of contamination is from the person drawing the patient sample (e.g., a doctor, phlebotomist, nurse, technician, etc.). Specifically, equipment, supplies, and/or devices used during a patient sample procurement process often include multiple fluidic interfaces (by way of example, but not limited to, patient to needle, needle to transfer adapter, transfer adapter to sample vessel, catheter hub to syringe, syringe to transfer adapter, needle/tubing to sample vessels, and/or any other fluidic interface or any combination thereof) that can each introduce points of potential contamination. In some instances, such contaminants may thrive in a culture medium and/or may be identified by another non-culture based diagnostic technology and eventually may yield a false positive and/or a false negative microbial test result, which may inaccurately reflect the presence or lack of such microbes within the patient (i.e., in vivo).

Such inaccurate results because of contamination and/or other sources of adulteration that compromise the purity of the sample are a concern when attempting to diagnose or treat a wide range of suspected illnesses, diseases, infections, patient conditions or other maladies of concern. For example, false negative results from microbial tests may result in a misdiagnosis and/or delayed treatment of a patient illness, which, in some cases, could result in the death of the patient. Conversely, false positive results from microbial tests may result in the patient being unnecessarily subjected to one or more anti-microbial therapies, which may cause serious side effects to the patient including, for example, death, as well as produce an unnecessary burden and expense to the health care system due to extended length of patient stay and/or other complications associated with erroneous treatments. The use of diagnostic imaging equipment attributable to these false positive results is also a concern from both a cost as well as patient safety perspective as unnecessary exposure to concentrated radiation associated with a variety of imaging procedures (e.g., CT scans) has many known adverse impacts on long-term patient health.

In some instances, devices and/or systems can be used to reduce the likelihood of contamination, adulteration, and/or the like of bodily fluid samples for testing. For example, some known devices can be configured to collect, divert, separate, and/or isolate or sequester an initial volume of bodily fluid that may be more likely to contain contaminants such as dermally residing microbes or the like. Some such devices, however, can be cumbersome, non-intuitive, perceived as difficult to use, inappropriate or unusable as intended for the target patient population, etc. In addition, some such devices can require training, user observation, intervention by more than one user, and/or can otherwise present challenges that can lead to limited efficacy based on variables including environmental, educational, clinician skill, patient condition, and/or the like. In some instances, such challenges can complicate the collection of consistently high quality samples that are non-contaminated, sterile, unadulterated, etc., which in turn, can impact the validity of test result outcomes.

On the other hand, some known passive diversion devices and/or systems (e.g., systems that do not specifically utilize or rely on direct user intervention, interaction, manipulation, and/or the like) may fail to adequately divert, sequester, and/or isolate a clinically desired and efficacious pre-sample volume of bodily fluid due to clinical realities such as, for example, the time required to fill a sequestration reservoir with a meaningful volume of fluid. In some instances, the operation of some known passive devices is dependent on a positive pressure applied by a bodily fluid source (e.g., a patient's blood pressure). The positive pressure applied by the bodily fluid source, however, may be insufficient to result in flow dynamics and/or flow rates that makes use of such devices practical in various clinical settings (including emergency rooms and other intensive settings). For example, the patient population with symptoms requiring diagnostic testing noted above commonly are in such physical condition that attaining vascular access and/or collection of bodily fluid samples can be difficult due to a hypotensive state (i.e., low blood pressure), hypovolemic state (i.e., low blood volume), and/or other physical challenges (e.g., severe dehydration, obesity, difficult and/or inaccessible vasculature, etc.). Such states or physical conditions can result in difficulty in providing sufficient blood flow and/or pressure to achieve passive filling of a sequestration chamber, channel, reservoir, container (or other diversion volume) consistently with sufficient volume to meet clinically validated, evidence-based efficacy and results in diverting, sequestering, and/or isolating contaminants which otherwise can lead to distorted, inaccurate, falsely positive, falsely negative, and/or otherwise adulterated diagnostic test results. The challenges associated with this approach (e.g., relying on a positive pressure differential applied by the bodily fluid source without utilizing a specific external energy source and/or negative pressure to facilitate collection of an appropriate and clinically efficacious initial volume of bodily fluid) can render it impractical as failure rates can be unacceptably high for the fragile patient population from whom these samples are collected.

As such, a need exists for fluid diversion devices and methods for procuring bodily fluid samples with reduced contaminants such as dermally residing microbes and/or other contaminants exterior to the bodily fluid source that result in consistent bodily fluid collection (e.g., from a general patient population and/or a challenging patient population). Some such devices and methods can include, for example, bodily fluid collection with the assistance of various sources of external energy and/or negative pressure. Furthermore, a need exists for such devices that are user-friendly, demonstrate consistent efficacy, and address the challenges associated with collecting samples from patients with challenging health circumstances and/or physical characteristics that impact the ability to collect bodily fluid samples.

SUMMARY

Devices and methods for procuring bodily fluid samples with reduced contaminants such as dermally residing microbes and/or other contaminants exterior to the bodily fluid source are described herein. In some embodiments, a system includes a housing, a flow controller, and a fluid collection device. The housing has an inlet and an outlet, and forms a sequestration portion. The inlet is configured to be placed in fluid communication with a bodily fluid source. The sequestration portion is configured to receive an initial volume of bodily fluid from the bodily fluid source. The flow controller is at least partially disposed in the sequestration portion of the housing and is configured to transition from a first state to a second state. The fluid collection device is configured to be fluidically coupled to the outlet to produce a negative pressure differential within at least a portion of the housing. The negative pressure differential is operable to draw the initial volume of bodily fluid into the sequestration portion when the flow controller is in the first state and is operable to draw the sample volume of bodily fluid through the outlet and into the fluid collection device when the flow controller is in the second state.

DETAILED DESCRIPTION

Figure 1:
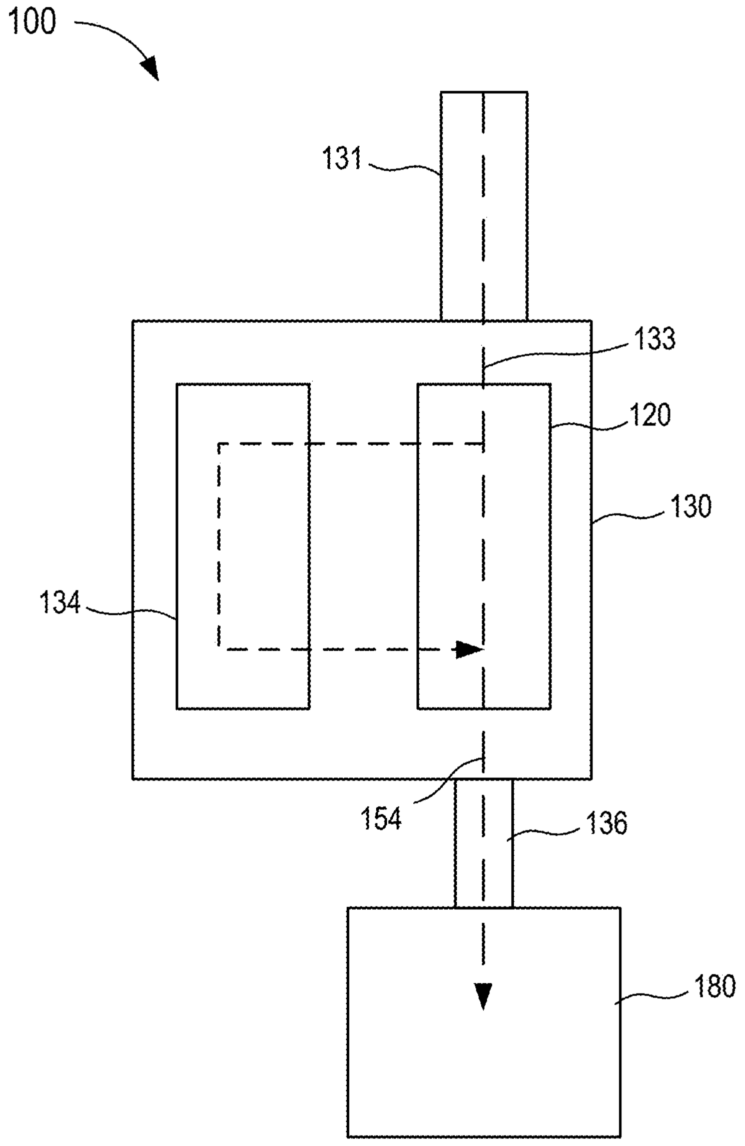
FIG. 1 is a schematic illustration of a fluid control device according to an embodiment.
Figure 2:
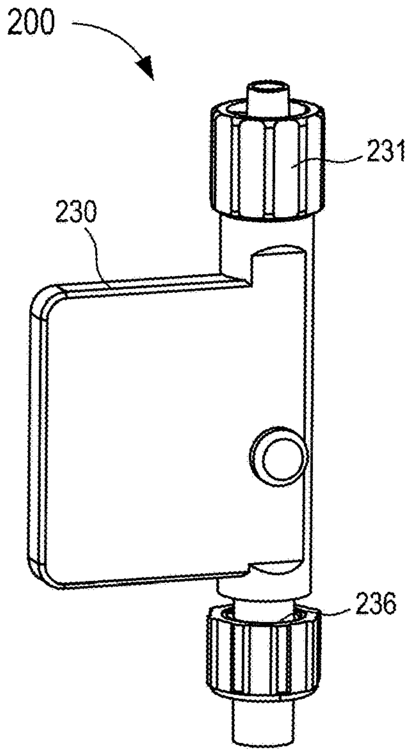
FIGS. 2-5 are various views of a fluid control device according to an embodiment.

Devices and methods for collecting, diverting, sequestering, isolating, etc. an initial volume of bodily fluid to reduce contamination in subsequently procured bodily fluid samples are described herein. Any of the fluid control devices described herein can be configured to receive, procure, and/or transfer a flow, bolus, volume, etc., of bodily fluid. A first reservoir, channel, flow path, or portion of the device can receive an initial amount of the bodily fluid flow, which then can be substantially or fully sequestered (e.g., contained or retained, circumvented, isolated, segregated, vapor-locked, separated, and/or the like) in or by the first reservoir or first portion of the device. In some instances, contaminants such as dermally residing microbes or the like can be included and/or entrained in the initial amount of the bodily fluid and likewise are sequestered in or by the first reservoir or first portion of the device. Once the initial amount is sequestered, any subsequent amount of the bodily fluid flow can be diverted, channeled, directed, flow controlled (e.g., manually, automatically, and/or semi-automatically) to a second reservoir, second portion of the device, and/or any additional flow path(s). Thus, with the initial amount sequestered, any additional and/or subsequent amount(s) of bodily fluid flow are substantially free from contaminants that may otherwise produce inaccurate, distorted, adulterated, falsely positive, falsely negative, etc., results in some diagnostics and/or testing. In some instances, the initial amount of bodily fluid also can be used, for example, in other testing such as those less affected by the presence of contaminants, can be discarded as a waste volume, can be infused back into the patient, and/or can be used for any other suitable clinical application.

In some embodiments, a feature of the fluid control devices and/or methods described herein is the use of an external negative pressure source (e.g., provided by a fluid collection device or any other suitable means) to (1) overcome physical patient challenges which can limit and/or prevent a sufficient pressure differential (e.g., a differential in blood pressure to ambient air pressure) to fully engage the sequestration chamber and/or to transition fluid flow to the fluid collection device; (2) result in proper filling of the sequestration chamber with a clinically validated and/or desirable volume of bodily fluid; (3) result in efficient, timely, and/or user-accepted consistency with bodily fluid collection process; and/or (4) provide a means of manipulating and/or automatically transitioning fluid flow (e.g., movement of physical components of the system or changing, switching, engaging, and/or otherwise employing or achieving desired fluid flow dynamics) to enable sequestration and/or isolation of the initial sample and collection of a subsequent sample.

In some embodiments, a fluid control device includes an inlet and an outlet. The inlet is configured to be placed in fluid communication with a bodily fluid source or an intermediary bodily fluid transfer device and the outlet is configured to be placed in fluid communication with a fluid collection device such as, for example, a sample reservoir, a syringe, a lumen-containing device, and/or any other suitable bodily fluid collection and/or transfer device. The fluid control device has a first state in which a negative pressure differential produced from an external source (e.g., the fluid collection device such as a sample reservoir, a syringe, a vessel, and/or any suitable intermediary fluid reservoir) is applied to the fluid control device to draw an initial volume of bodily fluid from the bodily fluid source, through the inlet, and into a sequestration and/or diversion portion of the fluid control device (which can be formed by or in the fluid control device or coupled thereto). The fluid control device has a second state in which (1) the sequestration chamber sequesters the initial volume, and (2) the negative pressure differential draws a subsequent volume of bodily fluid, being substantially free of contaminants, from the bodily fluid source, through the fluid control device, and into the fluid collection device.

In some embodiments, a system includes a housing, a flow controller, and a fluid collection device. The housing has an inlet and an outlet, and forms a sequestration portion. The inlet is configured to be placed in fluid communication with a bodily fluid source. The sequestration portion is configured to receive an initial volume of bodily fluid from the bodily fluid source. The flow controller is at least partially disposed in the sequestration portion of the housing and is configured to transition from a first state to a second state. The fluid collection device is configured to be fluidically coupled to the outlet to produce a negative pressure differential within at least a portion of the housing. The negative pressure differential is operable to draw the initial volume of bodily fluid into the sequestration portion when the flow controller is in the first state and is operable to draw the sample volume of bodily fluid through the outlet and into the fluid collection device when the flow controller is in the second state.

In some embodiments, an apparatus includes a housing and an actuator coupled to the housing. The housing has an inlet configured to be placed in fluid communication with a bodily fluid source and an outlet configured be placed in fluid communication with a fluid collection device. The housing forms a sequestration portion that is configured to receive an initial volume of bodily fluid from the bodily fluid source. The actuator has a first configuration in which a first fluid flow path places the inlet in fluid communication with the sequestration portion and a second configuration in which a second fluid flow path places the inlet in fluid communication with the outlet. The fluid collection device is configured to be placed in fluid communication with the outlet to produce a negative pressure differential (1) within the first fluid flow path that is operable to draw the initial volume of bodily fluid into the sequestration portion when the actuator is in the first configuration, and (2) within the second fluid flow path that is operable to draw a sample volume of bodily fluid into the fluid collection device when the actuator is in the second configuration.

In some embodiments, a method of using a fluid control device to obtain a bodily fluid sample with reduced contamination includes establishing fluid communication between a bodily fluid source and an inlet of the fluid control device. A fluid collection device is coupled to an outlet of the fluid control device and is configured to produce a negative pressure differential within at least a portion of the fluid control device. An initial volume of bodily fluid is received from the inlet and into a sequestration portion of the fluid control device in response to the negative pressure differential. In response to contact with a portion of the initial volume of bodily fluid, a flow controller disposed in the sequestration portion is transitioned from a first state in which the flow controller allows a flow of a gas through the flow controller and prevents a flow of bodily fluid through the flow controller, to a second state in which the flow controller prevents a flow of gas and bodily fluid through the flow controller. The initial volume of bodily fluid is sequestered in the sequestration portion after the flow controller is transitioned to the second state and a subsequent volume of bodily fluid is transferred from the inlet to an outlet in fluid communication with a fluid collection device.

As used in this specification and the claims, the singular forms “a,” “an” and “the” include plural referents unless the context clearly dictates otherwise. Thus, for example, the term “a member” is intended to mean a single member or a combination of members, “a material” is intended to mean one or more materials, or a combination thereof.

As used herein, the terms “about,” “approximate,” and/or “substantially” when used in connection with stated value and/or other geometric relationships is intended to convey that the structure so defined is nominally the value stated and/or the geometric relationship described. In some instances, the terms “about,” “approximately,” and/or “substantially” can generally mean and/or can generally contemplate plus or minus 10% of the value or relationship stated. For example, about 0.01 would include 0.009 and 0.011, about 0.5 would include 0.45 and 0.55, about 10 would include 9 to 11, and about 1000 would include 900 to 1100. While a value stated may be desirable, it should be understood that some variance may occur as a result of, for example, manufacturing tolerances or other practical considerations (such as, for example, the pressure or force applied through a portion of a device, conduit, lumen, etc.). Accordingly, the terms “about,” “approximately,” and/or “substantially” can be used herein to account for such tolerances and/or considerations.

As used herein, “bodily fluid” can include any fluid obtained directly or indirectly from a body of a patient. For example, “bodily fluid” includes, but is not limited to, blood, cerebrospinal fluid, urine, bile, lymph, saliva, synovial fluid, serous fluid, pleural fluid, amniotic fluid, mucus, sputum, vitreous, air, and the like, or any combination thereof.

As used herein, the words “proximal” and “distal” refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As described in further detail herein, any of the devices and methods can be used to procure bodily fluid samples with reduced contamination by, for example, diverting a “pre-sample” volume of bodily fluid prior to collecting a “sample” volume of bodily fluid. Each of the terms “pre-sample,” “first,” and/or “initial,” can be used interchangeably to describe and/or refer to an amount, portion, or volume of bodily fluid that is transferred, diverted, and/or sequestered prior to procuring the “sample” volume. In some embodiments, the terms “pre-sample,” “first,” and/or “initial” can refer to a predetermined, defined, desired, or given volume, portion, or amount of bodily fluid. For example, in some embodiments, a predetermined and/or desired pre-sample volume of bodily fluid can be about 0.1 milliliter (mL), about 0.2 mL, about 0.3 mL, about 0.4 mL, about 0.5 mL, about 1.0 mL, about 2.0 mL, about 3.0 mL, about 4.0 mL, about 5.0 mL, about 10.0 mL, about 20 mL, about 50 mL, and/or any volume or fraction of a volume therebetween. In other embodiments, the pre-sample volume can be greater than 50 mL or less than 0.1 mL. In some specific embodiments, a predetermined and/or desired pre-sample volume can be between about 0.1 mL and about 5.0 mL. In other embodiments, the pre-sample volume can be, for example, a drop of bodily fluid, a few drops of bodily fluid, a combined volume of any number of lumen that form, for example, a flow path (or portion thereof) from the bodily fluid source to an initial collection chamber, portion, reservoir, etc. (e.g., a sequestration chamber).

On the other hand, the terms “sample,” “second,” and/or “subsequent” when used in the context of a volume of bodily fluid can refer to a volume, portion, or amount of bodily fluid that is either a random volume or a predetermined or desired volume of bodily fluid collected after transferring, diverting, sequestering, and/or isolating the pre-sample volume of bodily fluid. For example, in some embodiments, a desired sample volume of bodily fluid can be about 10 mL to about 60 mL. In other embodiments, a desired sample volume of bodily fluid can be less than 10 mL or greater than 60 mL. In some embodiments, for example, a sample volume can be at least partially based on one or more tests, assays, analyses, and/or processes to be performed on the sample volume.

The embodiments described herein can be configured to selectively transfer bodily fluid to one or more fluid collection device(s). In some embodiments, a fluid collection device can include, but is not limited to, any suitable vessel, container, reservoir, bottle, adapter, dish, vial, syringe, device, diagnostic and/or testing machine, and/or the like. By way of specific example, in some instances, any of the embodiments and/or methods described herein can be used to transfer a sample volume into a sample reservoir such as any of those described in detail in U.S. Pat. No. 8,197,420 entitled, "Systems and Methods for Parenterally Procuring Bodily-Fluid Samples with Reduced Contamination," filed Dec. 13, 2007 ("the '420 patent"), the disclosure of which is incorporated herein by reference in its entirety.

In some embodiments, a sample reservoir can be a sample or culture bottle such as, for example, an aerobic culture bottle or an anaerobic culture bottle. In this manner, the culture bottle can receive a bodily fluid sample, which can then be tested (e.g., via in vitro diagnostic (IVD) tests, and/or any other suitable test) for the presence of, for example, Gram-Positive bacteria, Gram-Negative bacteria, yeast, fungi, and/or any other organism. In some instances, the culture bottle can receive a bodily fluid sample and the culture medium (disposed therein) can be tested for the presence of any suitable organism. If such a test of the culture medium yields a positive result, the culture medium can be subsequently tested using a PCR-based system to identify a specific organism. Moreover, as described in further detail herein, in some instances, diverting a pre-sample or initial volume of bodily fluid can reduce and/or substantially eliminate contaminants in the bodily fluid sample that may otherwise lead to inaccurate test results.

Any of the sample containers, reservoirs, bottles, dishes, vials, etc., described herein can be devoid of contents prior to receiving a sample volume of bodily fluid or can include, for example, any suitable additive, culture medium, substances, enzymes, oils, fluids, and/or the like. For example, in some embodiments, a sample reservoir can include an aerobic or anaerobic culture medium (e.g., a nutrient rich and/or environmentally controlled medium to promote growth, and/or other suitable medium(s)), which occupies at least a portion of the inner volume defined by the sample reservoir. In some embodiments, a sample reservoir can include, for example, any suitable additive or the like such as, heparin, citrate, ethylenediaminetetraacetic acid (EDTA), oxalate, SPS, and/or the like, which similarly occupies at least a portion of the inner volume defined by the sample reservoir. In other embodiments, a sample reservoir can be any suitable container used to collect a specimen.

While the term "culture medium" can be used to describe a substance configured to react with organisms in a bodily fluid (e.g., microorganisms such as bacteria) and the term "additive" can be used to describe a substance configured to react with portions of the bodily fluid (e.g., constituent cells of blood, serum, synovial fluid, etc.), it should be understood that a sample reservoir can include any suitable substance, liquid, solid, powder, lyophilized compound, gas, etc. Moreover, when referring to an "additive" within a sample reservoir, it should be understood that the additive could be a culture medium, such as an aerobic culture medium and/or an anaerobic culture medium contained in a culture bottle, an additive and/or any other suitable substance or combination of substances contained in a culture bottle and/or any other suitable reservoir such as those described above. That is to say, the embodiments described herein can be used with any suitable fluid reservoir or the like containing any suitable substance. Furthermore, any of the embodiments and/or methods described herein can be used to transfer a volume of bodily fluid to a reservoir (or the like) that does not contain a culture medium, additive, and/or any other substance prior to receiving a flow of bodily fluid.

While some of the embodiments are described herein as being used for procuring bodily fluid for one or more culture sample testing, it should be understood that the embodiments are not limited to such a use. Any of the embodiments and/or methods described herein can be used to transfer a flow of bodily fluid to any suitable device that is placed in fluid communication therewith. Thus, while specific examples are described herein, the devices, methods, and/or concepts are not intended to be limited to such specific examples.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly (butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

The embodiments described herein and/or portions thereof can include components formed of one or more parts, features, structures, etc. When referring to such components it should be understood that the components can be formed by a singular part having any number of sections, regions, portions, and/or characteristics, or can be formed by multiple parts or features. For example, when referring to a structure such as a wall or chamber, the structure can be considered as a single structure with multiple portions, or multiple, distinct substructures or the like coupled to form the structure. Thus, a monolithically constructed structure can include, for example, a set of substructures.

Such a set of substructures may include multiple portions that are either continuous or discontinuous from each other. A set of substructures can also be fabricated from multiple items or components that are produced separately and are later joined together (e.g., via a weld, an adhesive, or any suitable method).

Referring now to the drawings, FIG. 1 is a schematic illustration of a fluid control device 100 according to an embodiment. Generally, the fluid control device 100 (also referred to herein as "control device" or "device") is configured to withdraw bodily fluid from a patient. A first portion or amount (e.g., an initial amount) of the withdrawn bodily fluid is sequestered from a second portion or amount (e.g., a subsequent amount) of the withdrawn bodily fluid which can be subsequently used for additional testing, discarded, and/or reinfused into the patient. In this manner, contaminants or the like can be sequestered within the first portion or amount, leaving the second portion or amount substantially free of contaminants. The second portion or amount of bodily fluid can then be used as a biological sample in one or more tests for the purpose of medical diagnosis and/or treatment (e.g., a blood culture test or the like), as described in more detail herein. The first portion or amount of bodily fluid can be discarded as waste or can be used in any suitable test that is less likely to produce false, inaccurate, distorted, inconsistent, and unreliable results as a result of potential contaminants contained therein. In other instances, the first portion or amount of bodily fluid can be infused back into the patient.

The control device 100 includes a housing 130 that has and/or forms an inlet 131, at least one outlet 136, and a sequestration chamber 134. The inlet 131 is configured to fluidically couple to a lumen-containing device, which in turn, can place the housing 130 in fluid communication with a bodily fluid source. For example, the housing 130 can be coupled to and/or can include a lumen-containing device that is in fluid communication with the inlet 131 and that is configured to be percutaneously disposed in a patient (e.g., a butterfly needle, intravenous (IV) catheter, peripherally inserted central catheter (PICC), syringe, sterile tubing, intermediary lumen-containing device, and/or bodily-fluid transfer device or the like). Thus, bodily fluid can be transferred from the patient and/or other bodily fluid source to the housing 130 via the inlet 131, as described in further detail herein. The outlet(s) 136 can be placed in fluid communication with a fluid collection device 180 (e.g., a fluid or sample reservoir, syringe, evacuated container, etc.). As such, the control device 100 can be used and/or manipulated to selectively transfer a volume of bodily fluid from a bodily fluid source, through the inlet 131, the housing 130, and the outlet(s) 136 to the fluid collection device 180, as described in further detail herein.

The housing 130 defines one or more fluid flow paths 133 between the inlet 131 and the sequestration chamber 134 and/or one or more fluid flow paths 154 between the inlet 131 and the outlet 136. The housing 130 of the device 100 can be any suitable shape, size, and/or configuration. For example, in some embodiments, the housing 130 can have a size that is at least partially based on a volume of bodily fluid at least temporarily stored, for example, in the sequestration chamber 134. As described in further detail herein, the control device 100 and/or the housing 130 can be configured to transition between operating modes such that bodily fluid flows through at least one of the fluid flow paths 133 and/or 154. Moreover, the control device 100 and/or the housing 130 can be configured to transition automatically (e.g., based on pressure differential, time, electronically, saturation of a membrane, an absorbent and/or barrier material, etc.) or via intervention (e.g., user intervention, mechanical intervention, or the like).

The sequestration chamber 134 is at least temporarily placed in fluid communication with the inlet 131 via the fluid flow path(s) 133. As described in further detail herein, the sequestration chamber 134 is configured to (1) receive a flow and/or volume of bodily fluid from the inlet 131 and (2) sequester (e.g., separate, segregate, contain, retain, isolate, etc.) the flow and/or volume of bodily fluid therein. The sequestration chamber 134 can have any suitable arrangement such as, for example, those described herein with respect to specific embodiments. It should be understood, however, that the control device 100 and/or the housing 130 can have a sequestration chamber 134 in any suitable arrangement and is not intended to be limited to those shown and described herein. For example, in some embodiments, the sequestration chamber 134 can be at least partially formed by the housing 130. In other embodiments, the sequestration chamber 134 can be a reservoir placed and/or disposed within a portion of the housing 130. In other embodiments, the sequestration chamber 134 can be formed and/or defined by a portion of the fluid flow path 133. That is to say, the housing 130 can define one or more lumens and/or can include one or more lumen defining device(s) configured to receive a flow of bodily fluid from the inlet 131, thereby defining the fluid flow path 133. In such embodiments, at least a portion of the lumen and/or a portion of the lumen defining device(s) can form and/or can define the sequestration chamber 134.

The sequestration chamber 134 can have any suitable volume and/or fluid capacity. For example, in some embodiments, the sequestration chamber 134 can have a volume and/or fluid capacity between about 0.25 mL and about 5.0 mL. In some embodiments, the sequestration chamber 134 can have a volume measured in terms of an amount of bodily fluid (e.g., the initial or first amount of bodily fluid) configured to be transferred in the sequestration chamber 134. For example, in some embodiments, the sequestration chamber 134 can have a volume sufficient to receive an initial volume of bodily fluid as small as a microliter or less of bodily fluid (e.g., a volume as small as 20 drops of bodily fluid, 10 drops of bodily fluid, 5 drops of bodily fluid, a single drop of bodily fluid, or any suitable volume therebetween). In other embodiments, the sequestration chamber 134 can have a volume sufficient to receive an initial volume of bodily fluid up to, for example, about 5.0 mL, 10.0 mL, 15 mL, 20 mL, 30 mL, 40 mL, 50 mL, or more. In some embodiments, the sequestration chamber 134 can have a volume that is equal to a fraction of and/or a multiple of at least some of the volumes of one or more lumen(s) placing the sequestration chamber 134 in fluid communication with the bodily fluid source.

Although not shown in FIG. 1, in some embodiments, the sequestration chamber 134 can include any suitable arrangement, configuration, and/or feature, and/or can be formed of one or more materials configured to interact with a portion of the bodily fluid transferred into the sequestration chamber 134. For example, in some embodiments, the housing 130 can include an absorbent and/or hydrophilic material disposed within the sequestration chamber 134. Accordingly, when bodily fluid is transferred into the sequestration chamber 134, the absorbent and/or hydrophilic material can absorb, attract, retain, expand, and/or otherwise interact with at least a portion of the bodily fluid, which in turn, can sequester and/or retain at least an initial portion of the bodily fluid within the sequestration chamber 134, as described in further detail herein. In other embodiments, the sequestration chamber 134 can include and/or can be formed of an expandable or collapsible material configured to transition between a first state (e.g., while an initial portion of the bodily fluid is being transferred into the sequestration chamber 134) to a second state (e.g., after the initial portion of the bodily fluid is transferred into the sequestration chamber 134). In some embodiments, a force associated with and/or resulting from such a material expanding or collapsing can be operable to transition the housing 130 and/or the device 100 from a first state, position, configuration, etc. to a second state, position, configuration, etc. In some embodiments, the sequestration chamber 134 and/or any other suitable portion of the housing 130 can include one or more chemicals, compounds, and/or the like configured to chemically interact with bodily fluid transferred through a portion of the housing 130, which can be operable to transition the control device 100 and/or the housing 130 between the first state and the second state (e.g., via a force or any other suitable means).

In some embodiments, the control device 100 and/or the housing 130 can include and/or define a flow controller 120 configured to selectively control a flow of fluids (e.g., gas or liquids) through a portion of the control device 100. For example, in some embodiments, the flow controller 120 can control a flow of bodily fluid through the control device 100 (or housing 130) and/or otherwise selectively control a flow of bodily fluid through at least one of the fluid flow paths 133 and/or 154. The flow controller 120 can be, for example, a valve, a membrane, a diaphragm, a restrictor, a vent, a selectively permeable member (e.g., a fluid impermeable barrier or seal that at least selectively allows the passage of air or gas therethrough), a port, a junction, an actuator, and/or the like, or any suitable combination thereof. In some embodiments, the flow controller 120 can be configured to selectively control (at least in part) a flow of fluids into and/or out of the sequestration chamber 134 and/or any other suitable portion of the housing 130. In this context, the flow of fluids, for example, can be a liquid such as water, oil, dampening fluid, bodily fluid, and/or any other suitable liquid, and/or can be a gas such as air, oxygen, carbon dioxide, helium, nitrogen, ethylene oxide, and/or any other suitable gas. For example, in some embodiments, a wall or structure of the housing 130 can define an opening, aperture, port, orifice, and/or the like that is in fluid communication with the sequestration chamber 134. In such embodiments, the flow controller 120 can be, for example, a semi-permeable member or membrane disposed in or about the opening to selectively allow a flow of air or gas through the opening while limiting or substantially preventing a flow of fluid (e.g., bodily fluid such as blood) through the opening.

In some embodiments, one or more flow controllers 120 or the like can be configured to facilitate air (or other fluid) displacement through one or more portions of the control device 100, which in some instances, can result in a pressure differential across one or more portions of the control device 100 or can result in and/or allow for a pressure equalization across one or more portions of the housing 130. In some embodiments, the control device 100 can be configured to selectively transfer a volume of bodily fluid to the sequestration chamber 134 or to the outlet 136 based at least in part on a pressure differential between two or more portions of the control device 100. In some embodiments, the pressure differential can result from fluidically coupling the outlet 136 to the fluid collection device 180, which can define and/or can be configured to produce a negative pressure (e.g., an evacuated reservoir, a syringe, a pressure charged canister, and/or other source or potential energy to create a vacuum or pressure differential). In other embodiments, the pressure differential can result from a change in volume and/or temperature. In still other embodiments, the pressure differential can result from at least a portion of the control device 100, the housing 130, and/or other portions of the flow path being evacuated and/or charged (e.g., the sequestration chamber 134 and/or any other suitable portion). In some embodiments, the pressure differential can be established automatically or via direct or indirect intervention (e.g., by the user).

Moreover, a flow of a fluid (e.g., gas and/or liquid) resulting from a pressure differential can be selectively controlled via one or more flow controllers 120 that can, for example, transition between one or more operating conditions to control the fluid flow. In some embodiments, for example, the flow controller 120 can be an actuator or the like configured to transition between one or more operating conditions or states to establish fluid communication between one or more portions of the control device 100 and/or configured to sequester one or more portions of the control device 100 (e.g., the sequestration chamber 134). In some embodiments, the flow controller 120 can be member or device formed of an absorbent material configured to selectively allow fluid flow therethrough. For example, such an absorbent material can be transitioned from a first state in which the material allows a flow of gas (e.g., air) therethrough but prevents a flow of liquid (e.g., bodily fluid) therethrough, to a second state in which the material substantially prevents a flow of gas and liquid therethrough. In other embodiments, the flow controller 120 can include one or more valves, membranes, diaphragms, and/or the like. In some embodiments, the flow controller 120 can include any suitable combination of devices, members, and/or features. It should be understood that the flow controllers included in the embodiments described herein are presented by way of example and not limitation. Thus, while specific flow controllers are described herein, it should be understood that fluid flow can be controlled through the control device 100 by any suitable means.

The outlet(s) 136 is/are in fluid communication with and/or is/are configured to be placed in fluid communication with the fluid flow paths 133 and/or 154. As shown in FIG. 1, the outlet 136 can be any suitable outlet, opening, port, stopcock, lock, seal, coupler, valve (e.g. one-way, check valve, duckbill valve, umbrella valve, and/or the like), etc. and is configured to be fluidically coupled to the fluid collection device 180 (e.g., a fluid reservoir, culture sample bottle, syringe, container, vial, dish, receptacle, pump, adapter, and/or any other suitable collection or transfer device). In some embodiments, the outlet 136 can be monolithically formed with the fluid collection device 180. In other embodiments, the outlet 136 can be at least temporarily coupled to the fluid collection device 180 via an adhesive, a resistance fit, a mechanical fastener, a threaded coupling, a piercing or puncturing arrangement, any number of mating recesses, and/or any other suitable coupling or combination thereof. Similarly stated, the outlet 136 can be physically (e.g., mechanically) and/or fluidically coupled to the fluid collection device 180 such that an interior volume defined by the fluid collection device 180 is in fluid communication with the outlet 136. In still other embodiments, the outlet 136 can be operably coupled to the fluid collection device 180 via an intervening structure (not shown in FIG. 1), such as a flexible sterile tubing. In some embodiments, the arrangement of the outlet 136 can be such that the outlet 136 is physically and/or fluidically sealed prior to coupling to the fluid collection device 180. In some embodiments, the outlet 136 can be transitioned from a sealed configuration to an unsealed configuration in response to being coupled to the fluid collection device 180 and/or in response to a negative pressure differential between an environment within the outlet 136 and/or housing 130 and an environment within the fluid collection device 180.

The fluid collection device 180 can be any suitable device for at least temporarily containing a bodily fluid, such as, for example, any of those described in detail above. For example, in some embodiments, the fluid collection device 180 can be a single-use disposable collection tube(s), a syringe, a vacuum-based collection tube(s), an intermediary bodily-fluid transfer device, and/or the like. In some embodiments, the fluid collection device 180 can be substantially similar to or the same as known sample containers such as, for example, a Vacutainer® (manufactured by BD), a BacT/ALERT® SN or BacT/ALERT® FA (manufactured by Biomerieux, Inc.), and/or any suitable reservoir, vial, microvial, microliter vial, nanoliter vial, container, microcontainer, nanocontainer, and/or the like. In some embodiments, the fluid collection device 180 can be a sample reservoir that includes a vacuum seal that maintains negative pressure conditions (vacuum conditions) inside the sample reservoir, which in turn, can facilitate withdrawal of bodily fluid from the patient, through the control device 100, and into the sample reservoir, via a vacuum or suction force, as described in further detail herein. In embodiments in which the fluid collection device 180 is an evacuated container or the like, the user can couple the fluid collection device 180 to the outlet 136 to initiate a flow of bodily fluid from the patient such that a first or initial portion of the bodily fluid is transferred into and sequestered by the sequestration chamber 134 and such that any subsequent portion or volume of bodily fluid bypasses and/or is otherwise diverted away from the sequestration chamber 134 and flows into the fluid collection device 180, as described in further detail herein.

Although the outlet 136 of the control device 100 and/or the housing 130 is described above as being fluidically coupled to and/or otherwise placed in fluid communication with the fluid collection device 180, in other embodiments, the control device 100 can be used in conjunction with any suitable bodily fluid collection device and/or system. For example, in some embodiments, the control device 100 described herein can be used in any suitable fluid transfer device such as those described in U.S. Patent Publication No. 2015/0342510 entitled, "Sterile Bodily-Fluid Collection Device and Methods," filed Jun. 2, 2015 (referred to herein as the "'510 publication"), the disclosure of which is incorporated herein by reference in its entirety. More particularly, the control device 100 can be used in an "all-in-one" or pre-assembled device (e.g., such as those described in the '510 publication) to receive and sequester an initial volume of bodily fluid such that contaminants in subsequent volumes of bodily fluid are reduced and/or eliminated.

As described above, the device 100 can be used to procure a bodily fluid sample having reduced contamination from microbes such as, for example, dermally residing microbes, and/or the like. For example, in some instances, a user such as a doctor, physician, nurse, phlebotomist, technician, etc. can manipulate the device 100 to establish fluid communication between the inlet 131 and the bodily fluid source (e.g., a vein of a patient, cerebral spinal fluid (CSF) from the spinal cavity, urine collection, and/or the like). As a specific example, in some instances, the inlet 131 can be coupled to and/or can include a needle or the like that can be manipulated to puncture the skin of the patient and to insert at least a portion of the needle in the vein of the patient, thereby placing the inlet 131 in fluid communication with the bodily fluid source (e.g., the vein, an IV catheter, a PICC, etc.).

In some embodiments, once the inlet 131 is placed in fluid communication with the bodily fluid source (e.g., the portion of the patient), the outlet 136 can be fluidically coupled to the fluid collection device 180. As described above, in some embodiments, the fluid collection device 180 can be any suitable reservoir, container, and/or device configured to receive a volume of bodily fluid. For example, the fluid collection device 180 can be an evacuated reservoir or container that defines a negative pressure and/or can be a syringe that can be manipulated to produce a negative pressure. In some instances, coupling the outlet 136 to the fluid collection device 180 selectively exposes at least a portion of the fluid flow paths 133 and/or 154 to the negative pressure, thereby resulting in a negative pressure differential operable in drawing bodily fluid from the bodily fluid source (e.g., the patient), through the inlet 131, and into the housing 130.

In some embodiments, the arrangement of the housing 130 is such that when a volume of bodily fluid is transferred to and/or through the inlet 131, an initial portion of the volume of bodily fluid (also referred to herein as an "initial volume" or a "first volume") flows from the inlet 131, through at least a portion of the fluid flow path 133, and into the sequestration chamber 134. That is to say, in some embodiments, the control device 100 and/or the housing 130 can be in first or initial state in which the initial portion or volume of bodily fluid can flow in or through at least a portion the fluid flow path 133 and into the sequestration chamber 134. For example, in some embodiments, the initial state of the control device 100 and/or the housing 130 can be one in which one or more flow controllers 120 (e.g., valves, membranes, diaphragms, restrictors, vents, air permeable and fluid impermeable barriers, ports, actuators, and/or the like, or a combination thereof) are in a first state in which the fluid flow path 133 is exposed to the negative pressure differential via the sequestration chamber 134. In other words, the negative pressure within or created by the fluid collection device 180 can result in a negative pressure (or negative pressure differential) within at least a portion of the sequestration chamber 134 that is operable in drawing an initial flow of bodily fluid into the sequestration chamber 134 when one or more flow controllers 120 is/are in a first or initial state.

For example, in some embodiments, the flow controller 120 can be an actuator or the like that includes a valve (e.g. one-way valve, check valve, duckbill valve, umbrella valve, and/or the like), a selectively permeable member (e.g., a fluid impermeable barrier or seal that allows at least selective passage of gas or air), a selectively permeable membrane, a diaphragm, and/or the like that is at least temporarily fluidically coupled to a flow path between the fluid collection device 180 and the sequestration chamber 134 (e.g., at least a portion of the fluid flow path 154). While in some embodiments the flow controller 120 examples noted above can be, for example, known off-the-shelf components that are used in medical devices to control the flow of fluids and air, in other embodiments, the flow controller 120 can be a custom, proprietary, and/or specifically tailored component integrated into the device 100. When the flow controller 120 is in the first or initial state, the flow controller 120 can allow a flow of fluid therethrough in response to the negative pressure of the fluid collection device 180. In some embodiments, the flow controller 120 or a portion or component thereof is configured to allow only a flow of air or gas through the flow controller 120 and is configured to limit and/or substantially prevent a flow of liquid (e.g., bodily fluid) through the flow controller 120. As such, the fluid collection device 180 can produce a negative pressure differential within the sequestration chamber 134 that is operable to draw an initial portion and/or amount of bodily fluid into the sequestration chamber 134 when the flow controller 120 is in a first or initial state without allowing the initial portion of bodily fluid to flow into the fluid flow path 154 and/or otherwise out of the sequestration chamber 134.

Although not shown in FIG. 1, in some embodiments, the control device 100 and/or the housing 130 can include a member, device, mechanism, feature, etc. configured to modulate a magnitude of the negative pressure to which the sequestration chamber 134 is exposed. For example, in some embodiments, a housing can include a valve, a membrane, a porous material, a restrictor, an orifice, and/or any other suitable member, device, and/or feature configured to modulate pressure. In some embodiments, modulating and/or controlling a magnitude of the pressure to which the sequestration chamber 134 is exposed can, in turn, modulate a magnitude of pressure exerted on the bodily fluid and/or within a vein of a patient. In some instances, such pressure modulation can reduce, for example, hemolysis of a blood sample and/or a likelihood of collapsing a vein (e.g., which is particularly important in fragile patients needing microbial and/or other diagnostic testing associated with use of the control device 100). In addition, the modulation of the negative pressure can, for example, at least partially control a rate at which the control device 100 transitions between a first configuration or state and a second configuration or state. In some embodiments, modulating the negative pressure can act like a timer. For example, a time between the introduction of the negative pressure differential and the transitioning of the control device 100 from the first state to the second state can be known, predetermined, calculated, and/or controlled. As such, in some instances, modulating the negative pressure can at least partially control an amount or volume of bodily fluid transferred into the sequestration chamber 134 (i.e., can control a volume of the initial amount of bodily fluid).

The initial portion and/or amount of bodily fluid can be any suitable volume of bodily fluid, as described above. For example, in some instances, the control device 100 and/or the housing 130 can remain in the first state until a predetermined and/or desired volume (e.g., the initial volume) of bodily fluid is transferred to the sequestration chamber 134. In some embodiments, the initial volume can be associated with and/or at least partially based on a volume of the sequestration chamber 134. In other embodiments, the initial volume can be associated with and/or at least partially based on an amount or volume of bodily fluid that can be absorbed by an absorbent material, an expandable material, a hydrophilic material, a wicking material, and/or other suitable material disposed in the sequestration chamber 134. In other embodiments, the initial volume of bodily fluid can be associated with and/or at least partially based on an amount or volume of bodily fluid that can be transferred into the sequestration chamber 134 in a predetermined time. In still other embodiments, the initial volume can be associated with and/or at least partially based on an amount or volume of bodily fluid that is sufficient to fully wet or saturate a semi-permeable member or membrane otherwise configured to selectively expose the sequestration chamber 134 to the negative pressure of the fluid collection device 180 (i.e., the flow controller 120 such as an air permeable and liquid impermeable member or membrane). In other words, in some embodiments, the initial volume of bodily fluid can be a volume sufficient to transition one or more flow controllers 120 to a second state (e.g., a saturated or fully wetted state). In still other embodiments, the control device 100 and/or the housing 130 can be configured to transfer a volume of bodily fluid (e.g., the initial volume) into the sequestration chamber 134 until a pressure differential between the sequestration chamber 134 and the fluid flow path 133 and/or the bodily fluid source is brought into substantial equilibrium and/or is otherwise reduced below a desired threshold.

After the initial volume of bodily fluid is transferred and/or diverted into the sequestration chamber 134, the initial volume is sequestered, segregated, retained, contained, isolated, etc. in the sequestration chamber 134. For example, in some embodiments, the transitioning of the one or more flow controllers 120 from a first state to a second state can be operable to sequester and/or retain the initial portion of the bodily fluid in the sequestration chamber 134. As described in further detail herein, in some instances, contaminants such as, for example, dermally residing microbes or the like dislodged during the venipuncture event, other external sources of contamination, colonization of catheters and PICC lines that are used to collect samples, and/or the like can be entrained and/or included in the initial volume of the bodily fluid and thus, are sequestered in the sequestration chamber 134 when the initial volume is sequestered therein.

With the initial volume transferred and/or diverted into the sequestration chamber 134, the device 100 can transition to the second state in which a subsequent volume(s) of bodily fluid can flow through at least a portion the fluid flow paths 133 and/or 154 from the inlet 131 to the outlet 136. In some embodiments, the control device 100 and/or the housing 130 can passively and/or automatically transition (e.g., without user intervention) from the first state to the second state once the initial volume of bodily fluid is sequestered in the sequestration chamber 134. For example, in some embodiments, filling the sequestration chamber 134 to capacity and/or fully saturating, wetting, and/or impregnating an absorbent or similar material disposed between the sequestration chamber 134 and the fluid collection device 180 can be such that further transfer of bodily fluid into the sequestration chamber 134 is limited and/or substantially prevented due to a removal or diversion of the negative pressure. In other embodiments, the control device 100 and/or the housing 130 can be manually transitioned or transitioned in response to at least an indirect interaction by a user. For example, in some embodiments, a user can transition the control device 100 and/or the housing 130 from the first state to the second state by actuating an actuator or the like (e.g., actuating the flow controller 120 or a portion thereof). In still other embodiments, at least a portion of the initial volume of bodily fluid can transition the control device 100 and/or the housing 130 from the first state to the second state. For example, the control device 100 can include a flow controller 120 that is and/or that includes a bodily fluid activated switch, valve, port, and/or the like. In other embodiments, a volume of bodily fluid can move and/or displace one or more flow controller 120 (e.g., actuators or the like) that can, for example, open a port, flow path, and/or outlet. In still other embodiments, a user can manipulate such a flow controller 120 (e.g., switch, valve, port, actuator, etc.) to transition the control device 100 and/or the housing 130 from the first state to the second state.

With the fluid collection device 180 fluidically coupled to the outlet 136 and with the control device 100 and/or the housing 130 being in the second state (e.g., the initial volume of bodily fluid is sequestered in or by the sequestration chamber 134), any subsequent volume(s) of the bodily fluid can flow from the inlet 131, through at least one of the fluid flow paths 133 and/or 154, through the outlet 136, and into the fluid collection device 180. Thus, as described above, sequestering the initial volume of bodily fluid in the sequestration chamber 134 prior to collecting or procuring one or more sample volumes of bodily fluid reduces and/or substantially eliminates an amount of contaminants in the one or more sample volumes. Moreover, in some embodiments, the arrangement of the control device 100 and/or the housing 130 can be such that the control device 100 and/or the housing 130 cannot transition to the second state prior to collecting and sequestering the initial volume in the sequestration chamber 134.

FIGS. 2-5 illustrate a fluid control device 200 according to an embodiment. The fluid control device 200 can be similar in at least form and/or function to the fluid control device 100 described above with reference to FIG. 1. Accordingly, portions of the fluid control device 200 that can be similar to portions of the fluid control device 100 are not described in further detail herein.

As shown in FIGS. 2-5, the fluid control device 200 (also referred to herein as "control device" or "device") includes a housing 230 having an inlet 231, an outlet 236, and an actuator 250. As described above with reference to the control device 100, the inlet 231 is configured to be placed in fluid communication with a bodily fluid source to receive a flow of bodily fluid therefrom (e.g., via a lumen-containing device such as a needle, IV catheter, PICC line, or the like). The outlet 236 is configured to be fluidically coupled to a fluid collection device such as, for example, a sample reservoir, a syringe, and/or other intermediary bodily fluid transfer device or vessel (e.g., a transfer device similar to those described in the '510 publication), and/or the like.

As described above with reference to the housing 130, the housing 230 defines one or more fluid flow paths 233 between the inlet 231 and a sequestration chamber 234 and/or one or more fluid flow paths 254 between the inlet 231 and the outlet 236. The housing 230 of the device 200 can be any suitable shape, size, and/or configuration. For example, in some embodiments, the housing 230 can be substantially similar in at least form and/or function to the housing 130 described above with reference to FIG. 1. The sequestration chamber 234 of the housing 230 is at least temporarily placed in fluid communication with the inlet 231 via the fluid flow path(s) 233. Moreover, the sequestration chamber 234 can be selectively placed in fluid communication with the fluid flow path 254 such that at least air or gas can be transferred therebetween, as described in further detail herein.

As described in further detail herein, the sequestration chamber 234 is configured to (1) receive a flow and/or volume of bodily fluid from the inlet 231 and (2) sequester (e.g., separate, segregate, contain, retain, isolate, etc.) the flow and/or volume of bodily fluid therein. The sequestration chamber 234 can have any suitable shape, size, and/or configuration. For example, in some embodiments, the sequestration chamber 234 can have any suitable size, volume, and/or fluid capacity such as, for example, those described above with reference to the sequestration chamber 134. In the embodiment shown in FIGS. 2-5, the sequestration chamber 234 can be at least partially formed by the housing 230 that defines a lumen or flow path. In some embodiments, at least a portion of the fluid flow path 233 can extend through a portion of the housing 230 to form and/or define at least a portion of the sequestration chamber 234. As shown in FIGS. 2-5, the sequestration chamber 234 and/or a portion of the fluid flow path 233 forming the sequestration chamber 234 can have a serpentine configuration or the like. In other embodiments, the sequestration chamber 234 can have any suitable arrangement. For example, in some embodiments, a housing can include a sequestration chamber that is formed by a flexible tubing or the like that can be arranged in any suitable shape and/or configuration.

In some embodiments, the housing 230 and/or the sequestration chamber 234 can include, form, and/or define a flow controller 242. The flow controller 242 can be, for example, a valve, membrane, diaphragm, restrictor, vent, a selectively permeable member (e.g., a fluid impermeable barrier or seal that allows at least selective passage of gas or air such as, for example, a blood barrier and/or the like), port, etc. (collectively referred to herein as a "flow controller") configured to selectively control (at least in part) a flow of fluids into and/or out of the sequestration chamber 234 and/or any other suitable portion of the housing 230. More particularly, in the embodiment shown in FIGS. 2-5, the flow controller 242 is a selectively permeable fluid barrier (e.g., a blood barrier) that includes and/or is formed of a porous material configured to selectively allow a flow of gas therethrough but to prevent a flow of a liquid therethrough.

As shown, the flow controller 242 is positioned within the housing 230 to selectively establish fluid communication between the sequestration chamber 234 and the fluid flow path 254. Thus, with the flow controller 242 being configured as a semi-permeable member, the flow controller 242 can be configured to at least temporarily allow a gas or air to transfer between the fluid flow path 254 and the sequestration chamber 234 and can be configured to substantially prevent a flow of liquid between the fluid flow path 254 and the sequestration chamber 234, as described in further detail herein.

The outlet 236 of the housing 230 is in fluid communication with and/or is configured to be placed in fluid communication with the fluid flow paths 233 and/or 254. As shown in FIGS. 2-5, the outlet 236 can be any suitable outlet, opening, port, lock, seal, coupler, etc. and is configured to be fluidically coupled to a fluid collection device such as a sample reservoir, a syringe, container, and/or other sample vessel. In some embodiments, the outlet 236 can be monolithically formed with the fluid collection device or can be at least temporarily coupled to the fluid collection device, as described above with reference to the outlet 136 of the housing 130. The fluid collection device can be any suitable reservoir, container, and/or device for containing a bodily fluid, such as, for example, any of those described in detail above with reference to the fluid collection device 180. More particularly, in some embodiments, the outlet 236 can be configured to couple to an evacuated sample reservoir. As such, the user can couple the sample reservoir to the outlet 236 to initiate a flow of bodily fluid from the patient such that a first or initial portion of the bodily fluid is transferred into and sequestered by the sequestration chamber 234 and such that any subsequent portion or volume of bodily fluid bypasses and/or is otherwise diverted away from the sequestration chamber 234 and flows into the sample reservoir.

Figure 3:
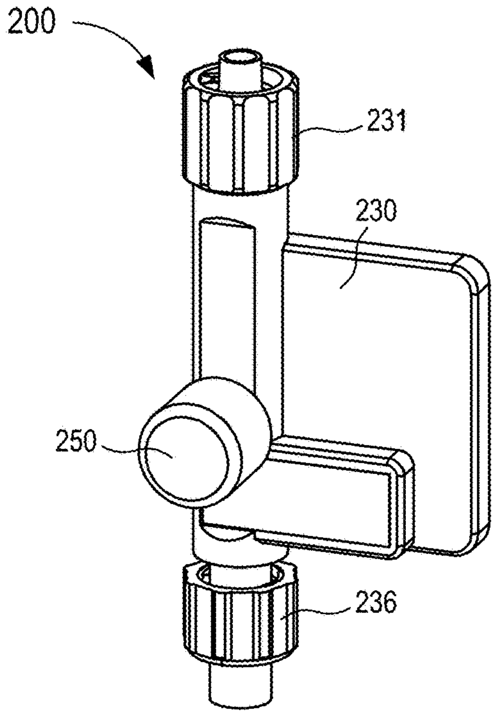
Figure 4:
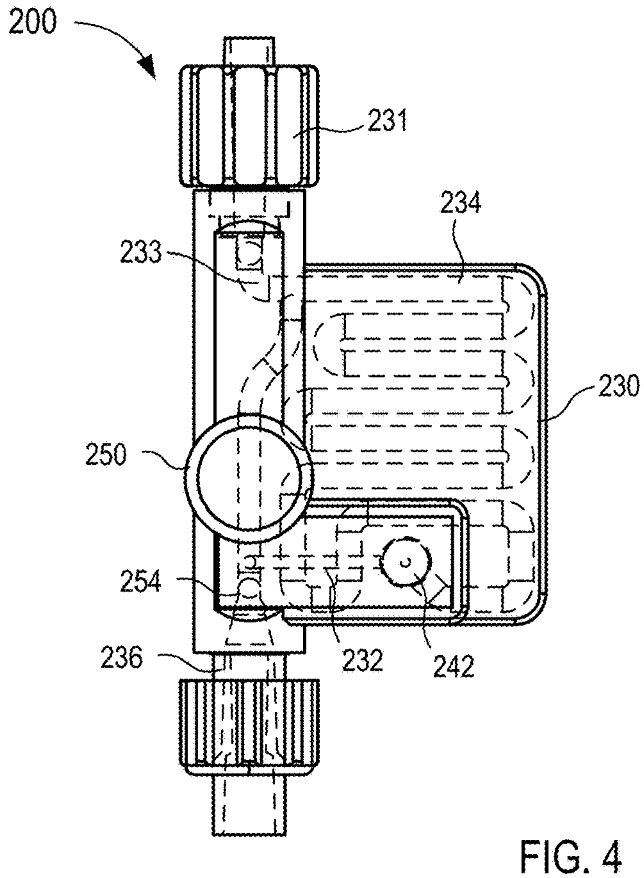
Figure 5:
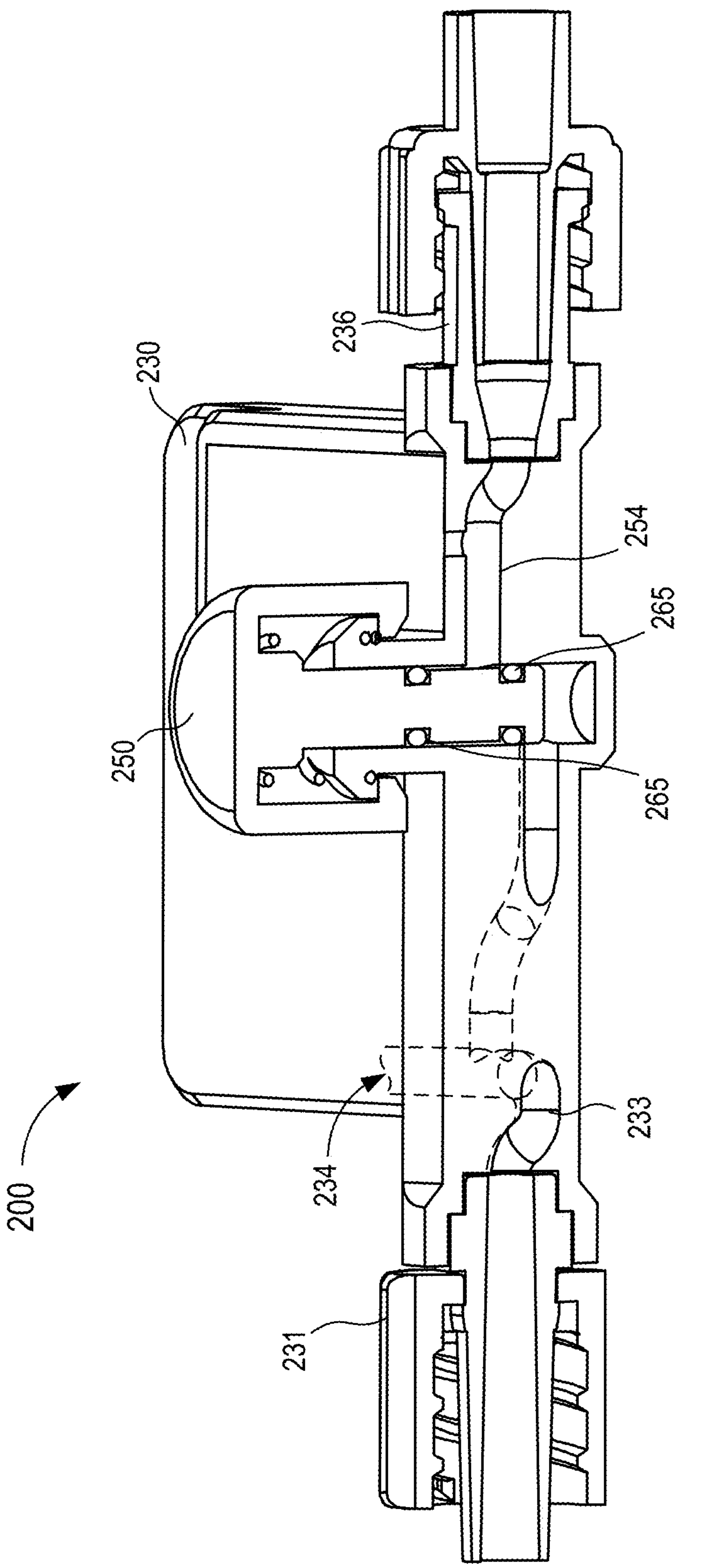

As shown in FIGS. 3-5, the housing 230 includes and/or is coupled to the actuator 250 configured to selectively control a flow of bodily fluid through the housing 230. More particularly, the actuator 250 is disposed, for example, between a portion of the fluid flow path 233 and a portion of the fluid flow path 254. While the actuator 250 is shown in FIGS. 3-5 as being positioned apart from, away from, and/or downstream of a junction between the fluid flow path 233 and the sequestration chamber 234, in other embodiments, the actuator 250 can be disposed at any suitable position within the housing 230. For example, in some embodiments, the actuator 250 can be positioned at and/or can form at least a portion of a junction between the fluid flow path 233, the sequestration chamber 234, and the fluid flow path 254.

The actuator 250 can be any suitable shape, size, and/or configuration. For example, in some embodiments, the actuator 250 can be any suitable member or device configured to transition between a first state and a second state. In the embodiment shown in FIGS. 2-5, the actuator 250 is configured to isolate, sequester, separate, and/or otherwise prevent fluid communication between the fluid flow path 233 and the fluid flow path 254 when in the first state and is configured to place the fluid flow path 233 in fluid communication with the fluid flow path 254 when in the second state. In some embodiments, for example, the actuator 250 can be a valve, plunger, seal, membrane, flap, plate, and/or the like. As shown, for example, in FIG. 5, the actuator 250 can include one or more seals 265 configured to selectively establish fluid communication between the fluid flow channels 233 and 254 when the actuator 250 is transitioned from a first state to a second state (e.g., pressed, rotated, moved, activated, switched, slid, etc.).

Although the actuator 250 is particularly shown in FIGS. 2-5 and described above, in other embodiments, the control device 200 can include any suitable actuator or device configured to selectively establish fluid communication between the fluid flow path 233 and 254. Thus, while particularly shown in FIGS. 2-5, it should be understood that the control device 200 is presented by way of example only and not limitation. For example, while the actuator 250 is shown in FIGS. 2-5 as being disposed in a given position, in other embodiments, the actuator 250 can be placed at any suitable position along the housing 230. By way of example, in some embodiments, the actuator 250 can be disposed at the junction between the fluid flow path 233, the sequestration chamber 234, and the inlet 231. In such embodiments, a flow of bodily fluid can flow directly from the inlet 231 and into the sequestration chamber 234 when the actuator 250 is in the first state and can flow directly from the inlet 231 to the fluid flow path 254 when the actuator 250 is in the second state. In other words, the actuator 250 can form a portion of the sequestration chamber 234 such that when the actuator 250 is in the first state, bodily fluid flows from the inlet directly into the sequestration chamber 234. When the actuator 250 is actuated, placed, and/or transitioned to the second state, the actuator 250 can, for example, allow bodily fluid to flow directly from the inlet 231 to the fluid flow path 233. In such embodiments, the actuator 250 can prevent the formation of a junction between the inlet 231, the sequestration chamber 234, and the fluid flow path 233. Moreover, when in the second state, the actuator 250 can be operable in at least partially sequestering the sequestration chamber 234 from the inlet 231 and/or the fluid flow path 233.

In addition, the actuator 250 can be actuated and/or transitioned in any suitable manner. For example, in some embodiments, the actuator 250 can transition between the first and the second state in response to a manual actuation by the user (e.g., exerting a manual force on a button, slider, switch, rotational member, etc.). In other embodiments, the actuator 250 can be configured to automatically transition between the first state and the second state in response to a pressure differential (or lack thereof), a change in potential or kinetic energy, a change in composition or configuration (e.g., a portion of the actuator could at least partially dissolve or transform), and/or the like. In still other embodiments, the actuator 250 can be mechanically and/or electrically actuated or transitioned based on a predetermined time, volumetric flow rate, flow velocity, etc. While examples of actuators and/or ways in which an actuator can transition are provided herein, it should be understood that they have been presented by way of example only and not limitation. Thus, a control device 200 can include any suitable actuator configured to transition in any suitable manner.

As described above, the device 200 can be used to procure a bodily fluid sample having reduced contamination from microbes such as, for example, dermally residing microbes, and/or the like. For example, in some instances, a user such as a doctor, physician, nurse, phlebotomist, technician, etc. can manipulate the device 200 to establish fluid communication between the inlet 231 and the bodily fluid source (e.g., a vein of a patient). Once the inlet 231 is placed in fluid communication with the bodily fluid source (e.g., the portion of the patient), the outlet 236 can be fluidically coupled to the fluid collection device. As described above, in the embodiment shown in FIGS. 2-5, the fluid collection device can be, for example, an evacuated reservoir or container that defines a negative pressure and/or can be any other suitable negative pressure source.

Coupling the outlet 236 to the fluid collection device selectively exposes at least a portion of the fluid flow path 254 to the negative pressure within the fluid collection device. As described above, the flow controller 242 is in fluid communication with the fluid flow path 254 and the sequestration chamber 234. Thus, coupling the outlet 236 to the fluid collection device exposes the sequestration chamber to the negative pressure of the fluid collection device, thereby resulting in a negative pressure differential operable in drawing bodily fluid from the bodily fluid source (e.g., the patient), through the inlet 231, and into the housing 230. As described above with reference to the control device 100, the arrangement of the housing 230 is such that when a volume of bodily fluid is transferred to and/or through the inlet 231, an initial portion of the volume of bodily fluid (also referred to herein as an "initial volume" or a "first volume") flows from the inlet 231, through at least a portion of the fluid flow path 233, and into the sequestration chamber 234. That is to say, in some embodiments, the control device 200 and/or the housing 230 can be in first or initial state in which the initial portion or volume of bodily fluid can flow in or through at least a portion the fluid flow path 233 and into the sequestration chamber 234.

As described above, the housing 230 and/or the control device 200 can be in the initial state when the flow controller 242 and the actuator 250 are in a first state, position, configuration, etc. As such, the actuator 250 isolates, separates, segregates, sequesters and/or otherwise prevents direct fluid communication between the fluid flow paths 233 and 254. In addition, the inlet 231 is exposed to the negative pressure differential via the sequestration chamber 234. In other words, the negative pressure within the fluid collection device can result in a negative pressure (or negative pressure differential) within at least a portion of the sequestration chamber 234 that is operable in drawing an initial flow of bodily fluid from the inlet 233 into the sequestration chamber 234 when the housing 230 and/or control device 200 is in the first or initial state.

When the flow controller 242 is in the first or initial state, the flow controller 242 can allow a flow of fluid (e.g., a gas or air) therethrough in response to the negative pressure of the fluid collection device (e.g., a sample reservoir, a syringe, or other source of potential energy used to create negative pressure), as described above with reference to the housing 130. In some instances, it may be desirable to modulate and/or control a magnitude of the negative pressure differential. In the embodiment shown in FIGS. 2-5, for example, the housing 230 defines a restricted flow path 232 that places the flow controller 242 in fluid communication with the fluid flow path 254. More specifically, the restricted flow path 232 is a fluid flow path having a smaller diameter than at least the fluid flow path 254.

For example, in some embodiments, the restricted flow path 232 can have a diameter of about 0.0005", about 0.001", about 0.003", about 0.005", about 0.01", about 0.1", about 0.5" or more. In other embodiments, the restricted flow path 232 can have a diameter less than 0.0005" or greater than 0.5". In some embodiments, the restricted flow path 232 can have a predetermined and/or desired length of about 0.01", about 0.05", about 0.1", about 0.15", about 0.2", about 0.5", or more. In other embodiments, the restricted flow path 232 can have a predetermined and/or desired length that is less than 0.01" or more than about 0.5". Moreover, in some embodiments, a restricted flow path 232 can have any suitable combination of diameter and length to allow for and/or to provide a desired flow characteristic through at least a portion of the control device 200.

In this embodiment, the restricted flow path 232 having a smaller diameter results in a lower magnitude of negative pressure being applied through the sequestration chamber than a magnitude of negative pressure when the restricted flow path has a larger diameter. In some instances, modulating a magnitude of negative pressure can control a rate at which bodily fluid is transferred into the sequestration chamber 234. For example, in some embodiments, a fluid collection device and/or other suitable negative pressure source may produce a negative pressure differential having a magnitude (e.g., a negative magnitude) of about 0.5 pounds per square inch (PSI), about 1.0 PSI, about 2.0 PSI, about 3.0 PSI, about 4.0 PSI, about 5.0 PSI, about 10 PSI, about 12.5 PSI, or about 14.7 PSI (e.g., at or substantially at atmospheric pressure at about sea level). In some embodiments, a fluid collection device such as an evacuated container or the like can have a predetermined negative pressure of about 12.0 PSI. Accordingly, by controlling the diameter and/or length of the restricted flow path 232, the amount of negative pressure to which the sequestration chamber 234 is exposed and/or the rate at which the negative pressure is applied can be controlled, reduced, and/or otherwise modulated. In some instances, the use of the restricted flow path 232 can result in a delay or ramp up of the negative pressure exerted on or in the sequestration chamber.

Moreover, in this embodiment, the restricted flow path 232 is, for example, a gas flow path configured to receive a flow of gas or air but not a flow of a liquid (e.g., bodily fluid). In some embodiments, the diameter of the restricted flow path 232 can be sufficiently small to limit and/or prevent a flow of a liquid therethrough. In addition, the arrangement of the restricted flow path 232 being disposed between the fluid flow path 254 and the flow controller 242 is such that a flow of bodily fluid and/or any other liquid is substantially prevented by the flow controller 242 (e.g., a selectively permeable barrier or seal).

Although the pressure modulation is described above as being based on a diameter of the restricted flow path 232 (i.e., a single restricted flow path), it should be understood that this is presented by way of example only and not limitation. Other means of modulating the magnitude of negative pressure to which the sequestration chamber is exposed can include, for example, a porous material, a valve, a membrane, a diaphragm, a specific restriction, a vent, a deformable member or flow path, and/or any other suitable means. In other embodiments, a control device can include any suitable number of restricted flow paths, each of which can have substantially the same diameter or can have varied diameters. For example, in some embodiments, a control device can include up to 100 restricted flow paths or more. In such embodiments, each of the restricted flow paths can have a diameter of between about 0.0005" and about 0.1", between about 0.0005" and about 0.05", or between about 0.0005" and about 0.01". In some embodiments, multiple restricted flow paths can be configured to (1) selectively provide a flow path between the outlet 236 and the sequestration chamber 234 that exposes the sequestration chamber 234 to the negative pressure differential, and (2) act as a flow controller configured to selectively allow the passage of a gas and/or air while substantially preventing the passage of a liquid (e.g., bodily fluid).

In some embodiments, modulating and/or controlling a magnitude of the pressure to which the sequestration chamber 234 is exposed can, in turn, modulate a magnitude of pressure exerted on the bodily fluid and/or within a vein of a patient. In some instances, such pressure modulation can reduce, for example, hemolysis of a blood sample and/or a likelihood of collapsing a vein. In some instances, the ability to modulate and/or control an amount or magnitude of negative pressure can allow the control device 200 to be used across a large spectrum of patients that may have physiological challenges whereby negative pressure is often needed to facilitate collection of bodily fluid such as, for example, blood (i.e. pressure differential between atmospheric pressure and a patient's vascular pressure is not sufficient to facilitate consistent and sufficiently forceful flow) but not so much pressure that a rapid force flattens, collapses, caves-in, and/or otherwise inhibits patency and ability to collect blood.

The initial portion and/or amount of bodily fluid can be any suitable volume of bodily fluid, as described in detail above with reference to the control device 100. For example, in some instances, the initial volume can be associated with and/or at least partially based on an amount or volume of bodily fluid that is sufficient to fully wet or saturate the flow controller 242. In other words, in some embodiments, the initial volume of bodily fluid can be a volume sufficient to transition the flow controller 242 to a second state (e.g., a saturated or fully wetted state). In some embodiments, the flow controller 242 is placed in a sealed configuration when transitioned to the second state. That is to say, saturating and/or fully wetting the flow controller 242 (e.g., the semi-permeable material) places the flow controller 242 in a sealed configuration in which the flow controller 242 substantially prevents a flow of a liquid and a gas therethrough. Thus, transitioning the flow controller 242 to the second state sequesters, blocks, isolates, separates, segregates, and/or otherwise prevents flow through the flow controller 242 between the restricted flow path 232 and the sequestration chamber 234.

After the initial volume of bodily fluid is transferred and/or diverted into the sequestration chamber 234, the control device 200 and/or the housing 230 can be transitioned to its second state or operating mode to sequester, segregate, retain, contain, isolate, etc. the initial volume in the sequestration chamber 234. For example, as described above, the flow controller 242 is placed in the sealed configuration. In addition, the actuator 250 can be actuated to transition from its first state to its second state to establish fluid communication between the fluid flow paths 233 and 254. As such, the negative pressure otherwise exerted on or through the sequestration chamber 234 is now exerted on or through the fluid flow paths 233 and 254. In response, bodily fluid can flow from the inlet 231, through the fluid flow paths 233 and 254, through the outlet 236, and into the fluid collection device. In some embodiments, the transitioning of the flow controller 242 and the actuator 250 from their respective first states to their respective second states is operable to sequester and/or retain the initial portion of the bodily fluid in the sequestration chamber 234. As described in further detail herein, in some instances, contaminants such as, for example, dermally residing microbes or the like dislodged during the venipuncture event, can be entrained and/or included in the initial volume of the bodily fluid and thus, are sequestered in the sequestration chamber 234 when the initial volume is sequestered therein.

With the fluid collection device fluidically coupled to the outlet 236 and with the control device 200 and/or the housing 230 being in the second state (e.g., the initial volume of bodily fluid is sequestered in or by the sequestration chamber 234), any subsequent volume(s) of the bodily fluid can flow from the inlet 231, through the fluid flow paths 233 and 254, through the outlet 236, and into the fluid collection device. Thus, as described above, sequestering the initial volume of bodily fluid in the sequestration chamber 234 prior to collecting or procuring one or more sample volumes of bodily fluid reduces and/or substantially eliminates an amount of contaminants in the one or more sample volumes. Moreover, in some embodiments, the arrangement of the control device 200 and/or the housing 230 can be such that the control device 200 and/or the housing 230 cannot transition to the second state prior to collecting and sequestering the initial volume in the sequestration chamber 234.

Figure 6:
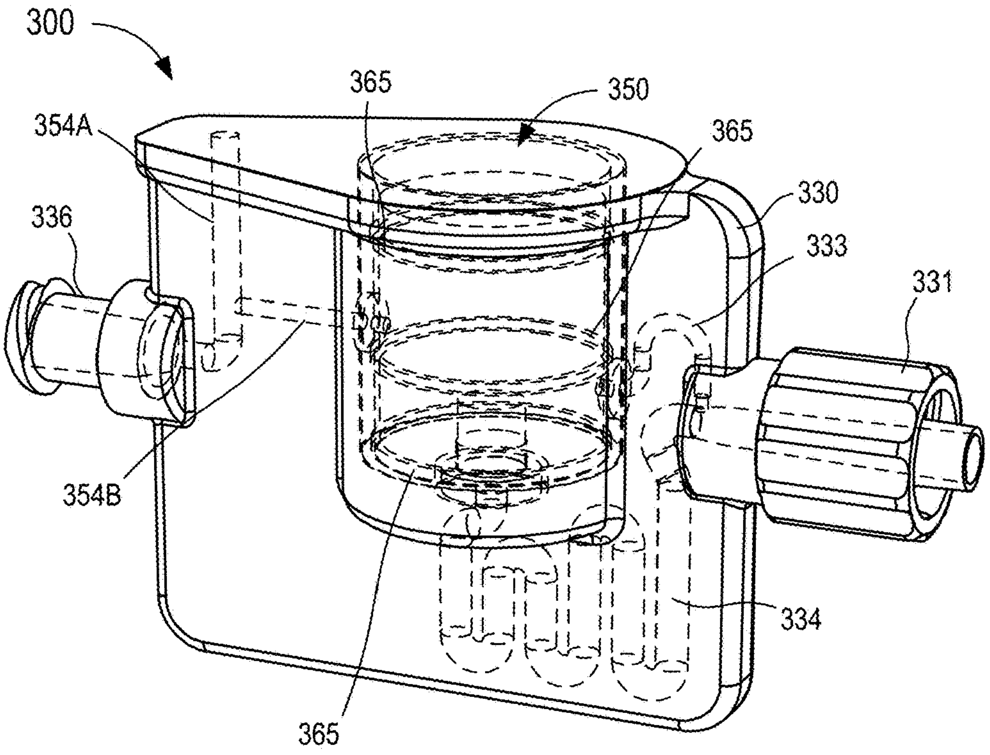
FIGS. 6-8 are various views of a fluid control device according to an embodiment.
Figure 7:
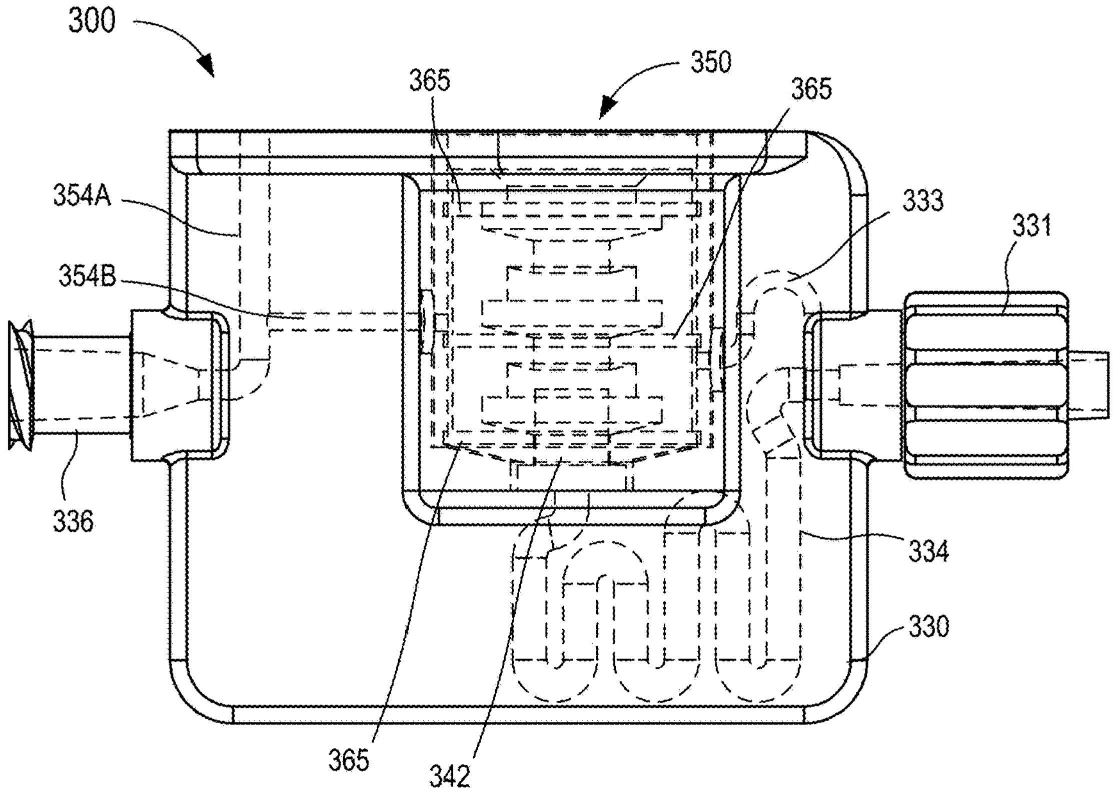
Figure 8:
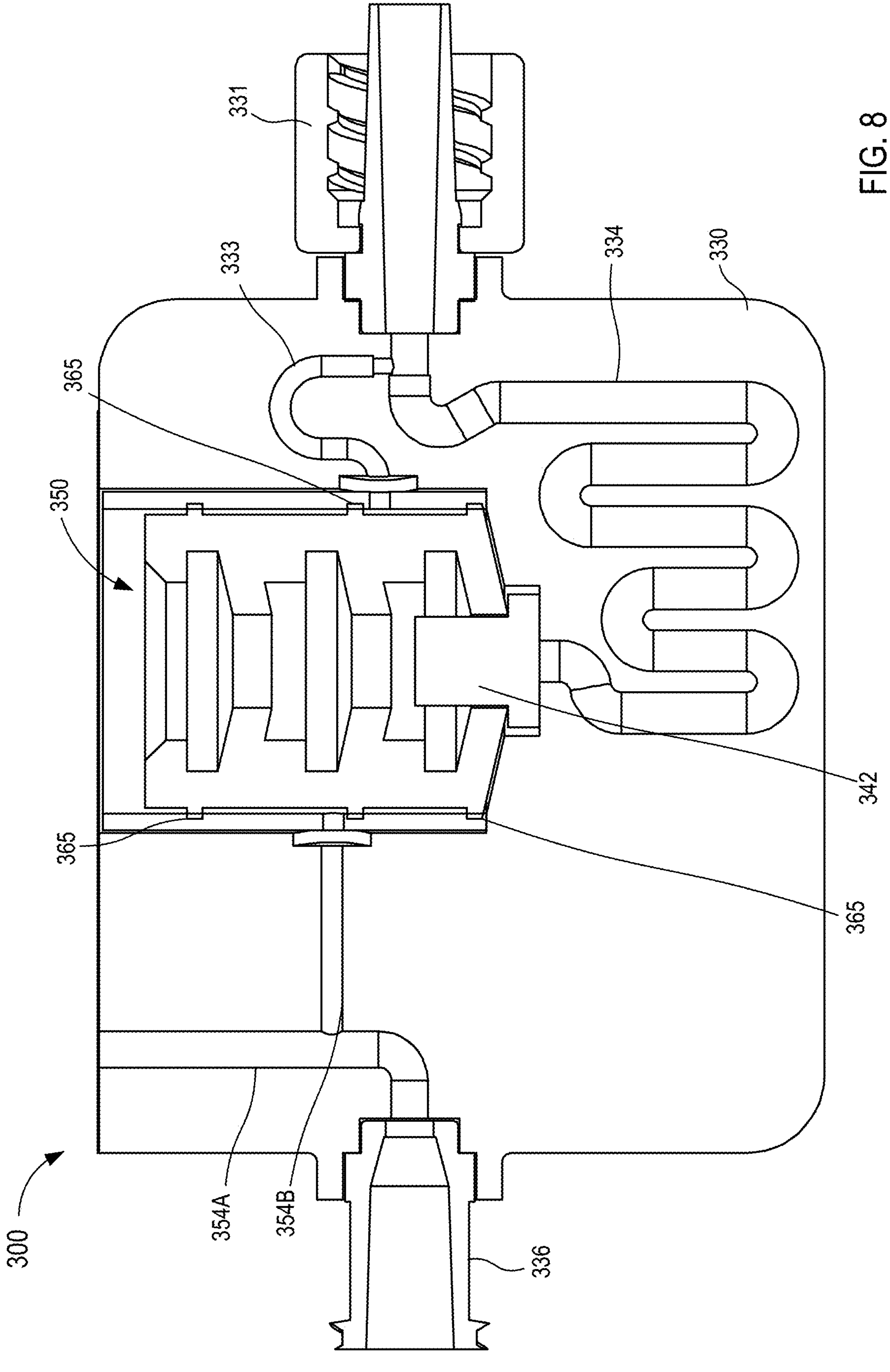

While the control device 200 is described above with reference to FIGS. 2-5 as including the actuator 250 configured to be moved (e.g., via a force applied by a user) between the first state and the second state, in other embodiments, a control device can include any suitable member, device, mechanism, etc. configured to selectively establish fluid communication between two or more fluid flow paths. For example, FIGS. 6-8 illustrate a fluid control device 300 according to an embodiment. The fluid control device 300 can be similar in at least form and/or function to the fluid control device 100 described above with reference to FIG. 1 and/or the fluid control device 200 described above with reference to FIGS. 2-5. Accordingly, portions of the fluid control device 300 that can be similar to portions of the fluid control devices 100 and/or 200 are not described in further detail herein.

As shown in FIGS. 6-8, the fluid control device 300 (also referred to herein as "control device" or "device") includes a housing 330 having an inlet 331 and an outlet 336, and including or being coupled to an actuator 350. As described above with reference to the control devices 100 and/or 200, the inlet 331 is configured to be placed in fluid communication with a bodily fluid source to receive a flow of bodily fluid therefrom (e.g., via a lumen-containing device such as a needle or the like). The outlet 336 is configured to be fluidically coupled to a fluid collection device (not shown in FIGS. 6-8).

As described above with reference to the housings 130 and/or 230, the housing 330 defines one or more fluid flow paths 333, 354A, and 354B configured to selectively place the inlet 331 in fluid communication with the sequestration chamber 334 and/or the outlet 336. The housing 330 of the device 300 can be any suitable shape, size, and/or configuration. For example, in some embodiments, the housing 330 can be substantially similar in at least form and/or function to the housings 130 and/or 230 described above. In some embodiments, the housing 330 can have a size that is at least partially based on a volume of bodily fluid at least temporarily stored, for example, in the sequestration chamber 334. The sequestration chamber 334 of the housing 330 is at least temporarily placed in fluid communication with the inlet 331 via the fluid flow path(s) 333. Moreover, the sequestration chamber 334 can be selectively placed in fluid communication with the fluid flow path 354A such that at least air or gas can be transferred therebetween, as described in further detail herein.

As described in further detail herein, the sequestration chamber 334 is configured to (1) receive a flow and/or volume of bodily fluid from the inlet 331 and (2) sequester (e.g., separate, segregate, contain, retain, isolate, etc.) the flow and/or volume of bodily fluid therein. The sequestration chamber 334 can have any suitable shape, size, and/or configuration. For example, in some embodiments, the sequestration chamber 334 can be substantially similar to the sequestration chamber 234 described above with reference to FIGS. 2-5 and thus, is not described in further detail herein. Likewise, the housing 330 and/or the sequestration chamber 334 include, form, and/or define a flow controller 342 that can be substantially similar to the flow controller 242 described above. As such, the flow controller 342 is positioned within the housing 330 to selectively establish fluid communication between the sequestration chamber 334 and the fluid flow path 354A, as described in further detail herein.

The outlet 336 of the housing 330 is in fluid communication with and/or is configured to be placed in fluid communication with the fluid flow paths 333, 354A, and/or 354B. In addition, the outlet 336 is configured to be fluidically coupled to a fluid collection device such as, for example, a sample reservoir, container, vial, negative pressure source, syringe, and/or intermediate control and/or transfer device (not shown in FIGS. 6-8). The outlet 336 and the fluid collection device can each be substantially similar to the outlet 236 and fluid collection device, respectively, described above with reference to the control device 200. Thus, the outlet 336 and fluid collection device are not described in further detail herein.

As shown in FIGS. 6-8, the housing 330 includes and/or is coupled to the actuator 350, which is configured to selectively control a flow of bodily fluid through the housing 330. In some embodiments, the actuator 350 can be substantially similar in at least function to the actuator 250 described above with reference to FIGS. 2-5. In this embodiment, however, the actuator 350 is arranged as a plunger and includes a set of seals 365 disposed along an outer surface of the plunger. Moreover, the actuator 350 has a substantially annular shape and is configured to at least temporarily receive and/or otherwise be disposed about a portion of the flow controller 342, as shown in FIG. 8. As described above with reference to the actuator 250, the actuator 350 is configured to isolate, sequester, separate, and/or otherwise prevent fluid communication between the fluid flow path 333 and the fluid flow path 354B when in the first state and is configured to place the fluid flow path 333 in fluid communication with the fluid flow path 354B when in the second state.

As described above, the device 300 can be used to procure a bodily fluid sample having reduced contamination from microbes such as, for example, dermally residing microbes, and/or the like. For example, in some instances, a user such as a doctor, physician, nurse, phlebotomist, technician, etc. can manipulate the device 300 to establish fluid communication between the inlet 331 and the bodily fluid source (e.g., a vein of a patient). Once the inlet 331 is placed in fluid communication with the bodily fluid source (e.g., the portion of the patient), the outlet 336 can be fluidically coupled to the fluid collection device. As described above, in the embodiment shown in FIGS. 6-8, the fluid collection device can be, for example, an evacuated reservoir, a syringe, and/or any container that defines a negative pressure.

Coupling the outlet 336 to the fluid collection device selectively exposes at least a portion of the fluid flow paths 354A and 354B to the negative pressure within and/or produced by the fluid collection device. The arrangement of the actuator 350 when in its first state, configuration, and/or position is such that the actuator 350 isolates the fluid flow path 354B from the fluid flow path 333 and as such, the fluid flow path 333 is not exposed to the negative pressure differential produced by the fluid collection device. As described above, the flow controller 342 is in fluid communication with the fluid flow path 354A and the sequestration chamber 334. More particularly, the annular arrangement of the actuator 350 allows the flow controller 342 to be in fluid communication with the fluid flow path 354A (see e.g., FIG. 8). Thus, coupling the outlet 336 to the fluid collection device exposes the sequestration chamber 334 to the negative pressure of the fluid collection device, thereby resulting in a negative pressure differential operable in drawing bodily fluid from the bodily fluid source (e.g., the patient), through the inlet 331, and into the housing 330. As described above with reference to the control devices 100 and 200, the arrangement of the housing 330 is such that when a volume of bodily fluid is transferred to and/or through the inlet 331, an initial portion of the volume of bodily fluid (also referred to herein as an "initial volume" or a "first volume") flows from the inlet 331 and into the sequestration chamber 334. That is to say, in some embodiments, the housing 330 can be in first or initial state in which the initial portion or volume of bodily fluid can flow from the inlet 331 and into the sequestration chamber 334.

As described above, the housing 330 and/or the control device 300 can be in the initial state when the flow controller 342 and the actuator 350 are in a first state, position, configuration, etc. As such, the actuator 350 isolates, separates, segregates, sequesters and/or otherwise prevents direct fluid communication between the fluid flow paths 333 and 354B. In addition, the inlet 331 is exposed to the negative pressure differential via the sequestration chamber 334. In other words, the negative pressure within or produced by the fluid collection device can result in a negative pressure (or negative pressure differential) within at least a portion of the sequestration chamber 334 that is operable in drawing an initial flow of bodily fluid from the inlet 331 into the sequestration chamber 334 when the housing 330 and/or control device 300 is in the first or initial state. As described in detail above, in some instances, it may be desirable to modulate and/or control a magnitude of the negative pressure differential by any suitable means such as those described herein.

The initial portion and/or amount of bodily fluid can be any suitable volume of bodily fluid, as described in detail above with reference to the control devices 100 and/or 200. For example, in some instances, the initial volume can be associated with and/or at least partially based on an amount or volume of bodily fluid that is sufficient to fully wet or saturate the flow controller 342. In other words, in some embodiments, the initial volume of bodily fluid can be a volume sufficient to transition the flow controller 342 to a second state (e.g., a saturated or fully wetted state). As described above with reference to the flow controller 242, the flow controller 342 is placed in a sealed configuration when transitioned to the second state. Thus, transitioning the flow controller 342 to the second state sequesters, blocks, isolates, separates, segregates, and/or otherwise prevents flow through the flow controller 342.

After the initial volume of bodily fluid is transferred and/or diverted into the sequestration chamber 334, the control device 300 and/or the housing 330 can be transitioned to its second state or operating mode to sequester, segregate, retain, contain, isolate, etc. the initial volume in the sequestration chamber 334. As described above, the flow controller 342 is placed in the sealed configuration and thus, substantially prevents a flow of fluid therethrough. In this embodiment, the arrangement of the actuator 350 is such that when the flow controller 342 is placed in the sealed configuration, at least a portion of the negative pressure otherwise being exerted through the flow controller 342 is instead exerted on the actuator 350, which in turn, is sufficient to transition the actuator 350 from its first state to its second state. For example, in some embodiments, the negative pressure is operable to move the actuator 350 from a first position (e.g., the first state) to a second position (e.g., the second state), thereby establishing fluid communication between the fluid flow paths 333 and 354B.

More particularly, moving the actuator 350 to its second position (or otherwise transitioning the actuator 350 to its second state), moves and/or transitions the seals 365 relative to the fluid flow paths 333 and 354B such that fluid communication is established therebetween. As such, the negative pressure otherwise exerted on or through the sequestration chamber 334 is now exerted on or through the fluid flow paths 333 and 354B. In response, bodily fluid can flow from the inlet 331, through the fluid flow paths 333 and 354B, through the outlet 336, and into the fluid collection device. In some embodiments, the transitioning of the flow controller 342 and the actuator 350 from their respective first states to their respective second states is operable to sequester and/or retain the initial portion of the bodily fluid in the sequestration chamber 334. As described in further detail herein, in some instances, contaminants such as, for example, dermally residing microbes or the like dislodged during the venipuncture event, can be entrained and/or included in the initial volume of the bodily fluid and thus, are sequestered in the sequestration chamber 334 when the initial volume is sequestered therein.

With the fluid collection device fluidically coupled to the outlet 336 and with the control device 300 and/or the housing 330 being in the second state (e.g., the initial volume of bodily fluid is sequestered in or by the sequestration chamber 334), any subsequent volume(s) of the bodily fluid can flow from the inlet 331, through the fluid flow paths 333 and 354B, through the outlet 336, and into the fluid collection device. Thus, as described above, sequestering the initial volume of bodily fluid in the sequestration chamber 334 prior to collecting or procuring one or more sample volumes of bodily fluid reduces and/or substantially eliminates an amount of contaminants in the one or more sample volumes. Moreover, in some embodiments, the arrangement of the housing 330 can be such that housing 330 cannot transition to the second state prior to collecting and sequestering the initial volume in the sequestration chamber 334.

Figure 9:
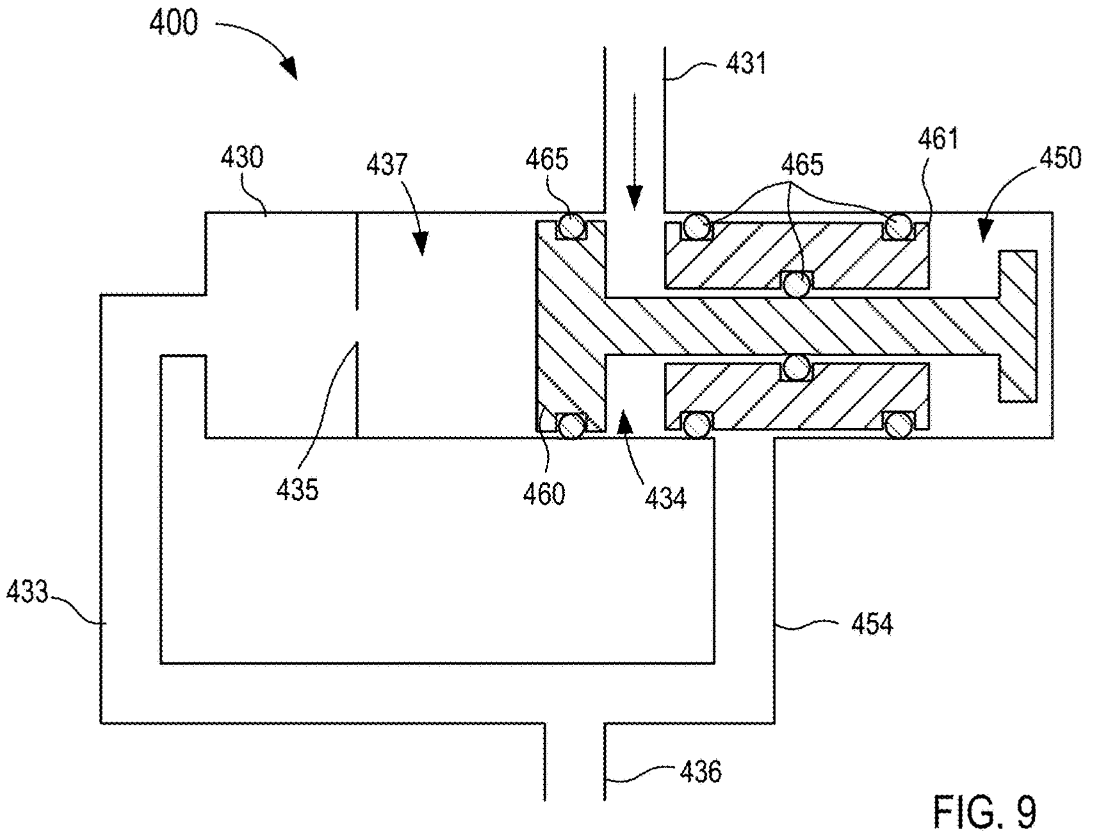
FIGS. 9 and 10 are front view illustrations of a fluid control device in a first operating mode and a second operating mode, respectively, according to an embodiment.
Figure 10:
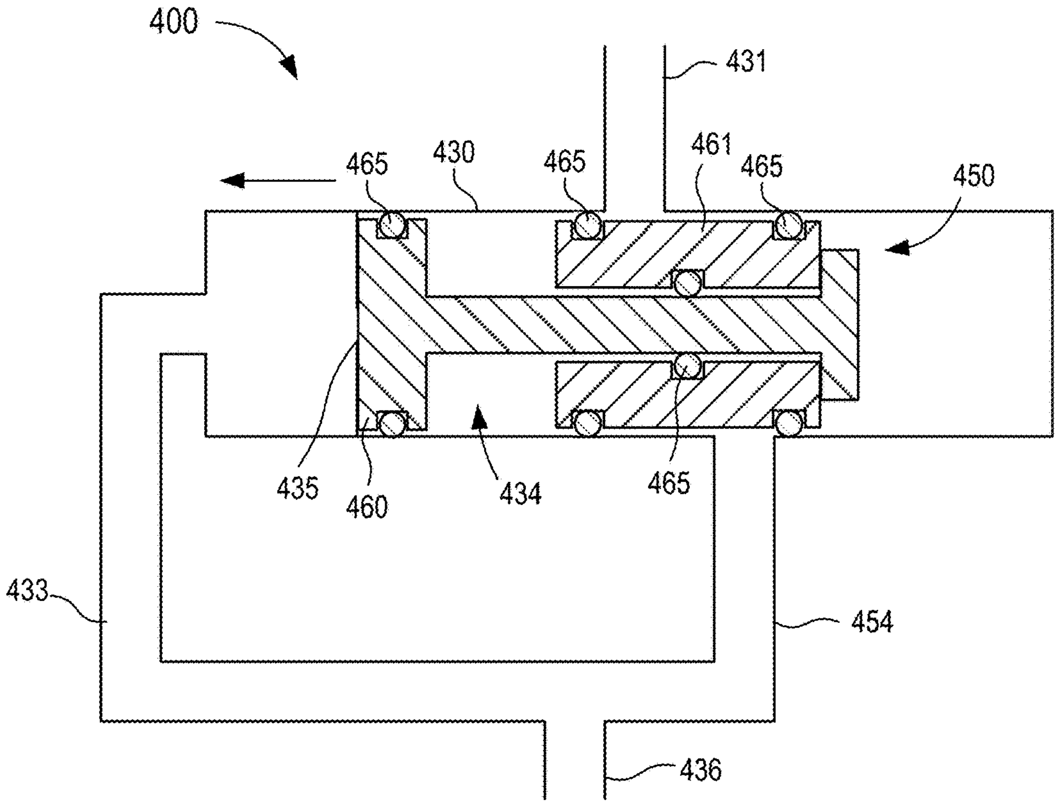

FIGS. 9 and 10 illustrate a fluid control device 400 according to an embodiment. The fluid control device 400 can be similar in at least form and/or function to the fluid control device 100 described above with reference to FIG. 1, the fluid control device 200 described above with reference to FIGS. 2-5, and/or the fluid control device 300 described above with reference to FIGS. 6-8. Accordingly, portions of the fluid control device 400 that can be similar to portions of the fluid control devices 100, 200, and/or 300 are not described in further detail herein.

As shown in FIGS. 9 and 10, the fluid control device 400 (also referred to herein as "control device" or "device") includes a housing 430 having an inlet 431 and an outlet 436, and having and/or being coupled to an actuator 450. As described above with reference to the control devices 100, 200, and/or 300, the inlet 431 is configured to be placed in fluid communication with a bodily fluid source to receive a flow of bodily fluid therefrom (e.g., via a lumen-containing device such as a needle or the like). The outlet 436 is configured to be fluidically coupled to a fluid collection device (not shown in FIGS. 9 and 10).

As described above, the housing 430 of the control device 400 is configured to (1) receive a flow and/or volume of bodily fluid via the inlet 431 and (2) sequester (e.g., separate, segregate, contain, retain, isolate, etc.) the flow and/or volume of bodily fluid within the sequestration chamber 434. The housing 430 can be any suitable shape, size, and/or configuration. In some embodiments, the housing 430 can have a size that is at least partially based on a volume of bodily fluid at least temporarily stored, for example, in the sequestration chamber 434. For example, in the embodiment shown in FIGS. 9 and 10, the housing 430 is arranged (at least in part) as a syringe-like device or the like, as described in further detail herein.

The housing 430 defines fluid flow paths 433 and 454 that are selectively in fluid communication with the outlet 436 and that selectively receive a flow of fluid therethrough (e.g., a liquid and/or a gas). The outlet 436 of the housing 430 is in fluid communication with and/or is configured to be placed in fluid communication with the fluid flow paths 433 and/or 454. In addition, the outlet 436 is configured to be fluidically coupled to a fluid collection device (not shown in FIGS. 9 and 10). The outlet 436 and the fluid collection device can each be substantially similar to the outlet 236 and fluid collection device, respectively, described above with reference to the control device 200. Thus, the outlet 436 and fluid collection device are not described in further detail herein.

The housing 430 includes and/or is coupled to the actuator 450 configured to selectively control a flow of bodily fluid through the housing 430. In this embodiment, the actuator 450 includes a first plunger 460 and a second plunger 461 movably disposed within the housing 430 and configured to at least partially define the sequestration chamber 434. More specifically, the actuator 450 is configured to move between a first state in which the inlet 431 is placed in fluid communication with the sequestration chamber 434 (FIG. 9) and a second state in which the inlet 431 is placed in fluid communication with the outlet 436 via the fluid flow path 454 (FIG. 10). In this embodiment, when the actuator 450 and/or housing 430 is in the first state, the inlet 431 is in fluid communication with a portion of the housing 430 defined between the first plunger 460 and the second plunger 461.

When in the first state, the first plunger 460 is disposed in a position such that a dampening chamber 437 is defined by the housing 430 on a side of the first plunger 460 opposite the sequestration chamber 434. As shown, the dampening chamber 437 is configured to be placed in fluid communication with the fluid flow path 433 via a port 435. The port 435 can be an opening, a valve, a membrane, a diaphragm, and/or any other suitable flow controller or the like configured to at least selectively establish fluid communication between the fluid flow path 433 and the dampening chamber 437. Furthermore, when the actuator 450 and/or the housing 430 is in the first state, the dampening chamber 437 includes and/or contains a dampening fluid 456 such as a gas (compressed or uncompressed) and/or a liquid (e.g., water, oil, dampening fluid, and/or any other suitable liquid).

When the actuator 450 and/or housing 430 are in the first state, the second plunger 461 is disposed in a position within the housing 430 such that one or more seals 465 formed by or coupled to the second plunger 461 fluidically isolate, separate, and/or sequester the inlet 431 from the fluid flow path 454. In addition, the second plunger 461 and/or the seals 465 formed by or coupled thereto fluidically isolate the fluid flow path 454 from the sequestration chamber 434. Thus, when the actuator 450 and/or control device 400 are in the first state, the inlet 431 is in fluid communication with the sequestration chamber 434 and is fluidically isolated from the fluid flow paths 433 and 454 as well as the outlet 436 (see FIG. 9). As described in further detail herein, the actuator 450 and/or the control device 400 can be configured to transition to the second state in which the sequestration chamber 434 is sequestered within the housing 430 and the inlet 431 is placed in fluid communication with the fluid flow path 454 (see FIG. 10).

As described above, the device 400 can be used to procure a bodily fluid sample having reduced contamination from microbes such as, for example, dermally residing microbes, and/or the like. For example, in some instances, a user such as a doctor, physician, nurse, phlebotomist, technician, etc. can manipulate the device 400 to establish fluid communication between the inlet 431 and the bodily fluid source (e.g., a vein of a patient). Once the inlet 431 is placed in fluid communication with the bodily fluid source (e.g., the portion of the patient), the outlet 436 can be fluidically coupled to the fluid collection device. As described above, in the embodiment shown in FIGS. 9 and 10 the fluid collection device can be, for example, an evacuated reservoir or container that defines a negative pressure.

As shown in FIG. 9, the actuator 450 and/or the control device 400 can be in a first or initial state prior to coupling the outlet 436 to the fluid collection device. Thus, the fluid flow path 433 is in fluid communication with the dampening chamber 437 and the fluid flow path 454 is fluidically isolated from the inlet 431 and the sequestration chamber 434 (e.g., via the second plunger 461). As described above, coupling the outlet 436 to the fluid collection device exposes at least a portion of the fluid flow paths 433 and 454 to the negative pressure within the fluid collection device. When the actuator 450 and/or the control device 400 are in the first state, the second plunger 461 isolates the housing 430 and/or the sequestration chamber 434 from the negative pressure exerted via the fluid flow path 454. Conversely, the negative pressure exerted through the fluid flow path 433 can be operable in exerting at least a portion of the negative pressure on the dampening chamber 437 (e.g., via the port 435). In some embodiments, for example, the port 435 can be transitioned from a closed configuration to an open configuration in response to the negative pressure.

The negative pressure exerted through the fluid flow path 433 is operable in transitioning the actuator 450 from a first state to a second state. For example, in some embodiments, the negative pressure differential draws the dampening fluid 456 from the dampening chamber 437 and into the fluid flow path 433 or a secondary chamber or the like. Moreover, the negative pressure urges the first plunger 460 to transition and/or move relative to the housing 430 from a first configuration or position to a second configuration or position. In some embodiments, the transitioning and/or moving of the first plunger 460 can be such that a volume of the housing 430 defined between the first plunger 460 and the second plunger 461 is increased (i.e., a volume of the sequestration chamber 434 is increased). In some embodiments, the increase in the volume of the sequestration chamber 434 results in a negative pressure therein, which in turn, can be operable in drawing an initial volume of bodily fluid through the inlet 431 and into the sequestration chamber 434. In other words, the negative pressure of the fluid collection device indirectly results in a negative pressure differential between the inlet 431 and the sequestration chamber 434 that is operable in drawing the initial volume of bodily fluid into the sequestration chamber 434.

As shown in FIG. 10, movement of the first plunger 460 results in a similar movement of the second plunger 461. For example, in some embodiments, the arrangement of the actuator 450 is such that after the first plunger 460 has moved a predetermined amount (and/or after the volume of the sequestration chamber 434 has been increased a predetermined amount) and an initial volume of bodily fluid has been drawn into the sequestration chamber 434, the second plunger 461 is moved or transitioned from a first position and/or configuration to a second position and/or configuration. As such, the actuator 450 is placed in its second state in which the sequestration chamber 434 is sequestered from the inlet 431. In addition, the second plunger 461 and/or the seals 465 coupled thereto place the inlet 431 in fluid communication with the fluid flow path 454. Thus, the negative pressure otherwise exerted on or through the fluid flow path 433 is now exerted on or through the fluid flow path 454. In response, bodily fluid can flow from the inlet 431, through the fluid flow path 454, through the outlet 436, and into the fluid collection device.

In some embodiments, the transitioning of the actuator 450 from the first state to the second state is operable to sequester and/or retain the initial portion of the bodily fluid in the sequestration chamber 434. As described in further detail herein, in some instances, contaminants such as, for example, dermally residing microbes or the like dislodged during the venipuncture event, can be entrained and/or included in the initial volume of the bodily fluid and thus, are sequestered in the sequestration chamber 434 when the initial volume is sequestered therein. Thus, as described above, sequestering the initial volume of bodily fluid in the sequestration chamber 434 prior to collecting or procuring one or more sample volumes of bodily fluid reduces and/or substantially eliminates an amount of contaminants in the one or more sample volumes. Moreover, in some embodiments, the arrangement of the housing 430 can be such that housing 430 cannot transition to the second state prior to collecting and sequestering the initial volume in the sequestration chamber 434.

As described above with reference to the control devices 100, 200, and/or 300, the control device 400 is configured to modulate an amount of negative pressure exerted on the first plunger 460 when the actuator 450 is in the first state. Specifically, in this embodiment, the dampening fluid 456 disposed in the dampening chamber 437 reduces a magnitude of the negative pressure exerted on the first plunger 460. As such, the rate at which the actuator 450 and/or control device 400 is transitioned from the first state to the second state can be controlled. Moreover, in some instances, exposing the housing 430 to the full magnitude of the negative pressure may result transitioning the actuator 450 and/or the control device 400 from the first state to the second state prior to receiving the initial volume of bodily fluid in the sequestration chamber 434. Thus, modulating the magnitude of the pressure can ensure a desired volume of bodily fluid is transferred into the sequestration chamber 434. Although shown in FIGS. 9 and 10 as modulating the negative pressure via the dampening fluid 456, it should be understood that this is presented by way of example only and not limitation. Any other suitable means of dampening and/or modulating a magnitude of the negative pressure can be used to control the transitioning of the actuator 450 and/or housing 430.

Figure 12:
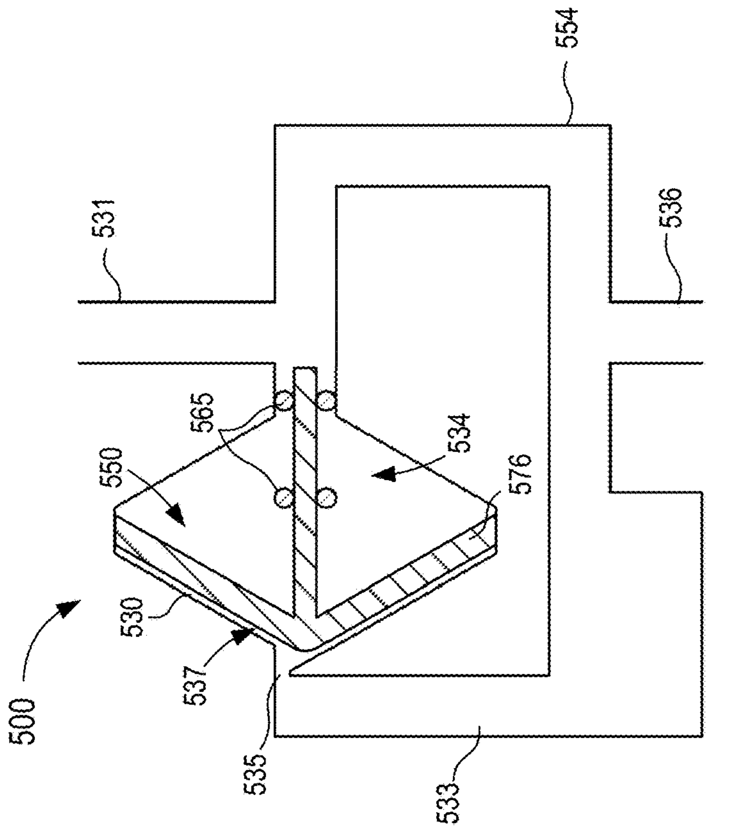
FIGS. 11 and 12 are front view illustrations of a fluid control device in a first operating mode and a second operating mode, respectively, according to an embodiment.
Figure 11:
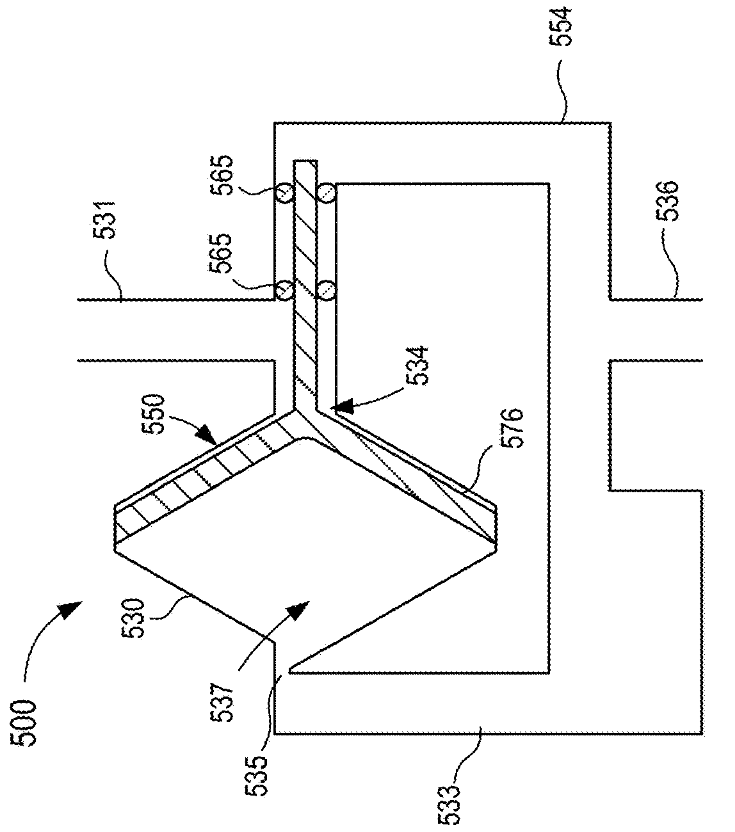

Although the housing 430 is shown in FIGS. 9 and 10 and described above as including the plungers 460 and 461 and being in a syringe-like configuration, in other embodiments, a housing can include any other suitable means for controlling fluid flow therethrough. For example, FIGS. 11 and 12 illustrate a fluid control device 500 according to an embodiment. The fluid control device 500 can be similar in at least form and/or function to any of the fluid control devices 100, 200, 300, and/or 400. Accordingly, portions of the fluid control device 500 that can be similar to portions of the fluid control devices 100, 200, 300, and/or 400 are not described in further detail herein. As shown in FIGS. 11 and 12, the fluid control device 500 (also referred to herein as "control device" or "device") includes a housing 530 having an inlet 531 and an outlet 536, and having and/or being coupled to an actuator 550. As described above with reference to the control devices 100, 200, 300, and/or 400, the inlet 531 is configured to be placed in fluid communication with a bodily fluid source to receive a fluid of bodily fluid therefrom (e.g., via a lumen-containing device such as a needle or the like). The outlet 536 is configured to be fluidically coupled to a fluid collection device (not shown in FIGS. 11 and 12). The inlet 531, the outlet 536, and the fluid collection device can be substantially similar to those described above and thus, are not described in further detail herein.

As described above, the housing 530 of the control device 500 is configured to (1) receive a flow and/or volume of bodily fluid via the inlet 531 and (2) sequester (e.g., separate, segregate, contain, retain, isolate, etc.) the flow and/or volume of bodily fluid within the sequestration chamber 534. The housing 530 can be any suitable shape, size, and/or configuration. In some embodiments, the housing 530 can have a size that is at least partially based on a volume of bodily fluid at least temporarily stored, for example, in the sequestration chamber 534. For example, in the embodiment shown in FIGS. 11 and 12, the housing 530 can be arranged in a substantially similar manner as the housing 430 described above with reference to FIGS. 9 and 10. As described in further detail herein, the housing 530 can differ from the housing 430, by arranging the actuator 550 as, for example, a diaphragm rather than one or more plungers.

The housing 530 defines a set of fluid flow paths 533 and 554 in fluid communication with the outlet 536 and configured to selectively receive a flow of fluid therethrough (e.g., a liquid and/or a gas). The housing 530 includes and/or is coupled to the actuator 550 configured to selectively control a flow of bodily fluid through the housing 530. In this embodiment, the actuator 550 includes a diaphragm 576 movably disposed within the housing 530 and configured to at least partially define the sequestration chamber 534. More specifically, the actuator 550 is configured to move between a first state in which the inlet 531 is placed in fluid communication with the sequestration chamber 534 (FIG. 11) and a second state in which the inlet 531 is placed in fluid communication with the outlet 536 via the fluid flow path 554 (FIG. 12).

As shown in FIG. 11, when the actuator 550 and/or control device 500 is in the first state, the inlet 531 is in fluid communication with a portion of the housing 530 defined between the diaphragm 576 and one or more seals 565. Moreover, the diaphragm 576 is disposed in a first state such that a dampening chamber 537 is defined by the housing 530 on a side of the diaphragm 576 opposite the sequestration chamber 534, as described above with reference to the housing 430. As shown, the dampening chamber 537 is configured to be placed in fluid communication with the fluid flow path 533 via a port 535. The port 535 can be an opening, a valve, a membrane, a diaphragm, and/or any other suitable flow controller or the like configured to at least selectively establish fluid communication between the fluid flow path 533 and the dampening chamber 537. Furthermore, when the actuator 550 and/or the control device 500 is in the first state, the dampening chamber 537 includes and/or contains a dampening fluid such as a gas (compressed or uncompressed) and/or a liquid (e.g., water, oil, dampening fluid, and/or any other suitable liquid). As described above with reference to the control devices 400, the arrangement of the dampening chamber 537, the dampening fluid, and the port 535 can be configured to modulate an amount of negative pressure exerted on the diaphragm 576 when the actuator 550 is in the first state. Although shown in FIGS. 11 and 12 as modulating the negative pressure via the dampening fluid, it should be understood that this is presented by way of example only and not limitation. Any other suitable means of dampening and/or modulating a magnitude of the negative pressure can be used to control the transitioning of the actuator 550 and/or the control device 500.

As described above with reference to the actuator 450, when the actuator 550 and/or the control device 500 are in the first state, the one or more seals 565 are disposed in a position within the housing 530 such that the one or more seals 565 fluidically isolate, separate, and/or sequester the inlet 531 from the fluid flow path 554. In addition, the one or more seals 565 fluidically isolate the fluid flow path 554 from the sequestration chamber 534. Thus, when the actuator 550 and/or the control device 500 are in the first state, the inlet 531 is in fluid communication with the sequestration chamber 534 and fluidically isolated from the fluid flow paths 533 and 554 as well as the outlet 536 (see FIG. 11). As described in further detail herein, the actuator 550 and/or the control device 500 housing 530 can be configured to transition to the second state in which the sequestration chamber 534 is sequestered within the housing 530 and the inlet 531 is placed in fluid communication with the fluid flow path 554 (see FIG. 12).

As described in detail above, the device 500 can be used to procure a bodily fluid sample having reduced contamination from microbes such as, for example, dermally residing microbes, and/or the like. For example, in some instances, a user can place the inlet 531 in fluid communication with the bodily fluid source (e.g., the portion of the patient) and can fluidically couple the outlet 536 to the fluid collection device. As shown in FIG. 11, the actuator 550 and/or the device 500 can be in a first or initial state prior to coupling the outlet 536 to the fluid collection device. Thus, the fluid flow path 533 is in fluid communication with the dampening chamber 537 and the fluid flow path 554 is fluidically isolated from the inlet 531 and the sequestration chamber 534 (e.g., via the one or more seals 565), as described in detail above with reference to the control device 400 of FIGS. 9 and 10.

Coupling the outlet 536 to the fluid collection device selectively exposes at least a portion of the fluid flow paths 533 and 554 to the negative pressure within and/or produced by the fluid collection device. When the actuator 550 and/or the device 500 are in the first state, the one or more seals 565 isolate the housing 530 and/or the sequestration chamber 534 from the negative pressure exerted via the fluid flow path 554. Conversely, the negative pressure exerted through the fluid flow path 533 can be operable in exerting at least a portion of the negative pressure on the dampening chamber 537 (e.g., via the port 535). In some embodiments, for example, the port 535 can be transitioned from a closed configuration to an open configuration in response to the negative pressure. The negative pressure exerted through the fluid flow path 533 is operable in transitioning the actuator 550 from a first state to a second state. For example, in some embodiments, the negative pressure differential draws the dampening fluid from the dampening chamber 537 and into the fluid flow path 533. Moreover, the negative pressure urges the diaphragm 576 to transition, flip, move, switch, deform, etc., from a first configuration or state (FIG. 11) to a second configuration or state (FIG. 12). As described above with reference to the actuator 450, the transitioning of the diaphragm 576 from the first state to the second state can be such that a volume of the housing 530 defined between the diaphragm 576 and the one or more seals 565 is increased (i.e., a volume of the sequestration chamber 534 is increased), which in turn, results in a negative pressure therein that can be operable in drawing an initial volume of bodily fluid through the inlet 531 and into the sequestration chamber 534.

As shown in FIG. 12, movement of the diaphragm 576 results in a similar movement of the one or more seals 565 such that the one or more seals 565 are disposed on the same side of the inlet 531 as the diaphragm 576. Thus, the sequestration chamber 534 is sequestered within the housing 530. In addition, moving the one or more seals 565 is such that fluid communication is established between the inlet 531 and the fluid flow path 554. Thus, the negative pressure otherwise exerted on or through the fluid flow path 533 is now exerted on or through the fluid flow path 554. In response, bodily fluid can flow from the inlet 531, through the fluid flow path 554, through the outlet 536, and into the fluid collection device, as described in detail above. In some embodiments, the transitioning of the actuator 550 from the first state to the second state is operable to sequester and/or retain the initial portion of the bodily fluid in the sequestration chamber 534, which can include contaminants such as, for example, dermally residing microbes or the like dislodged during the venipuncture event. Thus, as described above, sequestering the initial volume of bodily fluid in the sequestration chamber 534 prior to collecting or procuring one or more sample volumes of bodily fluid reduces and/or substantially eliminates an amount of contaminants in the one or more sample volumes. Moreover, in some embodiments, the arrangement of the control device 500 and/or the housing 530 can be such that the control device 500 and/or the housing 530 cannot transition to the second state prior to collecting and sequestering the initial volume in the sequestration chamber 534.

Figure 13:
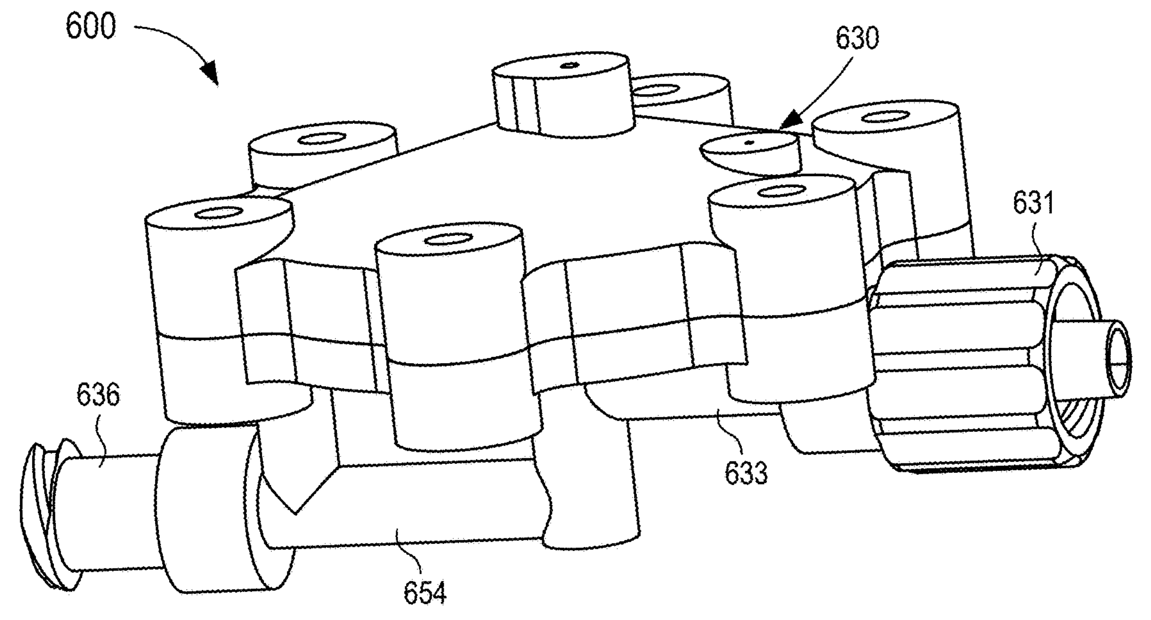
FIGS. 13-15B are various views of a fluid control device according to an embodiment.
Figure 14:
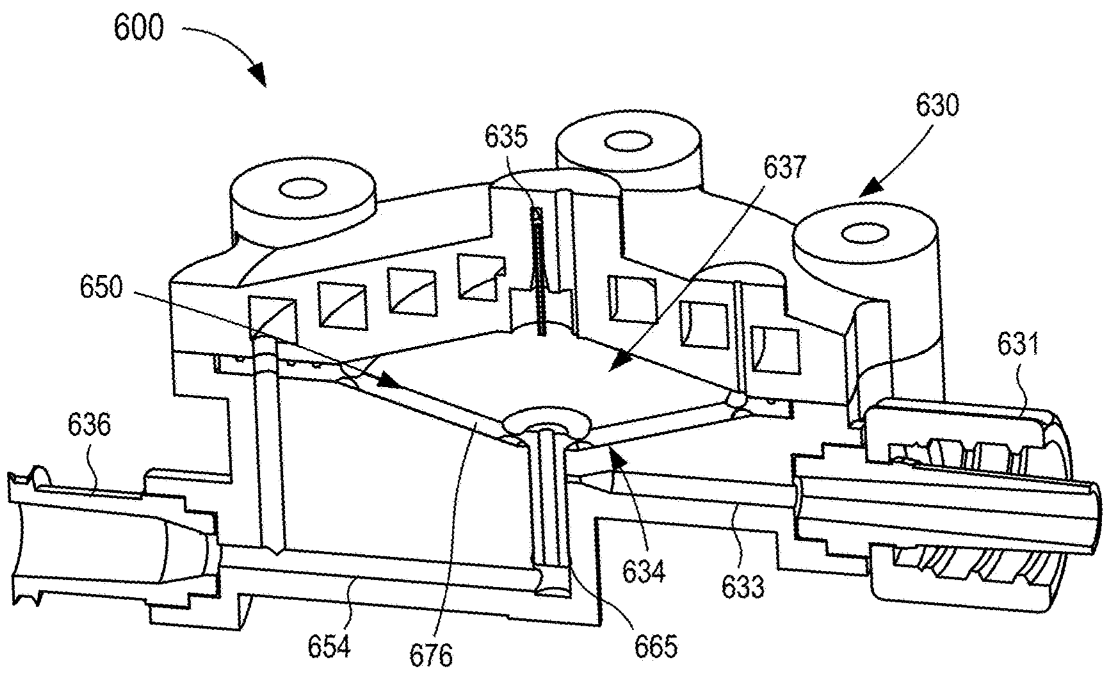
Figure 15A:
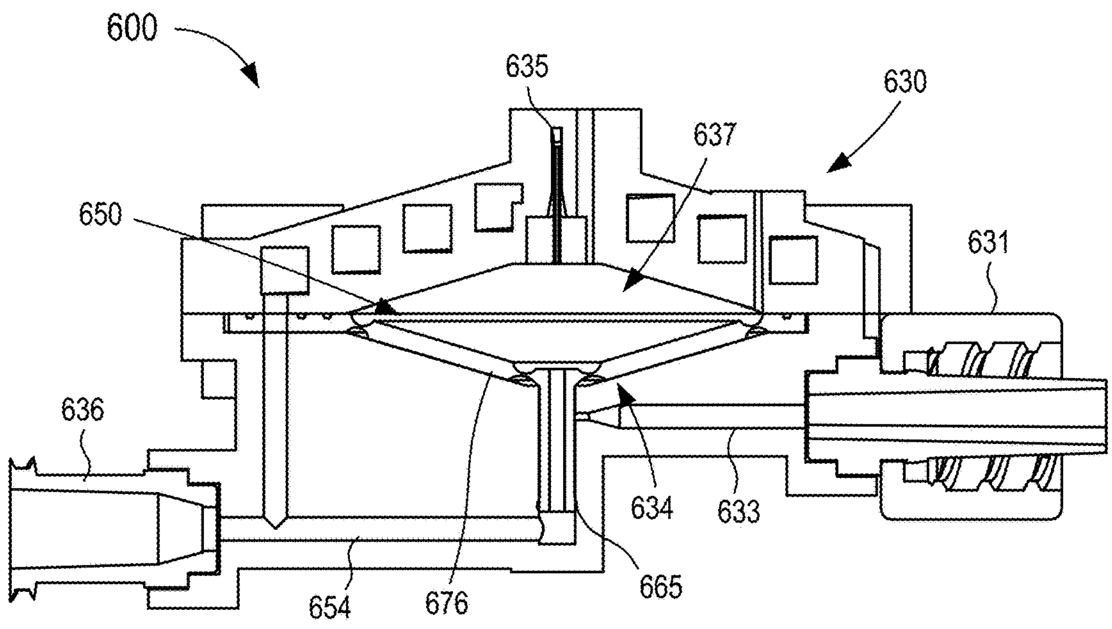
Figure 15B:
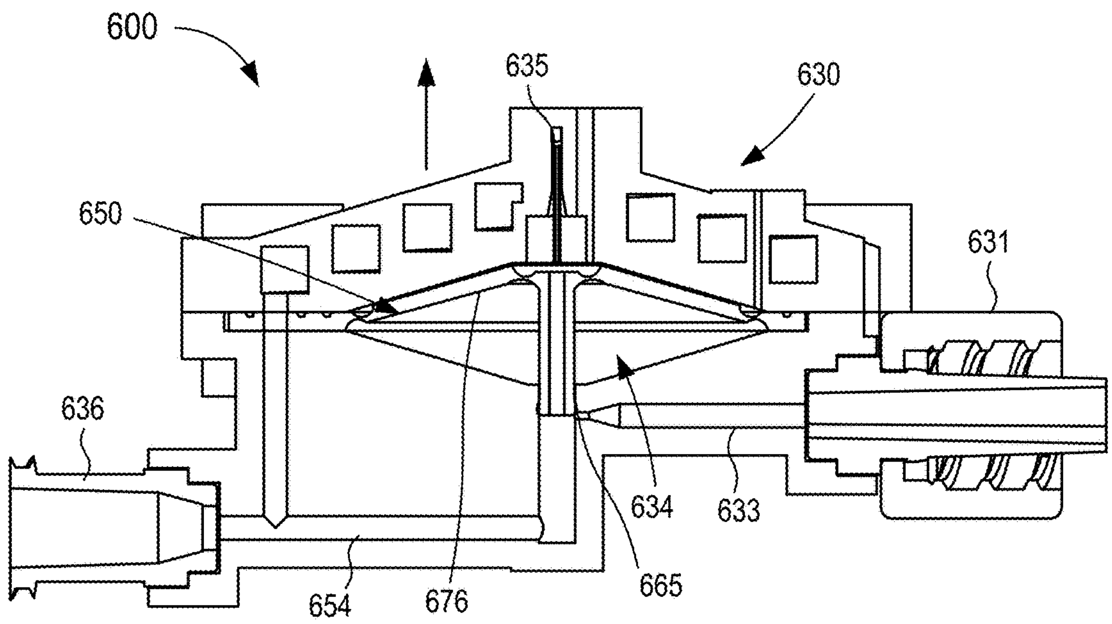

FIGS. 13-15 illustrate a fluid control device 600 according to an embodiment. The fluid control device 600 can be similar in at least form and/or function to any of the fluid control devices 100, 200, 300, 400, and/or 500. Accordingly, portions of the fluid control device 600 that can be similar to portions of the fluid control devices 100, 200, 300, 400, and/or 500 are not described in further detail herein. As shown in FIGS. 13-15, the fluid control device 600 (also referred to herein as "control device" or "device") includes a housing 630 having an inlet 631 and an outlet 636, and having and/or being coupled to an actuator 650. As described above with reference to the control devices 100, 200, 300, 500, and/or 500, the inlet 631 is configured to be placed in fluid communication with a bodily fluid source to receive a fluid of bodily fluid therefrom (e.g., via a lumen-containing device such as a needle or the like). The outlet 636 is configured to be fluidically coupled to a fluid collection device (not shown in FIGS. 13-15). The inlet 631, the outlet 636, and the fluid collection device can be substantially similar to those described above and thus, are not described in further detail herein.

As described above, the housing 630 of the control device 600 is configured to (1) receive a flow and/or volume of bodily fluid via the inlet 631 and (2) sequester (e.g., separate, segregate, contain, retain, isolate, etc.) the flow and/or volume of bodily fluid within a sequestration chamber 634 included in and/or at least partially formed by the housing 630. The housing 630 can be any suitable shape, size, and/or configuration. In some embodiments, the housing 630 can have a size that is at least partially based on a volume of bodily fluid at least temporarily stored, for example, in the sequestration chamber 634. For example, in the embodiment shown in FIGS. 13-15, the housing 630 can be arranged in a substantially similar manner as the housing 530 described above with reference to FIGS. 11 and 12. That is to say, the housing 630 includes an actuator 650 that is arranged as a diaphragm.

The housing 630 defines a set of fluid flow paths 633 and 654 in fluid communication with the outlet 636 and configured to selectively receive a flow of fluid therethrough (e.g., a liquid and/or a gas). The housing 630 includes and/or is coupled to the actuator 650 configured to selectively control a flow of bodily fluid through the housing 630. In this embodiment, the actuator 650 includes a diaphragm 676 movably disposed within the housing 630 and configured to at least partially define the sequestration chamber 634. More specifically, the actuator 650 is configured to move between a first state in which the inlet 631 is placed in fluid communication with the sequestration chamber 634 and a second state in which the inlet 631 is placed in fluid communication with the outlet 636 via the fluid flow path 654, as described in detail above with reference to the control device 500.

As shown in FIGS. 14 and 15, when the actuator 650 and/or the device 600 is in the first state, the inlet 631 is in fluid communication with a portion of the housing 630 defined between the diaphragm 676 and one or more seals 665. Moreover, the diaphragm 676 is disposed in a first state such that a dampening chamber 637 is defined by the housing 630 on a side of the diaphragm 676 opposite the sequestration chamber 634, as described above with reference to the housing 530. As shown, the dampening chamber 637 is configured to be placed in fluid communication with the fluid flow path 654 via a port 635 (such as those described above). Although not shown, when the actuator 650 and/or the device 600 is in the first state, the dampening chamber 637 includes and/or contains a dampening fluid such as a gas (compressed or uncompressed) and/or a liquid (e.g., water, oil, dampening fluid, and/or any other suitable liquid), that can be configured to modulate an amount of negative pressure exerted on the diaphragm, as described in detail above with reference to the control device 500. Although described as modulating the negative pressure via the dampening fluid, it should be understood that this is presented by way of example only and not limitation. Any other suitable means of dampening and/or modulating a magnitude of the negative pressure can be used to control the transitioning of the actuator 650 and/or device 600.

As described above with reference to the actuator 550, when the actuator 650 and/or the device 600 are in the first state, the seal 665 is disposed in a position within the housing 630 such that the seal 665 fluidically isolates, separates, and/or sequesters the inlet 631 from the fluid flow path 654. In addition, the seal 665 fluidically isolates the fluid flow path 654 from the sequestration chamber 634. Thus, when the actuator 650 and/or the device 600 are in the first state, the inlet 631 is in fluid communication with the sequestration chamber 634 and fluidically isolated from the fluid flow path 654 as well as the outlet 636. The actuator 650 and/or the device 600 can be configured to transition to the second state in which the sequestration chamber 634 is sequestered within the housing 630 and the inlet 631 is placed in fluid communication with the fluid flow path 654. Accordingly, the device 600 can be used to procure a bodily fluid sample having reduced contamination from microbes (e.g., dermally residing microbes and/or the like), in a substantially similar manner as the device 500 described above with reference to FIGS. 11 and 12. Thus, the functioning of the device 600 is not described in further detail herein.

Figure 16:
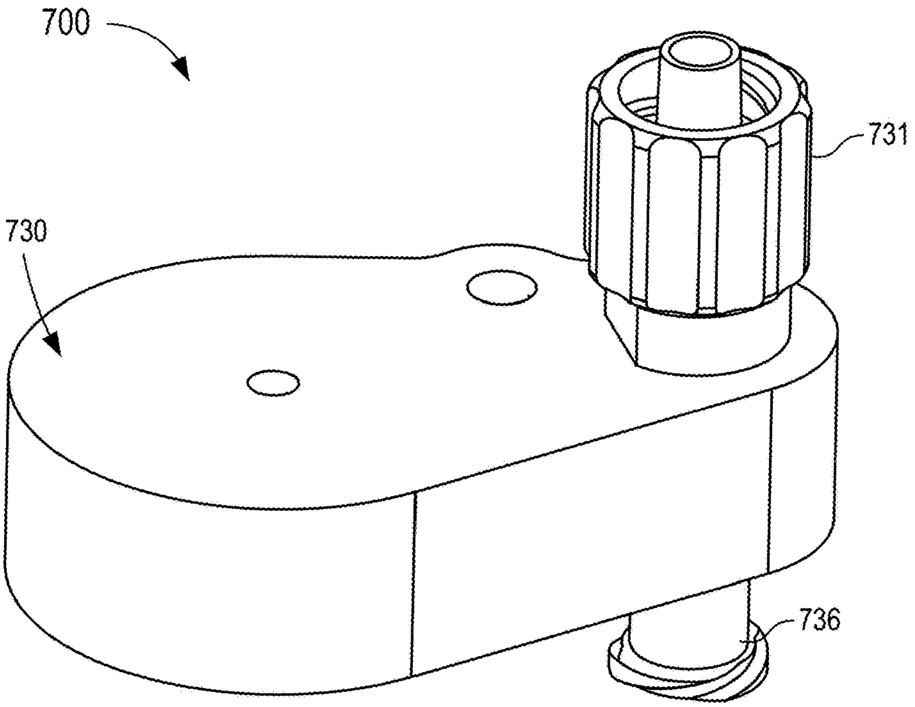
FIGS. 16-18 are various views of a fluid control device according to an embodiment.
Figure 17A:
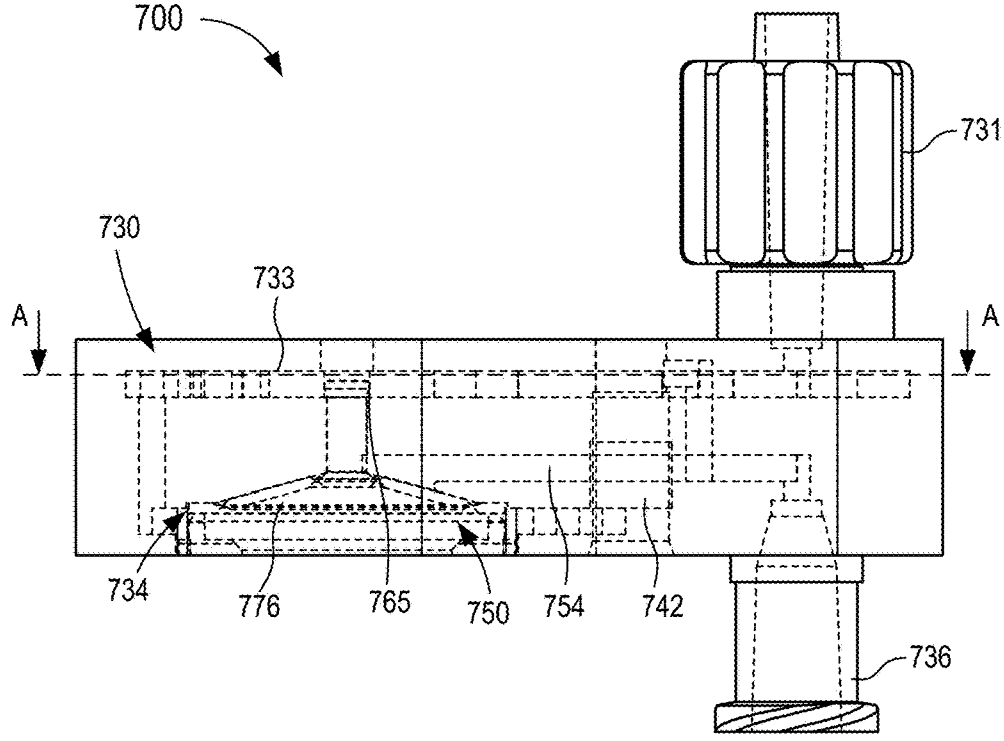
Figure 17B:
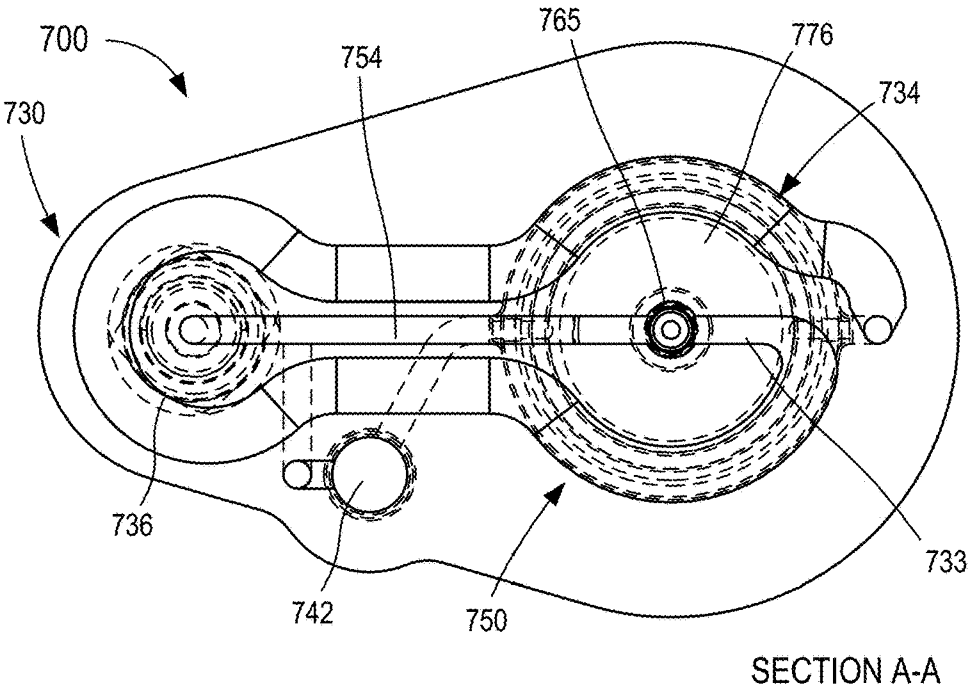
Figure 18:
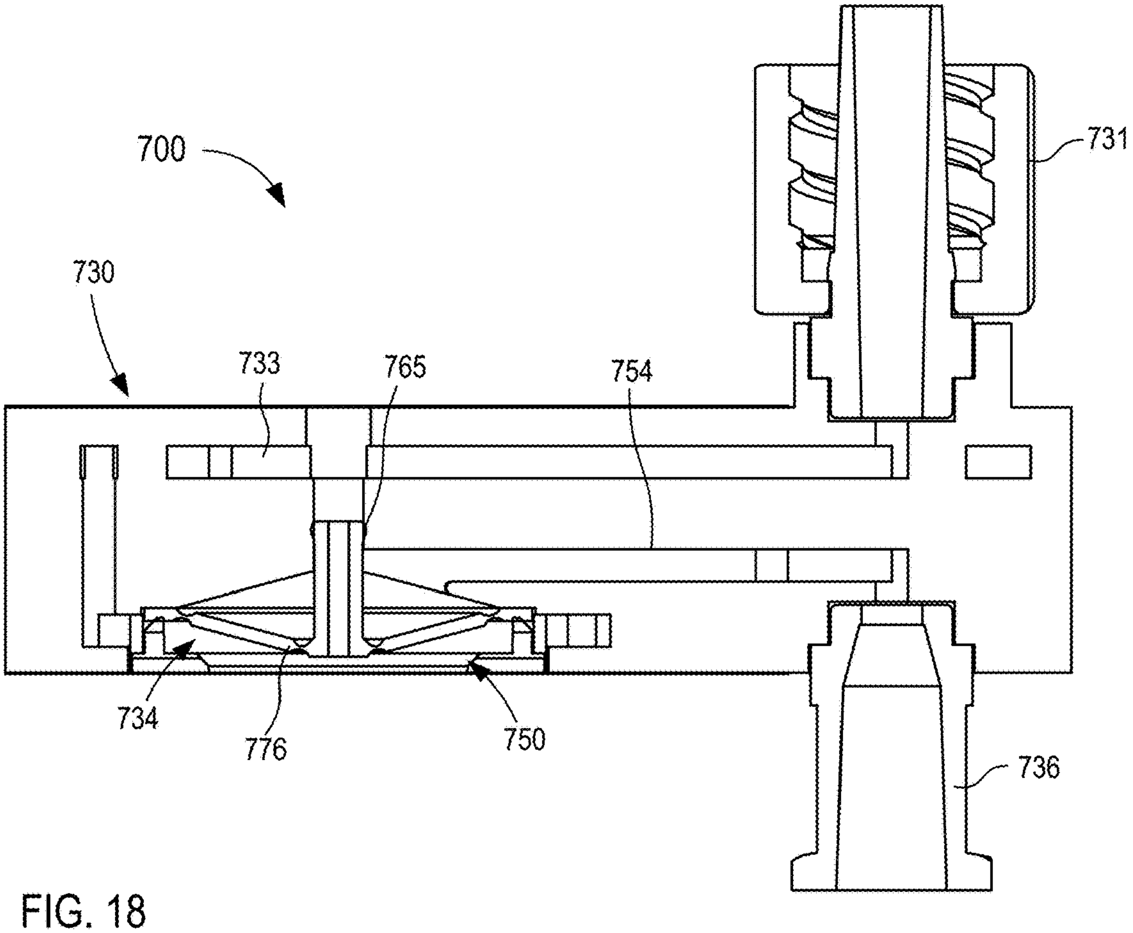

FIGS. 16-18 illustrate a fluid control device 700 according to an embodiment. The fluid control device 700 can be similar in at least form and/or function to any of the fluid control devices 100, 200, 300, 400, 500, and/or 600. Accordingly, portions of the fluid control device 700 that can be similar to portions of the fluid control devices 100, 200, 300, 400, 500, and/or 600 are not described in further detail herein. As shown in FIGS. 16-18, the fluid control device 700 (also referred to herein as "control device" or "device") includes a housing 730 having an inlet 731 and an outlet 736, and having or being coupled to an actuator 750. As described above with reference to the control devices 100, 200, 300, 400, 500, and/or 600, the inlet 731 is configured to be placed in fluid communication with a bodily fluid source to receive a fluid of bodily fluid therefrom (e.g., via a lumen-containing device such as a needle or the like). The outlet 736 is configured to be fluidically coupled to a fluid collection device (not shown in FIGS. 16-18). The inlet 731, the outlet 736, and the fluid collection device can be substantially similar to those described above and thus, are not described in further detail herein.

As described above, the housing 730 of the control device 700 is configured to (1) receive a flow and/or volume of bodily fluid via the inlet 731 and (2) sequester (e.g., separate, segregate, contain, retain, isolate, etc.) the flow and/or volume of bodily fluid within the sequestration chamber 734. The housing 730 can be any suitable shape, size, and/or configuration. In some embodiments, the housing 730 can have a size that is at least partially based on a volume of bodily fluid at least temporarily stored, for example, in the sequestration chamber 734. For example, in the embodiment shown in FIGS. 16-18, the housing 730 can be arranged in a substantially similar manner as the housings 530 and/or 630. That is to say, the housing 530 includes and/or is coupled to the actuator 750 that is arranged as a diaphragm.

The housing 730 defines a set of fluid flow paths 733 and 754 in fluid communication with the outlet 736 (see e.g., FIGS. 17A and 17B) and configured to selectively receive a flow of fluid therethrough (e.g., a liquid and/or a gas). The housing 730 includes and/or is coupled to the actuator 750 configured to selectively control a flow of bodily fluid through the housing 730. In this embodiment, the actuator 750 includes a diaphragm 776 movably disposed within the housing 730 and configured to at least partially define the sequestration chamber 734. More specifically, the actuator 750 is configured to move between a first state in which the inlet 731 is placed in fluid communication with the sequestration chamber 734 and a second state in which the inlet 731 is placed in fluid communication with the outlet 736 via the fluid flow path 754, as described in detail above with reference to the control device 500.

In the embodiment shown in FIGS. 16-18, when the actuator 750 and/or the device 700 are in the first state, the inlet 731 is in fluid communication with the sequestration chamber 734 formed by a portion of the housing 730 defined between the diaphragm 776 and a flow controller 742 (e.g., a selectively permeable fluid barrier or seal, and/or any other flow controller such as any of those described above). Moreover, the diaphragm 776 is disposed in a first state such that the fluid flow path 733 is in fluid communication with the sequestration chamber 734. As described above with reference to the actuator 550, when in the actuator 750 and/or device 700 are in the first state, the diaphragm 776 and/or the seal 765 are disposed in a position within the housing 730 such that the diaphragm 776 and/or the seal 765 fluidically isolate, separate, and/or sequester the inlet 731 from the fluid flow path 754. In addition, the diaphragm 776 and/or the seal 765 fluidically isolate the fluid flow path 754 from the sequestration chamber 734. Thus, when the actuator 750 and/or the device 700 are in the first state, the inlet 731 is in fluid communication with the sequestration chamber 734 and fluidically isolated from the fluid flow path 754.

As described above with reference to, for example, the control device 200, when the actuator 750 and/or the device 700 are in the first state, a negative pressure differential within the sequestration chamber 734 can result from the coupling of the fluid collection device to the outlet 736. More specifically, the fluid flow path 733 can be in fluid communication with the outlet 736 and the flow controller 742. When the flow controller 742 is in a first state, the flow controller 742 can allow a gas or air to pass therethrough. Thus, the negative pressure differential within the sequestration chamber 734 can result from the coupling of the fluid collection device to the outlet 736.

As shown in FIG. 18, the actuator 750 and/or the device 700 can be configured to transition to the second state in which the sequestration chamber 734 is sequestered within the housing 730 and the inlet 731 is placed in fluid communication with the fluid flow path 754, as described in detail above with reference to the control device 600. More particularly, an initial volume of bodily fluid can be transferred into the sequestration chamber 734, which in turn, can saturate, can wet, and/or otherwise can transition the flow controller 742 from the first or open state to a second or closed state. In some embodiments, the transitioning of the flow controller 742 from the first state to the second state is operable in isolating the fluid flow path 733 from the outlet 736. As such, a negative pressure exerted through the fluid flow path 754 can be operable in transitioning, switching, flipping, moving, deforming, and/or otherwise reconfiguring the diaphragm 776 such that the actuator 750 is placed in its second state. As such, the negative pressure of the fluid collection device can draw bodily fluid from the inlet 731, through the housing 730 (bypassing the sequestration chamber 734), through the fluid flow path 754 and the outlet 736, and into the fluid collection device, as described in detail above. Accordingly, the device 700 can be used to procure a bodily fluid sample having reduced contamination from microbes (e.g., dermally residing microbes and/or the like), in a manner substantially similar to one or more of the control devices 100, 200, 300, 400, 500, and/or 600 described in detail above. Thus, the functioning of the device 700 is not described in further detail herein.

In some embodiments, any of the control devices 100, 200, 300, 400, 500, 600, and/or 700 can be formed from any suitable components that can be manufactured, assembled, sterilized, and packaged as an assembly or integrated device. In such embodiments, a user can, for example, open a packaging containing such an assembly or integrated device and can use the device as described above with reference to the control devices 100, 200, 300, 400, 500, 600, and/or 700. In some embodiments, any of the control devices can be monolithically formed in whole or at least in part.

In some embodiments any of the control devices can be physically coupled, attached, formed, and/or otherwise mated to a fluid collection device (e.g., a sample reservoir, a syringe, a blood culture bottle, a collection vial, a fluid transfer container, and/or any other suitable reservoir, collection device, and/or transfer device) during a manufacturing process. This can be done prior to sterilization so the collection pathway(s) and connection interface(s) (e.g., where the control device couples to the fluid collection device) maintain a closed-system, mechanical diversion device within a sterile environment that is not subject to touch-point contamination from external sources. In this manner, in order for a user to transfer a sample volume to the fluid collection device, the user would be forced first to sequester, segregate, and/or isolate at least a portion of the initial bodily fluid volume or flow. In some embodiments, the coupling, mating, and/or attachment of the fluid control device to the fluid collection device can be executed such that the control device can be removed (physically decoupled, removed with a specific "key," and/or any other approach used to separate the control device from the fluid collection device) after use to allow access to the fluid collection device, which can then be placed in an incubator and/or any other type of analytical machine, and accessed for analysis and/or otherwise further processed. In some embodiments, such decoupling may be blocked, limited, and/or substantially prevented prior to use and unblocked or allowed after use. In other embodiments, the fluid control device and the fluid collection device can be permanently coupled and/or monolithically formed (at least in part) to prevent such decoupling.

While described above as being coupled and/or assembled, for example, during manufacturing, in other embodiments, however, a control device can include one or more modular components that can be selected by a user based on a desired use, preference, patient, etc. In such embodiments, the user can couple one or more modular components (packaged together or packaged separately) to form the desired fluid control device. For example, FIGS. 19-25 illustrate a modular fluid control device 800 according to an embodiment. The fluid control device 800 can be similar in at least form and/or function to the fluid control devices described herein. More specifically, portions of the fluid control device 800 can be similar to and/or substantially the same as corresponding portions of the fluid control device 200 described above with reference to FIGS. 2-5. Accordingly, such portions of the fluid control device 800 are not described in further detail herein.

The fluid control device 800 (also referred to herein as "control device" or "device") includes a housing 830 and an actuator 850. As described above, the control device 800 can be at least partially monolithically formed or can be otherwise preassembled during manufacturing. In other embodiments, the control device 800 can be at least partially modular such that a user can physically and fluidically couple the housing 830 and the actuator 850 to form the control device 800. The housing 830 of the device 800 can be any suitable shape, size, and/or configuration. For example, in the embodiment shown in FIGS. 19-25, the housing 830 can be, for example, relatively thin and substantially rectangular. In some embodiments, portions of the housing 830 can be substantially similar in at least form and/or function to the housing 230 described above with reference to FIGS. 2-5. Thus, while such portions are identified, similar components, features, and/or functions are not described in further detail herein.

Figure 19:
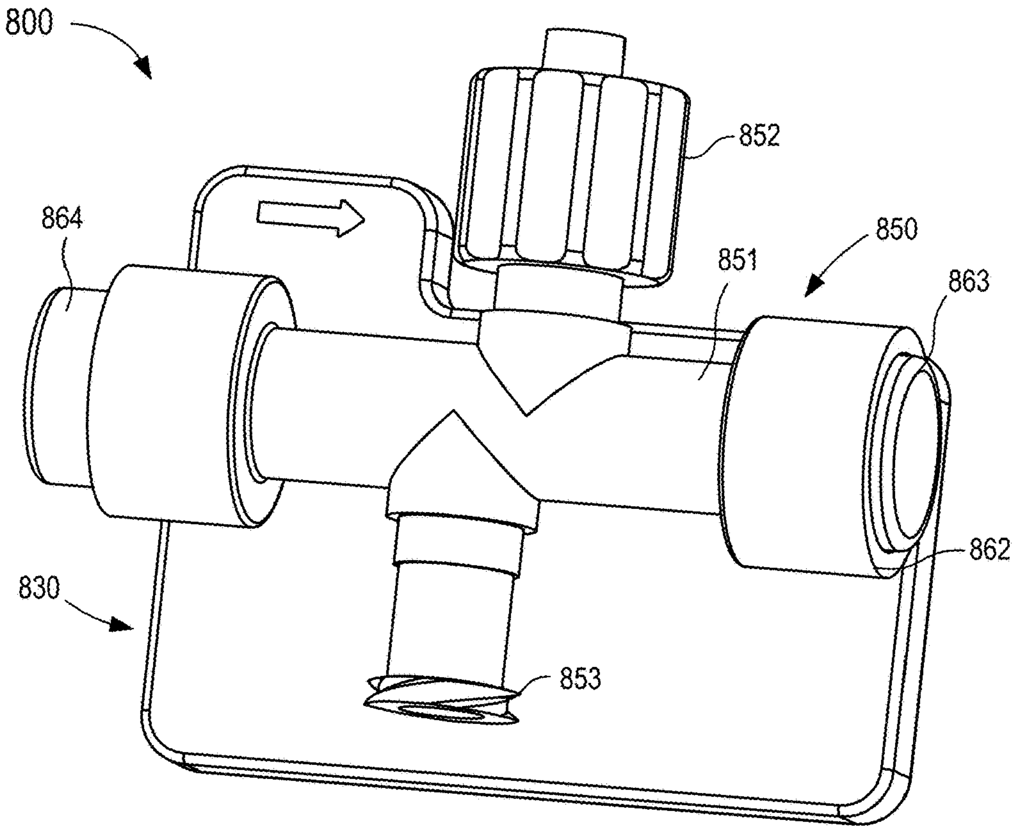
FIGS. 19-25 are various views of a fluid control device according to an embodiment.
Figure 20:
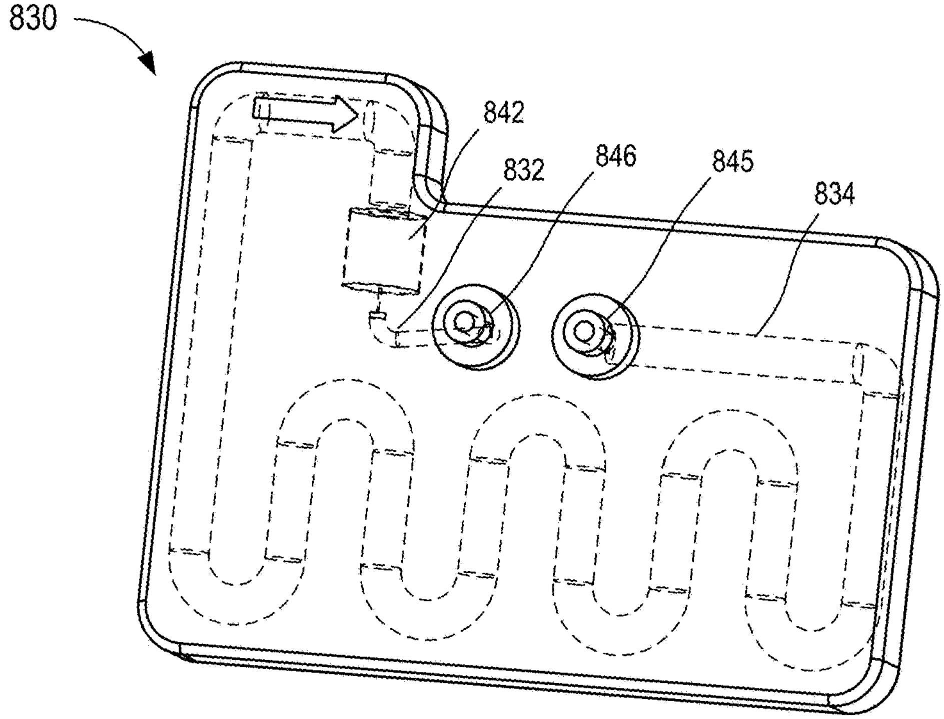

As shown in FIGS. 19 and 20, the housing 830 forms and/or defines a sequestration chamber 834 that is in selective fluid communication with a first port 845 and a second port 846. The first port 845 and the second port 846 are configured to be at least fluidically coupled to a portion of the actuator 850 to allow for selective fluid flow between the housing 830 and the actuator 850. As described in further detail herein, the sequestration chamber 834 is configured (1) to receive a selective flow and/or volume of bodily fluid from a portion of the actuator 850 via the first port 845, and (2) to sequester (e.g., separate, segregate, contain, retain, isolate, etc.) the flow and/or volume of bodily fluid (e.g., an initial or first flow and/or volume of bodily fluid or any portion thereof) within the sequestration chamber 834. The sequestration chamber 834 can have any suitable shape, size, and/or configuration. For example, in some embodiments, the sequestration chamber 834 can have any suitable size, volume, and/or fluid capacity such as, for example, those described above with reference to the sequestration chamber 134. In the embodiment shown in FIGS. 19-25, the sequestration chamber 834 can be, for example, a fluid flow path that extends through and/or that is defined by at least a portion of the housing 830. In some embodiments, the sequestration chamber 834 can be substantially similar in at least form and/or function to the sequestration chamber 234 described above with reference to FIGS. 2-5 and thus, is not described in further detail herein.

As shown in FIG. 20, the housing 830 includes and/or defines a flow controller 842 and a restricted flow path 832. The flow controller 842 can be, for example, a valve, membrane, diaphragm, restrictor, vent, a selectively permeable member, port, etc. configured to selectively control (at least in part) a flow of fluids into and/or out of the sequestration chamber 834 and/or any other suitable portion of the housing 830. For example, the flow controller 842 can be a selectively permeable fluid barrier (e.g., a blood barrier) that includes and/or is formed of a porous material configured to selectively allow a flow of gas therethrough but to prevent a flow of a liquid therethrough. In some embodiments, the flow controller 842 can be substantially similar to the flow controller 242 described in detail above with reference to FIGS. 2-5 and thus, is not described in further detail herein.

As shown, the restricted flow path 832 defined by the housing 830 is in fluid communication with the second port 846 and is positioned between the second port 846 and the flow controller 842 (or a portion of the housing 830 receiving or housing the flow controller 842). As described above with reference to the restricted flow path 232 shown in FIGS. 2-5, the restricted flow path 832 is a fluid flow path having a smaller diameter than, for example, one or more other flow paths defined by the housing 830 and/or actuator 850. For example, in some embodiments, the restricted flow path 832 can have a diameter between about 0.0005" to about 0.5" and can have a length between about 0.01" and about 0.5", as described above with reference to the restricted flow path 232. As described above, the smaller diameter of the restricted flow path 832 results in a lower magnitude of negative pressure being applied through the sequestration chamber 834 than a magnitude of negative pressure when the restricted flow path 832 has a larger diameter. In other words, the restricted flow path 832 can be configured to modulate an amount of negative pressure to which the sequestration chamber 834 is exposed. In some instances, modulating the amount of negative pressure can control a rate at which bodily fluid is transferred into the sequestration chamber 834. Moreover, in this embodiment, the restricted flow path 832 is, for example, a gas flow path configured to receive a flow of gas or air but not a flow of a liquid (e.g., bodily fluid), which can allow for a negative pressure differential sufficient to successfully collect the initial volume of bodily fluid and/or sufficient to transition at least a portion of the control device 800 to a second state, while limiting and/or substantially preventing a portion of the initial or first volume of bodily fluid from being drawn through the sequestration chamber 834 and the second port 846.

As shown in FIGS. 19-24, the actuator 850 includes a body 851 and an actuator rod 862. The body 851 of the actuator 850 includes an inlet 852 and an outlet 853. The inlet 852 and the outlet 853 can be substantially similar in at least form and/or function to the inlet 231 and the outlet 236, respectively, described above with reference to FIGS. 2-5. Thus, the inlet 852 is configured to be placed in fluid communication with a bodily fluid source to receive a flow of bodily fluid therefrom (e.g., via a lumen-containing device such as a needle, IV catheter, PICC line, or the like). The outlet 853 is configured to be fluidically coupled to a fluid collection device 880 such as, for example, a sample reservoir, a syringe, and/or other intermediary bodily fluid transfer device, adapter, or vessel (see e.g., FIG. 25) such as, for example, a transfer device similar to those described in the '510 publication.

Figure 21:
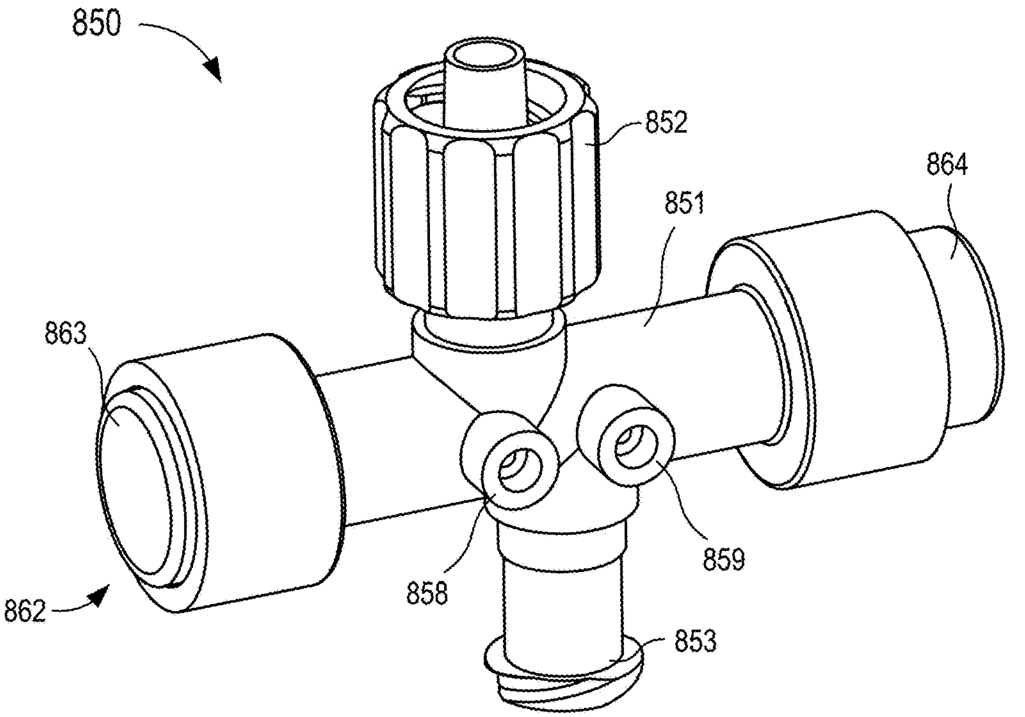
Figure 22:
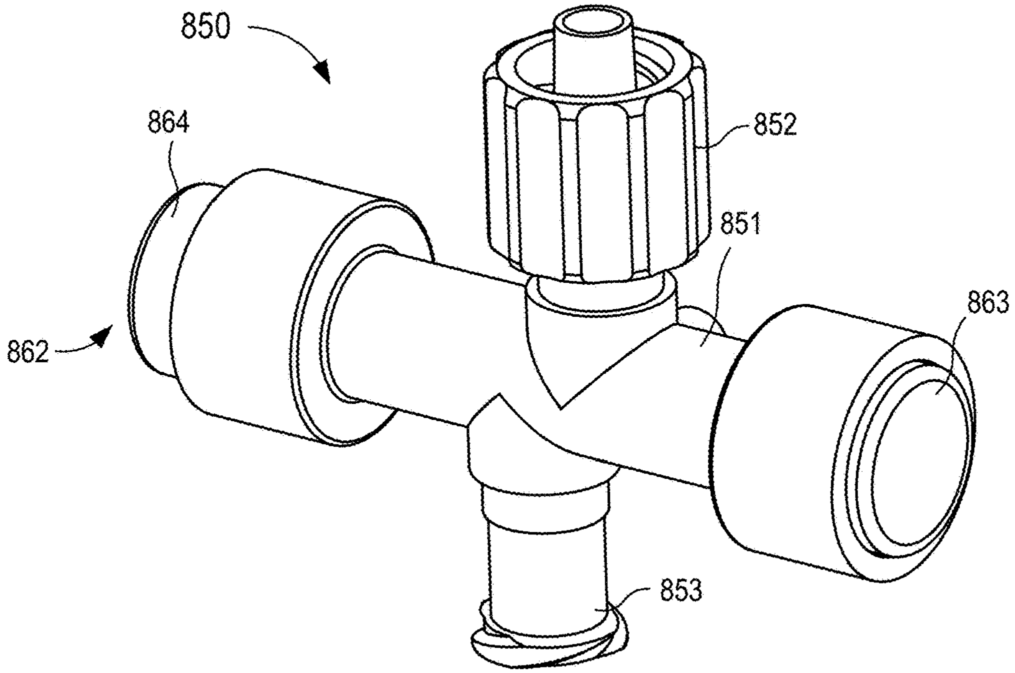

As shown in FIG. 21, the body 851 of the actuator 850 includes and/or defines a first port 858 and a second port 859. The first port 858 is in fluid communication with the inlet 852 and the second port 859 is in fluid communication with the outlet 853. In addition, the first port 858 and the second port 859 are configured to be at least fluidically coupled to the first port 845 and the second port 846, respectively, of the housing 830. As described in further detail herein, the actuator 850 can be transitioned between a first operating mode or state and a second operating mode or state to selectively control fluid flow through the ports 858 and 859 of the actuator 850 and the ports 845 and 846 of the housing 830, which in turn, can selectively control a flow of bodily fluid into and/or out of the sequestration chamber 834 of the housing 830.

In some embodiments, the arrangement of the ports 858 and 859 of the actuator 850 and the ports 845 and 846 of the housing 830 can allow for and/or otherwise can provide a means of physically coupling the housing 830 to the actuator 850 as well as fluidically coupling the housing 830 to the actuator 850. For example, in some embodiments, the ports 858 and 859 of the actuator 850 and the ports 845 and 846 of the housing 830 can form a friction fit, a press fit, an interference fit, and/or the like. In other embodiments, the ports 858 and 859 of the actuator 850 can be coupled to the ports 845 and 846, respectively, of the housing 830 via an adhesive, a mechanical fastener, an elastomeric coupling, a gasket, an o-ring(s), and/or any other suitable coupling means. In still other embodiments, the ports 858 and 859 of the actuator 850 can be physically and fluidically coupled to the ports 845 and 846, respectively, of the housing 830 via an intervening structure such as, for example, one or more sterile, flexible tubing(s). As such, the device 800 can be and/or can have, for example, a modular configuration in which the housing 830 can be at least fluidically coupled to the actuator 850.

In some embodiments, such a modular arrangement can allow a user to select a housing (or actuator) with one or more desired characteristics based on, for example, the intended purpose and/or use of the assembled device. In other embodiments, the modular arrangement can allow and/or facilitate one or more components with desired characteristics to be coupled and/or assembled during manufacturing. For example, in some instances, it may be desirable to select a housing that includes and/or defines a sequestration chamber having a particular or desired volume. As a specific example, when the device is being used to procure bodily fluid from a pediatric patient and/or a very sick patient (for example), it may be desirable to select a housing that defines and/or includes a sequestration chamber with a smaller volume than may otherwise be selected when the device is being used to procure bodily fluid from a seemingly healthy adult patient. Accordingly, such a modular arrangement can allow a user (e.g., a doctor, physician, nurse, technician, phlebotomist, etc.) to select a housing or an actuator having one or more desired characteristics based on, for example, the intended use of the device. In other instances, the modular arrangement can allow or facilitate assembly of a housing or an actuator having one or more desired characteristics during manufacturing without making significant changes to one or more manufacturing processes.

Figure 23:
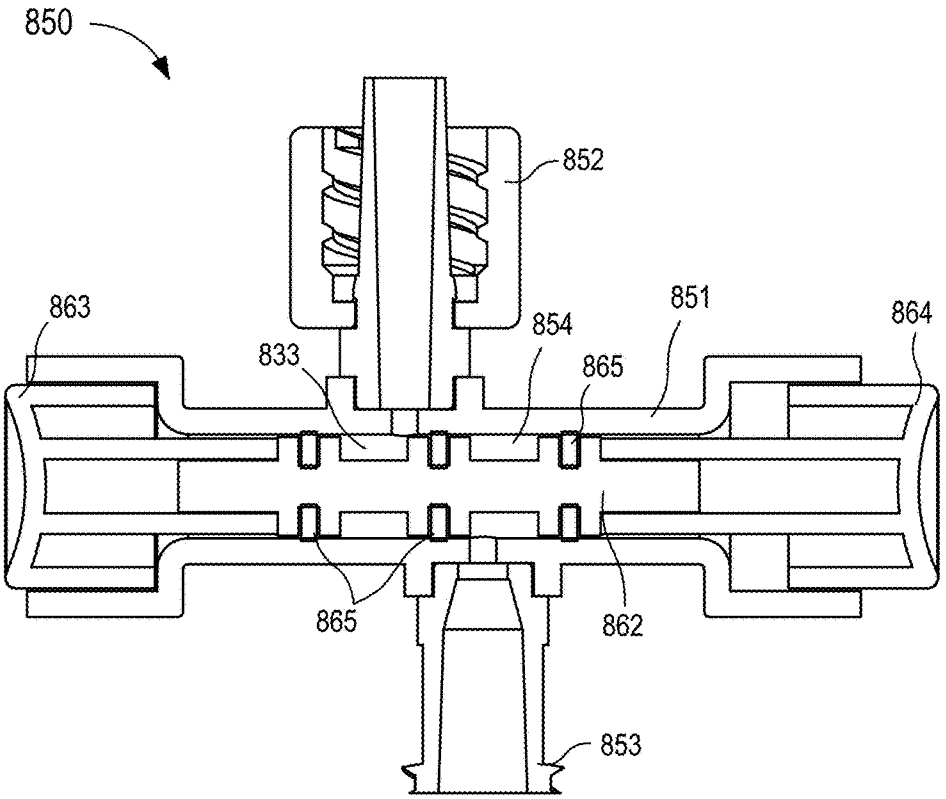
Figure 24:
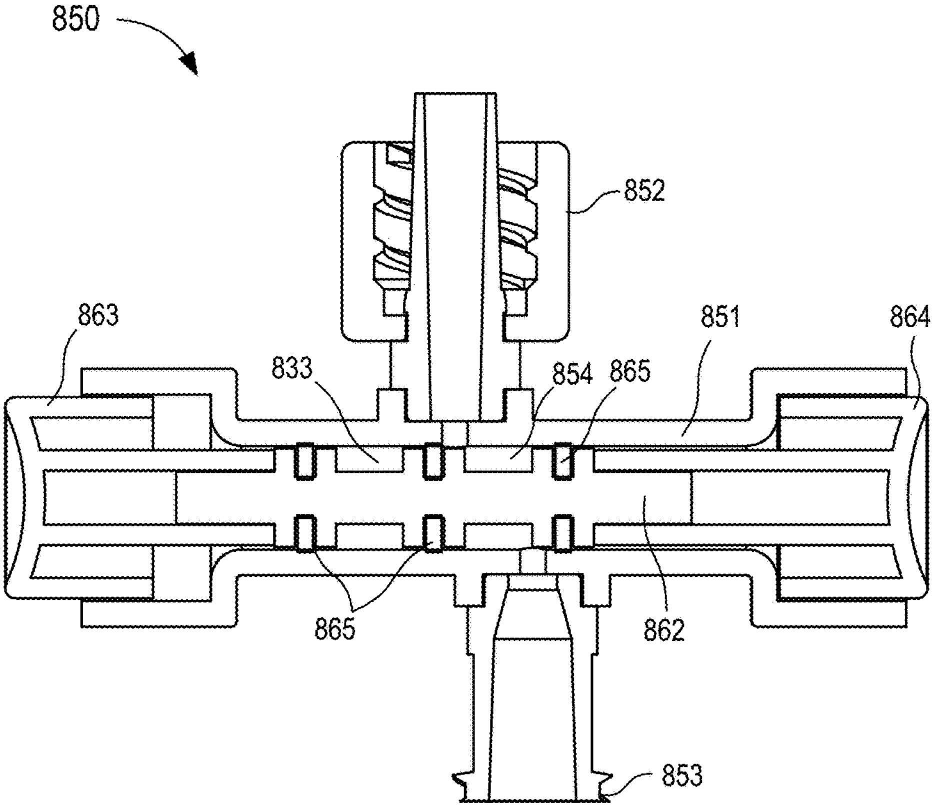

The actuator rod 862 of the actuator 850 is movably disposed within a portion of the body 851. The actuator rod 862 includes a first end portion 863 and a second end portion 864, at least one of which extends beyond the body 851 of the actuator 850 with the actuator rod 862 is disposed within the body 851 (see e.g., FIGS. 23 and 24). A portion of the actuator rod 862 includes and/or is coupled to a set of seals 865. The seals 865 can be, for example, o-rings, elastomeric over-molds, proud or raised dimensions or fittings, and/or the like. The arrangement of the actuator 862 and the body 851 of the actuator 850 can be such that an inner portion of the seals 865 forms a fluid tight seal with a surface of the actuator rod 862 and an outer portion of the seals 865 forms a fluid tight seal with an inner surface of the body 851. In other words, the seals 865 form one or more fluid tight seals between the actuator rod 862 and the inner surface of the body 851. As shown in FIGS. 23 and 24, the actuator rod 862 includes and/or is coupled to three seals 865 which form and/or define a first fluid flow path 833 within the body 851 of the actuator 850 and a second fluid flow path 854 within the body 851 of the actuator 850.

The actuator rod 862 is configured to be moved or transitioned relative to the body 851 between a first position or configuration and a second position or configuration. For example, in some instances, a force can be exerted on the first end portion 863 of the actuator rod 862 to place the actuator rod 862 in its first position and/or configuration, as shown in FIG. 23. The force exerted on the first end portion 863 of the actuator rod 862 can come from any suitable source. For example, a user can create the force with his or her hand or finger, a syringe, a positive or negative pressure source, and/or any other external energy source. When in the first position and/or configuration, the inlet 852 of the actuator 850 is in fluid communication with the first fluid flow path 833 and the outlet 853 of the actuator 850 is in fluid communication with the second fluid flow path 854. In some instances, a force can be exerted on the second end portion 864 of the actuator rod 862 to place the actuator rod 862 in its second position and/or configuration, as shown in FIG. 24. When in the second position and/or configuration, the inlet 852 and the outlet 853 of the actuator 850 are each in fluid communication with the second fluid flow path 854 while the first fluid flow path is sequestered, isolated, and/or otherwise not in fluid communication with the inlet 852 and the outlet 853. Although not shown, the first port 858 of the actuator 850 is in fluid communication with the first fluid flow path 833 and the second port 859 of the actuator 850 is in fluid communication with the second fluid flow path 854. As such, moving and/or transitioning the actuator rod 862 (or the actuator 850 in general) between the first position and the second position can be operable in selectively controlling a flow of fluid (e.g., bodily fluid) between the inlet 852 of the actuator 850 and the housing 830, or between the inlet 852 of the actuator 850 and the outlet 853 of the actuator 850, as described in further detail herein.

Figure 25:
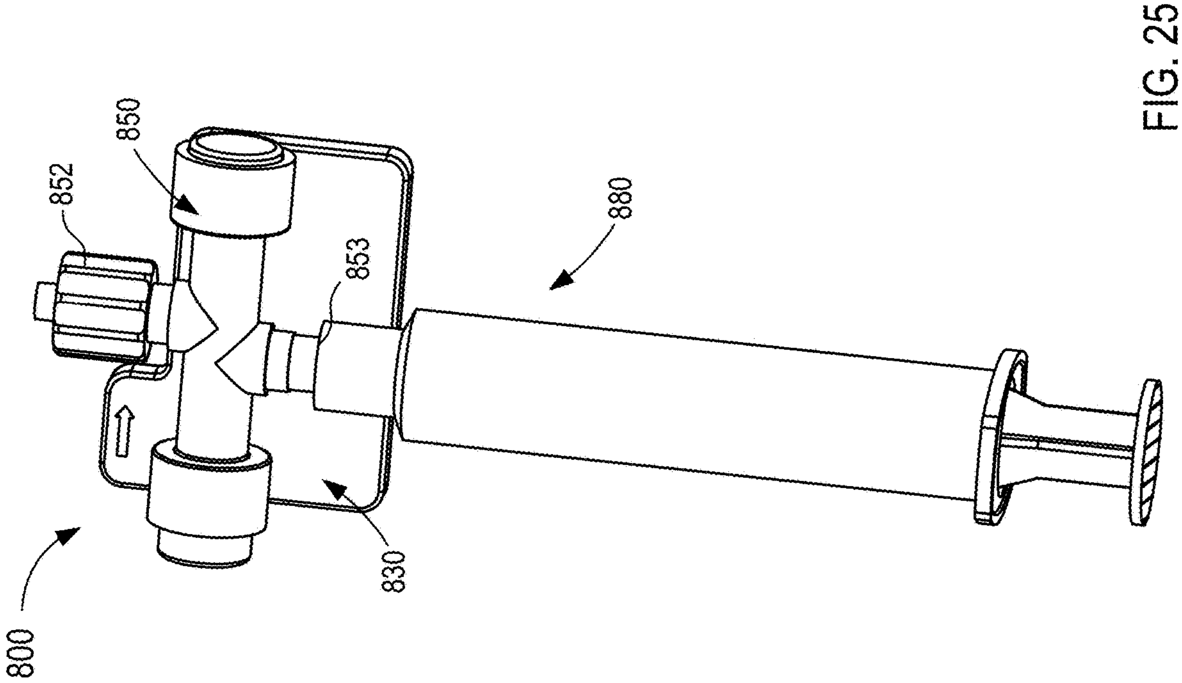

As described above, the device 800 can be used to procure a bodily fluid sample having reduced contamination from microbes such as, for example, dermally residing microbes, microbes external to the bodily fluid source, and/or the like. For example, in some instances, a user such as a doctor, physician, nurse, phlebotomist, technician, etc. can manipulate the device 800 to establish fluid communication between the inlet 852 and the bodily fluid source (e.g., a vein of a patient). Once the inlet 852 is placed in fluid communication with the bodily fluid source (e.g., the portion of the patient), the outlet 853 can be fluidically coupled to the fluid collection device 880. In the embodiment shown in FIGS. 19-25, the fluid collection device 880 can be, for example, a syringe (as shown in FIG. 25), and/or any other suitable container or device configured to define or produce a negative pressure or energy source.

As described in detail above with reference to, for example, the device 200, coupling the outlet 853 to the fluid collection device 880 selectively exposes at least a portion of the control device 800 to a negative pressure within and/or produced by the fluid collection device 880. More specifically, in the embodiment shown in FIGS. 19-25, coupling the outlet 853 to the fluid collection device 880 exposes the outlet 853 of the actuator 850 and the second fluid flow path 854 to the negative pressure within and/or produced by the fluid collection device 880. In addition, the second port 859 of the actuator 850 is in fluid communication with the second fluid flow path 854 and the second port 846 of the housing 830. The second port 846 of the housing 830, in turn, is in selective fluid communication with the sequestration chamber 834 via the flow controller 842 and the restricted flow path 832. For example, the device 800 and/or the flow controller 842 can be in a first operating state or mode in which the flow controller 842 allows a flow of gas (e.g., air) through the flow controller 842 while limiting and/or preventing a flow of liquid (e.g., bodily fluid such as blood) through the flow controller 842. Thus, coupling the fluid collection device 880 to the outlet 853 results in a negative pressure differential between the fluid collection device 880 (and/or any suitable negative pressure source) and the sequestration chamber 834.

As described above, the control device 800 can be in a first or initial state when the flow controller 842 and/or the actuator 850 are in a first state, position, configuration, etc. As such, the actuator rod 862 can be in its first position and/or configuration in which the first fluid flow path 833 is in fluid communication with the inlet 852. In addition, the first port 858 of the actuator 850 and the first port 845 of the housing 830 establish fluid communication between the sequestration chamber 834 and the first fluid flow path 833. Thus, the negative pressure within the fluid collection device 880 can result in a negative pressure (or negative pressure differential) within at least a portion of the sequestration chamber 834 that is operable in drawing an initial flow, portion, amount, or volume of bodily fluid from the inlet 852, through the first fluid flow path 833, and into the sequestration chamber 834 when the actuator 850 and/or control device 800 is in the first or initial state (e.g., when the actuator rod 862 is in its first state, position, and/or configuration). In some instances, the arrangement of the flow controller 842 and/or the restricted flow path 832 can be configured to restrict, limit, control, and/or otherwise modulate an amount or magnitude of negative pressure exerted on or through the sequestration chamber 834, as described in detail above with reference to the device 200.

The initial portion and/or amount of bodily fluid can be any suitable volume of bodily fluid, as described in detail above with reference to the control device 100. For example, in some instances, the initial volume can be associated with and/or at least partially based on an amount or volume of bodily fluid that is sufficient to fully wet or saturate the flow controller 842. In other words, in some embodiments, the initial volume of bodily fluid can be a volume sufficient to transition the flow controller 842 from a first state to a second state (e.g., a saturated or fully wetted state). In some embodiments, the flow controller 842 is placed in a sealed configuration when transitioned to the second state. That is to say, saturating and/or fully wetting the flow controller 842 (e.g., the semi-permeable material) places the flow controller 842 in a sealed configuration in which the flow controller 842 substantially prevents a flow of a liquid and a gas therethrough. Thus, transitioning the flow controller 842 to the second state sequesters, blocks, isolates, separates, segregates, and/or otherwise prevents flow through the flow controller 842 between the restricted flow path 832 and the sequestration chamber 834.

After the initial volume of bodily fluid is transferred and/or diverted into the sequestration chamber 834, the control device 800 and/or the actuator 850 can be transitioned to its second state or operating mode to sequester, segregate, retain, contain, isolate, etc. the initial volume in the sequestration chamber 834. For example, the actuator 850 can be actuated to transition from its first state to its second state, for example, by exerting a force on the second end portion 864 of the actuator rod 862. As such, the actuator rod 862 is moved and/or transitioned to its second state, position, and/or configuration in which the first fluid flow path 833 is sequestered and/or isolated from the inlet 852. With the flow controller 842 in the sealed configuration in response to the initial volume of bodily fluid being disposed in the sequestration chamber 834 and with the initial fluid flow path 833 sequestered and/or isolated from the inlet 852, the initial volume of bodily fluid is sequestered in the sequestration chamber 834. As described in detail above, in some instances, contaminants such as, for example, dermally residing microbes or the like dislodged during the venipuncture event, can be entrained and/or included in the initial volume of the bodily fluid and thus, are sequestered in the sequestration chamber 834 when the initial volume is sequestered therein.

As shown in FIG. 24, moving and/or transitioning the control device 800 and/or the actuator 850 to its second state or configuration establishes fluid communication between the inlet 852 and the outlet 853 via the second fluid flow path 854. As such, the negative pressure otherwise exerted on or through the sequestration chamber 834 is now exerted on or through the fluid flow path 854. In response, bodily fluid can flow from the inlet 852, through the fluid flow path 854, through the outlet 853, and into the fluid collection device 880. Thus, as described above, sequestering the initial volume of bodily fluid in the sequestration chamber 834 prior to collecting or procuring one or more sample volumes of bodily fluid reduces and/or substantially eliminates an amount of contaminants in the one or more sample volumes. Moreover, in some embodiments, the arrangement of the control device 800 can be such that the control device 800 cannot transition to the second state prior to collecting and sequestering the initial volume in the sequestration chamber 834, thereby reducing the likelihood of contaminants being transferred to the fluid collection device 880.

In some instances, it may be desirable to isolate the negative pressure source (e.g., the fluid collection device 880 from the inlet 853 such as, for example, if it is desirable to collect multiple samples of bodily fluid using multiple fluid collection device 880 (e.g., syringes). For example, in some instances, after filling the fluid collection device 880 the user can engage the actuator 850 and exert a force on the first end portion 863 of the actuator rod 862 to move and/or transition the actuator rod 862 from its second position and/or configuration toward its first position and/or configuration. As such, the second fluid flow path 854 no longer places the inlet 852 in fluid communication with the outlet 853. Moreover, the flow controller 842 can remain in the sealed state or configuration (e.g., fully saturated, wetted, and/or otherwise preventing flow therethrough) such that the outlet 853 is substantially sequestered or isolated from the rest of the control device 800. In some instances, the user can then remove the filled fluid collection device 880 (e.g., syringe) and can couple a new fluid collection device 880 (e.g., syringe) to the outlet 853. With the new fluid collection device 880 coupled to the outlet 853, the user can, for example, exert a force on the second end portion 864 of the actuator rod 862 to move and/or transition the actuator rod 862 back to its second position, state, and/or configuration, as described above.

Figure 26:
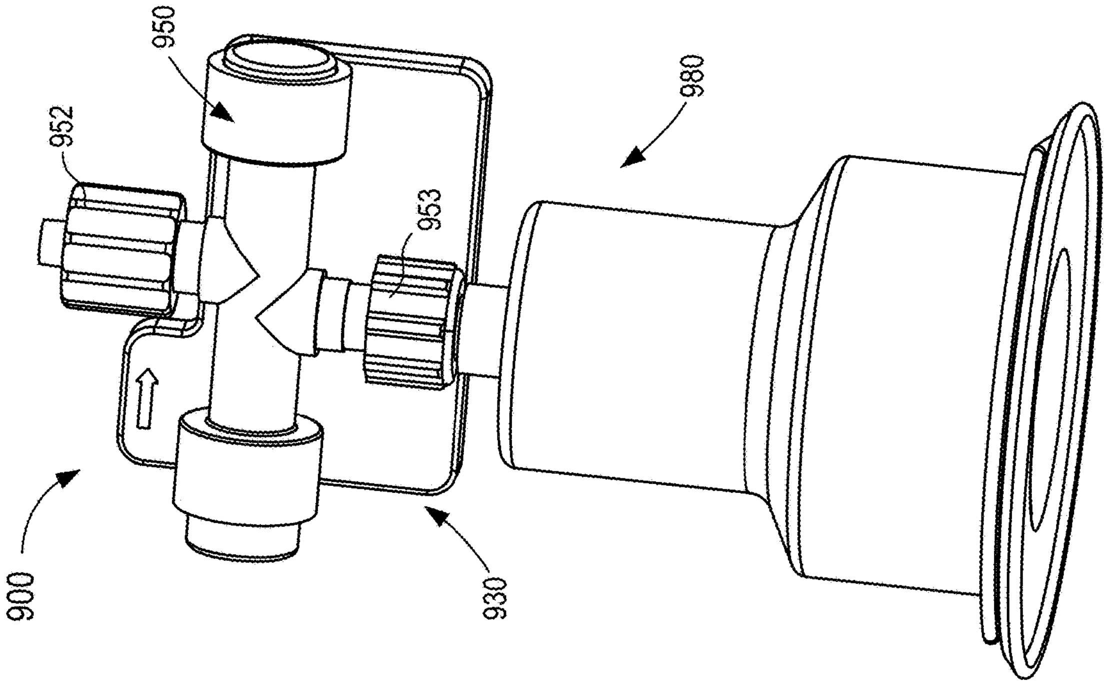
FIGS. 26-28 are each a perspective view of a fluid control device according to different embodiments.

While the fluid collection device 880 coupled to the device 800 is shown in FIG. 25 as being a syringe, in other embodiments, a control device can be physically and/or fluidically coupled to any suitable collection device. For example, FIG. 26 illustrates a fluid control device 900. As described above with reference to the control device 800, the fluid control device 900 includes a housing 930 and an actuator 950, which can be arranged, for example, in a modular configuration or the like. The actuator 950 includes an inlet 952 configured to be placed in fluid communication with a bodily fluid source and an outlet 953 configured to be coupled to a fluid collection device 980. In the embodiment shown in FIG. 26, the fluid collection device 980 is a transfer adapter configured to be coupled to one or more reservoirs such as, for example, an evacuated container, a sample bottle, a culture bottle, etc. In such embodiments, the reservoir can be sealed prior to being coupled to the transfer adapter (i.e., the fluid collection device 980) and once coupled the seal can be punctured, displaced, deformed, and/or otherwise unsealed to expose the outlet 953 to the negative pressure within the reservoir. Thus, the fluid control device 900 can function in a substantially similar manner to the control device 800 described above with reference to FIGS. 19-25.

While the fluid control device 800 is shown as including the actuator rod 862 that includes the first end portion 863 and the second portion 864 on which a force can be exerted to transition the device 800 between its first and second configurations, states, and/or positions, in other embodiments, a control device can include an actuator having any suitable configuration. For example, the fluid control device 900 includes an actuator rod 962 having only a single end portion that extends beyond the body 951 of the actuator 950, as shown in FIG. 26. In such embodiments, the device 900 can be used to fill a fluid collection device such as, for example, a sample reservoir, container, bottle, etc. and if it is desirable for more than one sample to be collected, the user can, for example, decouple the inlet 952 from a lumen-containing device and/or any suitable device otherwise placing the inlet 952 in fluid communication with the bodily fluid source. Once decoupled, the user can couple the inlet of a new control device 900 to the lumen-containing device and/or the like and can collect one or more additional samples in a manner similar to that described above with reference to the control device 800.

Figure 27:
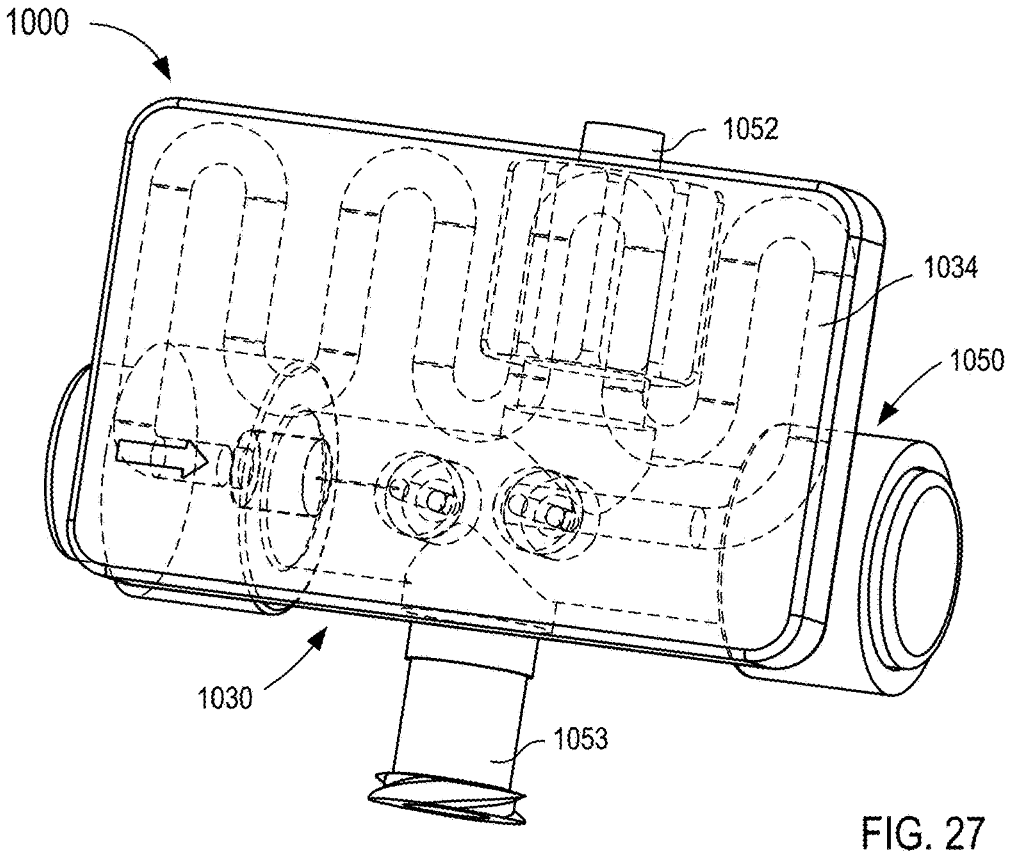

As described above, some fluid control device described herein can be and/or can have a modular configuration in which one or more components can be coupled to collectively form a fluid control device having a desired set of characteristics or the like. For example, the fluid control device 800 shown in FIGS. 19-25 includes the housing 830 and the actuator 850 in one modular arrangement. It should be understood, however, that a control device can have any suitable modular arrangement. For example, FIG. 27 illustrates a modular fluid control device 1000 according to an embodiment. The fluid control device (also referred to herein as "device") includes a housing 1030 forming and/or defining a sequestration chamber 1034, and an actuator 1050 forming and/or having an inlet 1052 and an outlet 1053. The device 1000 can be substantially similar to the control device 800 described in detail above but can be arranged such that housing 1030 is disposed in different position and/or orientation relative to the actuator 1050. In some embodiments, varying the arrangement may, for example, enhance usability, visibility, and/or the like and/or may otherwise allow for a more compact design.

Figure 28:
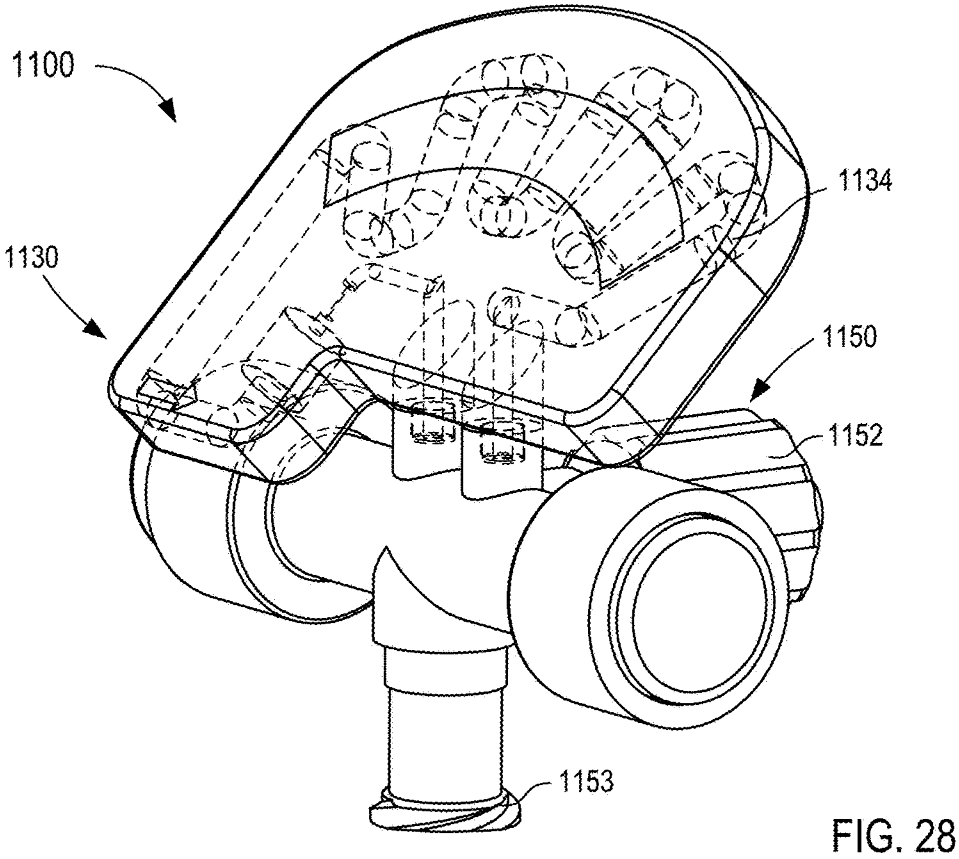

As another example, FIG. 28 illustrates a modular fluid control device 1100 according to an embodiment. The fluid control device (also referred to herein as "device") includes a housing 1130 forming and/or defining a sequestration chamber 1134, and an actuator 1150 forming and/or having an inlet 1152 and an outlet 1153. The device 1100 can be substantially similar to the control device 800 described in detail above but can be arranged such that housing 1130 is disposed in different position and/or orientation relative to the actuator 1150. Moreover, as shown in FIG. 28, the actuator 1150 can be arranged such that the inlet 1152 and the outlet 1153 are disposed in substantially perpendicular positions relative to one another. As described above, in some embodiments, varying the arrangement may, for example, enhance usability, visibility, and/or the like and/or may otherwise allow for a more compact design. While examples of modular fluid control devices are shown herein, it should be understood that such embodiments are presented by way of example and not limitation. Thus, while specific arrangements and/or orientations may be described herein, the devices and/or concepts described herein are not intended to be limited to those shown herein.

While the housings 230, 330, 830, 930, 1030, and 1130 have been shown and described herein as including and/or defining a sequestration chamber that is arranged in a serpentine-like configuration, in other embodiments, a housing and/or any other suitable portion of a control device can include and/or can define a sequestration chamber having any suitable configuration. For example, FIGS. 29-34 illustrate a fluid control device 1200 according to an embodiment. The fluid control device 1200 can be similar in at least form and/or function to the fluid control devices described herein. More specifically, portions of the fluid control device 1200 can be similar to and/or substantially the same as corresponding portions of the fluid control devices 200, 300, 800, 900, 1000, and/or 1100 described above. Accordingly, such portions of the fluid control device 1200 are not described in further detail herein.

The fluid control device 1200 (also referred to herein as "control device" or "device") includes a housing 1230 and an actuator 1250. As described above with reference to the control device 800, the control device 1200 can be arranged in a modular configuration such that the housing 1230 and the actuator 1250 can be physically and fluidically coupled to form the control device 1200. In other embodiments, the control device 1200 need not be modular. That is to say, in some embodiments, the control device 1200 can be assembled during manufacturing and delivered to a supplier and/or end user as an assembled device. In other embodiments, the control device can be monolithically formed and/or coupled to a fluid collection device in any suitable manner, as described in detail above.

The housing 1230 of the control device 1200 can be any suitable shape, size, and/or configuration. For example, in some embodiments, the housing 1230 can be substantially similar in at least form and/or function to the housing 830 described in detail above. Accordingly, such similar portions of the housing 1230 are identified below but may not be described in further detail herein.

Figure 29:
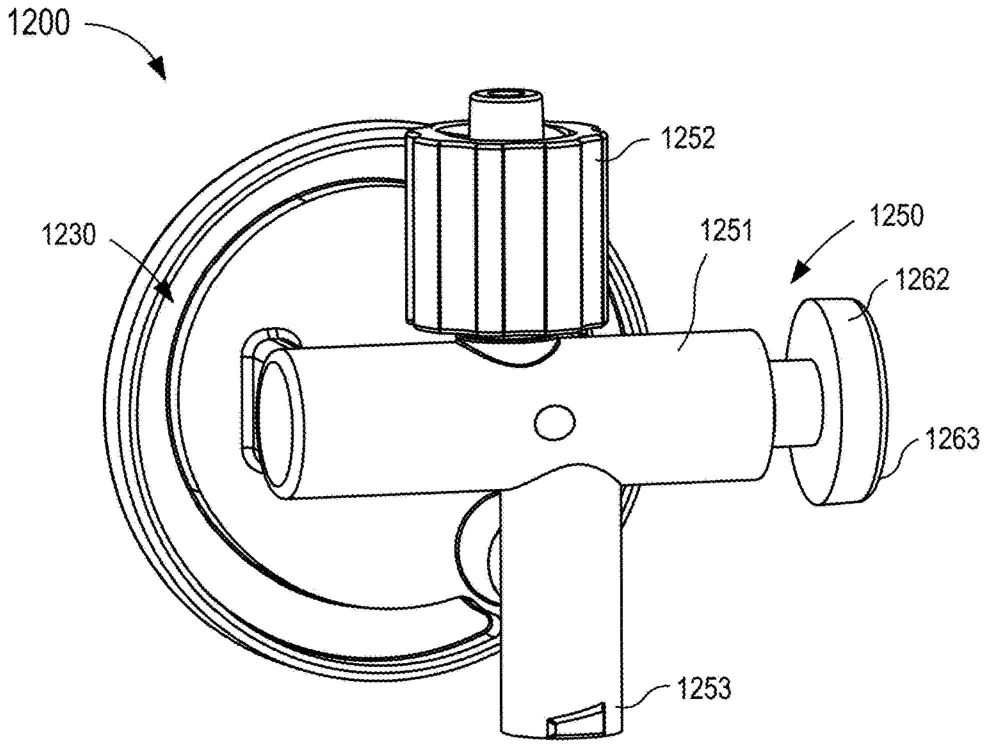
FIGS. 29-34 are various views of a fluid control device according to an embodiment.
Figure 30:
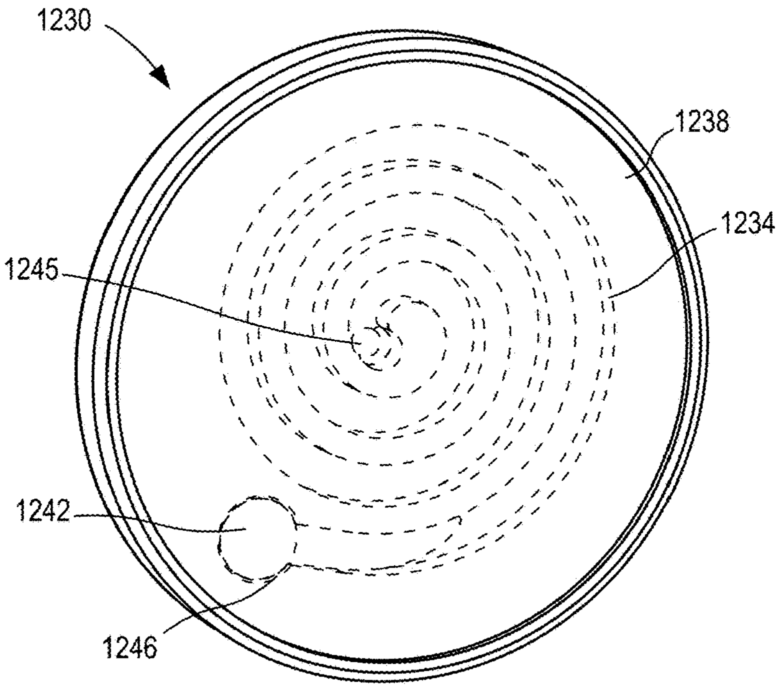
Figure 31:
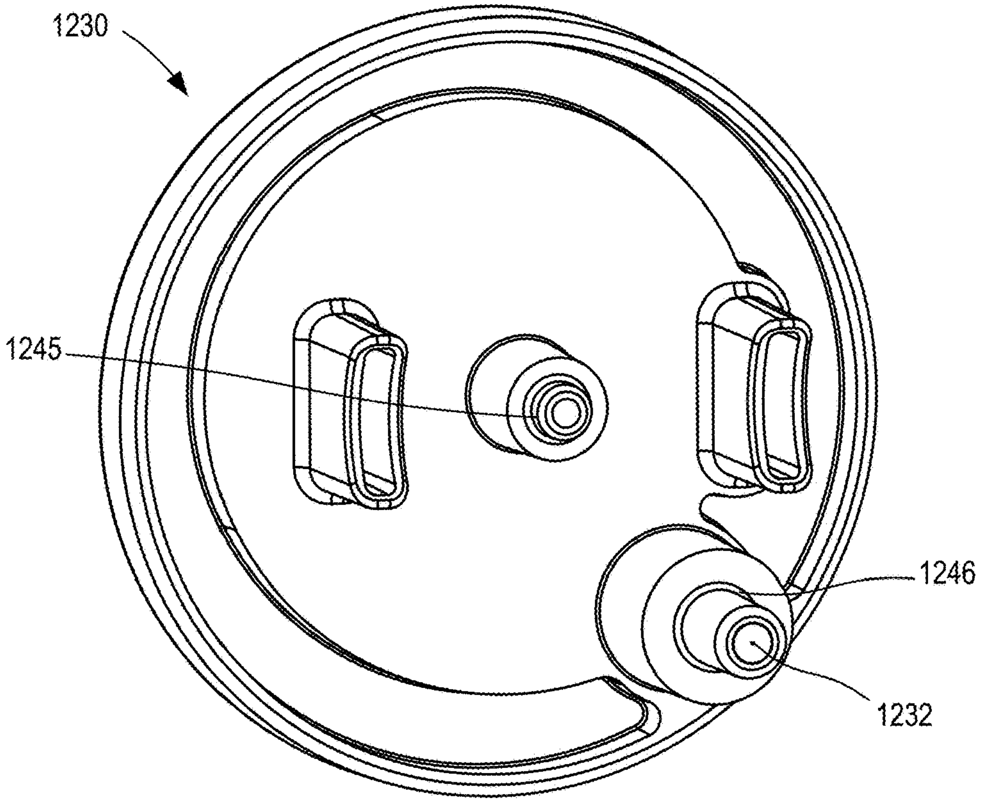

As shown in FIGS. 29-31, the housing 1230 forms and/or defines a sequestration chamber 1234 that is in selective fluid communication with a first port 1245 and a second port 1246. The second port 1246 is configured to receive, include, and/or define a flow controller 1242 (see e.g., FIG. 30) and a restricted flow path 1232 (see e.g., FIG. 31). Although shown as including the restricted flow path 1232, in other embodiments, a housing need not include or receive a restricted flow path (e.g., when excessive negative pressure being applied to the sequestration chamber 1234 is unlikely or otherwise not intended such as when a fluid collection device is a syringe or the like). The first port 1245 and the second port 1246 are configured to be at least fluidically coupled to a portion of the actuator 1250 to allow for selective fluid flow between the housing 1230 and the actuator 1250. As described in further detail herein, the sequestration chamber 1234 is configured (1) to receive a selective flow and/or volume of bodily fluid from a portion of the actuator 1250 via the first port 1245, and (2) to sequester (e.g., separate, segregate, contain, retain, isolate, etc.) the flow and/or volume of bodily fluid (e.g., an initial or first flow and/or volume of bodily fluid or any portion thereof) within the sequestration chamber 1234.

The sequestration chamber 1234 can have any suitable shape, size, and/or configuration. For example, in some embodiments, the sequestration chamber 1234 can have any suitable size, volume, and/or fluid capacity such as, for example, those described above with reference to the sequestration chamber 134. In the embodiment shown in FIGS. 29-34, the sequestration chamber 1234 can be, for example, a fluid flow path that extends through and/or that is defined by at least a portion of the housing 1230. In some embodiments, the sequestration chamber 1234 can be substantially similar in at least form and/or function to the sequestration chamber 834 described above with reference to FIGS. 19-25. The sequestration chamber 1234 and/or the housing 1230 can differ from the sequestration chamber 834 and/or the housing 830 by being arranged in a spiral configuration with the first port 1245 being in fluid communication with, for example, an inner portion of the spiraled sequestration chamber 1234 and the second port 1246 being in fluid communication with, for example, an outer portion of the spiraled sequestration chamber, as shown in FIG. 30. In some embodiments, the sequestration chamber 1234 can be, for example, a channel or the like formed in a portion of the housing 1230.

In some embodiments, the channel forming at least a portion of the sequestration chamber 1234 can have a relatively small cross-sectional shape and/or size that can reduce and/or substantially prevent a mixing of an initial volume of bodily fluid drawn into the sequestration chamber 1234 (channel) and a volume of air within the sequestration chamber 1234 (e.g., a volume of air that has not been vented or purged, as described in further detail herein). For example, in some instances, the relatively small cross-sectional shape and/or size of the sequestration chamber 1234 (channel), a surface tension associated with the bodily fluid flowing into the sequestration chamber 1234, and a contact angle between a surface of the housing 1230 forming the sequestration chamber 1234 and the bodily fluid flowing into the sequestration chamber 1234 can collectively limit and/or substantially prevent a mixing of the bodily fluid and a volume of air within the sequestration chamber 1234.

As shown in FIG. 30, the housing 1230 can include and/or can be coupled to a cover 1238 configured to enclose the channel, thereby forming the sequestration chamber 1234. The cover 1238 can be coupled to the housing 1230 in any suitable manner (e.g., via a friction fit, snap fit, interference fit, an adhesive, one or more mechanical fasteners, laser welding, ultrasonic welding, plasma techniques, annealing, heat boding and/or any other suitable coupling means or combination thereof). In other embodiments, the cover 1238 is monolithically formed with and/or coupled to the housing 1230. Moreover, in some embodiments, the cover 1238 can be at least partially transparent to allow a user to visualize a flow of bodily fluid through the sequestration chamber 1234. In some embodiments, the arrangement of the housing 1230 and the cover 1238 can, for example, facilitate one or more manufacturing processes and/or can facilitate use of the control device 1200.

As shown in FIG. 30, the housing 1230 includes and/or defines a flow controller 1242 and a restricted flow path 1232. The flow controller 1242 can be, for example, a valve, membrane, diaphragm, restrictor, vent, a selectively permeable member, port, etc. configured to selectively control (at least in part) a flow of fluids into and/or out of the sequestration chamber 1234 and/or any other suitable portion of the housing 1230. For example, the flow controller 1242 can be a selectively permeable fluid barrier (e.g., a blood barrier) that includes and/or is formed of a porous material configured to selectively allow a flow of gas therethrough but to prevent a flow of a liquid therethrough. As such, the flow controller 1242 can be configured to vent and/or purge a volume of air within the sequestration chamber 1234 through the flow controller 1242 in response to a negative pressure differential within a portion of the control device 1200. Such a venting and/or purging of the volume of air within the sequestration chamber 1234 can result in a suction force and/or negative pressure differential being exerted and/or applied in or on the sequestration chamber 1234 that is operable to draw in the initial volume of bodily fluid. Moreover, the use of a selectively permeable fluid barrier can allow for the venting and/or purging of air without allowing a volume of bodily fluid to pass through the flow controller 1242. Accordingly, in some embodiments, the flow controller 1242 can be substantially similar to the flow controller 242 described in detail above with reference to FIGS. 2-5 and thus, is not described in further detail herein.

The actuator 1250 of the control device 1200 can be any suitable shape, size, and/or configuration. For example, in some embodiments, the actuator 1250 can be substantially similar in at least form and/or function to the actuator 850 described in detail above. Accordingly, such similar portions of the actuator 1250 are identified below but may not be described in further detail herein.

Figure 32:
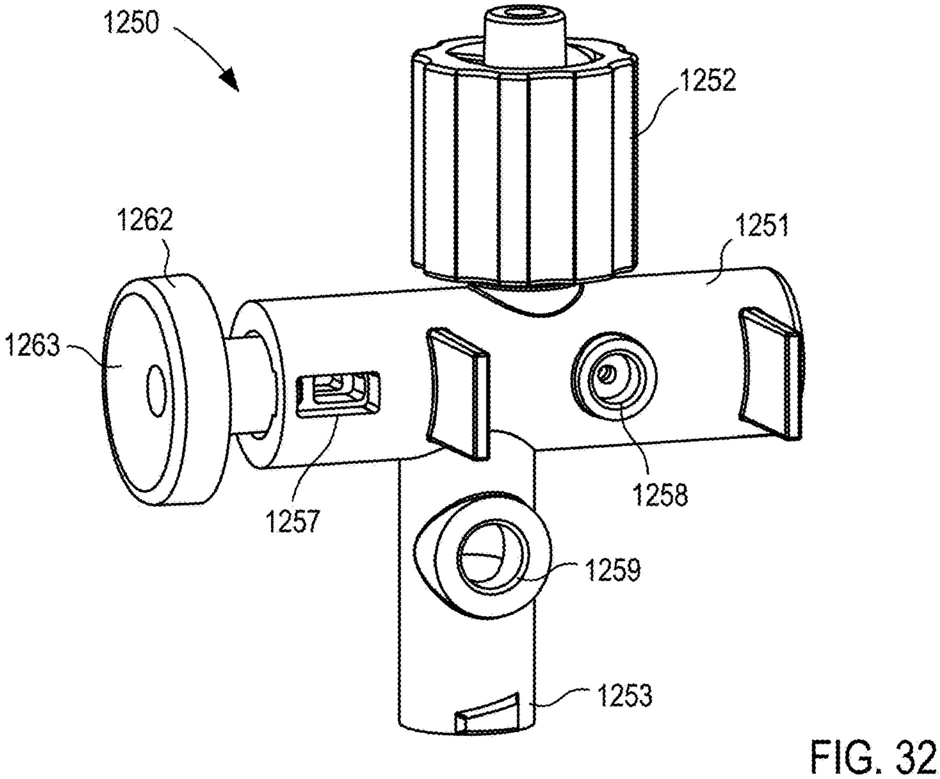
Figure 34:
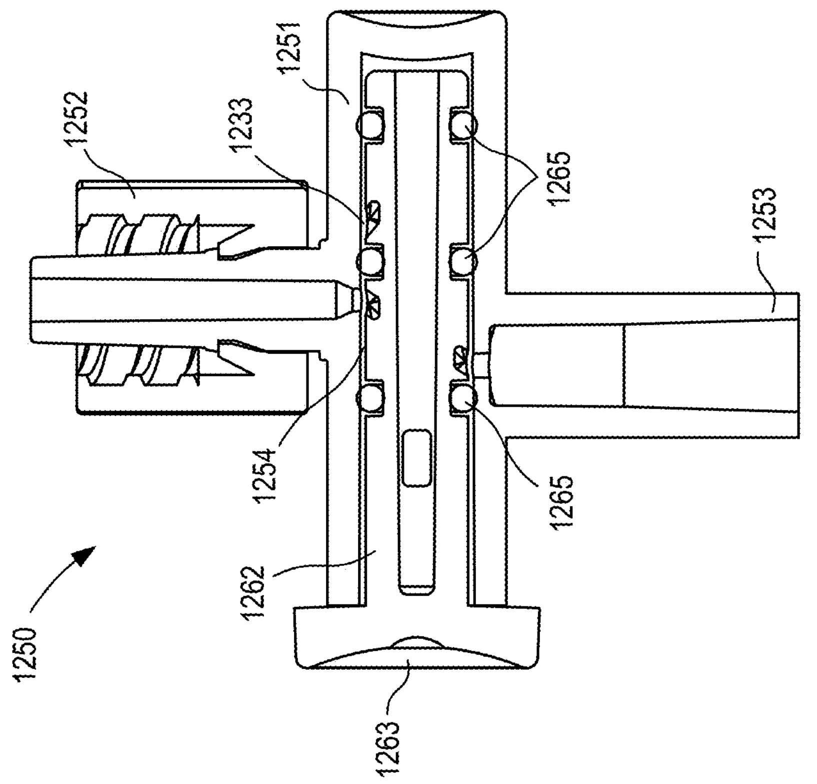
Figure 33:
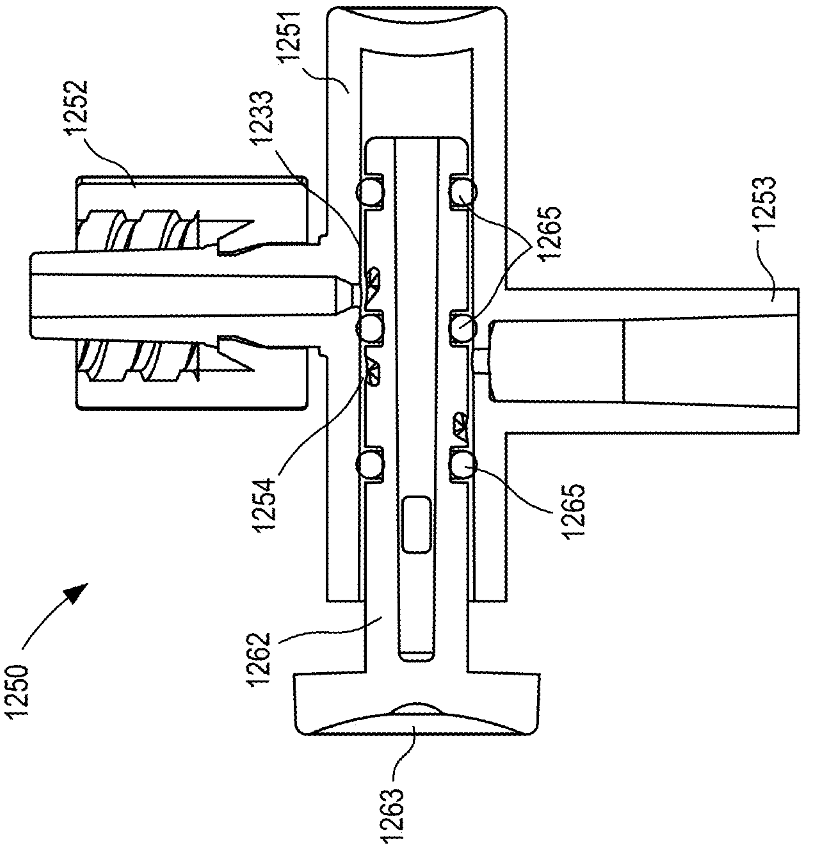

As shown in FIGS. 32-34, the actuator 1250 includes a body 1251 and an actuator rod 1262. The body 1251 of the actuator 1250 includes an inlet 1252 and an outlet 1253. The inlet 1252 and the outlet 1253 can be substantially similar in at least form and/or function to the inlet 852 and the outlet 853, respectively, described above with reference to FIGS. 19-25. Thus, the inlet 1252 is configured to be placed in fluid communication with a bodily fluid source to receive a flow of bodily fluid therefrom (e.g., via a lumen-containing device such as a needle, IV catheter, PICC line, or the like). The outlet 1253 is configured to be fluidically coupled to a fluid collection device (not shown in FIGS. 29-34) such as, for example, a sample reservoir, a syringe, and/or other intermediary bodily fluid transfer device, adapter, or vessel such as, for example, a transfer device similar to those described in the '510 publication. In some embodiments, such a transfer device can provide a negative pressure and/or can act as an external energy source to enable desired functionality and fluid flow path dynamics/characteristics of the control device 1200.

The body 1251 of the actuator 1250 includes and/or defines a first port 1258 and a second port 1259. The first port 1258 is in fluid communication with the inlet 1252 and the second port 1259 is in fluid communication with the outlet 1252. In addition, the first port 1258 and the second port 1259 are configured to be at least fluidically coupled to the first port 1245 and the second port 1246, respectively, of the housing 1230. In some embodiments, the arrangement of the ports 1258 and 1259 of the actuator 1250 and the ports 1245 and 1246 of the housing 1230 can allow for and/or otherwise can provide a means of physically coupling the housing 1230 to the actuator 1250 as well as fluidically coupling the housing 1230 to the actuator 1250. That is to say, in some embodiments, the arrangement of the ports 1258 and 1259 of the actuator 1250 and the ports 1245 and 1246 of the housing 1230 can allow for a modular configuration or arrangement as described above with reference to the control device 800. In other embodiments, the housing 1230 and/or actuator 1250 need not be modular.

In some embodiments, the body 1251 and the actuator rod 1262 collectively include and/or collectively form a lock configured to at least temporarily lock the actuator 1250. For example, in some embodiments, the body 1251 and the actuator rod 1262 can each define an opening 1257 in or through which a locking member can be disposed. In such embodiments, when the locking member (not shown in FIG. 32) is disposed in the openings 1257, the locking member can limit and/or substantially prevent the actuator rod 1262 from being moved relative to the body 1251. On the other hand, removing the locking member from the openings 1257 can allow the actuator rod 1262 to be moved relative to the body 1251. While described as forming a lock, in some embodiments, the body 1251 and the actuator rod 1262 collectively include and/or collectively form a feature and/or arrangement that can limit and/or substantially prevent the actuator rod 1262 from being pulled out of the body 1251. In such embodiments, the feature can be a snap, a lock, a catch, and/or any other suitable feature and/or arrangement.

As shown in FIGS. 33 and 34, a portion of the actuator rod 1262 includes and/or is coupled to a set of seals 1265. The seals 1265 can be, for example, o-rings, over-molded elastomeric material, raised protrusions, and/or the like. The arrangement of the actuator 1262 and the body 1251 of the actuator 1250 can be such that the seals 1265 form one or more fluid tight seals between the actuator rod 1262 and the inner surface of the body 1251, as described above with reference to the actuator 850. In the embodiment shown in FIGS. 33 and 34, the actuator rod 1262 includes and/or is coupled to three seals 1265 which form and/or define a first fluid flow path 1233 within the body 1251 of the actuator 1250 and a second fluid flow path 1254 within the body 1251 of the actuator 1250. In other embodiments, any number of seals may be used to achieve desired performance.

As described above with reference to the device 800, the device 1200 can be used to procure a bodily fluid sample having reduced contamination from microbes such as, for example, dermally residing microbes, microbes external to the bodily fluid source, and/or the like. For example, the actuator rod 1262 is configured to be moved or transitioned relative to the body 1251 between a first position or configuration and a second position or configuration. In some embodiments, the transition of the actuator rod 1262 can be achieved by and/or can otherwise result from user interaction and manipulation of the actuator rod 1262, automatically in response to negative pressure and associated flow dynamics within the device 1200, and/or enacted by or in response to an external energy source which creates dynamics that result in the transitioning of the actuator rod 1262. As shown in FIG. 33, when in the first position and/or configuration, the inlet 1252 of the actuator 1250 is in fluid communication with the first fluid flow path 1233, which in turn, is in fluid communication with the first port 1258. The outlet 1253 of the actuator 1250 is in fluid communication with the second fluid flow path 1254, which in turn, is in fluid communication with the second port 1259. Thus, when in the actuator 1250 and/or actuator rod 1262 is in the first position and/or configuration (e.g., when the control device 1200 is in a first state or operating mode), the negative pressure within the fluid collection device (not shown in FIGS. 29-34) can result in a negative pressure (or negative pressure differential) within at least a portion of the sequestration chamber 1234 that is operable in drawing at least a portion of an initial flow, amount, or volume of bodily fluid from the inlet 1252, through the first fluid flow path 1233, and into the sequestration chamber 1234. Moreover, in some instances, the initial volume and/or flow of bodily fluid can be transferred into the sequestration chamber 1234 until, for example, the bodily fluid disposed within the sequestration chamber 1234 transitions the flow controller 1242 from an open or unsealed configuration or state (e.g., one in which a flow of gas or air can be drawn therethrough) to a sealed configuration or state (e.g., one in which a flow of gas and liquid cannot be drawn therethrough).

In some instances, a force can be exerted on the end portion 1263 of the actuator rod 1262 to place the actuator rod 1262 and/or actuator 1250 in its second position and/or configuration, as shown in FIG. 34. As described above, in some instances, prior to exerting the force on the end portion 1263 of the actuator rod 1262, the actuator 1250 may be transitioned from a locked configuration or state to an unlocked configuration or state. When the actuator rod 1262 and/or the actuator 1250 is placed in its second position and/or configuration (e.g., when the control device 1200 is transitioned to a second state or operating mode), the inlet 1252 and the outlet 1253 of the actuator 1250 are each in fluid communication with the second fluid flow path 1254 while the first fluid flow path 1233 is sequestered, isolated, and/or otherwise not in fluid communication with the inlet 1252 and the outlet 1253. As described in detail above, in some instances, contaminants such as, for example, dermally residing microbes or the like dislodged during the venipuncture event or throughout the bodily fluid collection process, can be entrained and/or included in the initial volume of the bodily fluid and thus, are sequestered in the sequestration chamber 1234 when the initial volume is sequestered therein. As such, the negative pressure otherwise exerted on or through the sequestration chamber 1234 is now exerted on or through the second fluid flow path 1254. In response, bodily fluid can flow from the inlet 1252, through the second fluid flow path 1254, through the outlet 1253, and into the fluid collection device coupled to the outlet 1253. Accordingly, the device 1200 can function in a manner substantially similar to that of the device 800 and thus, the function of the device 1200 is not described in further detail herein.

FIGS. 35-40 illustrate a fluid control device 1300 according to an embodiment. The fluid control device 1300 can be similar in at least form and/or function to the fluid control devices described herein. More specifically, portions of the fluid control device 1300 can be similar to and/or substantially the same as corresponding portions of the fluid control devices 200, 300, 800, 900, 1000, 1100, and/or 1200 described above. Accordingly, such portions of the fluid control device 1300 are not described in further detail herein.

The fluid control device 1300 (also referred to herein as "control device" or "device") includes a housing 1330 and an actuator 1350. As described above with reference to the control devices 800, the control device 1300 can be arranged in a modular configuration such that the housing 1330 and the actuator 1350 can be physically and fluidically coupled to form the control device 1300. In other embodiments, the control device 1300 need not be modular. That is to say, in some embodiments, the control device 1300 can be assembled during manufacturing and delivered to a supplier and/or end user as an assembled device. In other embodiments, the device 1300 can be monolithically formed and/or collectively formed with, for example, a fluid collection device, as described above.

Figure 35:
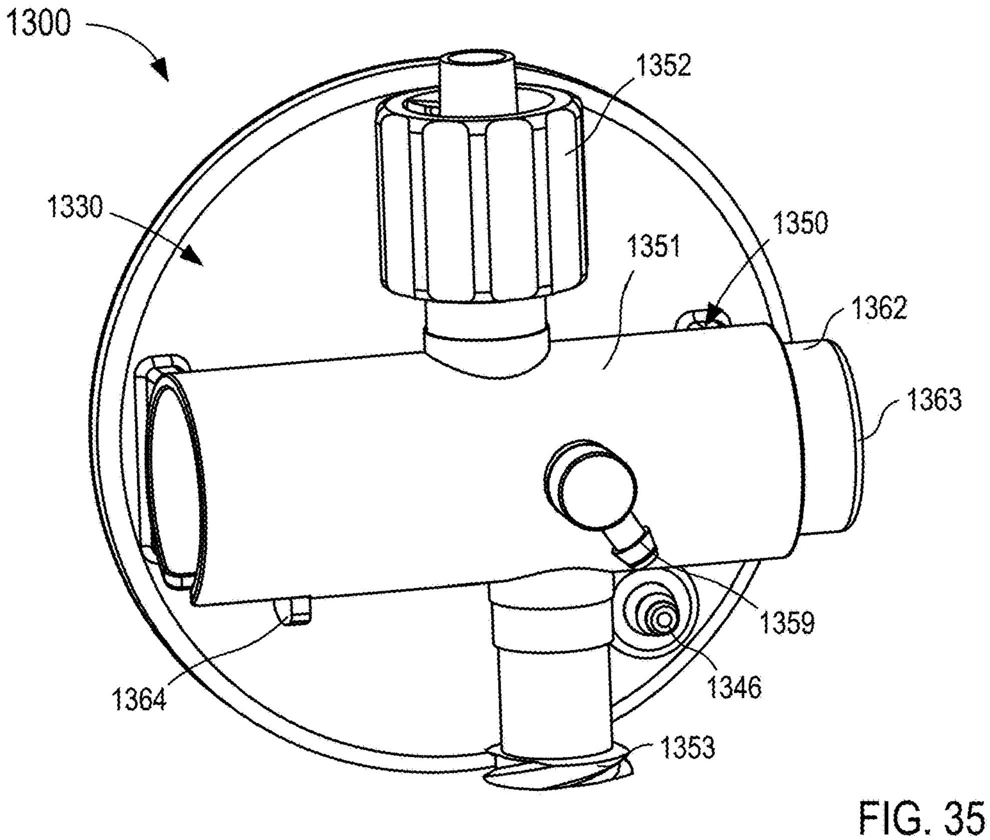
FIGS. 35-40 are various views of a fluid control device according to an embodiment.
Figure 36:
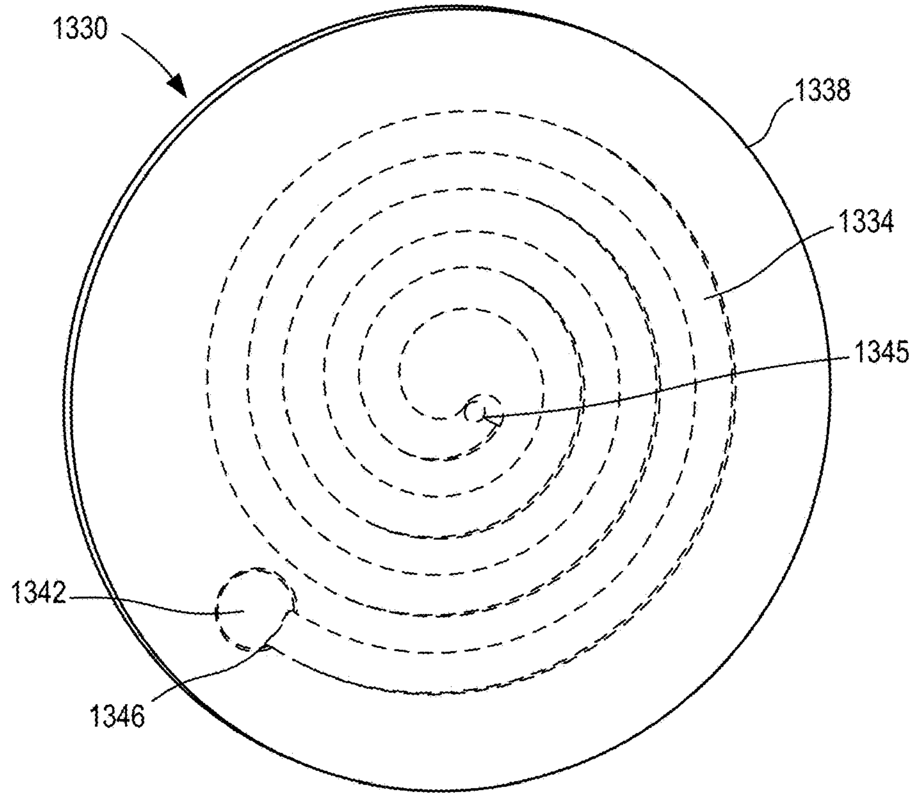
Figure 37:
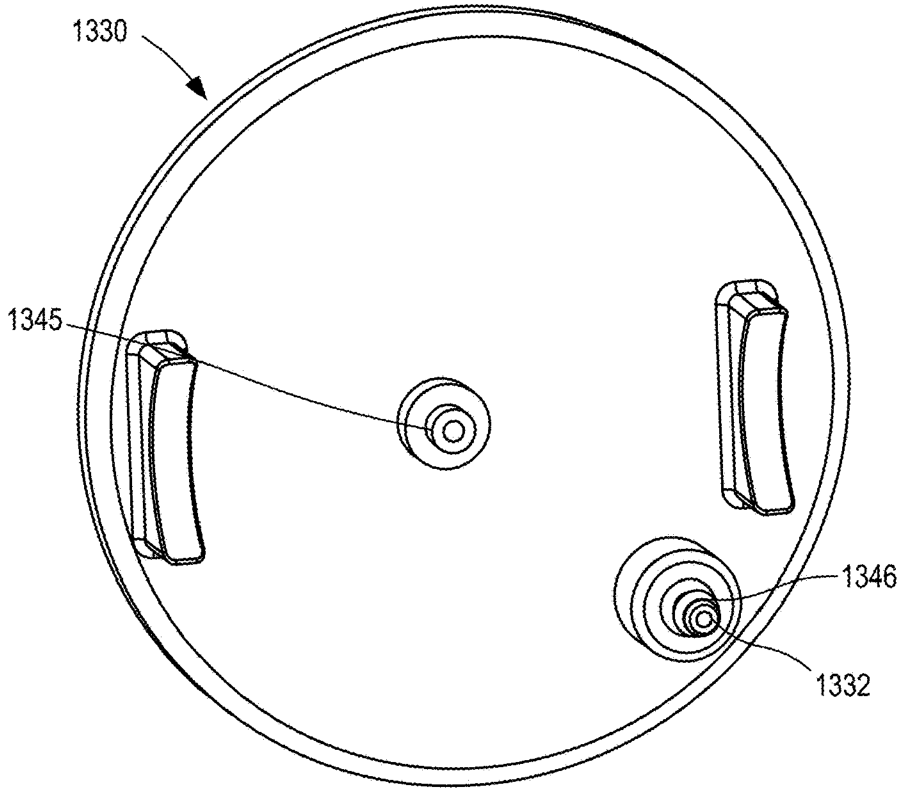

The housing 1330 of the control device 1300 can be any suitable shape, size, and/or configuration. As shown in FIGS. 35-37, the housing 1330 forms and/or defines a sequestration chamber 1334 that is in selective fluid communication with a first port 1345 and a second port 1346. The second port 1346 is configured to receive, include, and/or define a flow controller 1342 (see e.g., FIG. 36) and a restricted flow path 1332 (see e.g., FIG. 37). The first port 1345 and the second port 1346 are configured to be at least fluidically coupled to a portion of the actuator 1350 to allow for selective fluid flow between the housing 1330 and the actuator 1350. As described in further detail herein, the sequestration chamber 1334 is configured (1) to receive a selective flow and/or volume of bodily fluid from a portion of the actuator 1350 via the first port 1345, and (2) to sequester (e.g., separate, segregate, contain, retain, isolate, etc.) the flow and/or volume of bodily fluid (e.g., at least a portion of an initial or first flow and/or volume of bodily fluid) within the sequestration chamber 1334. The sequestration chamber 1334 can have any suitable shape, size, and/or configuration. For example, in some embodiments, the sequestration chamber 1334 can be, for example, a channel or the like formed in a portion of the housing 1330 and the housing 1330 can include and/or can be coupled to a cover 1338 configured to enclose the channel, thereby forming the sequestration chamber 1334. In some embodiments, the housing 1330 can be substantially similar in at least form and/or function to the housing 1230 described in detail above with reference to FIGS. 29-34. Accordingly, the housing 1330 is not described in further detail herein.

The actuator 1350 of the control device 1300 can be any suitable shape, size, and/or configuration. For example, in some embodiments, the actuator 1350 can be substantially similar in at least form and/or function to the actuators 850 and/or 1250 described in detail above. Accordingly, such similar portions of the actuator 1350 are identified below but may not be described in further detail herein.

Figure 38:
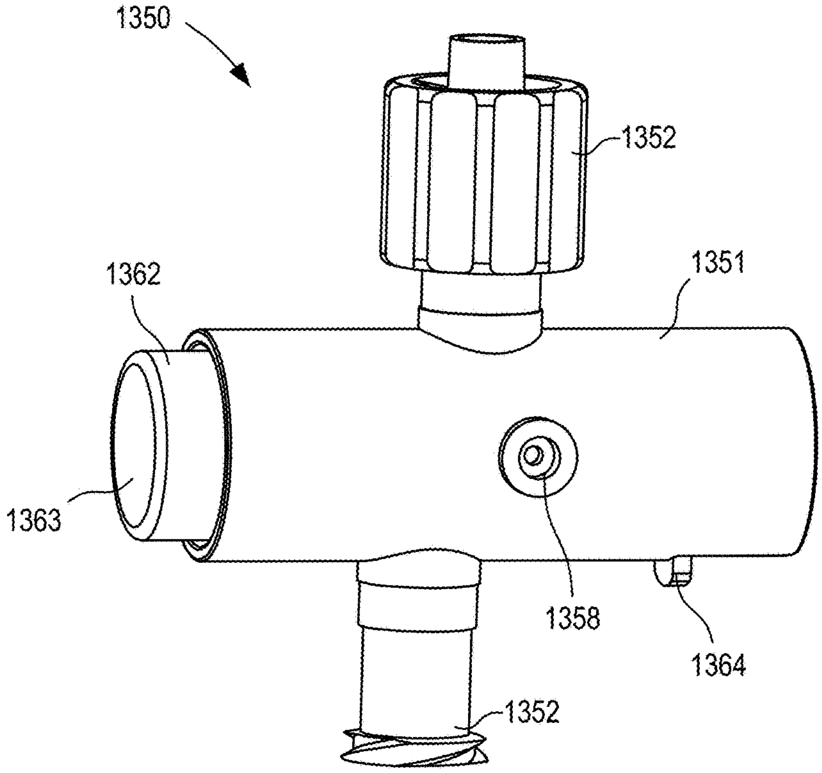
Figure 40:
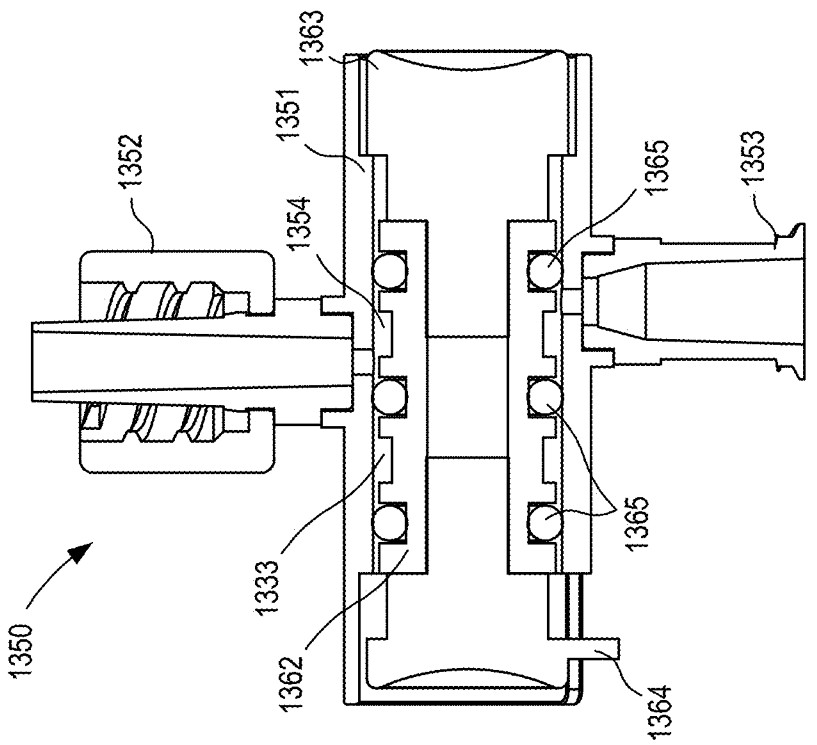
Figure 39:
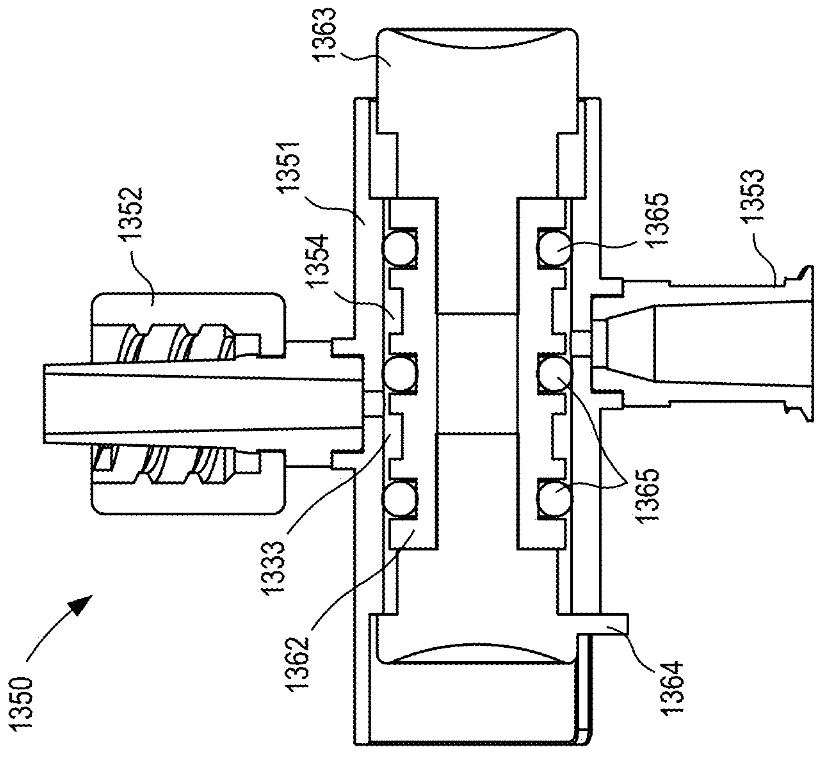
Figure 41:
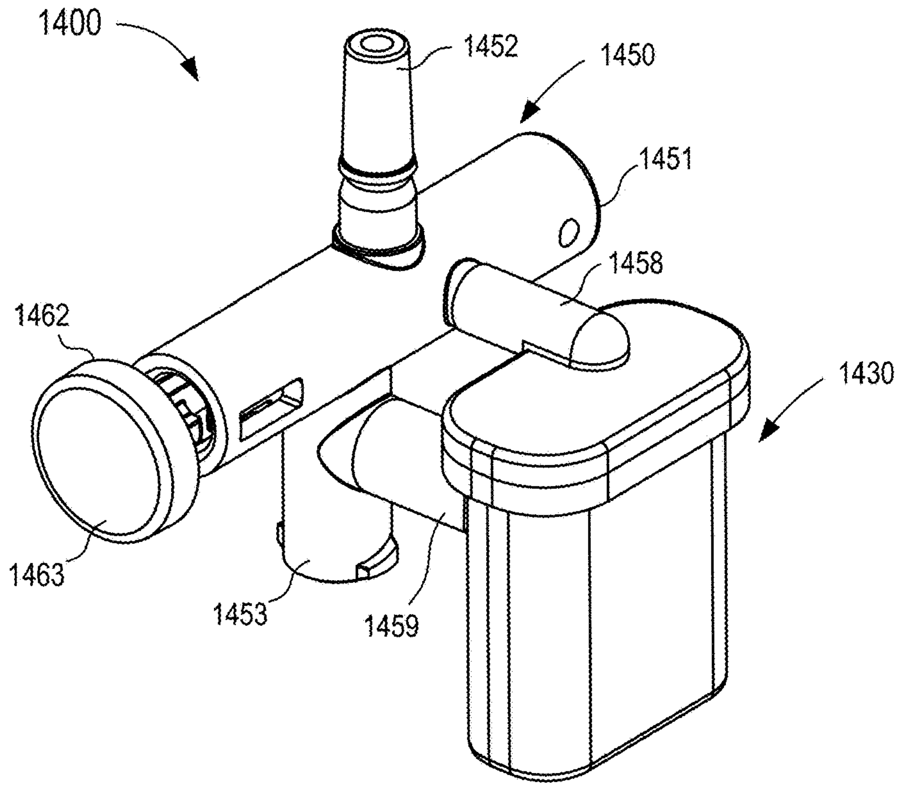
FIGS. 41-44 are various views of a fluid control device according to an embodiment.
Figure 42:
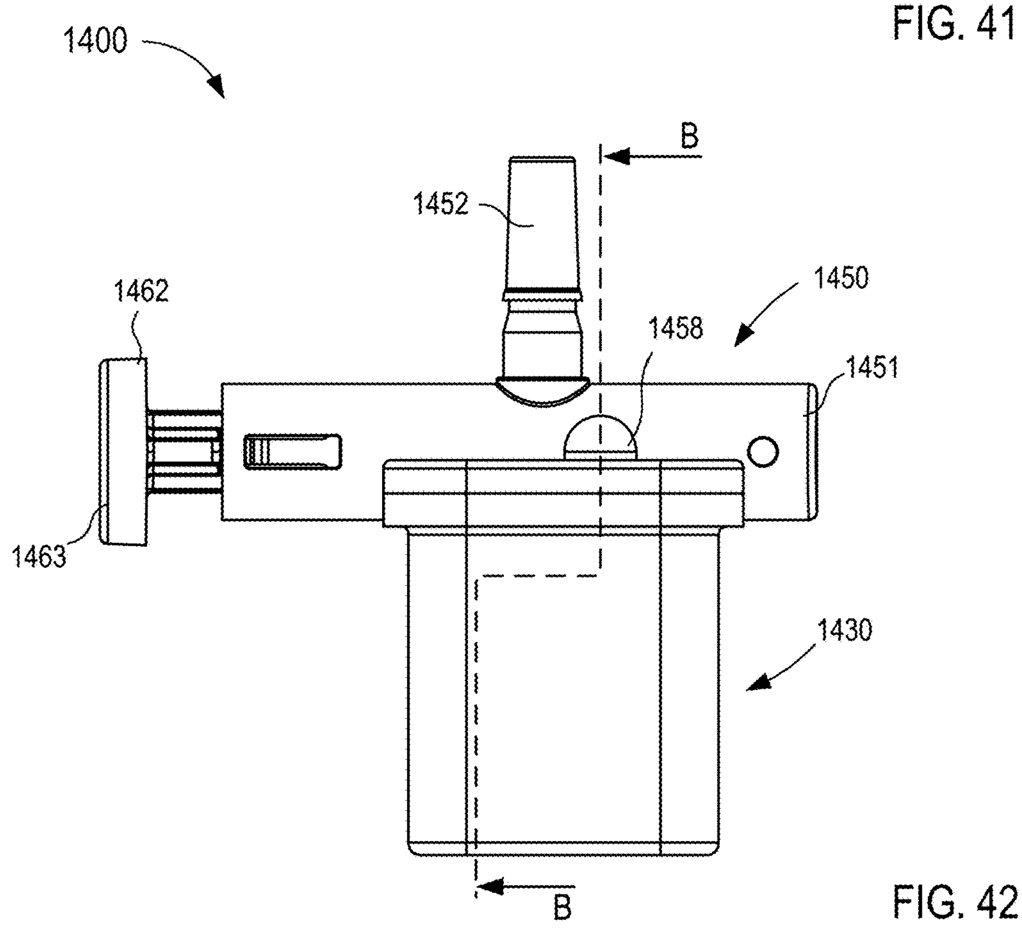

As shown in FIGS. 38-40, the actuator 1350 includes a body 1351 and an actuator rod 1362. The body 1351 of the actuator 1350 includes an inlet 1352 and an outlet 1353. The inlet 1352 and the outlet 1353 can be substantially similar in at least form and/or function to the inlet 852 and the outlet 853, respectively, described above with reference to FIGS. 19-25. Thus, the inlet 1352 is configured to be placed in fluid communication with a bodily fluid source to receive a flow of bodily fluid therefrom (e.g., via a lumen-containing device such as a needle, IV catheter, surgical tubing, other standard bodily-fluid transfer device, PICC line, or the like). The outlet 1353 is configured to be fluidically coupled to a fluid collection device (not shown in FIGS. 35-40) such as, for example, a sample reservoir, a syringe, and/or other intermediary bodily fluid transfer device, adapter, or vessel such as, for example, a transfer device similar to those described in the '510 publication.

The body 1351 of the actuator 1350 includes and/or defines a first port 1358 and a second port 1359. The first port 1358 is in fluid communication with the inlet 1352 and the second port 1359 is in fluid communication with the outlet 1353. In addition, the first port 1358 and the second port 1359 are configured to be at least fluidically coupled to the first port 1345 and the second port 1346, respectively, of the housing 1330. In some embodiments, the arrangement of the ports 1358 and 1359 of the actuator 1350 and the ports 1345 and 1346 of the housing 1330 can allow for and/or otherwise can provide a means of physically coupling the housing 1330 to the actuator 1350 as well as fluidically coupling the housing 1330 to the actuator 1350. That is to say, in some embodiments, the arrangement of the ports 1358 and 1359 of the actuator 1350 and the ports 1345 and 1346 of the housing 1330 can allow for a modular configuration or arrangement as described above with reference to the control device 800. In other embodiments, the housing 1330 and/or actuator 1350 need not be modular.

As shown in FIGS. 39 and 40, a portion of the actuator rod 1362 includes and/or is coupled to a set of seals 1365. The seals 1365 can be, for example, o-rings, elastomeric material, silicone or any other suitable material or configuration as described above with reference to the seals 1265. The arrangement of the actuator 1362 and the body 1351 of the actuator 1350 can be such that the seals 1365 form one or more fluid tight seals between the actuator rod 1362 and the inner surface of the body 1351, as described above with reference to the actuator 850. In the embodiment shown in FIGS. 33 and 34, the actuator rod 1362 includes and/or is coupled to three seals 1365 which form and/or define a first fluid flow path 1333 within the body 1351 of the actuator 1350 and a second fluid flow path 1354 within the body 1351 of the actuator 1350.

As described above with reference to the device 800, the device 1300 can be used to procure a bodily fluid sample having reduced contamination from microbes such as, for example, dermally residing microbes, microbes external to the bodily fluid source, and/or the like. For example, the actuator rod 1362 is configured to be moved or transitioned relative to the body 1351 between a first position or configuration and a second position or configuration. As shown in FIG. 39, when in the first position and/or configuration, the inlet 1352 of the actuator 1350 is in fluid communication with the first fluid flow path 1333, which in turn, is in fluid communication with the first port 1358. The outlet 1353 of the actuator 1350 is in fluid communication with the second fluid flow path 1354, which in turn, is in fluid communication with the second port 1359. Thus, when in the actuator 1350 and/or actuator rod 1362 is in the first position and/or configuration (e.g., when the control device 1300 is in a first state or operating mode), the negative pressure within the fluid collection device (not shown in FIGS. 35-40) can result in a negative pressure (or negative pressure differential) within at least a portion of the sequestration chamber 1334 that is operable in drawing at least a portion of an initial flow, amount, or volume of bodily fluid from the inlet 1352, through the first fluid flow path 1333, and into the sequestration chamber 1334. Moreover, in some instances, the initial volume and/or flow of bodily fluid can be transferred into the sequestration chamber 1334 until, for example, the bodily fluid disposed within the sequestration chamber 1334 transitions the flow controller 1342 from an open or unsealed configuration or state (e.g., one in which a flow of gas or air can be drawn therethrough) to a sealed configuration or state (e.g., one in which a flow of gas and liquid cannot be drawn therethrough).

In some instances, a force can be exerted on a first end portion 1363 of the actuator rod 1362 to place the actuator rod 1362 and/or actuator 1350 in its second position, state, operating mode, and/or configuration, as shown in FIG. 35. As described above, in some instances, prior to exerting the force on the first end portion 1363 of the actuator rod 1362, the actuator 1350 may be transitioned from a locked configuration or state to an unlocked configuration or state. In some embodiments, the transition of the actuator rod 1362 can be achieved by and/or can otherwise result from user interaction and manipulation of the actuator rod 1362, automatically in response to negative pressure and associated flow dynamics within the device 1300, and/or enacted by or in response to an external energy source which creates dynamics that result in the transitioning of the actuator rod 1362.

When the actuator rod 1362 and/or the actuator 1350 is placed in its second position and/or configuration (e.g., when the control device 1300 is transitioned to a second state or operating mode), the inlet 1352 and the outlet 1353 of the actuator 1350 are each in fluid communication with the second fluid flow path 1354 while the first fluid flow path 1333 is sequestered, isolated, and/or otherwise not in fluid communication with the inlet 1352 and the outlet 1353. As described in detail above, in some instances, contaminants such as, for example, dermally residing microbes or the like dislodged during the venipuncture event or throughout the bodily-fluid collection process, can be entrained and/or included in the initial volume of the bodily fluid and thus, are sequestered in the sequestration chamber 1334 when the initial volume is sequestered therein. As such, the negative pressure otherwise exerted on or through the sequestration chamber 1334 is now exerted on or through the second fluid flow path 1354. In response, bodily fluid can flow from the inlet 1352, through the second fluid flow path 1354, through the outlet 1353, and into the fluid collection device coupled to the outlet 1353. Accordingly, the device 1300 can function in a manner substantially similar to that of the device 800 and thus, the function of the device 1300 is not described in further detail herein.

In some instances, it may be desirable to isolate the negative pressure source (e.g., the fluid collection device from the inlet 1353 such as, for example, if it is desirable to collect multiple samples of bodily fluid using multiple fluid collection devices (e.g., syringes or the like). For example, in some instances, after filling the fluid collection device the user can engage the actuator 1350 and exert a force on a second end portion 1364 of the actuator rod 1362 to move and/or transition the actuator rod 1362 from its second position and/or configuration toward its first position and/or configuration. As such, the second fluid flow path 1354 no longer places the inlet 1352 in fluid communication with the outlet 1353. Moreover, the flow controller 1342 can remain in the sealed state or configuration (e.g., fully saturated, wetted, and/or otherwise preventing flow therethrough) such that the outlet 1353 is substantially sequestered or isolated from the rest of the control device 1300. In some instances, the user can then remove the filled fluid collection device and can couple a new fluid collection device to the outlet 1353. With the new fluid collection device coupled to the outlet 1353, the user can, for example, exert a force on the first end portion 1363 of the actuator rod 1362 to move and/or transition the actuator rod 1362 back to its second position, state, and/or configuration, as described above with reference to the actuator 850.

FIGS. 41-44 illustrate a fluid control device 1400 according to an embodiment. The fluid control device 1400 can be similar in at least form and/or function to the fluid control devices described herein. More specifically, portions of the fluid control device 1400 can be similar to and/or substantially the same as corresponding portions of the fluid control devices 200, 300, 800, 900, 1000, 1100, 1200, and/or 1300 described above. Accordingly, such portions of the fluid control device 1400 are not described in further detail herein.

The fluid control device 1400 (also referred to herein as "control device" or "device") includes a housing 1430 and an actuator 1450. As described above with reference to the control device 800, the control device 1400 can be arranged in a modular configuration such that the housing 1430 and the actuator 1450 can be physically and fluidically coupled to form the control device 1400. In other embodiments, the control device 1400 need not be modular. That is to say, in some embodiments, the control device 1400 can be assembled during manufacturing and delivered to a supplier and/or end user as an assembled device. In other embodiments, the device 1400 can be monolithically formed and/or collectively formed with, for example, a fluid collection device, as described above.

Figure 44:
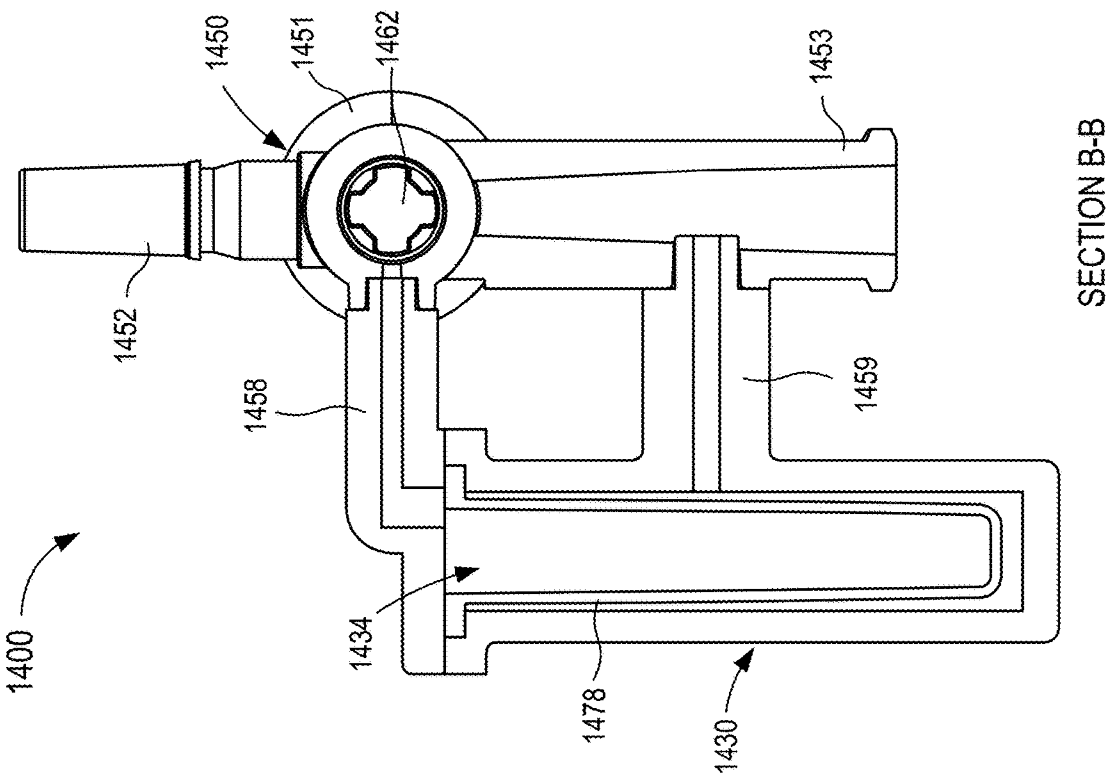
Figure 43:
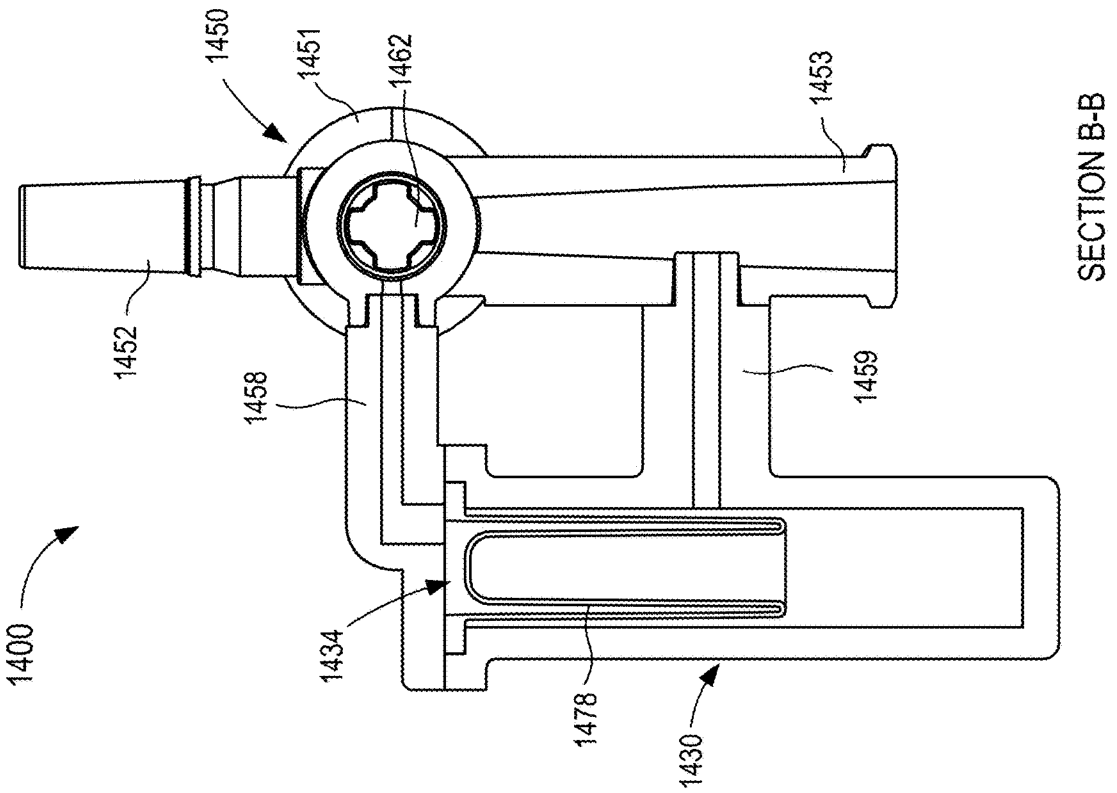
Figure 45:
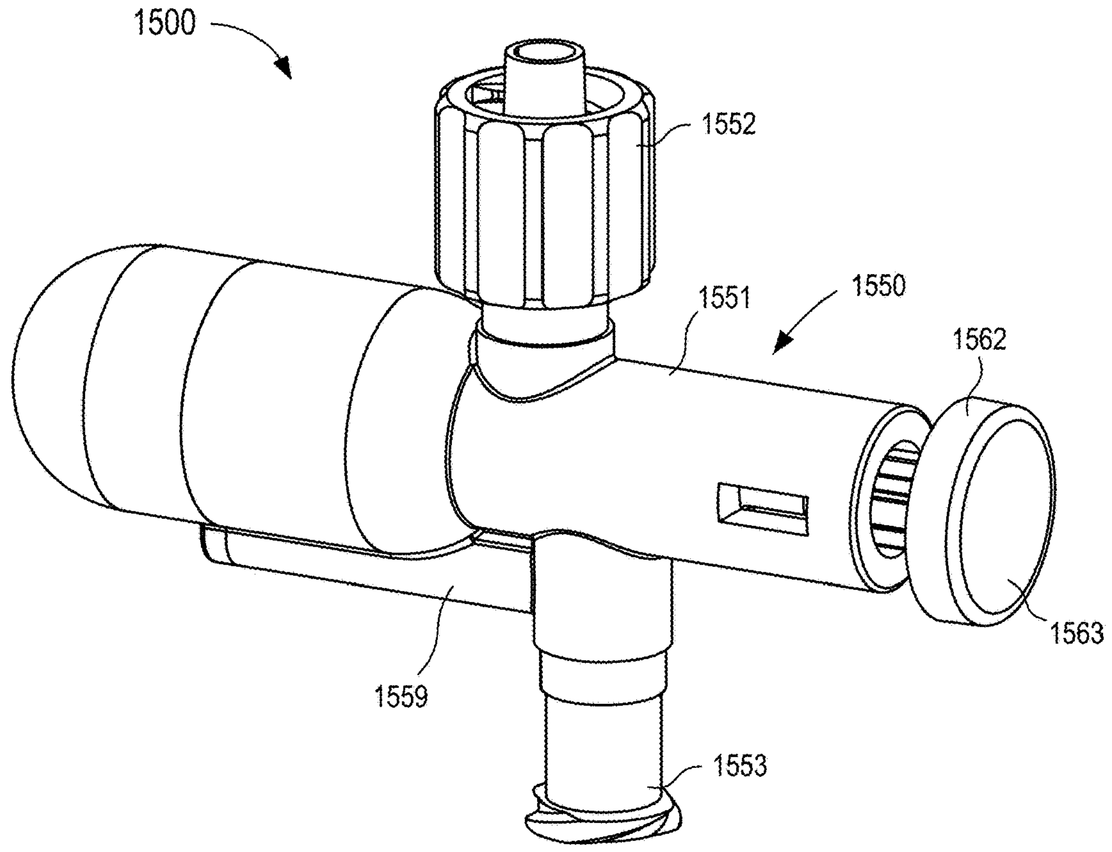
FIGS. 45-50 are various views of a fluid control device according to an embodiment.
Figure 46:
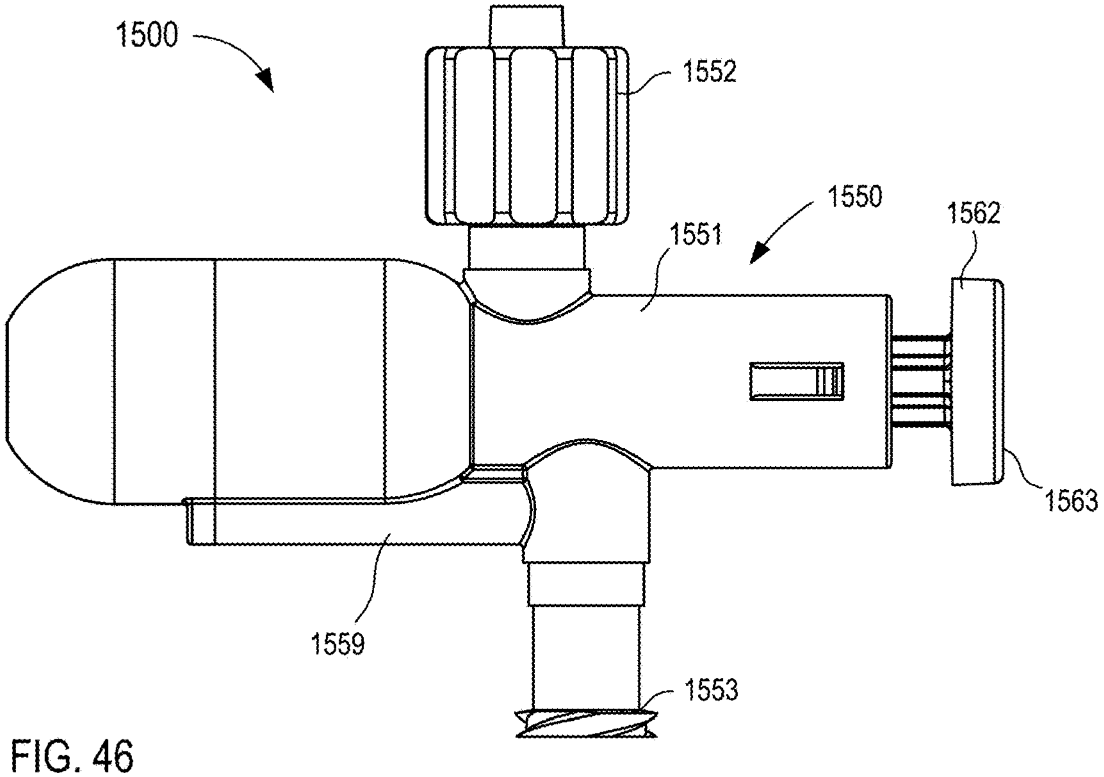
Figure 47:
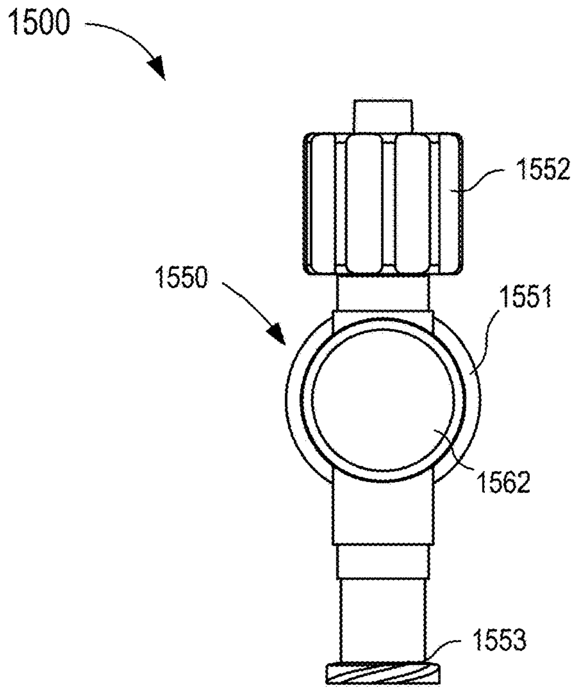

The housing 1430 of the control device 1400 can be any suitable shape, size, and/or configuration. The housing 1430 is configured to be in selective fluid communication with a portion of the actuator 1450 via a first port 1458 and a second port 1459. As shown in FIGS. 43 and 44, the housing 1430 includes a bladder 1478 that can be transitioned from a first configuration and/or state to a second configuration and/or state to form and/or define a sequestration chamber 1434. As described in further detail herein, the bladder 1478 is configured to transition from the first configuration and/or state (FIG. 43) to the second configuration and/or state (FIG. 44) to form and/or define the sequestration chamber 1434, which in turn, is configured to receive a selective flow and/or volume of bodily fluid from a portion of the actuator 1450 via the first port 1458. After the bladder 1478 is placed in the second configuration and/or state, the sequestration chamber 1434 can sequester (e.g., separate, segregate, contain, retain, isolate, etc.) the flow and/or volume of bodily fluid (e.g., at least a portion of an initial or first flow and/or volume of bodily fluid) within the sequestration chamber 1434.

While the bladder 1478 is particularly shown in FIGS. 43 and 44, in other embodiments, the bladder 1478 can be any suitable shape, size, and/or configuration. Similarly, the bladder 1478 can be formed of any suitable material (e.g., any suitable biocompatible material such as those described herein and/or any other suitable material). In some embodiments, the bladder 1478 can be arranged and/or configured as, for example, a bellows, an expandable bag, a flexible pouch, and/or any other suitable reconfigurable container or the like. In addition, the sequestration chamber 1434 formed by the bladder 1478 can have any suitable shape, size, and/or configuration. In some embodiments, the housing 1430 can be substantially similar in at least form and/or function to the housing 1230 and/or 1330 described in detail above with reference to FIGS. 29-34 and FIGS. 35-40, respectively. Accordingly, the housing 1430 is not described in further detail herein.

The actuator 1450 of the control device 1400 can be any suitable shape, size, and/or configuration. For example, in some embodiments, the actuator 1450 can be substantially similar in at least form and/or function to the actuators 850, 1250, and/or 1350 described in detail above. Accordingly, such similar portions of the actuator 1450 are identified below but may not be described in further detail herein.

As shown in FIGS. 41-44, the actuator 1450 includes a body 1451 and an actuator rod 1462. The body 1451 of the actuator 1450 includes an inlet 1452 and an outlet 1453. The inlet 1452 and the outlet 1453 can be substantially similar in at least form and/or function to the inlet 1252 and the outlet 1253, respectively, described above with reference to FIGS. 29-34. Thus, the inlet 1452 is configured to be placed in fluid communication with a bodily fluid source to receive a flow of bodily fluid therefrom (e.g., via a lumen-containing device such as a needle, IV catheter, surgical tubing, other standard bodily-fluid transfer device, PICC line, or the like). The outlet 1453 is configured to be fluidically coupled to a fluid collection device (not shown in FIGS. 41-44) such as, for example, a sample reservoir, a syringe, and/or other intermediary bodily fluid transfer device, adapter, or vessel such as, for example, a transfer device similar to those described in the '510 publication.

The body 1451 of the actuator 1450 includes and/or defines the first port 1458 and the second port 1459. Although not shown, the first port 1458 is configured to be in fluid communication with the inlet 1452 and the second port 1459 is configured to be in fluid communication with the outlet 1453. In addition, the first port 1458 is configured to be in fluid communication with the housing 1430 and more particularly, an inner volume or an inlet side of the bladder 1478 that forms the sequestration chamber 1434. The second port 1459 is configured to be in fluid communication with a portion of the housing 1430 defined between an inner surface of the housing 1430 and an outer surface of the bladder 1478. In other words, the second port 1459 is in fluid communication with a portion of the housing 1430 that is isolated and/or sequestered from the inner volume of the bladder 1478 that forms the sequestration chamber 1434. In some embodiments, the arrangement of the ports 1458 and 1459 of the actuator 1450 can allow for and/or otherwise can provide a means of physically coupling the housing 1430 to the actuator 1450 as well as fluidically coupling the housing 1430 to the actuator 1450. That is to say, in some embodiments, the arrangement of the ports 1458 and 1459 of the actuator 1450 can allow for a modular configuration or arrangement as described above with reference to the control device 800. In other embodiments, the housing 1430 and/or actuator 1450 need not be modular.

Although not shown in FIGS. 41-44, a portion of the actuator rod 1462 includes and/or is coupled to a set of seals. The seals can be, for example, o-rings, elastomeric material, silicone or any other suitable material or configuration as described above with reference to the seals 1265 and/or 1365. The arrangement of the actuator rod 1462 and the body 1451 of the actuator 1450 can be such that the seals form one or more fluid tight seals between the actuator rod 1462 and the inner surface of the body 1451, as described above with reference to the actuators 850, 1250, and/or 1350. Moreover, as described above with reference to the actuators 1250 and/or 1350, the actuator rod 1462 can include and/or can be coupled to a set seals which selectively form and/or define a first fluid flow path configured to place the inlet 1452 of the actuator 1450 in fluid communication with the first port 1458 (e.g., when in a first position, state, operating mode, and/or configuration) and a second fluid flow path configured to place the inlet 1452 in fluid communication with the outlet 1453 (e.g., when in a second position, state, operating mode, and/or configuration).

As described above with reference to the devices 800, 1200, and/or 1300, the device 1400 can be used to procure a bodily fluid sample having reduced contamination from microbes such as, for example, dermally residing microbes, microbes external to the bodily fluid source, and/or the like. For example, as described above with reference to the devices 1200 and/or 1300, the actuator rod 1462 can be configured to be moved or transitioned relative to the body 1451 between a first position or configuration and a second position or configuration. When in the first position and/or configuration, the inlet 1452 of the actuator 1450 is in fluid communication with, for example, the first fluid flow path, which in turn, is in fluid communication with the first port 1458 (not shown in FIGS. 41-44). The outlet 1453 of the actuator 1450 is in fluid communication with the second fluid flow path 1454, which in turn, is in fluid communication with the second port 1459. Thus, when in the actuator 1450 and/or actuator rod 1462 is in the first position and/or configuration (e.g., when the control device 1400 is in a first state or operating mode), the negative pressure within the fluid collection device (not shown in FIGS. 41-44) can result in a negative pressure (or negative pressure differential) within the portion of the housing 1430 defined between the inner surface of the housing 1430 and the outer surface of the bladder 1478.

As shown in FIG. 43, the bladder 1478 can be in a first state and/or configuration prior to the fluid collection device being coupled to the outlet 1453. In some embodiments, for example, the bladder 1478 can have a flipped, inverted, collapsed, and/or empty configuration prior to coupling the fluid collection device to the outlet 1453. As shown in FIG. 44, the bladder 1478 can be configured to transition from the first state and/or configuration to a second state and/or configuration in response to the negative pressure differential resulting from the coupling of the fluid collection device to the outlet 1453. In other words, the negative pressure differential can be operable to transition the bladder 1478 from a collapsed or unexpanded configuration and/or state to an expanded configuration and/or state. For example, in some embodiments, the transitioning of the bladder 1478 can be similar to the transitioning and/or "flipping" of the diaphragm 576, described above with reference to FIGS. 11 and 12.

As described above, the bladder 1478 can be configured to transition from the first configuration and/or state to the second configuration and/or state to form and/or define the sequestration chamber 1434. In some embodiments, the transitioning of the bladder 1478 results in an increase in an inner volume of the bladder 1478 (i.e., the sequestration chamber 1434). The increase in the inner volume can, in turn, result in a negative pressure differential between the sequestration chamber 1434 defined by the bladder 1478 and the inlet 1452 that is operable in drawing at least a portion of an initial flow, amount, or volume of bodily fluid from the inlet 1452, through the first port 1458, and into the sequestration chamber 1434. Moreover, in some instances, the initial volume and/or flow of bodily fluid can be transferred into the sequestration chamber 1434 until, for example, the bladder 1478 is fully expanded, and/or until the negative pressure differential is reduced and/or equalized.

Having transferred the initial volume of bodily fluid into the sequestration chamber 1434, a force can be exerted on a first end portion 1463 of the actuator rod 1462 to place the actuator rod 1462 and/or actuator 1450 in its second position, state, operating mode, and/or configuration, as described in detail above with reference to the devices 1200 and/or 1300. As described above, in some instances, prior to exerting the force on the first end portion 1463 of the actuator rod 1462, the actuator 1450 may be transitioned from a locked configuration or state to an unlocked configuration or state. In some embodiments, the transition of the actuator rod 1462 can be achieved by and/or can otherwise result from user interaction and manipulation of the actuator rod 1462, automatically in response to negative pressure and associated flow dynamics within the device 1400, and/or enacted by or in response to an external energy source which creates dynamics that result in the transitioning of the actuator rod 1462.

When the actuator rod 1462 and/or the actuator 1450 is placed in its second position and/or configuration (e.g., when the control device 1400 is transitioned to a second state or operating mode), the inlet 1452 and the outlet 1453 of the actuator 1450 are placed in fluid communication (e.g., via the second fluid flow path (not shown)) while the first fluid flow path (not shown) and/or the first port 1458 is sequestered, isolated, and/or otherwise not in fluid communication with the inlet 1452 and/or the outlet 1453. As described in detail above, in some instances, contaminants such as, for example, dermally residing microbes or the like dislodged during the venipuncture event or throughout the bodily-fluid collection process, can be entrained and/or included in the initial volume of the bodily fluid and thus, are sequestered in the sequestration chamber 1434 when the initial volume is sequestered therein. As such, the negative pressure otherwise exerted on or through the housing 1430 is now exerted on or through the outlet 1453 and the inlet 1452 via, for example, the second fluid flow path (not shown). In response, bodily fluid can flow from the inlet 1452, through the body 1451 of the actuator 1450, through the outlet 1453, and into the fluid collection device coupled to the outlet 1453. Accordingly, the device 1400 can function in a manner substantially similar to that of the devices 800, 1200, and/or 1300 and thus, the function of the device 1400 is not described in further detail herein.

While the device 1400 is described above as including the housing 1430 and the actuator 1450, in other embodiments, a fluid control device can have, for example, at least a partially integrated design. For example, FIGS. 45-50 illustrate a fluid control device 1500 according to an embodiment. The fluid control device 1500 can be similar in at least form and/or function to the fluid control devices described herein. More specifically, portions of the fluid control device 1500 can be similar to and/or substantially the same as corresponding portions of at least the fluid control device 1400 described above with reference to FIGS. 41-44. Accordingly, such portions of the fluid control device 1500 are not described in further detail herein.

The fluid control device 1500 (also referred to herein as "control device" or "device") includes an actuator 1550 having an actuator body 1551 and an actuator rod 1562. The actuator 1550 can be any suitable shape, size, and/or configuration. For example, in some embodiments, the actuator 1550 can be substantially similar in at least form and/or function to the actuators 850, 1250, 1350, and/or 1450 described in detail above. Accordingly, such similar portions of the actuator 1550 are identified below but may not be described in further detail herein.

As shown in FIGS. 45-50, the actuator 1550 includes an inlet 1552 and an outlet 1553, each of which is in fluid communication with the body 1551. The inlet 1552 and the outlet 1553 can be substantially similar in at least form and/or function to the inlet 1252 and the outlet 1253, respectively, described above with reference to FIGS. 29-34. Thus, the inlet 1552 is configured to be placed in fluid communication with a bodily fluid source to receive a flow of bodily fluid therefrom (e.g., via a lumen-containing device such as a needle, IV catheter, surgical tubing, other standard bodily-fluid transfer device, PICC line, or the like). The outlet 1553 is configured to be fluidically coupled to a fluid collection device (not shown in FIGS. 45-50) such as, for example, a sample reservoir, a syringe, and/or other intermediary bodily fluid transfer device, adapter, or vessel such as, for example, a transfer device similar to those described in the '510 publication.

Figure 48:
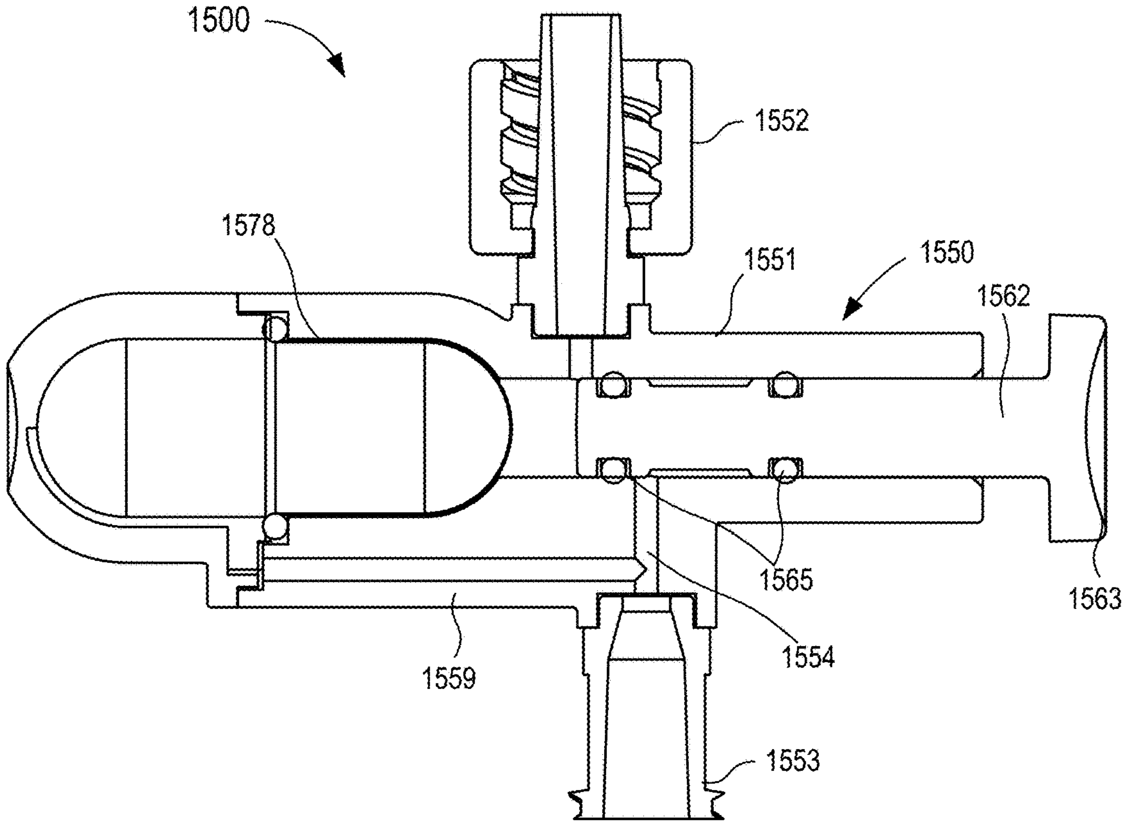
Figure 49:
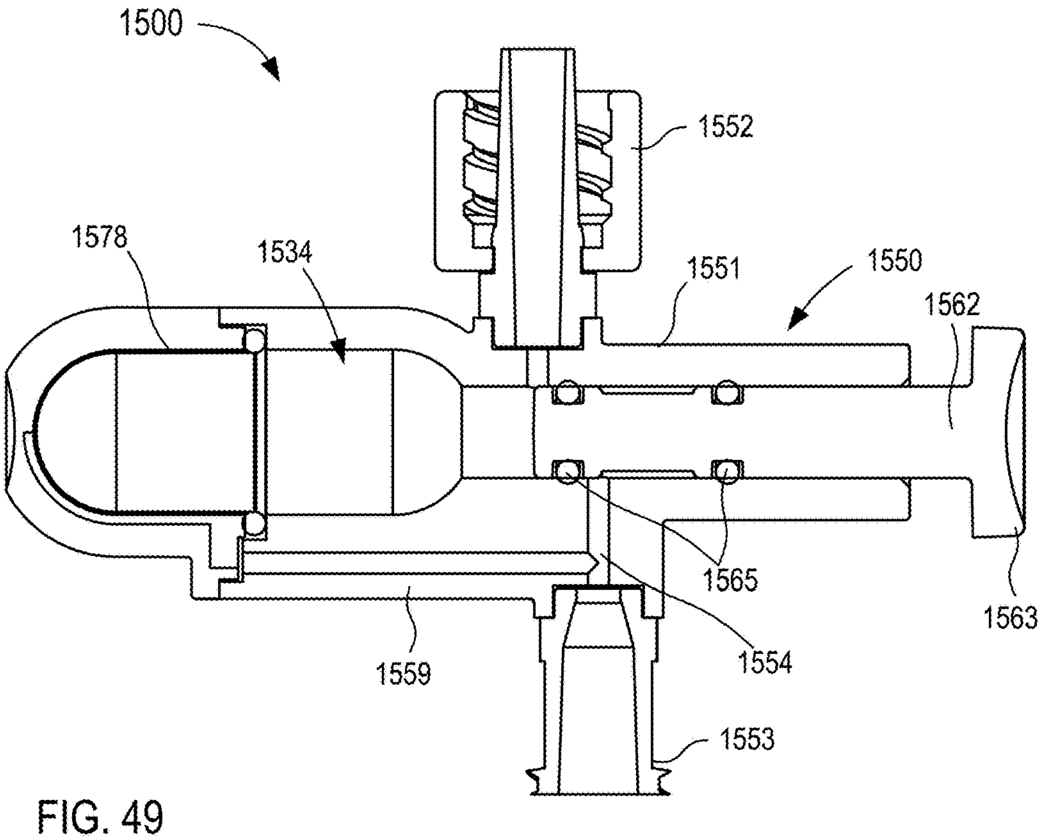
Figure 50:
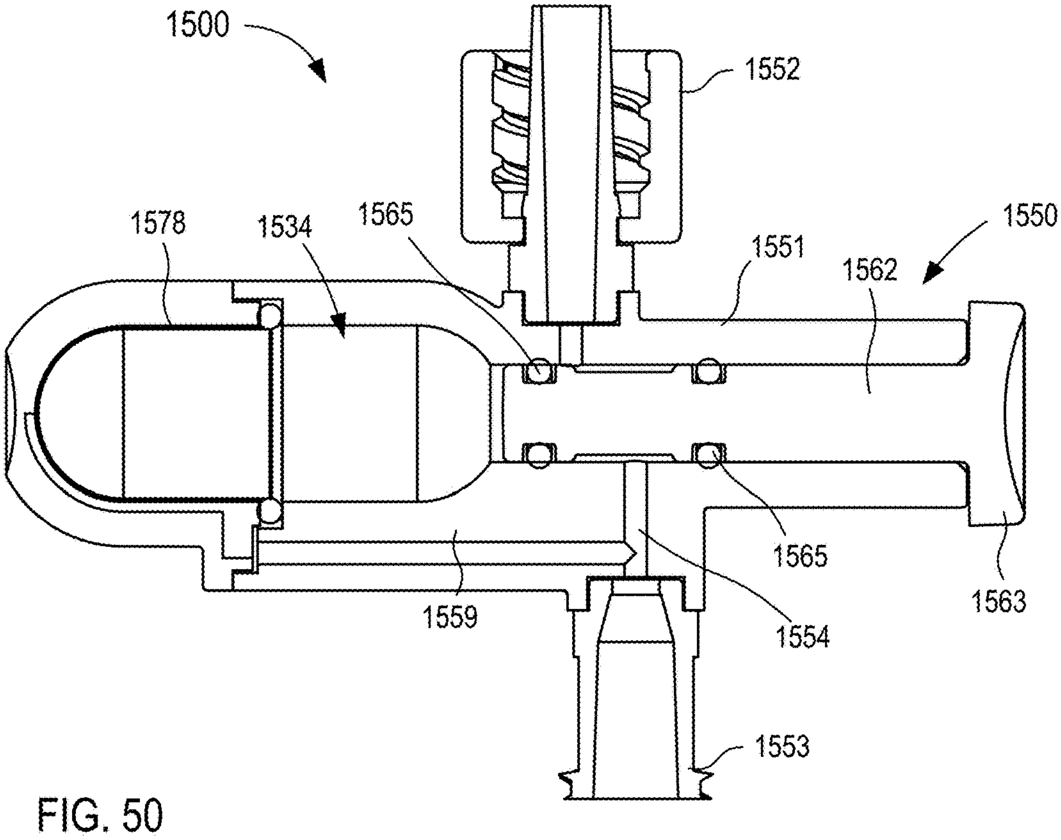

As shown in FIGS. 48-50, the actuator 1550 includes a bladder 1578 that can be transitioned from a first configuration and/or state (FIG. 48) to a second configuration and/or state (FIG. 49) to form and/or define a sequestration chamber 1534. As described in further detail herein, the bladder 1578 is configured to transition from the first configuration and/or state (FIG. 48) to the second configuration and/or state (FIGS. 49 and 50) to form and/or define the sequestration chamber 1534, which in turn, is configured to receive a selective flow and/or volume of bodily fluid from the inlet 1552. After the bladder 1578 is placed in the second configuration and/or state, the sequestration chamber 1534 can sequester (e.g., separate, segregate, contain, retain, isolate, etc.) the flow and/or volume of bodily fluid (e.g., at least a portion of an initial or first flow and/or volume of bodily fluid) within the sequestration chamber 1534. As such, the bladder 1578 can be substantially similar in at least form and/or function to the bladder 1478 described above with reference to FIGS. 41-44 and thus, is not described in further detail herein.

As shown in FIGS. 46 and 48-50, the body 1551 of the actuator 1550 includes and/or defines a port 1559 configured to be in fluid communication with the outlet 1553. In addition, the port 1559 defines a fluid flow path that is configured to be in fluid communication with a portion of the actuator 1550 defined between an inner surface of the body 1551 and an outer surface of the bladder 1578. In other words, the port 1559 is in fluid communication with a portion of the actuator 1550 that is isolated and/or sequestered from the inner volume of the bladder 1578 that forms and/or that is configured to form the sequestration chamber 1534.

As described above with reference to the devices 1200, 1300, and/or 1400, a portion of the actuator rod 1562 includes and/or is coupled to a set of seals 1565. The seals 1565 can be, for example, o-rings, elastomeric material, silicone or any other suitable material or configuration as described above with reference to the seals 1265 and/or 1365. The arrangement of the actuator rod 1562 and the body 1551 of the actuator 1550 can be such that the seals 1565 form one or more fluid tight seals between the actuator rod 1562 and the inner surface of the body 1551, as described above with reference to the actuators 850, 1250, and/or 1350. Moreover, as described above with reference to the actuators 1250 and/or 1350, the set seals 1565 can be arranged along the actuator rod 1562 to selectively form and/or define a fluid flow path 1554 that is sequestered from and/or fluidically isolated from the inlet 1552 when the actuator rod 1562 is in a first position and/or configuration and that is configured to place the inlet 1552 in fluid communication with the outlet 1553 when the actuator rod 1562 is in a second position and/or configuration.

As described above with reference to the devices 800, 1200, 1300, and/or 1400, the device 1500 can be used to procure a bodily fluid sample having reduced contamination from microbes such as, for example, dermally residing microbes, microbes external to the bodily fluid source, and/or the like. For example, as described above with reference to the devices 1200, 1300, and/or 1400, the actuator rod 1562 can be configured to be moved or transitioned relative to the body 1551 between the first position or configuration and the second position or configuration. When in the first position and/or configuration, the inlet 1552 of the actuator 1550 is in fluid communication with a fluid flow path, which in turn, is in fluid communication with a portion of the body 1551 that is disposed on an inlet side of the bladder 1578. In other words, the fluid flow path establishes fluid communication between the inlet 1553 and the bladder 1578 and/or the sequestration chamber 1534 at least partially defined by the bladder 1578 when the bladder 1578 is transitioned to the second configuration and/or state. The outlet 1553 of the actuator 1550 is in fluid communication with the port 1559. Thus, when in the actuator 1550 and/or actuator rod 1562 is in the first position and/or configuration (e.g., when the control device 1500 is in a first state or operating mode), the negative pressure within the fluid collection device (not shown in FIGS. 45-50) can result in a negative pressure (or negative pressure differential) within the portion of the actuator body 1551 defined between the inner surface of the body 1551 and the outer surface of the bladder 1578, as described above with reference to the device 1400.

As shown in FIG. 48, the bladder 1578 can be in a first state and/or configuration prior to the fluid collection device being coupled to the outlet 1553. In some embodiments, for example, the bladder 1578 can have a flipped, inverted, collapsed, and/or empty configuration prior to coupling the fluid collection device to the outlet 1553. Moreover, when the actuator rod 1562 is in the first position and/or configuration, the fluid flow path 1554 is fluidically isolated from the inlet 1552. Accordingly, as shown in FIG. 49, the bladder 1578 can be configured to transition from the first state and/or configuration to a second state and/or configuration in response to the negative pressure differential resulting from the coupling of the fluid collection device to the outlet 1553. In other words, the negative pressure differential can be operable to transition the bladder 1578 from a collapsed or unexpanded configuration and/or state to an expanded configuration and/or state. For example, in some embodiments, the transitioning of the bladder 1578 can be similar to the transitioning and/or "flipping" of the diaphragm 576, described above with reference to FIGS. 11 and 12. In other embodiments, the bladder 1578 can be configured to transition between a first state and/or configuration to a second state and/or configuration in any suitable manner such as any of those described herein.

As described above, the bladder 1578 can be configured to transition from the first configuration and/or state to the second configuration and/or state to form and/or define the sequestration chamber 1534. In some embodiments, the transitioning of the bladder 1578 results in an increase in an inner volume of the bladder 1578 (i.e., the sequestration chamber 1534). The increase in the inner volume can, in turn, result in a negative pressure differential between the sequestration chamber 1534 defined by the bladder 1578 and the inlet 1552 that is operable in drawing at least a portion of an initial flow, amount, or volume of bodily fluid from the inlet 1552 and a portion of the actuator body 1551, and into the sequestration chamber 1534. Moreover, in some instances, the initial volume and/or flow of bodily fluid can be transferred into the sequestration chamber 1534 until, for example, the bladder 1578 is fully expanded, and/or until the negative pressure differential is reduced and/or equalized.

Having transferred the initial volume of bodily fluid into the sequestration chamber 1534, a force can be exerted on a first end portion 1563 of the actuator rod 1562 to place the actuator rod 1562 and/or actuator 1550 in its second position, state, operating mode, and/or configuration, as described in detail above with reference to the devices 1200 and/or 1300. As described above, in some instances, prior to exerting the force on the first end portion 1563 of the actuator rod 1562, the actuator 1550 may be transitioned from a locked configuration or state to an unlocked configuration or state. In some embodiments, the transition of the actuator rod 1562 can be achieved by and/or can otherwise result from user interaction and manipulation of the actuator rod 1562, automatically in response to negative pressure and associated flow dynamics within the device 1500, and/or enacted by or in response to an external energy source which creates dynamics that result in the transitioning of the actuator rod 1562.

When the actuator rod 1562 and/or the actuator 1550 is placed in its second position and/or configuration (e.g., when the control device 1500 is transitioned to a second state or operating mode), the inlet 1552 and the outlet 1553 of the actuator 1550 are placed in fluid communication via the fluid flow path 1554 while the sequestration chamber 1534 is sequestered, isolated, and/or otherwise not in fluid communication with the inlet 1552 and/or the outlet 1553. As described in detail above, in some instances, contaminants such as, for example, dermally residing microbes or the like dislodged during the venipuncture event or throughout the bodily-fluid collection process, can be entrained and/or included in the initial volume of the bodily fluid and thus, are sequestered in the sequestration chamber 1534 when the initial volume is sequestered therein.

As described above with reference to the devices 1200 and/or 1300, transitioning the actuator rod 1562 to the second position and/or configuration is such that the fluid flow path 1554 places the inlet 1552 in fluid communication with the outlet 1553. For example, transitioning the actuator rod 1562 to the second position and/or configuration can move the seals 1565 relative to the inlet 1552 such that the fluid flow path 1554 is placed in fluid communication with both the inlet 1552 and the outlet 1553. As such, the negative pressure otherwise exerted on the outer surface of the bladder 1578 is now exerted on or through the outlet 1553 and the inlet 1552 via the fluid flow path 1554. In response, bodily fluid can flow from the inlet 1552, through the fluid flow path 1554, through the outlet 1553, and into the fluid collection device coupled to the outlet 1553. Accordingly, the device 1500 can function in a manner substantially similar to that of the devices 800, 1200, 1300, and/or 1400 and thus, the function of the device 1500 is not described in further detail herein.

Figure 52:
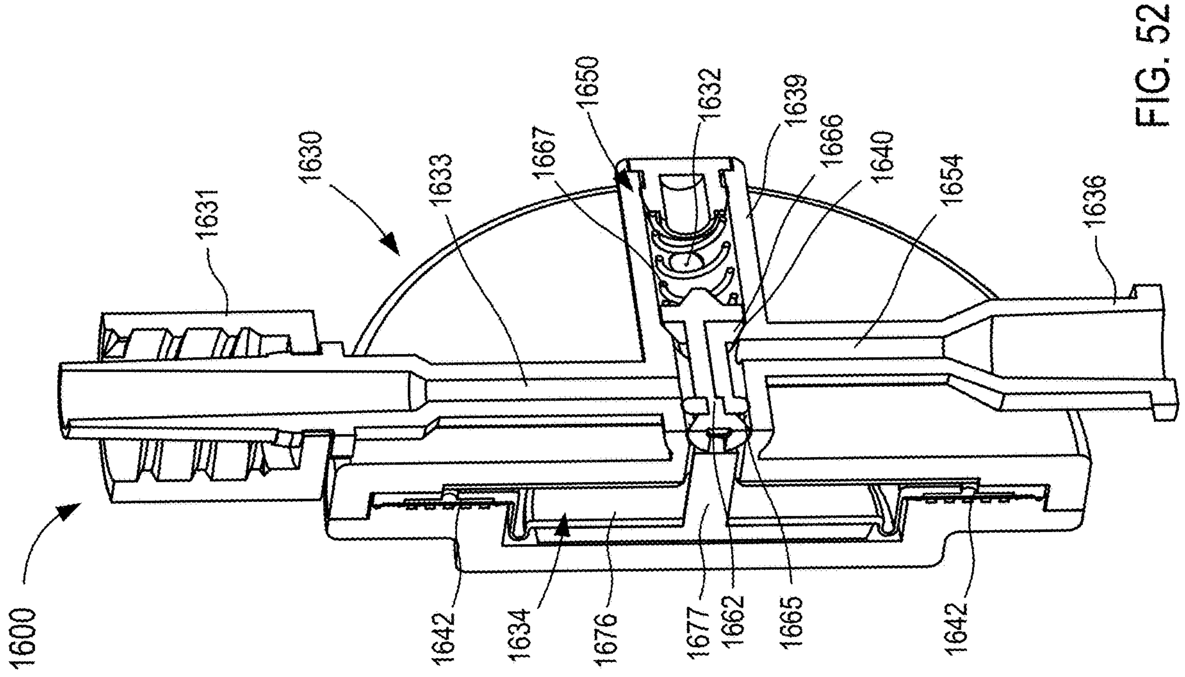
FIGS. 51 and 52 are cross-sectional views of a fluid control device according to an embodiment.
Figure 51:
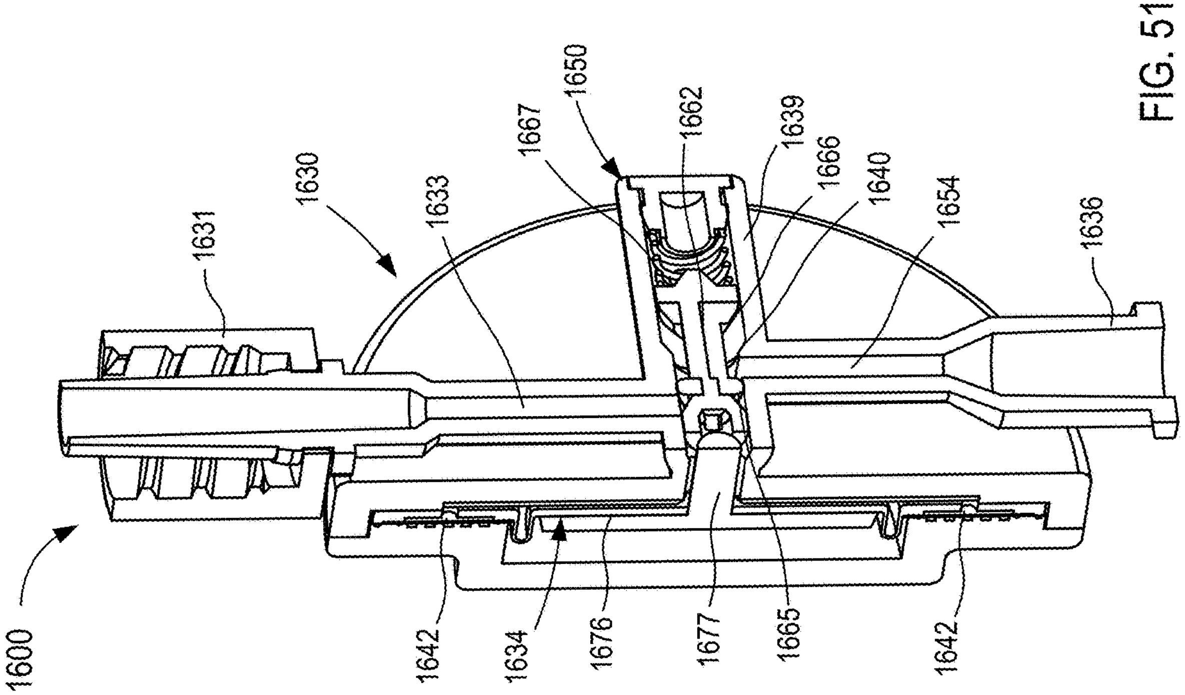

While the actuators 850, 1250, 1350, 1450, and 1550 have been described in detail above as being transitioned in response to an external force such as, for example, a force exerted by a user, in other embodiments, a fluid control device can include one or more actuators that can be transitioned in response to any suitable force, input, change of state or configuration, etc. For example, FIGS. 51 and 52 illustrate a portion of a fluid control device 1600 according to an embodiment. The fluid control device 1600 can be similar in at least form and/or function to the fluid control devices described herein. More specifically, portions of the fluid control device 1600 can be similar to and/or substantially the same as corresponding portions of at least the fluid control devices 500, 600, and/or 700 described above. Accordingly, such portions of the fluid control device 1600 are not described in further detail herein.

As shown in FIGS. 51 and 52, the fluid control device 1600 (also referred to herein as "control device" or "device") includes a housing 1630 having an inlet 1631 and an outlet 1636, and having and/or being coupled to an actuator 1650. As described in further detail herein, the housing 1630 defines a set of fluid flow paths 1633 and 1654 configured to establish fluid communication between one or more portions of the housing 1630 to selectively receive a flow of fluid therethrough (e.g., a liquid and/or a gas). The inlet 1631 is configured to be placed in fluid communication with a bodily fluid source to receive a flow of bodily fluid therefrom (e.g., via a lumen-containing device such as a needle or the like, as described in detail above). The outlet 1636 is configured to be fluidically coupled to a fluid collection device (not shown in FIGS. 51 and 52). The inlet 1631, the outlet 1636, and the fluid collection device can be substantially similar to those described above and thus, are not described in further detail herein.

The housing 1630 can be any suitable shape, size, and/or configuration. In some embodiments, the housing 1630 can have a size that is at least partially based on a volume of bodily fluid configured to be at least temporarily stored within one or more portions of the housing 1630. As described above, the housing 1630 of the control device 1600 is configured to (1) receive a flow and/or volume of bodily fluid via the inlet 1631 and (2) sequester (e.g., separate, segregate, contain, retain, isolate, etc.) the flow and/or volume of bodily fluid within a sequestration chamber 1634 included in and/or at least partially formed by the housing 1630. In some embodiments, aspects of the housing 1630 can be substantially similar, for example, to aspects of the housings 630, 730, and/or 830. Accordingly, some portions and/or aspects of the housing 1630 are not described in further detail herein.

The housing 1630 includes and/or is coupled to the actuator 1650 configured to selectively control a flow of bodily fluid through the housing 1630. In this embodiment, the actuator 1650 includes a diaphragm 1676 and an actuator rod 1662 having a set of seals (e.g., seals 1665 and 1666). As described in further detail herein, the diaphragm 1676 and the actuator rod 1662 are configured to transition, move, and/or otherwise reconfigure within the housing 1630 in response to a negative pressure differential within at least a portion of the device. More specifically, the actuator 1650 is configured to move between a first state in which the inlet 1631 is placed in fluid communication with the sequestration chamber 1634 and a second state in which the inlet 1631 is placed in fluid communication with the outlet 1636 via the fluid flow path 1654, as described in detail above with reference to the control device 500.

In some embodiments, the diaphragm 1676 can be similar to, for example, the diaphragms 576, 676, and/or 776 described in detail above. Accordingly, the diaphragm 1676 can be at least partially disposed in a sequestration portion of the housing 1630 to define and/or to form at least a portion of the sequestration chamber 1634. As described in detail above, the diaphragm 1676 can be configured to transition, move, flip, and/or otherwise reconfigure from a first state to a second state in response to a negative pressure differential, which can be operable to draw an initial volume of bodily fluid into the sequestration chamber 1634 and/or to sequester the initial volume of bodily fluid in the sequestration chamber 1634 once disposed therein. Moreover, as shown in FIGS. 51 and 52, the diaphragm 1676 can include and/or can be coupled to a flow controller 1642. The flow controller 1642 can be any suitable flow controller such as any of those described herein. For example, in some embodiments, the flow controller 1642 can be a semi-permeable member or membrane such as an air permeable/liquid impermeable barrier (e.g., a blood barrier).

As described in detail above, the flow controller 1642 can be configured to transition from a first state in which the flow controller 1642 allows a flow of gas (e.g., air) to pass through the flow controller 1642 while preventing a flow of liquid (e.g., bodily fluid) to pass therethrough, to a second state in which the flow controller 1642 limits and/or substantially prevents a flow of gas and liquid to pass through the flow controller 1642. In some embodiments, the flow controller 1642 can be configured to transition from the first state to the second state in response to contact with, for example, the initial volume of bodily fluid (e.g., at least a portion of the initial volume of bodily fluid can wet or saturate the flow controller 1642 to place the flow controller 1642 in the second state).

While the diaphragms 576, 676, and 776 are shown and described above as including a pin, rod, post, and/or the like that include and/or are coupled to one or more seals (e.g., the seals 565, 665, and 765, respectively), in the embodiment shown in FIGS. 51 and 52, the diaphragm 1676 includes a pin 1677 (e.g., a rod, an extension, a protrusion, a latch, a lock, and/or any other suitable feature, member, and/or mechanism) that does not include and/or is not coupled to a seal. For example, in this embodiment, the pin 1677 extends through a portion of the housing 1630 to selectively engage a portion of the actuator rod 1662, which in turn includes one or more seals (e.g., the seals 1665 and 1666), as described in further detail herein.

As shown in FIGS. 51 and 52, the actuator rod 1662 is movably disposed in, for example, an actuator portion 1639 of the housing 1630. The actuator rod 1662 includes a first seal 1665 and a second seal 1666 and is in contact with an energy storage member 1667 such as a spring or the like disposed within the actuator portion 1639 of the housing 1630. In the embodiment shown in FIGS. 51 and 52, the arrangement of the actuator 1650 can be such that a first end portion of the actuator rod 1662 is in selective contact with the pin 1677 of the diaphragm 1676 and a second end portion of the actuator rod 1662 (opposite the first end portion) is in contact with and/or otherwise is engaged with the energy storage member 1667.

As shown in FIG. 51, when the actuator 1650 is in a first state, the pin 1677 of the diaphragm 1676 can engage the actuator rod 1662 to maintain the actuator rod 1662 in a first or initial state and/or position in which the energy storage member 1667 has a relatively high potential energy (e.g., the energy storage member 1667 can be a spring maintained and/or held in a compressed state when in the first state). Furthermore, the first seal 1665 coupled to and/or disposed on the actuator 1662 is in a first or initial position in which the fluid flow path 1633 establishes fluid communication between the inlet 1631 and the sequestration chamber 1634 when the actuator 1650 is in the first state. As shown, the second seal 1666 coupled to and/or disposed on the actuator rod 1662 is likewise in a first or initial position in which the second seal 1666 is spaced apart from a seal surface 1640 formed by at least a portion of the actuator portion 1639 of the housing 1630.

In some embodiments, the separation of the second seal 1666 from the seal surface 1640 can be such that the fluid flow path 1654 places the outlet 1636 in fluid communication with the sequestration chamber 1634 via a restricted flow path 1632 (see FIG. 52). In some embodiments, the restricted flow path 1632 can be similar in at least form and/or function to any of the restricted flow paths described herein (e.g., the restricted flow paths 232, 832, 1232, and/or 1332). As such, the restricted flow path 1632 can be configured to modulate a magnitude of a negative pressure differential applied on or in the sequestration chamber 1634 and/or a rate at which a negative pressure differential increases within the sequestration chamber 1634. In other embodiments, the outlet 1636 can be in fluid communication with the sequestration chamber 1634 via any suitable flow path, port, opening, valve, etc. In other words, in some embodiments, the control device 1600 need not include the restricted flow path 1632.

As shown in FIG. 51, when the actuator 1650 is in the first state, the actuator rod 1662 can be maintained in a first state or position in which the fluid flow path 1633 places the inlet 1631 in fluid communication with the sequestration chamber 1634, and the fluid flow path 1654 places the outlet 1636 in fluid communication with the sequestration chamber 1634 via the restricted flow path 1632. Accordingly, when a fluid collection device (such as those described herein) is coupled to the outlet 1636, a negative pressure defined in and/or otherwise produced by the fluid collection device can be operable to draw the initial volume of bodily fluid into the sequestration chamber 1634.

As described in detail above, the actuator 1650 can be transitioned to a second state and/or configuration in response to the initial volume being transferred into the sequestration chamber 1634. For example, in some embodiments, the initial volume of bodily fluid can be drawn into the sequestration chamber 1634 in response to a negative pressure being exerted through the flow controller 1642 (e.g., the selectively permeable membrane). In some instances, at least a portion of the bodily fluid drawn into the sequestration chamber 1634 can come into contact with the flow controller 1642, which in turn, can transition the flow controller 1642 from the first state to the second state (e.g., the flow controller 1642 limits and/or substantially prevents a flow of gas and liquid therethrough). As such, a negative pressure exerted on a surface of the diaphragm 1676 can build and can become sufficient to transition, move, and/or flip the diaphragm from a first state and/or configuration to a second state and/or configuration (see FIG. 52). In some embodiments, the transitioning of the diaphragm 1676 can correspond with and/or can be in response to the flow controller 1642 being transitioned from the first state to the second state (e.g., becoming fully wetted or the like, as described in detail above). In other embodiments, the diaphragm 1676 can transition before or after the flow controller 1642 has transitioned from the first state to the second state. In still other embodiments, the control device 1600 need not include the flow controller 1642 and the diaphragm 1676 can be configured to transition in response to being exposed to the negative pressure differential produced by the fluid collection device. In some such embodiments, the diaphragm 1676 (and/or at least a portion thereof) can be configured to act in a similar manner to the flow controller 1642 by transitioning from the first state to the second state in a predictable and/or predetermined manner after being exposed to a predetermined negative pressure differential or a predetermined rate of change in negative pressure. Moreover, the transitioning of the diaphragm 1676 can be automatic (e.g., is not a result of user intervention).

As shown in FIG. 52, when the diaphragm 1676 is transitioned, moved, flipped, etc., the pin 1677 can be moved within the housing 1630 and relative to the actuator rod 1662. More particularly, the transitioning of the diaphragm 1676 can move the pin 1677 a sufficient amount that the pin 1677 is disengaged from the actuator rod 1662. As such, the energy storage member 1667 (e.g., spring) can be configured to release and/or convert at least a portion of its potential energy. As a specific example, in this embodiment, moving the pin 1677 can allow the spring 1667 to expand from a first or compressed state to a second or substantially uncompressed state. The transitioning of the energy storage member 1667 (e.g., spring) from the first state to the second state, in turn, moves the actuator rod 1662 within the actuator portion 1639 from a first state and/or position to a second state and/or position.

As shown in FIG. 52, when the actuator rod 1662 is in the second state and/or position, the first seal 1665 can be placed in a second or subsequent position in which the first seal 1665 sequesters the sequestration chamber 1634 from the inlet 1631. Similarly, the second seal 1666 can be placed in a second or subsequent position in which the second seal 1666 is pushed (e.g., by the energy storage member 1667) against the seal surface 1640, which in turn, sequesters the flow controller 1642 from the fluid flow path 1654. Furthermore, the placement of the first seal 1665 and the second seal 1666 when the actuator rod 1662 is in the second state and/or position is such that the fluid flow path 1633 is placed in fluid communication with the fluid flow path 1654. Thus, a negative pressure differential produced by the fluid collection device coupled to the outlet 1636 can be operable to draw a subsequent volume of bodily fluid from the inlet 1631, through the fluid flow path 1633 and 1654, through the outlet 1636, and into the fluid collection device. Moreover, the collecting and sequestering of the initial volume of bodily fluid can result in the subsequent volume(s) of bodily fluid being substantially free from contaminants, as described in detail above.

Figure 53:
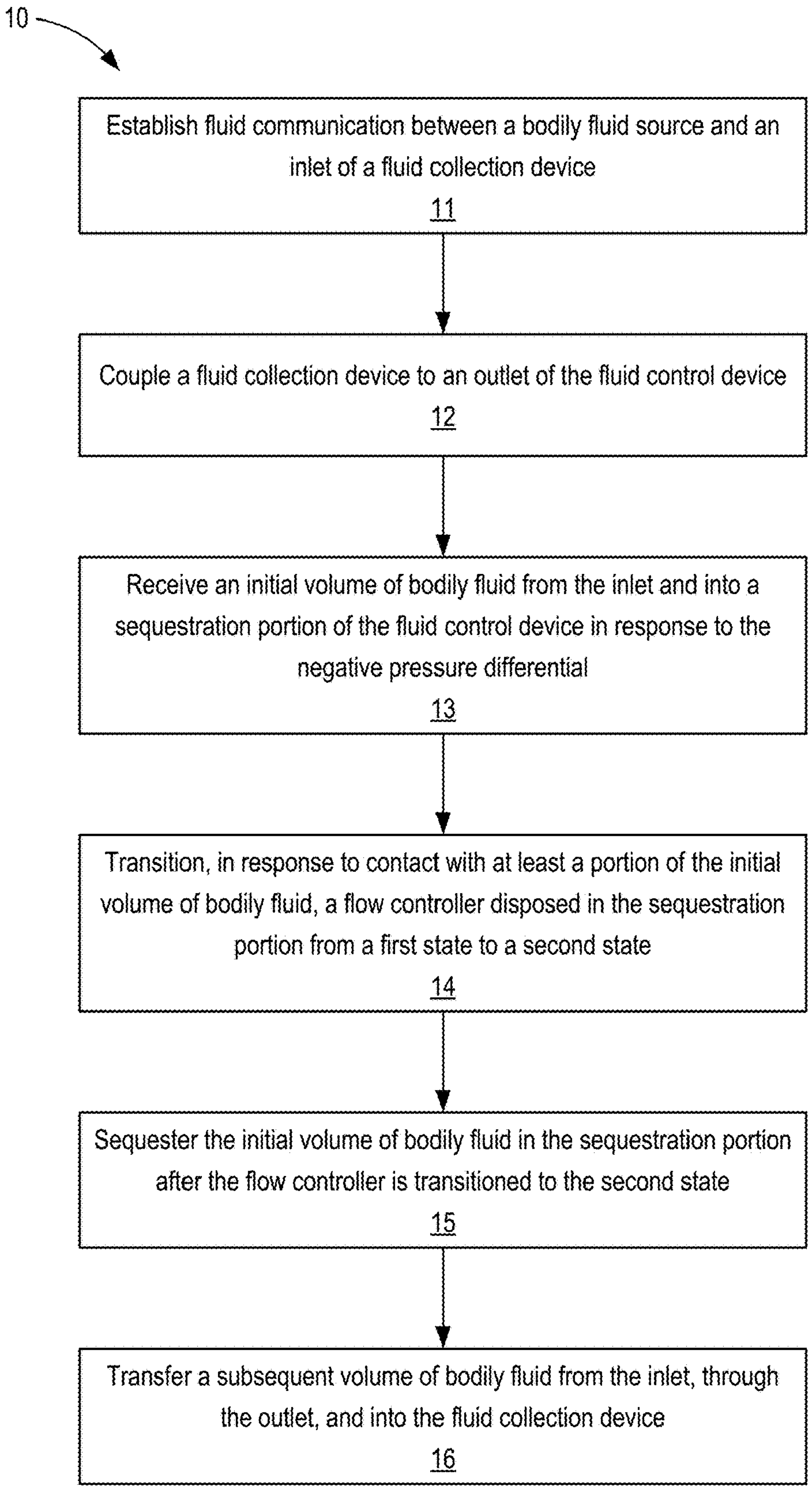
FIG. 53 is a flowchart illustrating a method of using a fluid control device according to an embodiment.

Referring now to FIG. 53, a flowchart is presented illustrating a method 10 of using a fluid control device to obtain a bodily fluid sample with reduced contamination according to an embodiment. The fluid control device can be similar to and/or substantially the same as any of the fluid control devices described in detail above. The method 10 includes establishing fluid communication between a bodily fluid source and an inlet of the fluid collection device, at 11. For example, in some embodiments, a user can manipulate the fluid control device to physically and/or fluidically couple the inlet to a lumen-containing device (e.g., a needle, IV, PICC line, etc.) in fluid communication with a patient.

A fluid collection device is coupled to an outlet of the fluid control device, at 12. The coupling of the fluid collection device to the outlet is configured to produce a negative pressure differential within at least a portion of the fluid control device, as described in detail above. In some embodiments, for example, the fluid collection device can be a sample bottle or container that defines a negative pressure. In other embodiments, the fluid collection device can be a syringe or the like that can be manipulated to produce a negative pressure. Accordingly, a negative pressure differential can be produced within one or more portions of the fluid control device, as described above with reference to the control devices 100, 200, 300, 400, 500, 600, 700, 800, 900, 1000, 1100, 1200, 1300, 1400, 1500, and/or 1600.

An initial volume of bodily fluid is received from the inlet and into a sequestration portion of the fluid control device in response to the negative pressure differential, at 13. For example, in some embodiments, the sequestration portion can be similar to and/or substantially the same as the sequestration chamber 1234 described above with reference to FIGS. 29-34. In other embodiments, the sequestration portion can be similar to and/or substantially the same as the sequestration chamber 1634. In still other embodiments, the sequestration portion can be similar to and/or substantially the same as any of the sequestration chambers described herein. Furthermore, in some instances, the initial volume of bodily fluid can include contaminants entrained therein, which may otherwise result in false results during testing of a bodily fluid sample.

In response to contact with at least a portion of the initial volume of bodily fluid, a flow controller disposed in the sequestration portion is transitioned from a first state in which the flow controller allows a flow of a gas through the flow controller and prevents a flow of bodily fluid through the flow controller, to a second state in which the flow controller prevents a flow of gas and bodily fluid through the flow controller, at 14. For example, in some embodiments, the flow controller can be a selectively permeable member or membrane (e.g., a fluid or blood barrier and/or the like), as described above with reference to the flow controller 242. In other embodiments, the flow controller can be similar to and/or substantially the same as any of the flow controllers described herein. Thus, in some embodiments, the contact with at least the portion of the initial volume of bodily fluid can, for example, wet or saturate the flow controller such that the flow controller limits and/or substantially prevents a flow of gas and liquid (e.g., bodily fluid) therethrough. In other embodiments, the flow controller can be a bladder and/or diaphragm that is configured to be transitioned in response to a negative pressure differential. For example, in such embodiments, a flow controller can be a substantially impermeable bladder or diaphragm that can transition from a first state to a second state when a negative pressure differential applied to a surface of the bladder and/or diaphragm exceeds a threshold amount of negative pressure.

The initial volume of bodily fluid is sequestered in the sequestration portion after the flow controller is transitioned to the second state, at 15. For example, in some embodiments, the fluid control device can include an actuator and/or any other suitable feature or mechanism configured to transition after the flow controller is placed in its second configuration to sequester the initial volume of bodily fluid. In some embodiments, the actuator can transition from a first state to a second state to automatically sequester the initial volume of bodily fluid in the sequestration portion, as described above with reference to, for example, the actuator 1650. In other embodiments, the actuator can transition from a first state to a second state in response to a force exerted by a user, as described above with reference to, for example, the actuator 850. In still other embodiments, the fluid control device can sequester the initial volume of bodily fluid in the sequestration portion in any suitable manner such as those described herein.

After sequestering the initial volume of bodily fluid, a subsequent volume of bodily fluid is transferred from the inlet, through the outlet, and into the fluid collection device, at 16. As described in detail above, in some instances, sequestering the initial volume of bodily fluid in the sequestration portion of the fluid control device can likewise sequester contaminants contained in the initial volume. Accordingly, contaminants in the subsequent volume of bodily fluid can be reduced or substantially eliminated.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. For example, while the control devices 100, 200, 300, 400, 500, 600, 700, 800, 900, 1000, 1100, 1200, 1300, 1400, and/or 1500 are described as transferring a bodily fluid into the device as a result of a negative pressure within a fluid collection device, in other embodiments, the devices described herein can be used with any suitable device configured to establish a pressure differential (e.g., a negative pressure differential). For example, in some embodiments, an outlet of a control device can be coupled to a syringe or pump. In other embodiments, a control device can include a pre-charged sequestration chamber, a vented sequestration chamber, a manually activated device configured to produce a negative pressure, an energy source (e.g., a chemical energy source, a kinetic energy source, and/or the like), and/or any other suitable means of defining and/or forming a pressure differential within a portion of the control device. Moreover, as described above, the control devices can be coupled to such collection devices by a user (e.g., doctor, nurse, technician, physician, etc.) or can be coupled or assembled during manufacturing. In some embodiments, pre-assembling a control device and a collection device (e.g., a sample container or syringe) can, for example, force compliance with a sample procurement protocol that calls for the sequestration of an initial amount of bodily fluid prior to collecting a sample volume of bodily fluid.

While some of the embodiments described above include a flow controller and/or an actuator having a particular configuration and/or arrangement, in other embodiments, a fluid control device can include any suitable flow controller and/or actuator configured to selectively control a flow of bodily fluid through one or more portions of the fluid control device. For example, while some embodiments include an actuator such as a diaphragm or the like having one or more seals arranged as an O-ring or an elastomeric over-mold, which is/are moved with the diaphragm and relative to a portion of the device (e.g., the inlet, the outlet, or any other suitable portion) when the diaphragm is transitioned or flipped from a first state to a second state, in other embodiments, a fluid control device can include one or more seals having any suitable configuration. For example, in some embodiments, a fluid control device can include one or more seals arranged as an elastomeric sheet or the like that is/are fixedly coupled to a portion of the control device. In such embodiments, a portion of an actuator such as a pin or rod extending from a diaphragm (see e.g., FIGS. 11 and 12) can extend through an opening defined in the one or more elastomeric sheets, which in turn, form a substantially fluid tight seal with an outer surface of the pin or rod. As such, when the actuator (e.g., diaphragm) is transitioned from a first state to a second state, the portion of the actuator (e.g., the pin or rod) can move through one or more of the elastomeric sheets. In other words, the portion of the actuator moves relative to the one or more elastomeric sheets, which in turn, remain in a substantially fixed position relative to the portion of the control device. In some embodiments, the removal or the portion of the actuator can allow a flow of fluid through the opening defined by the one or more elastomeric sheets that was otherwise occluded by the portion of the actuator. Accordingly, the one or more elastomeric sheets can function in a similar manner as any of the seals described herein. Moreover, in some embodiments, such an arrangement may, for example, reduce an amount of friction associated with forming the desired fluid tight seals, which in turn, may obviate the use of a lubricant otherwise used to facilitate the movement of the seals within the control device.

While the diaphragms (e.g., diaphragms 576, 676, and 776) are described herein as being configured to transition, move, flip, and/or otherwise reconfigure in response to an amount of negative pressure exerted on a surface of the diaphragm exceeding a threshold amount of negative pressure, in other embodiments, a fluid control device can include any suitable actuator or the like configured to transition, move, flip, and/or otherwise reconfigure in response to being exposed to a desired and/or predetermined amount of negative pressure. For example, in some embodiments, a fluid control device can include an actuator including and/or arranged as a movable member, plug, plunger, occlusion member, seal, and/or the like configured to selectively control a flow of fluid through at least a portion of the fluid control device. More particularly, the movable member or the like can be transitioned from a first state and/or position in which the movable member or the like is disposed in and/or otherwise occludes an opening, to a second state and/or position in which the movable member or the like is removed from the opening. In such embodiments, a negative pressure can be exerted through a portion of the device to transfer, for example, an initial volume of bodily fluid into a sequestration portion and/or chamber.

As described in detail above, in some embodiments, a device can include a flow controller such as a selectively permeable member or membrane, that can be configured to transition from a first state to a second state in response to being wetted (or otherwise transitioned) by the initial volume of bodily fluid. After transferring the initial volume of bodily fluid and after the flow controller is transitioned to its second state, an amount of negative pressure exerted on a surface of the movable member or the like may build until a magnitude of the negative pressure is sufficient to pull or move the movable member out of the opening, thereby allowing a flow of bodily fluid through the opening that was otherwise occluded by the movable member. In this manner, the movable member can function similar to any of the diaphragms described herein (e.g., the diaphragm 576, 676, and/or 776) that are configured to transition or flip from a first state to a second state. In such embodiments, the movable member can be, for example, an elastomeric plug, cork, plunger, and/or any other suitable member that can be moved or "popped" out of such an opening or portion of a flow path.

While some of the embodiments described above include a flow controller and/or actuator that selectively establishes fluid communication between a sequestration chamber and a fluid collection device (e.g., a sample reservoir, a syringe, and/or any other suitable source of negative pressure) in other embodiments, a control device can be arranged to transfer a flow of bodily fluid in response to negative pressure differentials resulting from any suitable portion(s) of the device. For example, while the control device 200 is described above as including the flow controller 242 and the restricted flow path 232 that selectively place the sequestration chamber 234 in fluid communication with the sample reservoir until the flow controller 242 is transitioned to a sealed or closed state (e.g., until the flow controller 242 is sufficiently wetted), in other embodiments, a control device can include a sequestration chamber that is a pre-sealed evacuated and/or charged chamber such that establishing fluid communication between an inlet and the sequestration chamber results in a negative pressure differential that is sufficient to draw an initial volume of bodily fluid into the sequestration chamber. In such embodiments, the control device can be configured to transfer bodily fluid to the sequestration chamber until the pressure differential is sufficiently reduced and/or until pressures otherwise substantially equalize. Moreover, in some such embodiments, the sequestration chamber and/or the inlet can include a coupler, an actuator, a needle, a septum, a port, and/or any other suitable member that can establish fluid communication therebetween (e.g., that can transition the sequestration chamber from a sealed to an unsealed configuration).

While some of the embodiments described above include a flow controller and/or actuator that physically and/or mechanically sequesters one or more portions of a fluid control device, in other embodiments, a fluid control device need not physically and/or mechanically sequester one or more portions of the fluid control device. For example, in some embodiments, an actuator such as the actuator 1250 can be transitioned from a first state in which an initial volume of bodily fluid can flow from an inlet to a sequestration chamber or portion, to a second state in which (1) the sequestration chamber or portion is physically and/or mechanically sequestered and (2) the inlet is in fluid communication with an outlet of the fluid control device. In other embodiments, however, an actuator and/or any other suitable portion of a fluid control device can transition from a first state in which an initial volume of bodily fluid can flow from an inlet to a sequestration chamber or portion, to a second state in which the inlet is placed in fluid communication with the outlet without physically and/or mechanically sequestering (or isolating) the sequestration chamber or portion. When such a control device is in the second state, one or more features and/or geometries of the control device can result in a preferential flow of bodily fluid from the inlet to the outlet and the initial volume of bodily fluid can be retained in the sequestration chamber or portion without physically and/or mechanically being sequestered or isolated.

While the restricted flow path 232 is described above as modulating and/or controlling a magnitude of negative pressure applied on or through at least a portion of the device 200, in other embodiments, a control device can include any suitable feature, mechanism, and/or device configured to modulate, create, and/or otherwise control one or more pressure differentials through at least a portion of the control device. For example, in some embodiments, a user can transition and/or move an actuator to change (e.g., reduce or increase) the size of one or more portions of a fluid flow path or fluid flow interface within a portion of the control device to manually modulate and/or otherwise control an amount or magnitude of negative pressure within one or more portions of a control device.

Although various embodiments have been described as having particular features, concepts, and/or combinations of components, other embodiments are possible having any combination or sub-combination of any features, concepts, and/or components from any of the embodiments described herein. For example, as described above, the device 700 includes concepts, features, and/or elements of the devices 200 and 600. As another example, any of the embodiments described herein can include a lock or other suitable feature configured to at least temporarily maintain one or more components in a desired position, state, arrangement, and/or configuration. As another example, any of the embodiments described herein can include and/or can define a sequestration chamber and/or portion that is configured similar to, for example, the sequestration chamber 1234 described above with reference to FIG. 30. In other words, any of the fluid control devices described herein can include a sequestration chamber that is arranged and/or formed as a channel. In some embodiments, a channel forming at least a portion of a sequestration chamber can have a relatively small cross-sectional shape and/or size that can reduce and/or substantially prevent mixing of air and bodily fluid as the initial volume of bodily fluid is drawn into the channel, as described above with reference to the sequestration chamber 1234. Moreover, such a channel can have a spiral shape and/or configuration similar to the sequestration chamber 1234 described above and/or can have any other suitable shape and/or configuration.

As another example, any of the control devices described herein can include a flow controller arranged as a selectively permeable member or membrane as described above, for example, with reference to the flow controller 242. More particularly, while the control device 600 is not described as including a flow controller, in other embodiments, a portion of the diaphragm 676 can include and/or can form a flow controller formed, at least in part, of a selectively permeable material. In such embodiments, the flow controller can be configured to allow a volume of the sequestration chamber and/or portion 634 to be vented in response to being exposed to the negative pressure differential (as described above). In other words, a volume of air can be drawn out of (e.g., vented from or purged from) the sequestration chamber 634 via the flow controller in response to the negative pressure differential within a portion of the fluid control device 600. In some instances, such an arrangement can allow for a reduction in a size and/or volume of the sequestration chamber 634 because a volume of air otherwise occupying a portion of the sequestration chamber 634 is vented or purged through the flow controller in response to the negative pressure differential.

By way of another example, any of the embodiments described herein can include any suitable actuator and/or flow controller configured to selectively control fluid flow through at least a portion of the device. Specifically, a flow controller or the like can be one or more of a selectively permeable material or membrane, a valve, a diaphragm, and/or any other suitable flow controller. While some of the embodiments have been described as including an actuator rod configured to be transitioned from a first configuration or position to a second configuration or position (e.g., the actuator rod 1262 of the actuator 1250), in other embodiments, any actuator described herein can include an actuator rod configured to transition from between a first position and second position to at least temporarily isolate an outlet of the device from one or more other portions of the device (e.g., as described above with reference to the actuators 850 and/or 1350). In some embodiments, such an actuator can be configured for use with a given and/or predetermined collection device such as, for example, a syringe. In other embodiments, such an actuator can be used with any suitable collection device.

In some embodiments, the specific configurations of the various components can also be varied. For example, the size and specific shape of the various components can be different from the embodiments shown, while still providing the functions as described herein. For example, while a portion of the actuator body 1551, sequestration chamber 1534, and/or the bladder 1578 are shown in FIGS. 45-50 as being substantially tubular having a round or substantially semi-circular end portion, in other embodiments, the portion of the actuator body 1551, sequestration chamber 1534, and/or bladder 1578 can have any suitable shape and/or size. In some embodiments, varying the size and/or shape of such components may reduce an overall size of the device 1500 and/or may increase the ergonomics of the device 1500 without changing the function of the device 1500. As a specific example, a housing, sequestration chamber, and/or bladder may have a substantially cylindrical shape with a relatively flat end portion or the like. Moreover, in some embodiments, a control device can include a bladder that is configured to "flip" similar to the diaphragms described above in response to being exposed to a negative pressure differential. In other embodiments, a bladder can be configured to gradually transition (e.g., unroll, unfold, unfurl, and/or otherwise reconfigure) from the first state to the second state. In some instances, controlling a rate at which a bladder is transitioned may allow for a modulation and/or control of a negative pressure differential produced within the sequestration chamber.

In other embodiments, a device may include a bladder (similar in form and/or function to the bladders 1478 and/or 1578) disposed in a housing having a size, shape, and/or profile similar to the housings 1230 and/or 1330. In some such embodiments, the bladder can define a volume that is similar in shape and/or size the overall size, and/or shape of the housing (e.g., cylindrical with a relatively low profile or height). In some instances, such an arrangement can allow at least a portion of an initial volume of bodily fluid to remain in contact with a surface of the bladder (or diaphragm or other actuator), which can provide a visual indication to the user regarding the bodily fluid being transferred into the sequestration chamber. In other embodiments, a housing similar to the housing 1230 can define a spiral channel or any other suitable channel and can include a bladder disposed within at least a portion of that channel. In such embodiments, the bladder can function similarly to the bladder 1578 in which the bladder expands, opens, and/or otherwise increases in volume in response to being exposed to a negative pressure differential. In some embodiments, a bladder can define an enclosed volume configured to receive an initial volume of bodily fluid. In other embodiments, the bladder and a portion of the housing (e.g., a surface defining the sequestration chamber and/or channel) can collectively define the volume configured to receive the initial volume of bodily fluid. In this manner, a fluid control device can include a bladder configured to conform to any suitable shape, feature, channel, and/or configuration of a housing in which it is disposed. In some embodiments, the size and shape of the various components can be specifically selected for a desired rate and/or volume of bodily fluid flow into a fluid reservoir.

In some embodiments, the size and/or shape of the various components can be specifically selected for a desired or intended usage. For example, in some embodiments, a device such as those described herein can be configured for use with or on seemingly healthy adult patients. In such embodiments, the device can include a sequestration chamber that has a first volume (e.g., about 0.5 ml to about 5.0 ml). In other embodiments, a device such as those described herein can be configured for use with or on, for example, very sick patients and/or pediatric patients. In such embodiments, the device can include a sequestration chamber that has a second volume that is less than the first volume (e.g., less than about 0.5 ml). Thus, it should be understood that the size, shape, and/or arrangement of the embodiments and/or components thereof can be adapted for a given use unless the context explicitly states otherwise.

Although not shown, any of the devices described herein can include an opening, port, coupler, septum, Luer-Lok, gasket, valve, threaded connecter, standard fluidic interface, etc. (referred to for simplicity as a "port") in fluid communication with the sequestration chamber. In some such embodiments, the port can be configured to couple to any suitable device, reservoir, pressure source, etc. For example, in some embodiments, the port can be configured to couple to a reservoir, which in turn, can allow a greater volume of bodily fluid to be diverted and/or transferred into the sequestration chamber. In other embodiments, the port can be coupled to a negative pressure source such as an evacuated container, a pump, a syringe, and/or the like to collect a portion of or the full volume of bodily fluid in the sequestration chamber, channel, reservoir, etc. and use that volume of bodily fluid (e.g., the pre-sample volume) for additional clinical and/or in vitro diagnostic testing purposes. In other embodiments, the port can be configured to receive a probe, sampling tool, testing device, and/or the like that can be used to perform one or more tests (e.g., tests not sensitive to potential contamination) on the initial volume while the initial volume is disposed or sequestered in the sequestration chamber. In still other embodiments, the port can be coupled to any suitable pressure source or infusion device configured to infuse the initial volume of bodily fluid sequestered in the sequestration chamber back into the patient and/or bodily fluid source (e.g., in the case of pediatric patients, very sick patients, patients having a low blood volume, and/or the like). In other embodiments, the sequestration channel, chamber, and/or reservoir can be configured with the addition of other diagnostic testing components integrated into the chamber (e.g., a paper test) such that the initial bodily fluid is used for that test.

In still other embodiments, the sequestration chamber, channel, and/or reservoir can be designed, sized, and configured to be removable and compatible with testing equipment and/or specifically accessible for other types of bodily fluid tests commonly performed on patients with suspected conditions. By way of example, a patient with suspected sepsis commonly has blood samples collected for lactate testing, procalcitonin testing, and blood culture testing. All of the fluid control devices described herein can be configured such that the sequestration chamber, channel, reservoir, etc. can be removed (e.g., after receiving the initial volume of bodily fluid) and the bodily fluid contained therein can be used for these additional testing purposes before or after the subsequent sample is collected for microbial testing.

Although not shown, in some embodiments, a fluid control device can include one or more lumen, channels, flow paths, etc. configured to selectively allow for a "bypass" flow of bodily fluid, where an initial amount or volume of bodily fluid can flow from the inlet, through the lumen, cannel, flow path, etc. to bypass the sequestration chamber, and into the collection device. In some embodiments, the fluid control device can include an actuator having, for example, at least three states-a first in which bodily fluid can flow from the inlet to the sequestration chamber, a second in which bodily fluid can flow from the inlet to the outlet after the initial volume is sequestered in the sequestration chamber, and a third in which bodily fluid can flow from the inlet, through the bypass flow path, and to the outlet. In other embodiments, the control device can include a first actuator configured to transition the device between a first and second state, as described in detail above with reference to specific embodiments, and can include a second actuator configured to transition the device to a bypass configuration or the like. In still other embodiments, the control device can include any suitable device, feature, component, mechanism, actuator, controller, etc. configured to selectively place the fluid control device in a bypass configuration or state.

Any of the embodiments described herein can be used in conjunction with any suitable fluid transfer, fluid collection, and/or fluid storage device such as, for example, the fluid reservoirs described in the '420 patent. In some instances, any of the embodiments described herein can be used in conjunction with any suitable transfer adapter, fluid transfer device, fluid collection device, and/or fluid storage devices such as, for example, the devices described in the '510 Publication and/or any of the devices described in U.S. Patent Publication No. 2015/0246352 entitled, "Apparatus and Methods for Disinfection of a Specimen Container," filed Mar. 3, 2015; U.S. Pat. No. 8,535,241 entitled, "Fluid Diversion Mechanism for Bodily-Fluid Sampling," filed Oct. 12, 2012; U.S. Pat. No. 9,060,724 entitled, "Fluid Diversion Mechanism for Bodily-Fluid Sampling," filed May 29, 2013; U.S. Pat. No. 9,155,495 entitled, "Syringe-Based Fluid Diversion Mechanism for Bodily-Fluid Sampling," filed Dec. 2, 2013; U.S. Patent Publication No. 2016/0361006 entitled, "Devices and Methods for Syringe Based Fluid Transfer for Bodily-Fluid Sampling," filed Jun. 13, 2016; U.S. Patent Publication No. 2018/0140240 entitled, "Systems and Methods for Sample Collection with Reduced Hemolysis," filed Nov. 20, 2017; and/or U.S. Patent Publication No. 2017/0065733 entitled, "Apparatus and Methods for Maintaining Sterility of a Specimen Container," filed Sep. 6, 2016, the disclosures of each of which are incorporated herein by reference in their entireties.

In some embodiments, a method of using a fluid control device such as those described herein can include the ordered steps of establishing fluid communication between a bodily fluid source (e.g., a vein of a patient or the like) and an inlet of a fluid control device. An outlet of the fluid control device is then placed in fluid communication with and/or otherwise engages a negative pressure source. Such a negative pressure source can be a sample reservoir, a syringe, an evacuated container, an intermediate transfer device, and/or the like. The fluid control device can be in a first state or operating mode when the outlet is coupled to the negative pressure source and, as such, a negative pressure differential is applied through the fluid control device that draws an initial volume of bodily fluid into a sequestration chamber of the fluid control device. For example, a negative pressure within a sample reservoir can be operable in drawing an initial volume of bodily fluid from a patient and into the sequestration chamber. Once the initial volume of bodily fluid is disposed in the sequestration chamber, the fluid control device is transitioned, either automatically or via user intervention, from the first state or operating mode to a second state or operating mode such that (1) the initial volume is sequestered in the sequestration chamber and (2) the fluid communication is established between the inlet and the outlet. The sequestration of the initial volume can be such that contaminants entrained in the flow of the initial volume are likewise sequestered within the sequestration chamber. With the initial volume of bodily fluid sequestered in the sequestration chamber and with fluid communication established between the inlet and the outlet, subsequent volumes of bodily fluid that are substantially free of contamination can be collected in one or more sample reservoirs.

While the method of using the fluid control device is explicitly described as including the recited ordered steps, in other embodiments, the ordering of certain events and/or procedures in any of the methods or processes described herein may be modified and such modifications are in accordance with the variations of the invention. Additionally, certain events and/or procedures may be performed concurrently in a parallel process when possible, as well as performed sequentially as described above. Certain steps may be partially completed or may be omitted before proceeding to subsequent steps. For example, while the devices are described herein as transitioning from a first state to a second state in a discrete operation or the like, it should be understood that the devices described herein can be configured to automatically and/or passively transition from the first state to the second state and that such a transitioning may occur over a period of time. In other words, the transitioning from the first state to the second state may, in some instances, be relatively gradual such that as a last portion of the initial volume of bodily fluid is being transferred into the sequestration chamber, the housing begins to transition from the first state to the second state. In some instances, the rate of change when transitioning from the first state to the second state can be selectively controlled to achieve one or more desired characteristics associated with the transition. Moreover, in some such instances, the inflow of the last portion of the initial volume can limit and/or substantially prevent bodily fluid already disposed in the sequestration chamber from escaping therefrom. Accordingly, while the transitioning from the first state to the second state may occur over a given amount of time, the sequestration chamber can nonetheless sequester the volume of bodily fluid disposed therein.

What is claimed is:

1. A device, comprising:

a housing having an inlet and an outlet, the housing defining each of a containment channel and a sampling channel;

a blood barrier disposed in the housing between the containment channel and the outlet, the blood barrier being gas permeable and blood impermeable;

a movable seal disposed in the housing, the movable seal configured, in a first state, to separate the inlet from at least a portion of the sampling channel such that a pressure differential between the inlet and the outlet causes a gas to flow from the containment channel through the blood barrier and a volume of blood to flow into the containment channel, the movable seal configured to transition to a second state due to an increase in a pressure differential across movable seal, wherein the increase in the pressure differential across the movable seal is a result of the volume of blood in the containment channel limiting gas flow through the blood barrier; and a lock configured to engage the movable seal to at least temporarily maintain the movable seal in the second position.

2. The device of claim 1, wherein the inlet is configured to be fluidically coupled to a patient.

3. The device of claim 1, wherein the outlet is configured to be fluidically coupled to a fluid collection device.

4. The device of claim 3, wherein fluidically coupling the outlet to the fluid collection device generates the pressure differential between the inlet and the outlet.

5. The device of claim 1, wherein the housing defines a flow path between an end portion of the containment channel and the outlet, a cross-sectional area of at least a portion of the flow path is configured to modulate the pressure differential between the inlet and the outlet as the volume of blood flows into the containment channel.

6. The device of claim 1, wherein the blood barrier is disposed at an end portion of the containment channel.

7. The device of claim 1, wherein the movable seal is formed from an elastomeric material.

8. The device of claim 1, wherein the movable seal is configured, in the second state, such that the sampling channel defines a portion of a flow path between the inlet and the outlet that receives a subsequent volume of blood.

9. The device of claim 8, wherein the housing is configured such that the containment channel contains the volume of blood to limit contamination of the subsequent volume of blood that flows through the flow path, which reduces false results in culture testing of the subsequent volume of blood.

10. The device of claim 1, wherein the transition of the movable seal from the first state to the second state includes the movable seal being moved from a first position to a second position.

11. The device of claim 10, wherein the movable seal is configured to move relative to the blood barrier.

12. The device of claim 1, wherein the housing has an inner surface that defines each of the containment channel and the sampling channel.

13. The device of claim 12, wherein the movable seal in the first state forms a seal with a portion of the inner surface to prevent the volume of blood from flowing through the sampling channel.

* * * * *